US012595477B2

(12) United States Patent
Li et al.

(10) Patent No.: US 12,595,477 B2
(45) Date of Patent: Apr. 7, 2026

(54) COMPLEMENT FACTOR B-MODULATING COMPOSITIONS AND METHODS OF USE THEREOF

(71) Applicant: ADARx Pharmaceuticals, Inc., San Diego, CA (US)

(72) Inventors: Zhen Li, San Diego, CA (US); Rui Zhu, San Diego, CA (US); Zhiqing (Joel) Zhou, San Diego, CA (US); Sean Studer, San Diego, CA (US); Kimberly Fultz, San Diego, CA (US); Jean da Silva Correia, San Diego, CA (US)

(73) Assignee: ADARx Pharmaceuticals, Inc., San Diego, CA (US)

( * ) Notice: Subject to any disclaimer, the term of this patent is extended or adjusted under 35 U.S.C. 154(b) by 601 days.

(21) Appl. No.: 18/058,664

(22) Filed: Nov. 23, 2022

(65) Prior Publication Data

US 2024/0043836 A1 Feb. 8, 2024

Related U.S. Application Data

(60) Provisional application No. 63/339,873, filed on May 9, 2022, provisional application No. 63/302,976, filed on Jan. 25, 2022, provisional application No. 63/287,952, filed on Dec. 9, 2021, provisional application No. 63/283,177, filed on Nov. 24, 2021.

(51) Int. Cl.
*C12N 15/11* (2006.01)
*A61P 3/00* (2006.01)

(52) U.S. Cl.
CPC ................ *C12N 15/11* (2013.01); *A61P 3/00* (2018.01); *C12N 2310/3125* (2013.01); *C12N 2310/315* (2013.01); *C12N 2310/323* (2013.01)

(58) Field of Classification Search
CPC ...................................................... C12N 15/11
See application file for complete search history.

(56) References Cited

U.S. PATENT DOCUMENTS

2016/0298124 A1 10/2016 Borodovsky et al.
2021/0123048 A1 4/2021 Dames et al.

FOREIGN PATENT DOCUMENTS

WO 2004/045543 A2 6/2004
WO 2005/116204 A1 12/2005
WO 2014/107763 A1 7/2014
WO 2015/038939 A2 3/2015
WO 2015/168635 A2 11/2015
WO 2021/222549 A1 11/2021
WO 2023/031359 A1 3/2023
WO WO-2023056446 A1 * 4/2023 ........... C12N 15/113
WO 2023/076451 A1 5/2023

OTHER PUBLICATIONS

Invitation to Pay Additional Fees for Application No. PCT/US2022/080448, mailed Feb. 27, 2023.
International Search Report and Written Opinion for Application No. PCT/US2022/080448, mailed May 1, 2023.
GENBANK Submission; NIH/NCBI, Accession No. NC_000006.12, Apr. 6, 2022. 3 pages.
GENBANK Submission; NIH/NCBI, Accession No. NM_001710.6, Dec. 28, 2022. 6 pages.
GENBANK Submission; NIH/NCBI, Accession No. NT_113891.3, Apr. 6, 2022. 2 pages.
International Preliminary Report on Patentability for Application No. PCT/US2022/080448, mailed Jun. 6, 2024.
Extended European Search Report mailed Dec. 19, 2025 for European Application No. 22899562.7.

* cited by examiner

*Primary Examiner* — Ekaterina Poliakova-Georgantas
(74) *Attorney, Agent, or Firm* — Wolf, Greenfield & Sacks, P.C.

(57) ABSTRACT

Aspects of the disclosure provide compounds, compositions, and methods for modulating the expression or activity of Complement Factor B (CFB). In certain aspects, the compounds, compositions, and methods of the disclosure can be used to reduce the expression of CFB mRNA in a cell or animal. In certain aspects, the compounds, compositions, and methods of the disclosure can be used to reduce the expression of CFB protein in a cell or animal.

19 Claims, No Drawings

Specification includes a Sequence Listing.

COMPLEMENT FACTOR B-MODULATING COMPOSITIONS AND METHODS OF USE THEREOF

CROSS-REFERENCE TO RELATED APPLICATIONS

This application claims the benefit of priority under 35 U.S.C. § 119(e) of U.S. Provisional Application No. 63/283,177, filed Nov. 24, 2021; U.S. Provisional Application No. 63/287,952, filed Dec. 9, 2021; U.S. Provisional Application No. 63/302,976, filed Jan. 25, 2022; and U.S. Provisional Application No. 63/339,873, filed May 9, 2022. The disclosure of each of the prior applications is considered part of and is incorporated by reference in its entirety in the disclosure of this application.

REFERENCE TO AN ELECTRONIC SEQUENCE LISTING

The contents of the electronic sequence listing (A127870010US04-SUBSEQ-JIB.xml; Size: 111,210 bytes; and Date of Creation: Feb. 6, 2023) is herein incorporated by reference in its entirety.

BACKGROUND

Complement Factor B (CFB) is an important component of the alternative pathway of complement activation. CFB is a serine protease secreted from the liver. CFB circulates in the blood as a single chain polypeptide. Upon activation of the alternative pathway, it is cleaved by complement factor D yielding the noncatalytic chain Ba and the catalytic subunit Bb. The active subunit Bb is a serine protease which associates with C3b to form the alternative pathway C3 convertase. Production of C3 convertase leads to the formation of C5 convertase which cleaves C5 and triggers events that result in the formation of the lytic membrane attack complex (MAC). The membrane attack complex forms transmembrane channels and disrupts the phospholipid bilayer of target cells, leading to cell lysis.

Inappropriate complement activation contributes to many different diseases, including, for example, atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia and reperfusion injury, and rheumatoid arthritis (RA). Accordingly, there is a need to find effective treatments for complement related diseases.

SUMMARY

The present disclosure provides compounds, compositions, and methods for modulating the expression or activity of Complement Factor B (CFB). In certain embodiments, the compounds, compositions, and methods can be used to reduce the expression of CFB mRNA in a cell or animal. In certain embodiments, the compounds, compositions, and methods can be used to reduce the amount of CFB protein in a cell or animal.

In certain embodiments, the animal has or is at risk of having a complement pathway related disease, disorder or condition or a symptom thereof. In certain embodiments, the disease, disorder, or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). Certain compounds, compositions and methods provided herein are directed to reducing tissue damage, for example ocular damage or kidney damage, related to dysregulation of the complement pathway. Certain compounds, compositions and methods provided herein are directed to reducing atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA) in an animal. In certain embodiments, the compounds and compositions provided herein are potent and tolerable and inhibit CFB expression, which can be used to treat, prevent, ameliorate, or slow progression of tissue damage, for example ocular damage or kidney damage, related to dysregulation of the complement pathway. In certain embodiments, the compounds and compositions provided herein are potent and tolerable and inhibit CFB expression, which can be used to treat, prevent, ameliorate, or slow progression of atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA).

In certain embodiments, the compounds and compositions comprise one or more features that are effective for increasing potency. In certain embodiments, the compounds and compositions comprise one or more features that are effective for increasing tolerability. In certain embodiments, compounds and compositions comprise one or more features that are effective for targeting the compound or composition to a cell or tissue. In certain embodiments, the compounds and compositions are more potent or have greater therapeutic value than compounds publicly disclosed.

DETAILED DESCRIPTION

It is to be understood that both the foregoing summary and the following detailed description are exemplary and explanatory only and are not restrictive of the embodiments, as claimed. The section headings used herein are for organizational purposes only and are not to be construed as limiting the subject matter described.

All documents, or portions of documents, cited in this application, including, but not limited to, patents, patent applications, articles, books, treatises, and GenBank, NCBI and other sequence reference records are hereby expressly incorporated by reference for the portions of the document discussed herein, as well as in their entirety as of the date of filing this application.

It is understood that the sequence set forth in each SEQ ID NO contained herein is independent of any modification to a sugar moiety, an internucleoside linkage, or a nucleobase even if shown in context with a modified compound. As such, compounds defined by a SEQ ID NO may comprise, independently, one or more modifications to a sugar moiety, an internucleoside linkage, or a nucleobase. Oligomeric compounds referenced by Compound Number or Ref ID NO indicate a combination of nucleobase sequence, chemical modification, and motif.

Herein, the use of the singular includes the plural unless specifically stated otherwise. For example, the articles "a" and "an" are used herein to refer to one or to more than one (i.e., to at least one) of the grammatical object of the article. By way of example, "an element" means one element or more than one element, e.g., a plurality of elements. As used herein, the use of "or" means "and/or" unless stated otherwise. Furthermore, the use of the term "including" as well as other forms, such as "includes" and "included," is not limiting and is used interchangeably with, the phrase "including but not limited to."

Definitions

Unless otherwise indicated, the following terms have the following meanings:

"Complement Factor B," used interchangeably with the term "CFB," refers to any nucleic acid or protein of CFB. Exemplary nucleotide and amino acid sequences of CFB can be found, for example, at GenBank Accession No. NM_001710.6 (incorporated herein as SEQ ID NO: 1), nucleotides 31946095 to 31952084 of GenBank Accession No. NC_000006.12 (incorporated herein as SEQ ID NO: 2), GenBank Accession No. NM_001710.6 (incorporated herein as SEQ ID NO: 3), and nucleotides 3423522 to 3429511 of GenBank Accession No. NT_113891.3 (incorporated herein as SEQ ID NO: 4). Additional examples of CFB sequences are readily available through publicly available databases, e.g., GenBank, UniProt, and OMIM. Further information on CFB can be found, for example, at https://www.ncbi.nlm.nih.gov/gene/?term=CFB. CFB, as used herein, also refers to variations of the CFB gene including variants provided in the SNP database. Numerous sequence variations within the CFB gene have been identified and may be found at, for example, NCBI dbSNP and UniProt (see, e.g., https://www.ncbi.nlm.nih.gov/snp/?term=CFB). "CFB mRNA" means an mRNA encoding a CFB protein. CFB may be referred to in either upper or lower case.

"CFB specific inhibitor" refers to any agent capable of specifically inhibiting CFB RNA and/or CFB protein expression or activity at the molecular level. For example, CFB specific inhibitors include nucleic acids (including oligonucleotide compounds), peptides, antibodies, small molecules, and other agents capable of inhibiting the expression of CFB RNA and/or CFB protein.

"2'-O-methoxyethyl" or "2'-MOE" means a 2'-$O(CH_2)_2$—$OCH_3$ modification. A 2'-O-methoxyethyl modified sugar is a modified sugar with 2'-$O(CH_2)_2$—$OCH_3$ in the place of the 2'-OH group of a ribosyl ring.

"5' start site" means the nucleotide of the target nucleic acid or region which is complementary to the 3'-most nucleoside of an antisense oligonucleotide.

"3' stop site" means the nucleotide of the target nucleic acid or region which is complementary to the 5'-most nucleoside of an antisense oligonucleotide.

"About" means within ±10% of a value. For example, if it is stated, "a compound achieved about 70% inhibition of CFB", it is implied that CFB levels are inhibited within a range of 60% and 80%. When about is present before a series of numbers or a range, it is understood that "about" can modify each of the numbers in the series or range.

"Administer" or "administering" refers to routes of introducing a compound or composition provided herein to an individual to perform its intended function. An example, routes of administration that can be used include, but are not limited to, parenteral administration, such as subcutaneous, intravenous, or intramuscular injection or infusion.

"Ameliorate" refers to an improvement or lessening of at least one indicator, sign, or symptom of an associated disease, disorder, or condition. In certain embodiments, amelioration includes a delay or slowing in the progression or severity of one or more indicators of a condition or disease. The progression or severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense oligonucleotide" or "antisense strand" means an oligonucleotide which includes a region that is complementary to a target nucleic acid, e.g., a CFB RNA or a region thereof.

"Complementarity" in reference to an oligonucleotide means the nucleobase sequence of such oligonucleotide or one or more regions thereof that is complementary to the nucleobase sequence of another oligonucleotide or nucleic acid or one or more regions thereof when the two nucleobase sequences are aligned in opposing directions. Complementary nucleobases, as described herein, are limited to the following pairs: adenine (A) and thymine (T), adenine (A) and uracil (U), and cytosine (C) and guanine (G) unless otherwise specified. Complementary oligonucleotides and/or nucleic acids need not have nucleobase complementarity at each nucleoside and may include one or more nucleobase mismatches. By contrast, "fully complementary" or "100% complementary" in reference to oligonucleotides means that such oligonucleotides have nucleobase matches at each nucleoside without any nucleobase mismatches.

"Composition" or "pharmaceutical composition" means a mixture of substances suitable for administering to an individual. For example, a composition may comprise one or more compounds or salt thereof and a sterile aqueous solution.

"Co-administration" means administration of two or more compounds in any manner in which the pharmacological effects of both are manifest in the patient. Co-administration does not require both compounds to be administered in a single pharmaceutical composition, in the same dosage form, by the same route of administration, or at the same time. The effects of both compounds need not manifest themselves at the same time. The effects need only be overlapping for a period of time and need not be coextensive. Co-administration includes parallel or sequential administration of the one or more compounds.

"Conjugate group" means a group of atoms that is attached to an oligonucleotide. A conjugate group is optionally attached to an oligonucleotide through a conjugate linker. A conjugate group may, for example, alter the distribution, targeting, or half-life of a compound into which it is incorporated. Conjugate groups include targeting moieties.

"Conjugate linker" means a group of atoms comprising at least one bond that connects a linked moiety to an oligonucleotide.

"Identity" in reference to an oligonucleotide means the nucleobase sequence of such oligonucleotide or one or more regions thereof that matches the nucleobase sequence of another oligonucleotide or nucleic acid or one or more regions thereof. Identity of an oligonucleotide to another oligonucleotide or nucleic acid need not require each nucleobase to match and may include one or more different nucleobases. By contrast, "fully identical" or "100% identity" in reference to oligonucleotides means that such oligonucleotides have the same nucleobase at each relative position over its length as the other oligonucleotide or nucleic acid.

"Individual" means a human or non-human animal selected for treatment or therapy.

"Inhibiting the expression or activity" with reference to a target nucleic acid or protein means to reduce or block the expression or activity of such target relative to the expression or activity in an untreated or control sample and does not necessarily indicate a total elimination of expression or activity.

As used herein, the term "internucleoside linkage" is the covalent linkage between adjacent nucleosides in an oligonucleotide. As used herein, "modified internucleoside linkage" means any internucleoside linkage other than a phosphodiester internucleoside linkage. "Phosphorothioate internucleoside linkage" is a modified internucleoside linkage in which one of the non-bridging oxygen atoms of a phosphodiester internucleoside linkage is replaced with a sulfur atom.

Representative internucleoside linkages having a chiral center include but are not limited to alkylphosphonates and phosphorothioates. Modified oligonucleotides comprising internucleoside linkages having a chiral center can be prepared as populations of modified oligonucleotides comprising stereorandom internucleoside linkages, or as populations of modified oligonucleotides comprising phosphorothioate linkages in particular stereochemical configurations as further described below. Unless otherwise indicated, chiral internucleoside linkages of modified oligonucleotides described herein can be stereorandom or in a particular stereochemical configuration.

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$), or carbon-14 ($^{14}C$). All isotopic variations of the compounds of the present disclosure, whether radioactive or not, are encompassed within the scope of the present disclosure.

The term "isotopic variant" refers to a therapeutic agent (e.g., a compound and/or modified oligonucleotide disclosed herein) that contains an unnatural proportion of an isotope at one or more of the atoms that constitute such a therapeutic agent. In certain embodiments, an "isotopic variant" of a therapeutic agent contains unnatural proportions of one or more isotopes, including, but not limited to, hydrogen (H), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^5N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$), sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine 123 ($^{123}I$), iodine-125 ($^{125}I$), iodine-127 ($^{127}I$), iodine-129 ($^{129}I$), and iodine-131 ($^{131}I$). In certain embodiments, an "isotopic variant" of a therapeutic agent contains unnatural proportions of one or more isotopes, including, but not limited to, hydrogen (H), deuterium ($^2H$), tritium ($^3H$), carbon-11 ($^{11}C$), carbon-12 ($^{12}C$), carbon-13 ($^{13}C$), carbon-14 ($^{14}C$), nitrogen-13 ($^{13}N$), nitrogen-14 ($^{14}N$), nitrogen-15 ($^{15}N$), oxygen-14 ($^{14}O$), oxygen-15 ($^{15}O$), oxygen-16 ($^{16}O$), oxygen-17 ($^{17}O$), oxygen-18 ($^{18}O$), fluorine-17 ($^{17}F$), fluorine-18 ($^{18}F$), phosphorus-31 ($^{31}P$), phosphorus-32 ($^{32}P$), phosphorus-33 ($^{33}P$) sulfur-32 ($^{32}S$), sulfur-33 ($^{33}S$), sulfur-34 ($^{34}S$), sulfur-35 ($^{35}S$), sulfur-36 ($^{36}S$), chlorine-35 ($^{35}Cl$), chlorine-36 ($^{36}Cl$), chlorine-37 ($^{37}Cl$), bromine-79 ($^{79}Br$), bromine-81 ($^{81}Br$), iodine-123 ($^{123}I$), iodine-125 ($^{125}I$), iodine-127 ($^{127}I$), iodine-129 ($^{129}I$), and iodine-131 ($^{131}I$).

It will be understood that, in a therapeutic agent (e.g., a compound and/or modified oligonucleotide disclosed herein), any hydrogen can be $^2H$, for example, or any carbon can be $^{13}C$, for example, or any nitrogen can be $^{15}N$, for example, or any oxygen can be $^{18}O$, for example, where feasible according to the judgment of one of skill. In certain embodiments, an "isotopic variant" of a therapeutic agent contains unnatural proportions of deuterium (D).

"Mismatch" or "non-complementary" means a nucleobase of a first oligonucleotide or nucleic acid that is not complementary to the corresponding nucleobase of a second oligonucleotide or nucleic acid when the first oligonucleotide/nucleic acid and second oligonucleotide/nucleic acid are aligned in an antiparallel orientation. For example, nucleobases including, but not limited to, a universal nucleobase, inosine, and hypoxanthine, are capable of hybridizing with at least one nucleobase but are still mismatched or non-complementary with respect to the nucleobase to which they are hybridized. As another example, a nucleobase of a first oligonucleotide/nucleic acid that is not capable of hybridizing to the corresponding nucleobase of a second oligonucleotide/nucleic acid when the first and second oligonucleotides are aligned in an antiparallel orientation is a mismatch or non-complementary nucleobase.

"Modified oligonucleotide" means an oligonucleotide, wherein at least one sugar, nucleobase, or internucleoside linkage is modified. In certain embodiments, the compounds described herein comprise at least one modified oligonucleotide.

"Modulating" refers to changing or adjusting a feature in a cell, tissue, organ, or organism. For example, modulating CFB RNA can mean to increase or decrease the level of CFB RNA and/or CFB protein in a cell, tissue, organ, or organism. A "modulator" effects the change in the cell, tissue, organ, or organism. For example, a CFB compound can be a modulator that decreases the amount of CFB RNA and/or CFB protein in a cell, tissue, organ, or organism.

"Motif" means the pattern of unmodified and modified sugar moieties, nucleobases, and/or internucleoside linkages, in an oligonucleotide.

"Nucleic acid" refers to molecules composed of monomeric nucleotides. A nucleic acid includes, but is not limited to, ribonucleic acids (RNA), deoxyribonucleic acids (DNA), single-stranded nucleic acids, and double-stranded nucleic acids.

"Nucleobase" means a heterocyclic moiety capable of pairing with a base of another nucleic acid. As used herein a "naturally occurring nucleobase" is adenine (A), thymine (T), cytosine (C), uracil (U), and guanine (G). A "modified nucleobase" is a naturally occurring nucleobase that is chemically modified. A "universal base" or "universal nucleobase" is a nucleobase other than a naturally occurring nucleobase and modified nucleobase and is capable of pairing with any nucleobase.

"Nucleobase sequence" means the order of contiguous nucleobases in a nucleic acid or oligonucleotide independent of any sugar or internucleoside linkage.

"Nucleoside" means a compound comprising a nucleobase and a sugar moiety. The nucleobase and sugar moiety are each, independently, unmodified or modified. "Modified nucleoside" means a nucleoside comprising a modified nucleobase and/or a modified sugar moiety. Modified nucleosides include abasic nucleosides, which lack a nucleobase.

"Oligomeric Compound" means a compound comprising one or more oligonucleotides and optionally one or more additional features, such as a conjugate group or terminal group. Examples of oligomeric compounds include single-stranded and double-stranded compounds, such as, oligonucleotides, antisense oligonucleotides, interfering RNA compounds (RNAi compounds), microRNA targeting oligonucleotides, occupancy-based compounds (e.g., mRNA processing or translation blocking compounds and splicing compounds). RNAi compounds include double-stranded compounds (e.g., short-interfering RNA (siRNA) and double-stranded RNA (dsRNA)) and single-stranded compounds (e.g., single-stranded siRNA (ssRNA), single-stranded RNAi (ssRNAi), short hairpin RNA (shRNA) and microRNA mimics) which work at least in part through the RNA-induced silencing complex (RISC) pathway resulting in sequence specific degradation and/or sequestration of a target nucleic acid through a process known as RNA interference (RNAi). The term "RNAi compound" is meant to be equivalent to other terms used to describe nucleic acid compounds that are capable of mediating sequence-specific RNA interference, for example, interfering RNA (iRNA), iRNA agent, RNAi agent, short interfering oligonucleotide, short interfering nucleic acid, short interfering modified oligonucleotide, chemically modified siRNA, and others. Additionally, the term "RNAi" is meant to be equivalent to other terms used to describe sequence-specific RNA interference.

"Oligonucleotide" means a polymer of linked nucleosides, each of which can be modified or unmodified, independent from one another.

The term "oligomeric duplex" means a duplex formed by two oligomeric compounds having complementary nucleobase sequences. Each oligomeric compound of an oligomeric duplex may be referred to as a "duplexed oligomeric compound." The oligonucleotides of each oligomeric compound of an oligomeric duplex may include non-complementary overhanging nucleosides. In some embodiments, the terms "duplexed oligomeric compound" and "modified oligonucleotide" are used interchangeably. In other embodiments, the terms "oligomeric duplex" and "compound" are used interchangeably.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Pharmaceutically acceptable carrier or diluent" means any substance suitable for use in administering to an individual. In certain embodiments, a pharmaceutically acceptable carrier or diluent aids the administration of a compound to and absorption by an individual and can be included in the compositions of the present disclosure without causing a significant adverse toxicological effect on the patient. Non-limiting examples of pharmaceutically acceptable excipients include water, NaCl, normal saline solutions, and the like. For example, a pharmaceutically acceptable carrier can be a sterile aqueous solution, such as PBS or water-for-injection. One of skill in the art will recognize that other pharmaceutical excipients are useful in the present disclosure.

"Pharmaceutically acceptable salts" means or refers to physiologically and pharmaceutically acceptable salts of compounds, such as oligomeric compounds or oligonucleotides, i.e., salts that retain the desired biological activity of the parent compound and do not impart undesired toxicological effects thereto. As used herein, a pharmaceutically acceptable salt is any salt of a compound provided herein which retains its biological properties and which is not toxic or otherwise undesirable for pharmaceutical use. The pharmaceutically acceptable salts of the therapeutic agents disclosed herein include salts that are prepared with relatively nontoxic acids or bases, depending on the particular substituents found on the compounds or modified oligonucleotides described herein.

When compounds of the present disclosure contain relatively acidic functionalities, base addition salts can be obtained by contacting the neutral form of such compounds with a sufficient amount of the desired base, either neat or in a suitable inert solvent.

When compounds of the present disclosure contain relatively basic functionalities, acid addition salts can be obtained by contacting the neutral form of such compounds with a sufficient amount of the desired acid, either neat or in a suitable inert solvent.

Thus, the compounds of the present disclosure may exist as salts, such as with pharmaceutically acceptable acids. Such salts may be derived from a variety of organic and inorganic counter-ions well known in the art. Such salts include, but are not limited to: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion or an aluminum ion, or alkali metal or alkaline earth metal hydroxides, such as sodium, potassium, calcium, magnesium, aluminum, lithium, zinc, and barium hydroxide, ammonia, or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N'-dibenzylethylene-diamine, chloroprocaine, diethanolamine, procaine, N-benzylphenethylamine, N-methylglucamine piperazine, tris(hydroxymethyl)-aminomethane, tetramethylammonium hydroxide, and the like (see, for example, Berge et al., "Pharmaceutical Salts," Journal of Pharmaceutical Science, 1977, 66, 1-19).

Pharmaceutically acceptable salts further include, by way of example only and without limitation, sodium, potassium, calcium, magnesium, ammonium, tetraalkylammonium, and the like, and when the compound contains a basic functionality, salts of non-toxic organic or inorganic acids, such as hydrohalides, e.g. hydrochloride and hydrobromide, sulfate, phosphate, sulfamate, nitrate, acetate, trifluoroacetate, trichloroacetate, propionate, hexanoate, cyclopentylpropionate, glycolate, glutarate, pyruvate, lactate, malonate, succinate, sorbate, ascorbate, malate, maleate, fumarate, tartarate, citrate, benzoate, 3-(4-hydroxybenzoyl)benzoate, picrate, cinnamate, mandelate, phthalate, laurate, methanesulfonate (mesylate), ethanesulfonate, 1,2-ethane-disulfonate, 2-hydroxyethanesulfonate, benzenesulfonate (besylate), 4-chlorobenzenesulfonate, 2-naphthalenesulfonate, 4-toluenesulfonate, camphorate, camphorsulfonate, 4-methylbicyclo[2.2.2]-oct-2-ene-1-carboxylate, glucoheptonate, 3-phenylpropionate, trimethylacetate, tert-butylacetate, lauryl sulfate, gluconate, benzoate, glutamate, hydroxynaphthoate, salicylate, stearate, cyclohexylsulfamate, quinate, muconate, and the like. In some embodiments, the pharmaceutically acceptable salt of the compounds and modified oligonucleotides disclosed herein is a sodium or a potassium salt. In some embodiments, the pharmaceutically acceptable salt of the compounds and modified oligonucleotides disclosed herein is a sodium salt.

The neutral forms of the compounds are preferably regenerated by contacting the salt with a base or acid and isolating the parent compound in the conventional manner. The parent form of the compound may differ from the various salt forms in certain physical properties, such as solubility in polar solvents. In embodiments, compounds of the present disclosure contain both basic and acidic functionalities that allow the compounds to be converted into either base or acid addition salts. The neutral forms of the compounds may be regenerated by contacting the salt with a base or acid and isolating the parent compound in a conventional manner. The parent form of the compounds differs from the various salt forms in certain physical properties, such as solubility in polar solvents, but, unless specifically indicated, the salts disclosed herein are equivalent to the parent form of the compound for the purposes of the present disclosure.

“Pharmaceutical agent” means a compound that provides a therapeutic benefit when administered to an individual.

“Phosphorothioate linkage” means a modified phosphate linkage in which one of the non-bridging oxygen atoms is replaced with a sulfur atom.

“Portion” means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an oligonucleotide.

“Prevent” refers to delaying or forestalling the onset, development or progression of a disease, disorder, or condition for a period of time.

“RNA interference compound” or “RNAi compound” means a compound that acts, at least in part, through an RNA-induced silencing complex (RISC) pathway or Ago2, but not through RNase H, to modulate a target nucleic acid and/or protein encoded by a target nucleic acid. RNAi compounds include, but are not limited to double-stranded siRNA, single-stranded siRNA, and microRNA, including microRNA mimics.

“Sense oligonucleotide” or “sense strand” means the strand of a double-stranded compound that includes a region that is substantially complementary to a region of the antisense strand of the compound.

“Specifically inhibit” with reference to a target nucleic acid or protein means to reduce or block expression or activity of the target nucleic acid or protein while minimizing or eliminating effects on non-target nucleic acids or proteins.

“Subunit” with reference to an oligonucleotide means a nucleotide, nucleoside, nucleobase or sugar or a modified nucleotide, nucleoside, nucleobase, or sugar as provided herein.

“Target nucleic acid,” “target RNA,” and “nucleic acid target” all mean a nucleic acid capable of being targeted by compounds described herein.

“Target region” means a portion of a target nucleic acid to which one or more compounds is targeted.

“Targeting moiety” means a conjugate group that provides an enhanced affinity for a selected target, e.g., molecule, cell or cell type, compartment, e.g., a cellular or organ compartment, tissue, organ, or region of the body, as, e.g., compared to a compound absent such a moiety.

“Terminal group” means a chemical group or group of atoms that is covalently linked to a terminus of an oligonucleotide.

“Therapeutically effective amount” or “effective amount” means an amount of a compound, pharmaceutical agent, or composition that provides a therapeutic benefit to an individual. A “therapeutically effective amount” or “effective amount” is an amount sufficient for a compound to accomplish a stated purpose relative to the absence of the compound (e.g., achieve the effect for which it is administered, treat, prevent, or ameliorate a disease or reduce one or more symptoms of a disease or condition). An example of a “therapeutically effective amount” or “effective amount” is an amount sufficient to contribute to the treatment, prevention, amelioration, or reduction of a symptom or symptoms of a disease. A “reduction” of a symptom or symptoms (and grammatical equivalents of this phrase) means decreasing of the severity or frequency of the symptom(s), or elimination of the symptom(s). A “prophylactically effective amount” of a drug is an amount of a drug that, when administered to a subject, will have the intended prophylactic effect, e.g., preventing or delaying the onset (or reoccurrence) of an injury, disease, pathology, or condition, or reducing the likelihood of the onset (or reoccurrence) of an injury, disease, pathology, or condition, or their symptoms. The term “therapeutically effective amount,” as used herein, refers to that amount of the therapeutic agent sufficient to provide a therapeutic benefit to an individual, such as treating, preventing, or ameliorating the disease or disorder or symptom thereof, as described above. For example, for the given parameter, a therapeutically effective amount will show an increase or decrease of at least 5%, 10%, 15%, 20%, 25%, 40%, 50%, 60%, 75%, 80%, 90%, or at least 100%. Therapeutic efficacy can also be expressed as “-fold” increase or decrease. For example, a therapeutically effective amount can have at least a 1.2-fold, 1.5-fold, 2-fold, 5-fold, or more effect over a control.

The terms “treating” or “treatment” refer to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient’s physical or mental well-being. The treatment or amelioration of symptoms can be based on objective or subjective parameters, including the results of a physical examination. The term “treating” and conjugations thereof, may include prevention of an injury, pathology, condition, or disease. In embodiments, treating is preventing. In embodiments, treating does not include preventing.

"Treating" or "treatment" as used herein (and as well-understood in the art) also broadly includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. In other words, "treatment" as used herein includes any cure, amelioration, or prevention of a disease. Treatment may prevent the disease from occurring; inhibit the disease's spread; relieve the disease's symptoms, fully or partially remove the disease's underlying cause, shorten a disease's duration, or do a combination of these things.

"Treating" and "treatment" as used herein include prophylactic treatment. Treatment methods include administering to a subject a therapeutically effective amount of a compound described herein. The administering step may consist of a single administration or may include a series of administrations. The length of the treatment period depends on a variety of factors, such as the severity of the condition, the age of the patient, the concentration of the compound, the activity of the compositions used in the treatment, or a combination thereof. It will also be appreciated that the effective dosage of an agent used for the treatment or prophylaxis may increase or decrease over the course of a particular treatment or prophylaxis regime. In some instances, chronic administration may be required. For example, the compositions are administered to the subject in an amount and for a duration sufficient to treat the patient.

"Treat" refers to administering a compound or pharmaceutical composition to an animal in order to effect an alteration or improvement of a disease, disorder, or condition in the animal.

Certain compounds of the present disclosure possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present disclosure. The compounds of the present disclosure do not include those that are known in art to be too unstable to synthesize and/or isolate. The present disclosure is meant to include compounds in racemic and optically pure forms. Optically active (R)- and (S)-, or (D)- and (L)-isomers may be prepared using chiral synthons or chiral reagents or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium, and which are readily converted from one isomeric form to another.

It will be apparent to one skilled in the art that certain compounds of this disclosure may exist in tautomeric forms, all such tautomeric forms of the compounds being within the scope of the disclosure.

Unless otherwise stated, structures depicted herein are also meant to include all stereochemical forms of the structure (i.e., the R and S configurations for each asymmetric center). Therefore, single stereochemical isomers as well as enantiomeric and diastereomeric mixtures of the present compounds are within the scope of the disclosure.

As used herein, "chirally enriched population" means a plurality of molecules of identical molecular formula, wherein the number or percentage of molecules within the population that contain a particular stereochemical configuration at a particular chiral center is greater than the number or percentage of molecules expected to contain the same particular stereochemical configuration at the same particular chiral center within the population if the particular chiral center were stereorandom. Chirally enriched populations of molecules having multiple chiral centers within each molecule may contain one or more stereorandom chiral centers. In certain embodiments, the molecules are modified oligonucleotides. In certain embodiments, the molecules are compounds comprising modified oligonucleotides.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}C$- or $^{14}C$-enriched carbon are within the scope of this disclosure.

As used herein, "stereorandom chiral center" in the context of a population of molecules of identical molecular formula means a chiral center having a random stereochemical configuration. For example, in a population of molecules comprising a stereorandom chiral center, the number of molecules having the (S) configuration of the stereorandom chiral center may be but is not necessarily the same as the number of molecules having the (R) configuration of the stereorandom chiral center. The stereochemical configuration of a chiral center is considered random when it is the results of a synthetic method that is not designed to control the stereochemical configuration. In certain embodiments, a stereorandom chiral center is a stereorandom phosphorothioate internucleoside linkage.

Certain Embodiments

In certain aspects, the disclosure relates to methods, compounds, and compositions for inhibiting CFB. In certain embodiments, CFB is specifically inhibited. In certain embodiments, CFB is specifically degraded. In certain embodiments, CFB expression is inhibited. In certain embodiments, CFB translation is inhibited. In certain embodiments, CFB activity is inhibited. In certain embodiments, CFB expression, translation, or activity is reduced by at least 10% relative to the expression, translation, or activity in an untreated or control sample. For example, in certain embodiments, CFB expression, translation, or activity is reduced by at least 10%, at least 20%, at least 30%, at least 40%, at least 50%, at least 60%, at least 70%, at least 80%, at least 90%, at least 95%, 10-50%, 25-50%, 25-75%, 50-75%, 50-99%, or 75-99% relative to the expression, translation, or activity in an untreated or control sample. In certain embodiments, CFB expression, translation, or activity is reduced as measured by any suitable assay, including but not limited to, an immunoassay, a hybridization-based assay, or a sequencing-based assay (e.g., RNA-Seq).

In certain aspects, the disclosure relates to compounds targeted to a CFB nucleic acid. In certain embodiments, the CFB nucleic acid has the sequence set forth in GENBANK Accession No. NM_001710.6 (incorporated herein as SEQ ID NO: 1), nucleotides 31946095 to 31952084 of GenBank Accession No. NC_000006.12 (incorporated herein as SEQ ID NO: 2), GenBank Accession No. NM_001710.6 (incorporated herein as SEQ ID NO: 3), and nucleotides 3423522 to 3429511 of GenBank Accession No. NT_113891.3 (incorporated herein as SEQ ID NO: 4).

In certain embodiments, the compound is an oligomeric compound. In certain embodiments, the compound is single-stranded. In certain embodiments, the compound is double-stranded.

Certain embodiments provide a compound comprising a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. Certain embodiments provide a compound comprising a modified oligonucleotide (e.g., of 14 to 30, for example, 14 to 23, linked nucleosides in length) having a nucleobase sequence comprising the nucleobase sequence of any one of SEQ ID NOs: 11-44 and 96-102.

Certain embodiments provide a compound comprising a modified oligonucleotide having a nucleobase sequence selected from any one of the nucleobase sequences of SEQ ID NOs: 11-44 and 96-102.

In certain embodiments, the modified oligonucleotide has a nucleobase sequence that is at least 80%, at least 85%, at least 90%, or at least 95% complementary to the nucleobase sequence of SEQ ID NO: 1 or 3. In certain embodiments, the modified oligonucleotide comprises at least one modification selected from a modified internucleoside linkage, a modified sugar, and a modified nucleobase. In certain embodiments, the compound is double-stranded.

Certain embodiments provide a compound comprising a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide.

In certain embodiments, the compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences provided in Tables 2 and 3, and a second modified oligonucleotide (e.g., of 14 to 30, for example, 14 to 23, linked nucleosides in length) having a region of complementarity to the first modified oligonucleotide.

Certain embodiments provide a compound comprising a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide.

Certain embodiments provide a compound comprising a first modified oligonucleotide having a nucleobase sequence selected from any one of the nucleobase sequences of SEQ ID NOs: 11-110 and a second modified oligonucleotide 19 to 23 linked nucleosides in length having a region of complementarity to the first modified oligonucleotide.

In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequences of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110.

In certain embodiments, the modified oligonucleotide or first modified oligonucleotide of any compound herein has a nucleobase sequence that has at least 80%, at least 85%, at least 90%, or at least 95% complementarity or identity to the nucleobase sequence of SEQ ID NO: 1 or 3 over its length. In certain embodiments, the modified oligonucleotide or first modified oligonucleotide has a nucleobase sequence that has at least 1, at least 2, or at least 3 mismatches to a region of a nucleobase sequence of SEQ ID NO: 1 or 3. In certain embodiments, the region of complementarity between the first strand and the second strand is 14 to 30 linked nucleosides in length. In certain embodiments, the region of complementarity between the first modified oligonucleotide or first strand and the second modified oligonucleotide or second strand is 14 to 23 linked nucleosides in length. In certain embodiments, the region of complementarity between the first modified oligonucleotide or first strand and the second modified oligonucleotide or second strand is 19 to 23 linked nucleosides in length. In certain embodiments, the region of complementarity between the first modified oligonucleotide or first strand and the second modified oligonucleotide or second strand is 21 to 23 linked nucleosides in length. In certain embodiments, the first modified oligonucleotide is fully complementary to the second modified oligonucleotide.

In certain embodiments, the first modified oligonucleotide of any preceding compound or other compound herein comprises at least one modification selected from a modified internucleoside linkage, a modified sugar, and a modified nucleobase. In certain embodiments, the second modified oligonucleotide of any preceding compound comprises at least one modification selected from a modified internucleoside linkage, a modified sugar, and a modified nucleobase. In certain embodiments, the modified internucleoside linkage is a phosphorothioate internucleoside linkage or a methylphosphonate internucleoside linkage. In certain embodiments, the phosphorothioate internucleoside linkage or methylphosphonate internucleoside linkage is at the 3' terminus of the first or second modified oligonucleotide or at the 5' terminus of the first modified oligonucleotide. In certain embodiments, the modified sugar comprises a modification selected from a halogen, an alkoxy group and a bicyclic sugar. In certain embodiments, the modified sugar comprises a 2'-F modification. In certain embodiments, the modified sugar comprises a 2'-OMe modification. In certain embodiments, each nucleoside of the first modified oligonucleotide comprises a modified sugar. In certain embodiments, each nucleoside of the second modified oligonucleotide comprises a modified sugar. In certain embodiments, the modified sugar comprises a modification selected from a halogen, an alkoxy group and a bicyclic sugar or a combination thereof. In certain embodiments, the modified sugar comprises a modification selected from 2'-MOE, 2'-F, and 2'-OMe or a combination thereof. In certain embodiments, the first modified oligonucleotide comprises no more than ten 2'-F sugar modifications. In certain embodiments, the second modified oligonucleotide comprises no more than five 2'-F sugar modifications.

In certain embodiments, the compound of any preceding embodiment comprises a conjugate group. In certain embodiments, the conjugate group is attached to the 5' end of the modified oligonucleotide. In certain embodiments, the conjugate group is a targeting moiety. In certain embodiments, the targeting moiety comprises one or more GalNAc. In certain embodiments, the modified oligonucleotide is the second modified oligonucleotide or sense oligonucleotide. In certain embodiments, the one or more GalNAc is attached to the 2' or 3' position of the ribosyl ring. In certain embodiments, the one or more GalNAc is attached to the 5' nucleoside of the modified oligonucleotide. In certain embodiments, the 5' nucleoside of a modified oligonucleotide is selected from the following Formulae or a salt, solvate, or hydrate thereof, wherein R is the portion of the modified oligonucleotide other than the 5' nucleoside:

Formula I

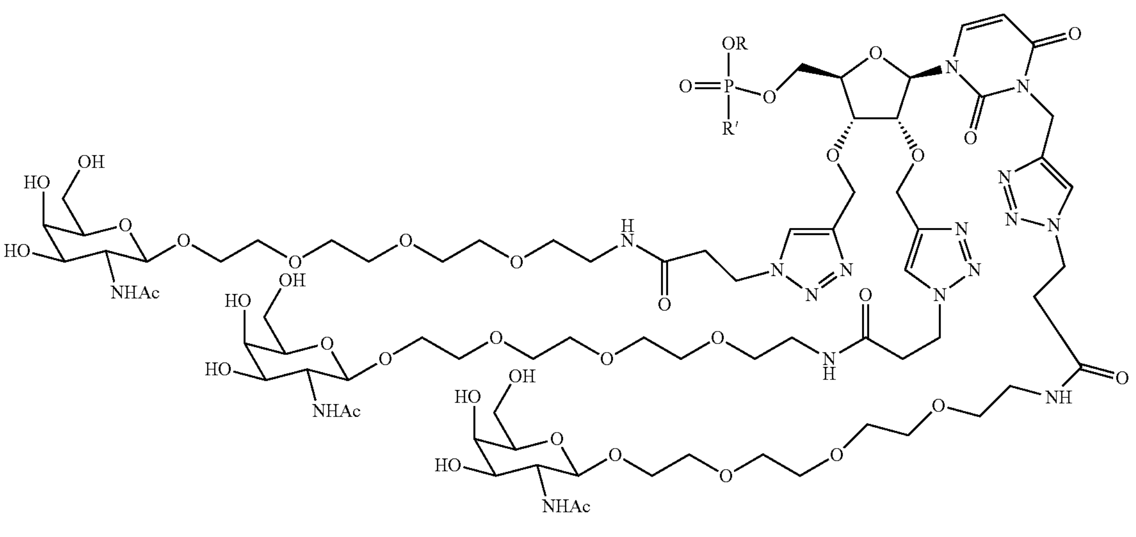

R = Oligo
R′ = $O^-$, $S^-$, OH, or SH

-continued
Formula II
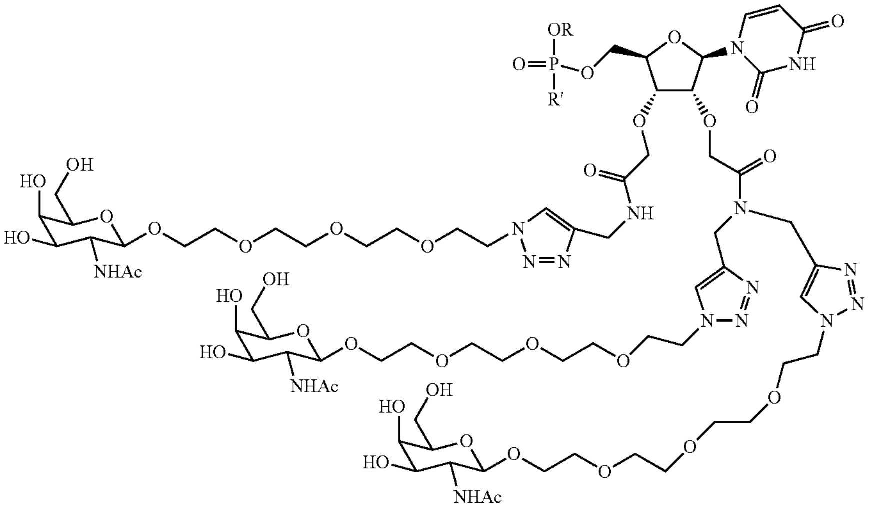
R = Oligo
R′ = O⁻, S⁻, OH, or SH
Formula III
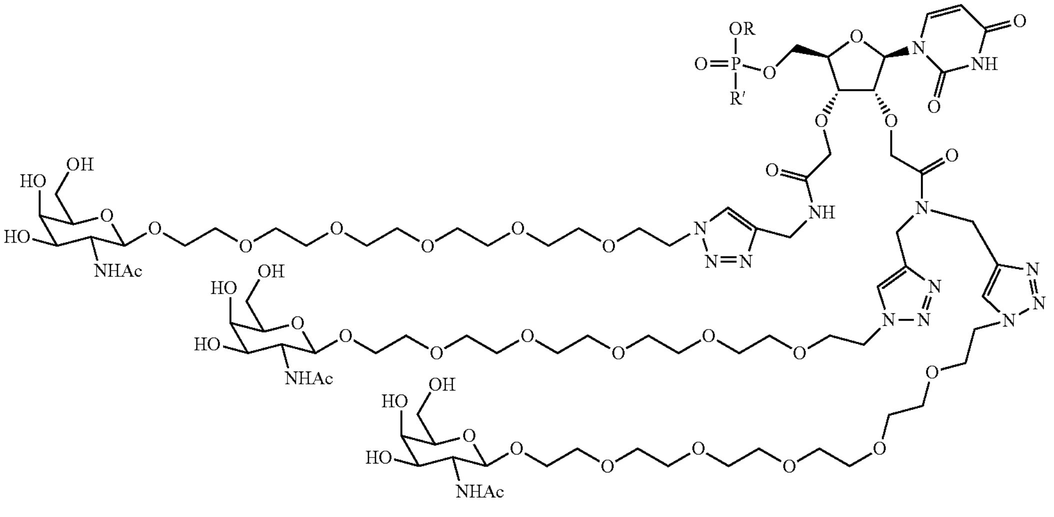
R = Oligo
R′ = O⁻, S⁻, OH, or SH -continued
Formula IV
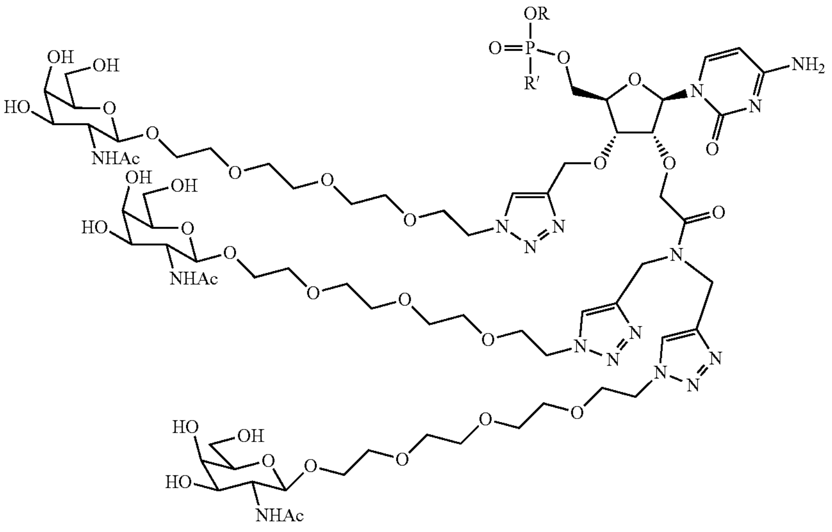
R = Oligo
R′ = O⁻, S⁻, OH, or SH
Formula V
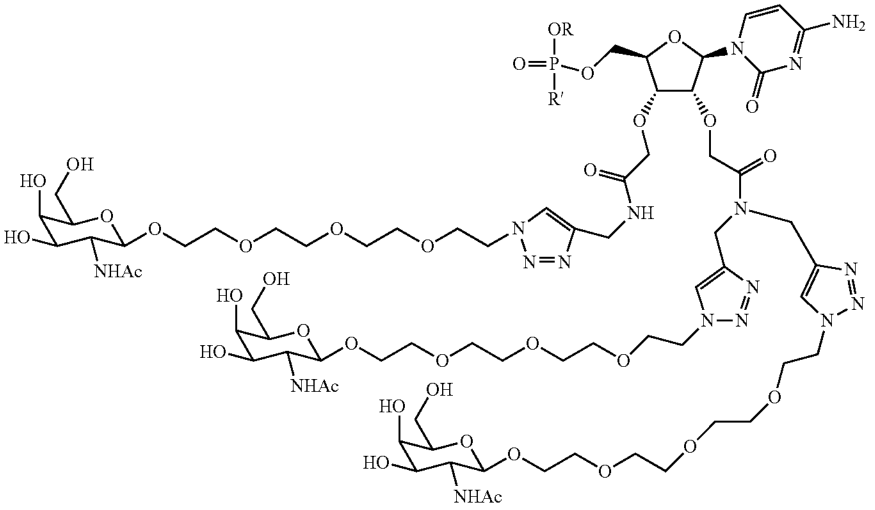
R = Oligo
R′ = O⁻, S⁻, OH, or SH -continued
Formula VI
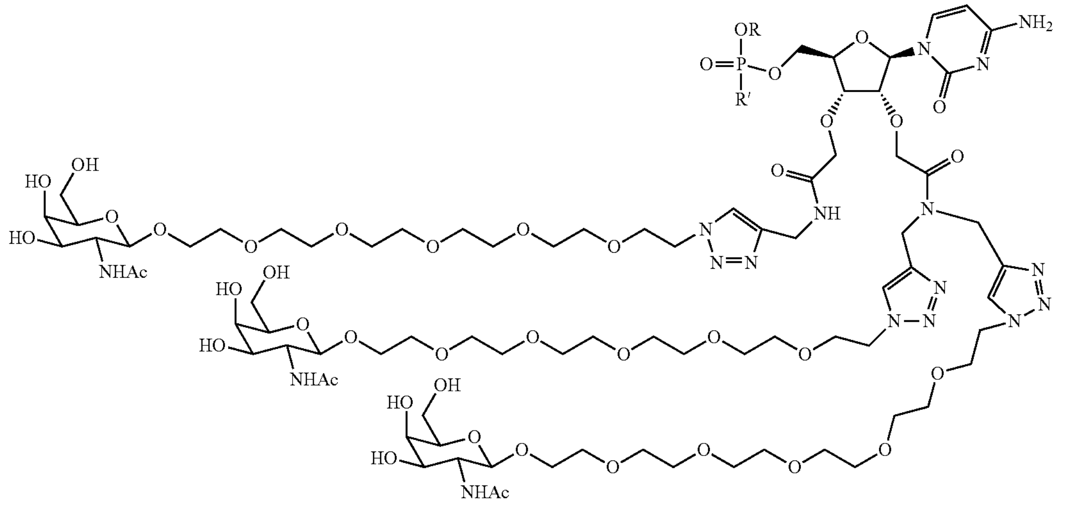
R = Oligo
R′ = O⁻, S⁻, OH, or SH
Formula VII
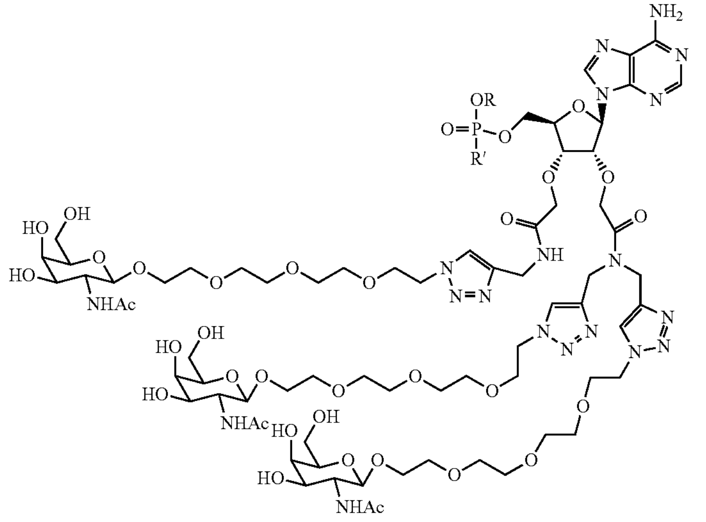
R = Oligo
R′ = O⁻, S⁻, OH, or SH -continued
Formula VIII
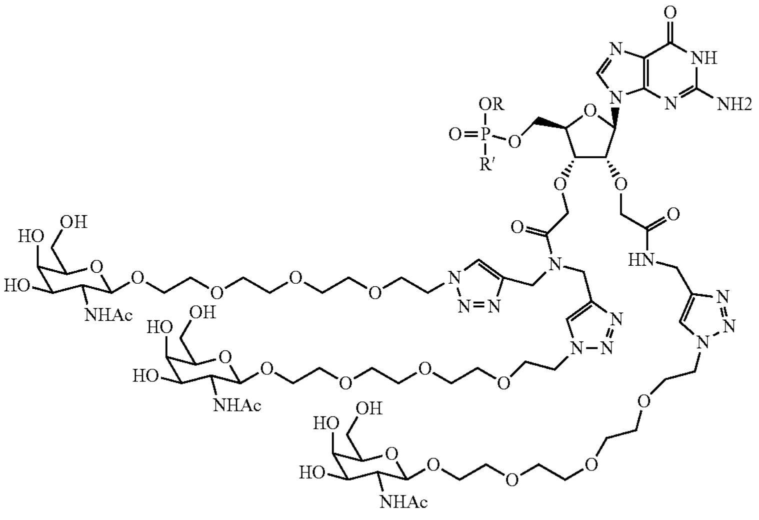
R = Oligo
R′ = O⁻, S⁻, OH, or SH
Formula XII
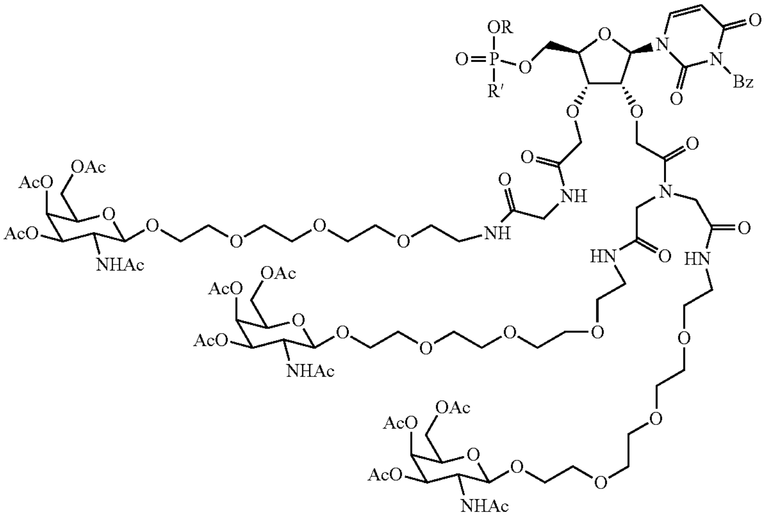
R = Oligo
R′ = O⁻, S⁻, OH, or SH In certain embodiments, the conjugate group according to Formula III is represented by the following Formula:

Formula III-A

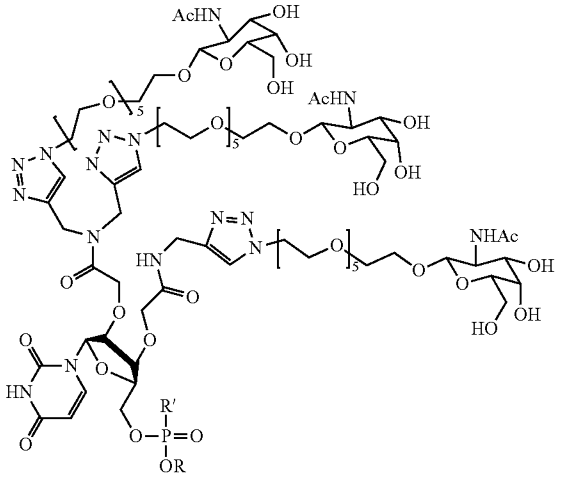

R = Oligo
R′ = O-, S-, OH, or SH

In certain embodiments, the conjugate group according to Formula V is represented by the following Formula:

Formula V-A

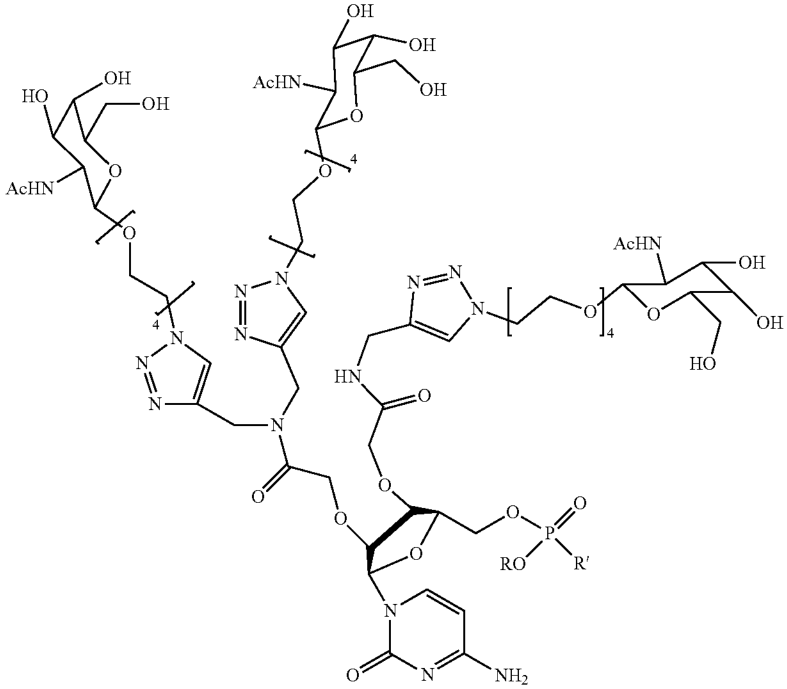

R = Oligo
R′ = O-, S-, OH, or SH

In certain embodiments, the conjugate group according to Formula VIII is represented by the following Formula:

Formula VIII-A

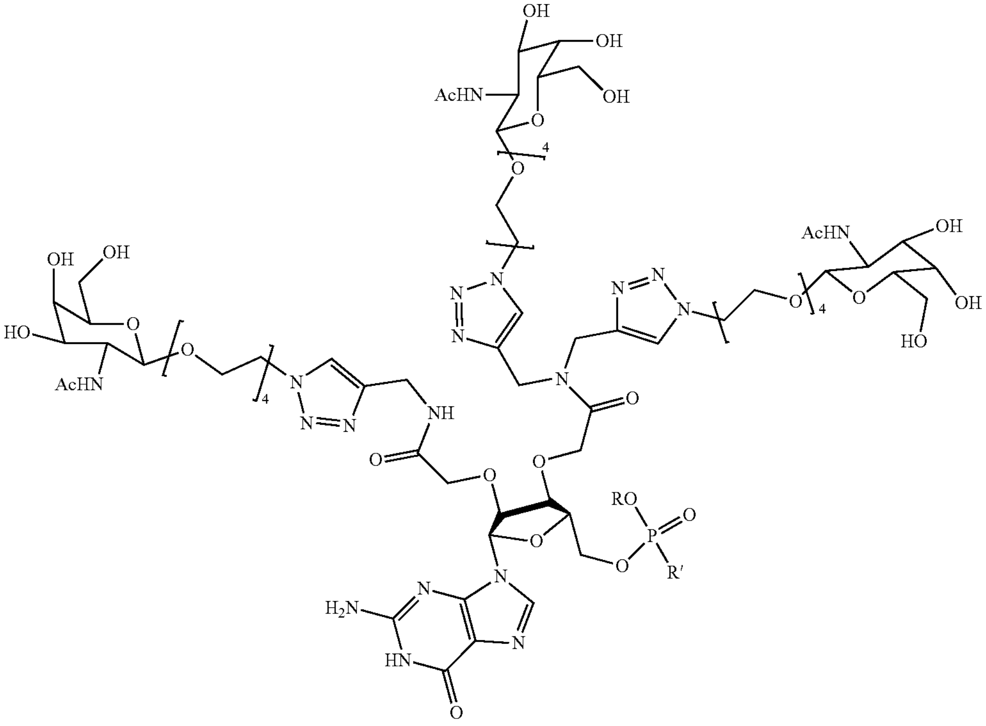

R = Oligo
R′ = O-, S-, OH, or SH

In certain embodiments, R' is OH. In certain embodiments, R' is SH. In certain embodiments, the 5' nucleoside of the modified oligonucleotide is Formula I and R' is OH. In certain embodiments, the 5' nucleoside of the modified oligonucleotide is Formula I and R' is SH. In certain embodiments, the 5' nucleoside of the modified oligonucleotide is Formula II and R' is OH. In certain embodiments, the 5' nucleoside of the modified oligonucleotide is Formula II and R' is SH. In certain embodiments, the 5' nucleoside of the modified oligonucleotide is Formula III and R' is OH. In certain embodiments, the 5' nucleoside of the modified oligonucleotide is Formula III and R' is SH. In certain embodiments, the 5' nucleoside of the modified oligonucleotide is Formula IV and R' is OH. In certain embodiments, the 5' nucleoside of the modified oligonucleotide is Formula IV and R' is SH. In certain embodiments, the 5' nucleoside of the modified oligonucleotide is Formula V and R' is OH. In certain embodiments, the 5' nucleoside of the modified oligonucleotide is Formula V and R' is SH. In certain embodiments, the 5' nucleoside of the modified oligonucleotide is Formula VI and R' is OH. In certain embodiments, the 5' nucleoside of the modified oligonucleotide is Formula VI and R' is SH. In certain embodiments, the 5' nucleoside of the modified oligonucleotide is Formula VII and R' is OH. In certain embodiments, the 5' nucleoside of the modified oligonucleotide is Formula VII and R' is SH. In certain embodiments, the 5' nucleoside of the modified oligonucleotide is Formula VIII and R' is OH. In certain embodiments, the 5' nucleoside of the modified oligonucleotide is Formula VIII and R' is SH. In certain embodiments, the 5' nucleoside of the modified oligonucleotide is Formula XII and R' is OH. In certain embodiments, the 5' nucleoside of the modified oligonucleotide is Formula XII and R' is SH.

In certain embodiments, R' is OH. In certain embodiments, R' is SH. In certain embodiments, the 5' nucleoside of the modified oligonucleotide is Formula I and R' is OH. In certain embodiments, the 5' nucleoside of the modified oligonucleotide is Formula I and R' is SH. In certain embodiments, the 5' nucleoside of the modified oligonucleotide is Formula II and R' is OH. In certain embodiments, the 5' nucleoside of the modified oligonucleotide is Formula II and R' is SH. In certain embodiments, the 5' nucleoside of the modified oligonucleotide is Formula III and R' is OH. In certain embodiments, the 5' nucleoside of the modified oligonucleotide is Formula III and R' is SH. In certain embodiments, the 5' nucleoside of the modified oligonucleotide is Formula IV and R' is OH. In certain embodiments, the 5' nucleoside of the modified oligonucleotide is Formula IV and R' is SH. In certain embodiments, the 5' nucleoside of the modified oligonucleotide is Formula V and R' is OH. In certain embodiments, the 5' nucleoside of the modified oligonucleotide is Formula V and R' is SH. In certain embodiments, the 5' nucleoside of the modified oligonucleotide is Formula VI and R' is OH. In certain embodiments, the 5' nucleoside of the modified oligonucleotide is Formula VI and R' is SH. In certain embodiments, the 5' nucleoside of the modified oligonucleotide is Formula VII and R' is OH. In certain embodiments, the 5' nucleoside of the modified oligonucleotide is Formula VII and R' is SH. In certain embodiments, the 5' nucleoside of the modified oligonucleotide is Formula VIII and R' is OH. In certain embodiments, the 5' nucleoside of the modified oligonucleotide is Formula VIII and R' is SH. In certain embodiments, the 5' nucleoside of the modified oligonucleotide is Formula XII and R' is OH. In certain embodiments, the 5' nucleoside of the modified oligonucleotide is Formula XII and R' is SH.

In certain embodiments, R' is O. In certain embodiments, R' is S. In certain embodiments, the 5' nucleoside of the modified oligonucleotide is Formula I and R' is O. In certain embodiments, the 5' nucleoside of the modified oligonucleotide is Formula I and R' is S. In certain embodiments, the 5' nucleoside of the modified oligonucleotide is Formula II and R' is O. In certain embodiments, the 5' nucleoside of the modified oligonucleotide is Formula II and R' is S. In certain embodiments, the 5' nucleoside of the modified oligonucleotide is Formula III and R' is O. In certain embodiments, the 5' nucleoside of the modified oligonucleotide is Formula III and R' is S. In certain embodiments, the 5' nucleoside of the modified oligonucleotide is Formula IV and R' is O. In certain embodiments, the 5' nucleoside of the modified oligonucleotide is Formula IV and R' is S. In certain embodiments, the 5' nucleoside of the modified oligonucleotide is Formula V and R' is O. In certain embodiments, the 5' nucleoside of the modified oligonucleotide is Formula V and R' is S. In certain embodiments, the 5' nucleoside of the modified oligonucleotide is Formula VI and R' is O. In certain embodiments, the 5' nucleoside of the modified oligonucleotide is Formula VI and R' is S. In certain embodiments, the 5' nucleoside of the modified oligonucleotide is Formula VII and R' is O. In certain embodiments, the 5' nucleoside of the modified oligonucleotide is Formula VII and R' is S. In certain embodiments, the 5' nucleoside of the modified oligonucleotide is Formula VIII and R' is O. In certain embodiments, the 5' nucleoside of the modified oligonucleotide is Formula VIII and R' is S. In certain embodiments, the 5' nucleoside of the modified oligonucleotide is Formula XII and R' is O. In certain embodiments, the 5' nucleoside of the modified oligonucleotide is Formula XII and R' is S.

Certain embodiments provide a compound comprising a first modified oligonucleotide selected from any one of Ref ID NOs: IA0478-490, IA0840, IA0842-846, IA0852-862, IA0872-882, IA0887-890, IA1010-1012, and IA1015-1018, IS0570-587, IS0969, IS0972-977, IS1023-1027, IS1029, IS1031-1037, IS1042-1046, IS1082, IS1085, IS1086, IS1091-1095, IS1108-1111, IS1236-1239, IS1242, IS1249, and IS1251-1254 and a second modified oligonucleotide 14 to 21 linked nucleosides in length fully complementary to the first modified oligonucleotide.

Certain embodiments provide a compound comprising a first modified oligonucleotide selected from any one of Ref ID NOs: IA0478-490, IA0840, IA0842-846, IA0852-862, IA0872-882, IA0887-890, IA1010-1012, and IA1015-1018 and a second modified oligonucleotide selected from any one of Ref ID NOs: IS0570-587, IS0969, IS0972-977, IS1023-1027, IS1029, IS1031-1037, IS1042-1046, IS1082, IS1085, IS1086, IS1091-1095, IS1108-1111, IS1236-1239, IS1242, IS1249, and IS1251-1254.

Certain embodiments provide a compound comprising a first modified oligonucleotide which is IA0840 and a second modified oligonucleotide which is IS0972.

Certain embodiments provide a compound comprising a first modified oligonucleotide which is IA0842 and a second modified oligonucleotide which is IS0974.

Certain embodiments provide a compound comprising a first modified oligonucleotide which is IA0888 and a second modified oligonucleotide which is IS1109.

Certain embodiments provide a compound comprising a first modified oligonucleotide which is IA0888 and a second modified oligonucleotide which is IS1236.

Certain embodiments provide a compound comprising a first modified oligonucleotide which is IA1010 and a second modified oligonucleotide which is IS1109.

Certain embodiments provide a compound comprising a first modified oligonucleotide which is IA1011 and a second modified oligonucleotide which is IS1239.

Certain embodiments provide a compound comprising a first modified oligonucleotide which is IA1012 and a second modified oligonucleotide which is IS1242. Certain embodiments provide a compound comprising a first modified oligonucleotide which is IA1016 and a second modified oligonucleotide which is IS1252.

Certain embodiments provide a compound comprising a first modified oligonucleotide which is IA1017 and a second modified oligonucleotide which is IS1253.

In certain embodiments, the compound of any foregoing embodiment is in a pharmaceutically acceptable salt form. In certain embodiments, the pharmaceutically acceptable salt is a sodium salt. In certain embodiments, the pharmaceutically acceptable salt is a potassium salt.

Certain embodiments provide a compound of any foregoing embodiments that is a stereoisomer.

In an aspect provided herein, is a modified oligonucleotide according to the following chemical structure:

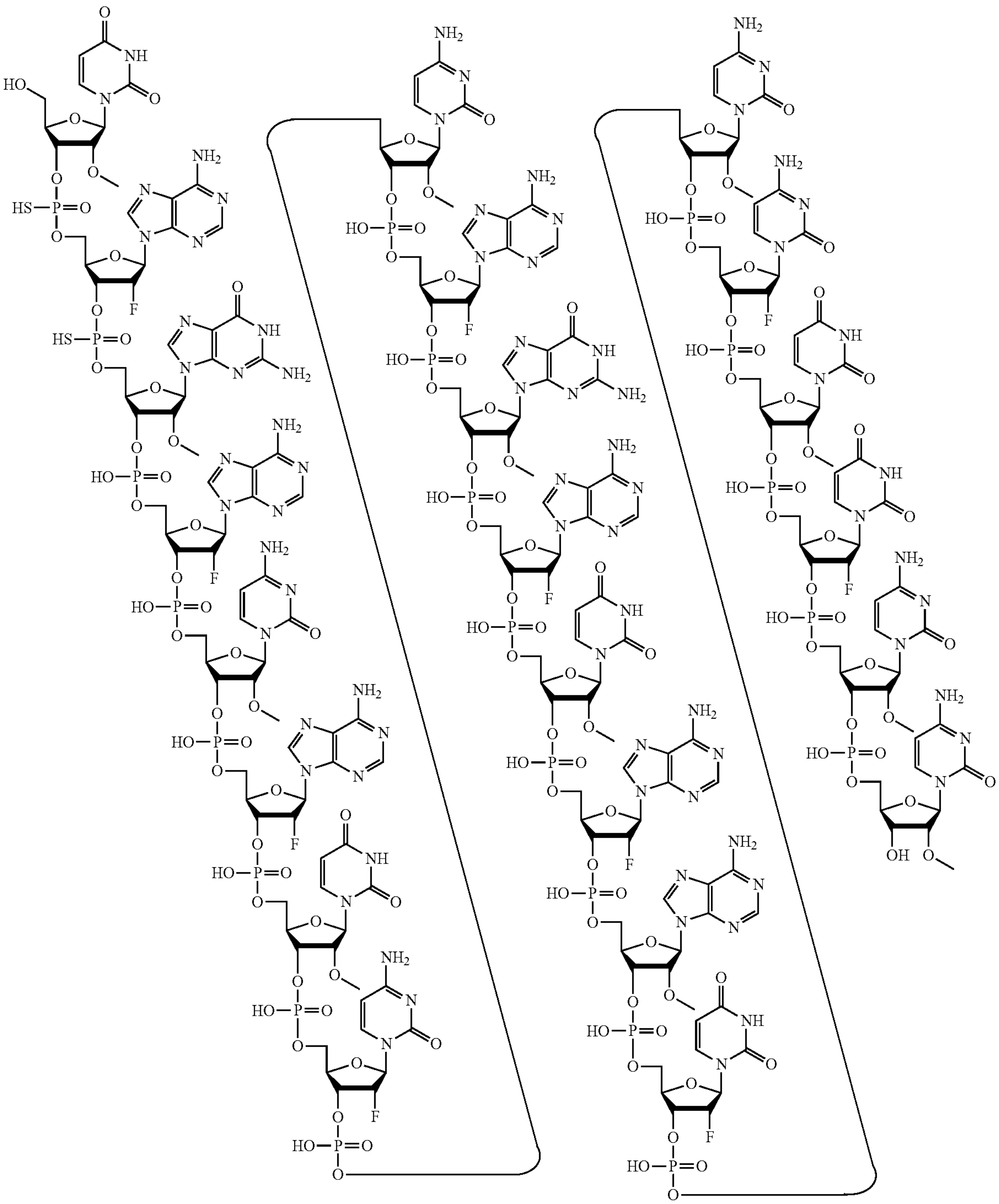
or a pharmaceutically acceptable salt or stereoisomer thereof. In certain embodiments, Ref ID NO: IA1016 is a modified oligonucleotide, or a pharmaceutically acceptable salt or stereoisomer thereof, according to the preceding chemical structure.
In an aspect provided herein, is a modified oligonucleotide according to the following chemical structure:

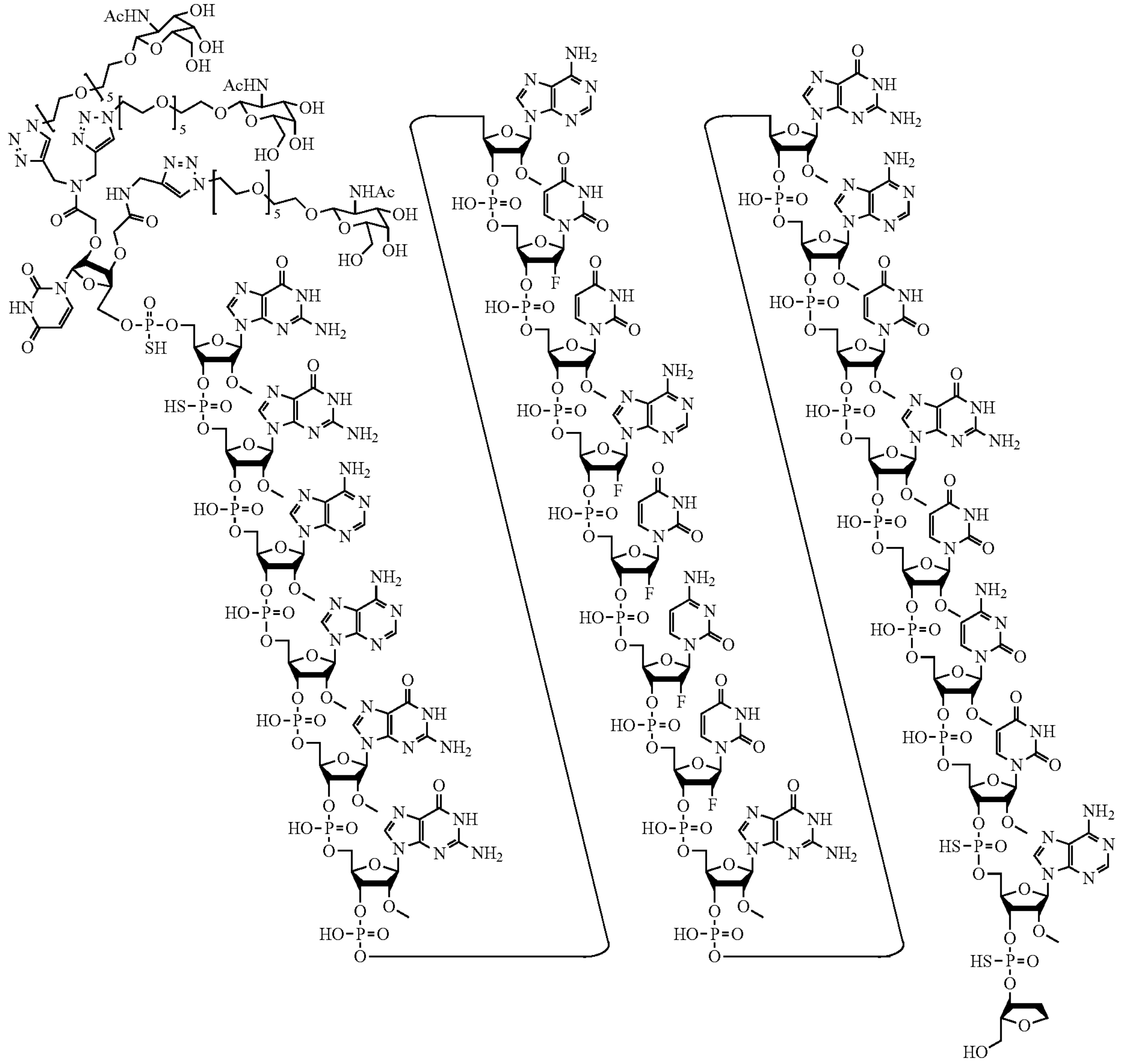
or a pharmaceutically acceptable salt or stereoisomer thereof. In certain embodiments, Ref ID NO: IS 1252 is a modified oligonucleotide, or a pharmaceutically acceptable salt or stereoisomer thereof, according to the preceding chemical structure.
In an aspect provided herein, is a modified oligonucleotide according to the following chemical structure:

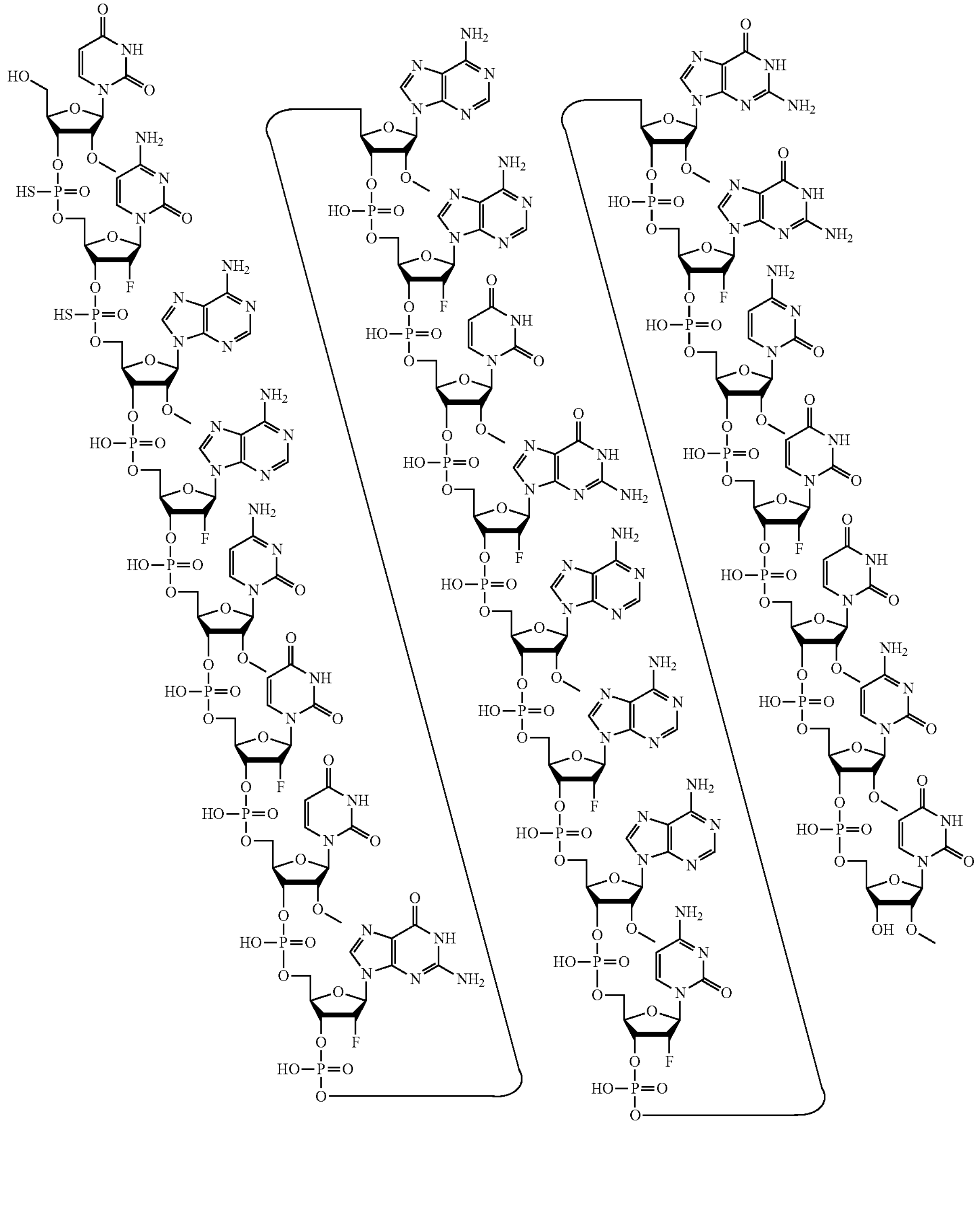
or a pharmaceutically acceptable salt or stereoisomer thereof. In certain embodiments, Ref ID NO: IA1017 is a modified oligonucleotide, or a pharmaceutically acceptable salt or stereoisomer thereof, according to the preceding chemical structure.
In an aspect provided herein, is a modified oligonucleotide according to the following chemical structure:

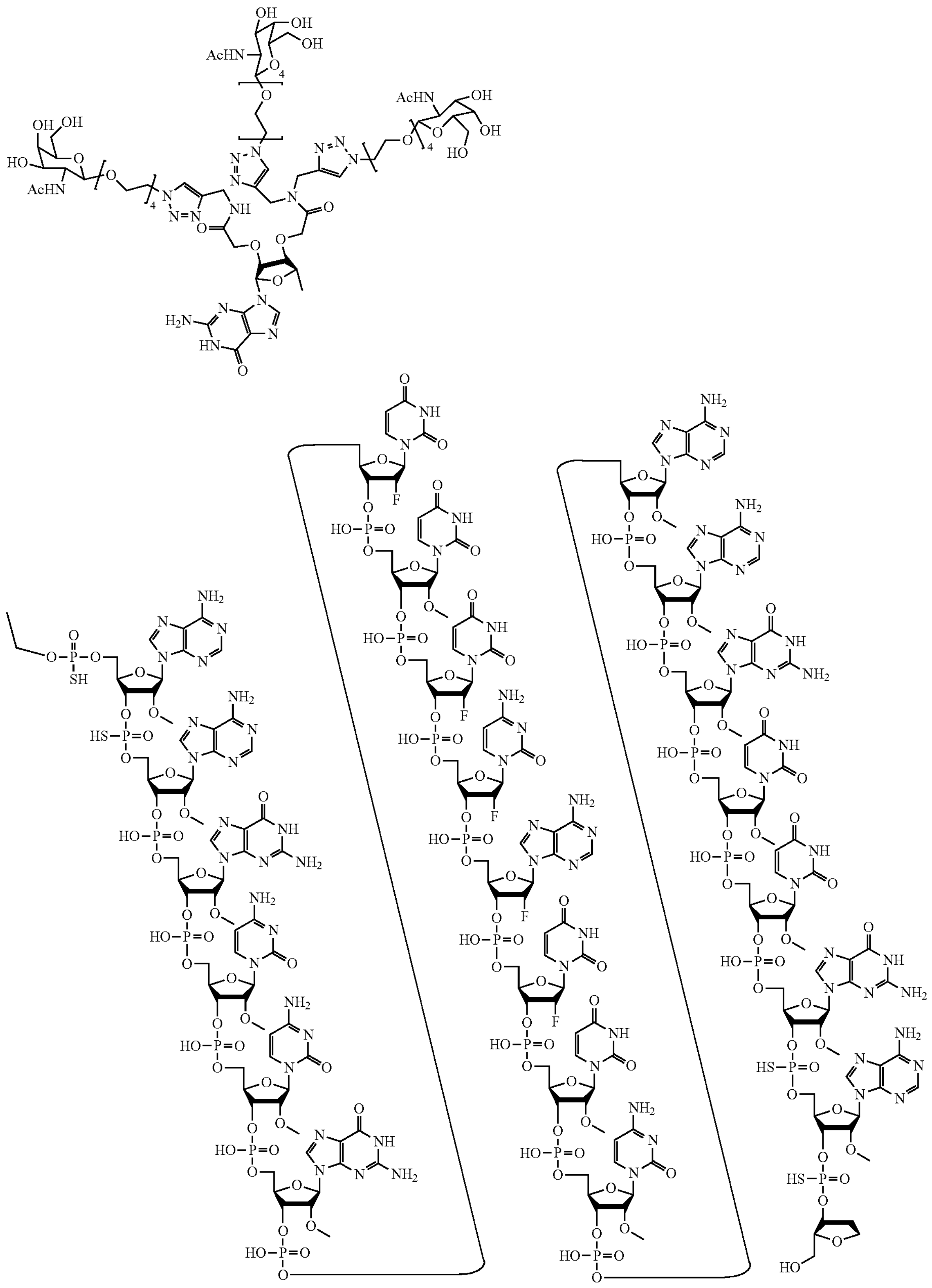

or a pharmaceutically acceptable salt or stereoisomer thereof. In certain embodiments, Ref ID NO: IS 1253 is a modified oligonucleotide, or a pharmaceutically acceptable salt or stereoisomer thereof, according to the preceding chemical structure.

In an aspect provided herein, is a modified oligonucleotide according to the following chemical structure:

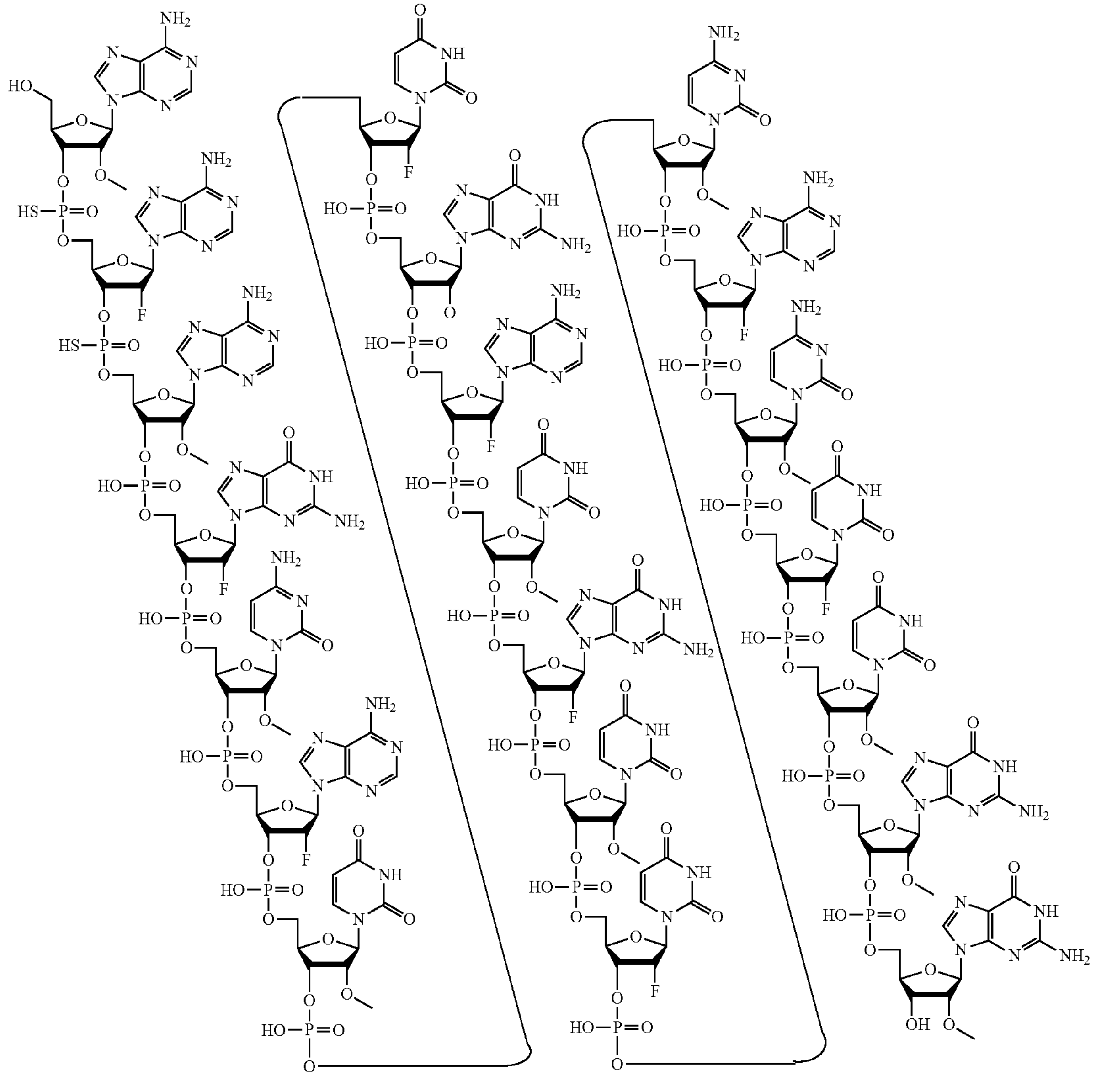

or a pharmaceutically acceptable salt or stereoisomer thereof. In certain embodiments, Ref ID NO: IA1010 is a modified oligonucleotide, or a pharmaceutically acceptable salt or stereoisomer thereof, according to the preceding chemical structure.

In an aspect provided herein, is a modified oligonucleotide according to the following chemical structure:

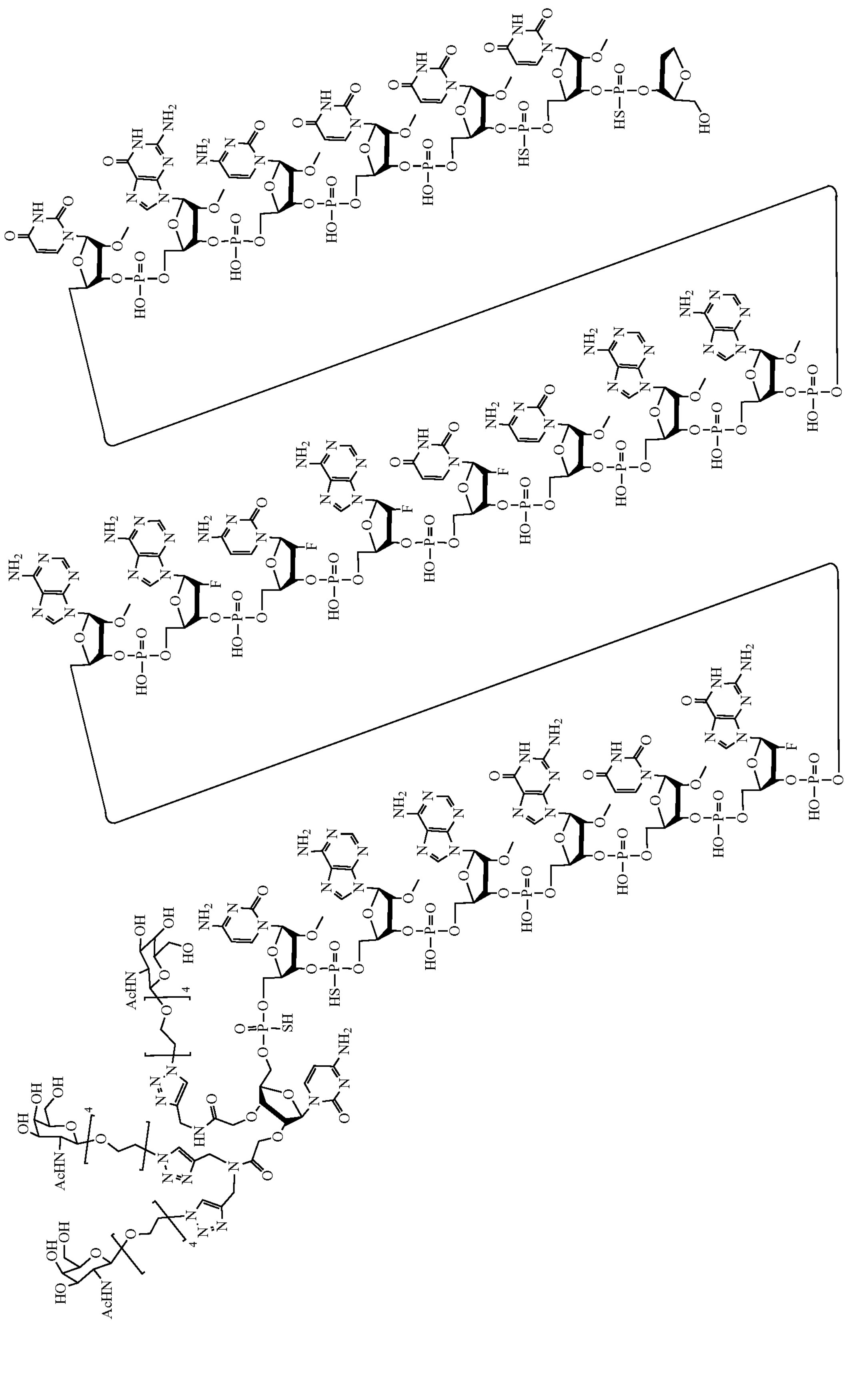

or a pharmaceutically acceptable salt or stereoisomer thereof. In certain embodiments, Ref ID NO: IS 1109 is a modified oligonucleotide, or a pharmaceutically acceptable salt or stereoisomer thereof, according to the preceding chemical structure.

In an aspect provided herein, is a modified oligonucleotide according to the following chemical structure:

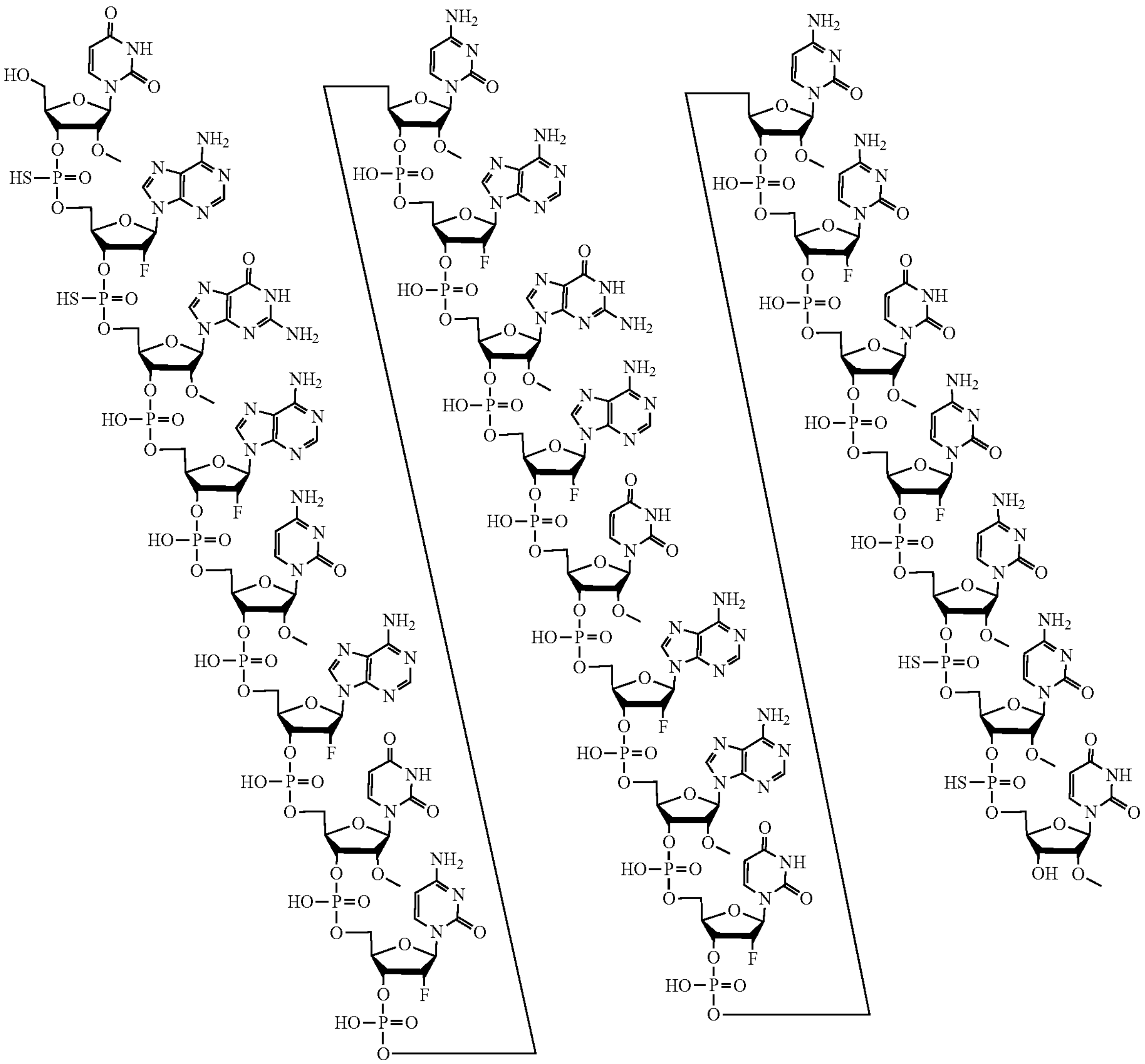

or a pharmaceutically acceptable salt or stereoisomer thereof. In certain embodiments, Ref ID NO: IA1011 is a modified oligonucleotide, or a pharmaceutically acceptable salt or stereoisomer thereof, according to the preceding chemical structure.

In an aspect provided herein, is a modified oligonucleotide according to the following chemical structure:

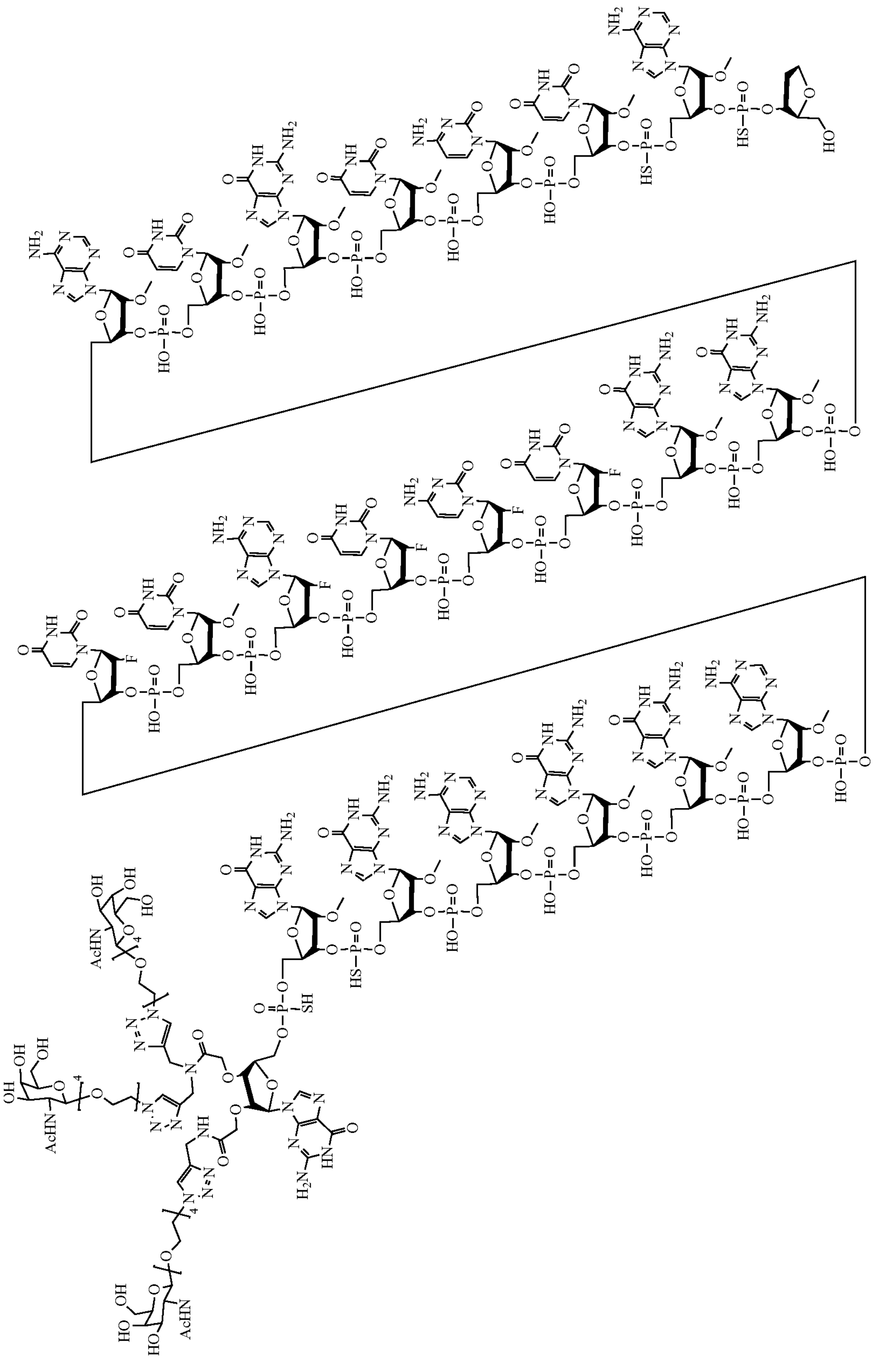

or a pharmaceutically acceptable salt or stereoisomer thereof. In certain embodiments, Ref ID NO: IS1239 is a modified oligonucleotide, or a pharmaceutically acceptable salt or stereoisomer thereof, according to the preceding chemical structure.

In an aspect provided herein, is a sodium salt of a modified oligonucleotide according to the following chemical structure:

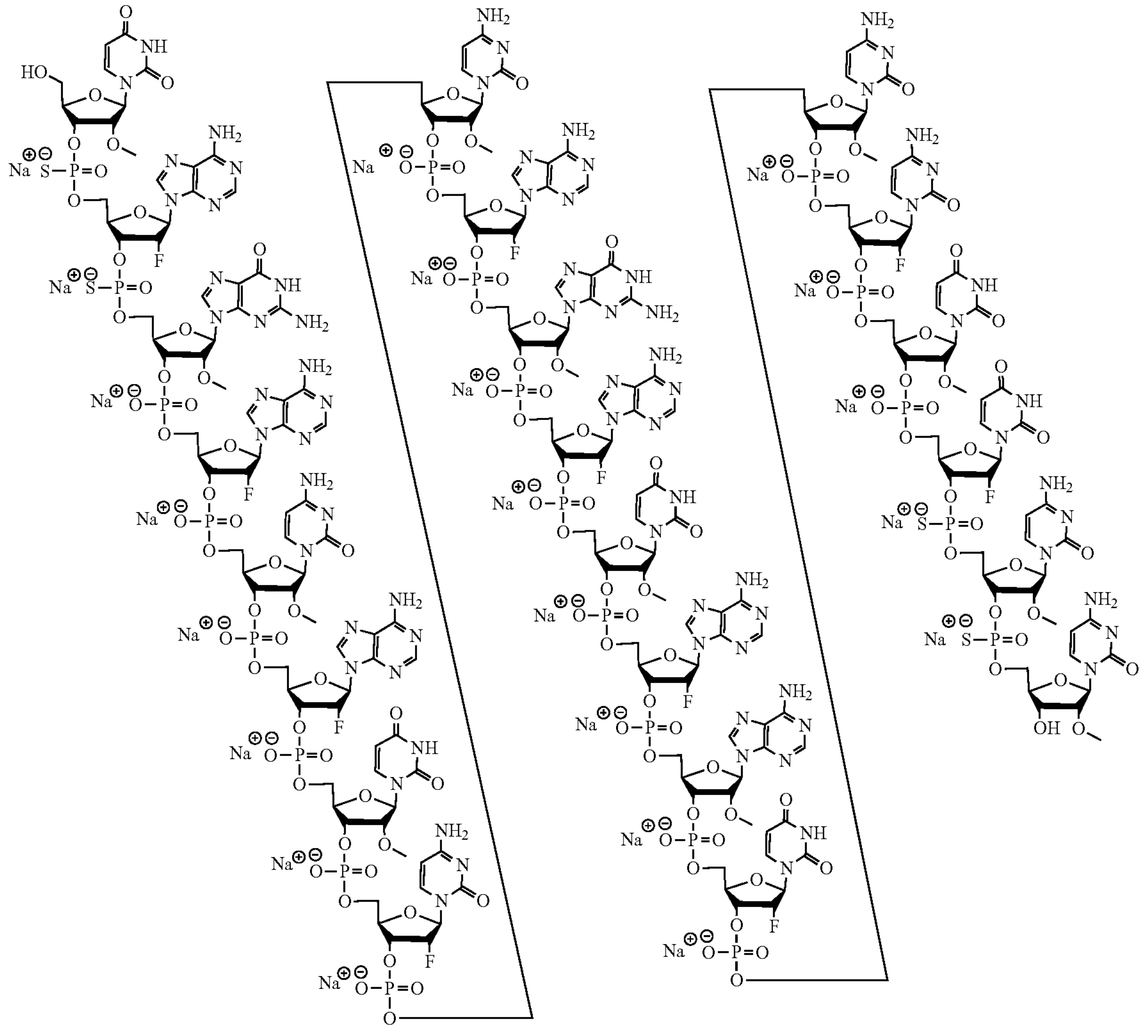

or a stereoisomer thereof. In certain embodiments, Ref ID NO: IA1016 is a modified oligonucleotide, or a stereoisomer thereof, according to the preceding chemical structure.

In an aspect provided herein, is a sodium salt of a modified oligonucleotide according to the following chemical structure:

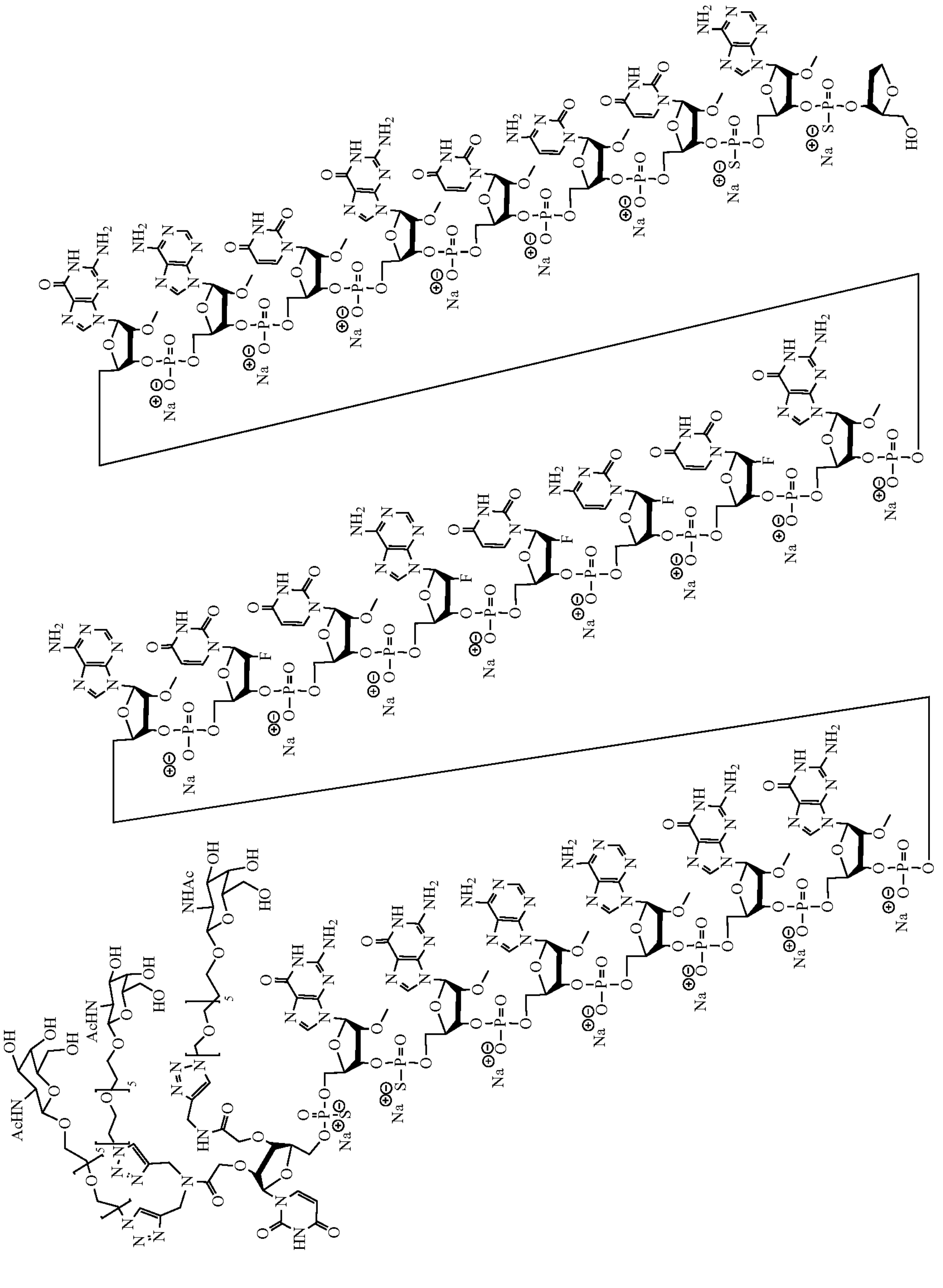

or a stereoisomer thereof. In certain embodiments, Ref ID NO: IS 1252 is a modified oligonucleotide, or a stereoisomer thereof, according to the preceding chemical structure.

In an aspect provided herein, is a sodium salt of a modified oligonucleotide according to the following chemical structure:

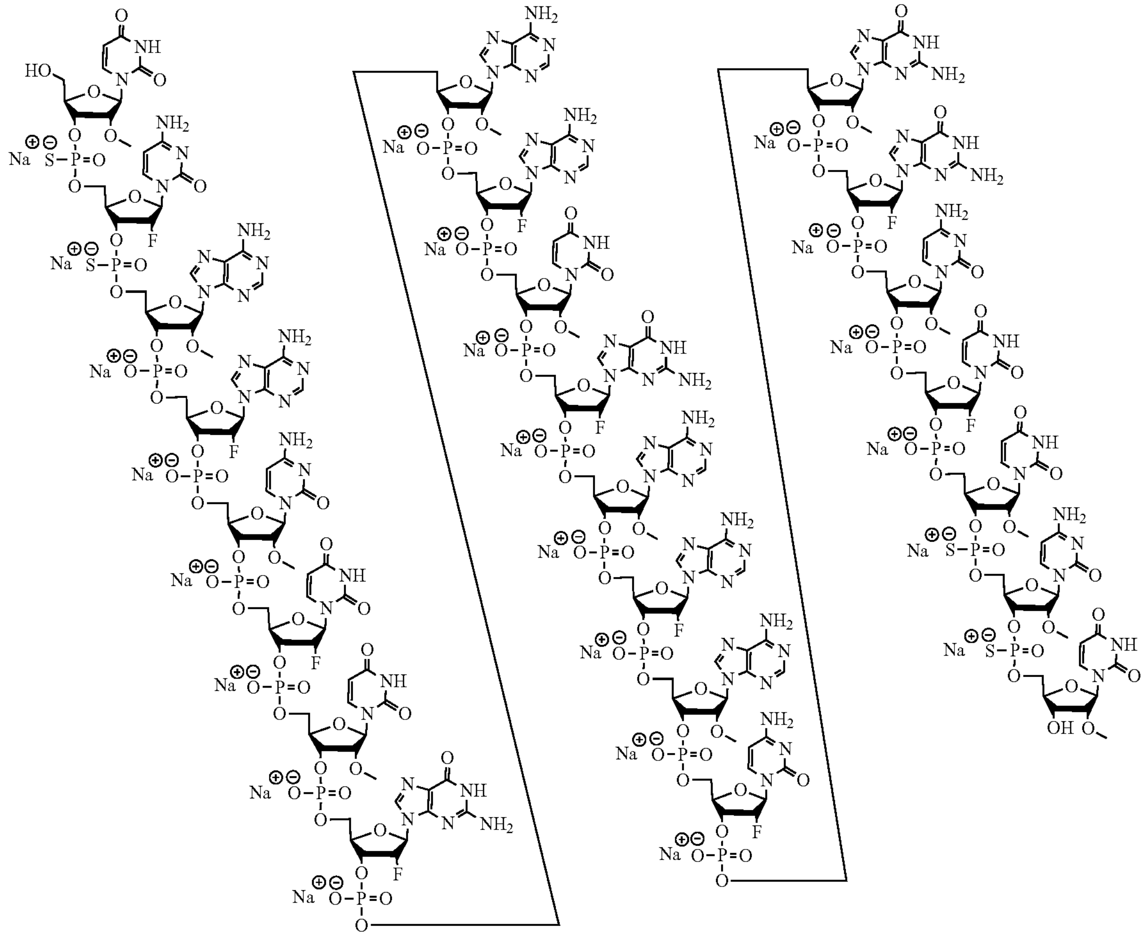

or a stereoisomer thereof. In certain embodiments, Ref ID NO: IA1017 is a modified oligonucleotide, or a stereoisomer thereof, according to the preceding chemical structure.

In an aspect provided herein, is a sodium salt of a modified oligonucleotide according to the following chemical structure:

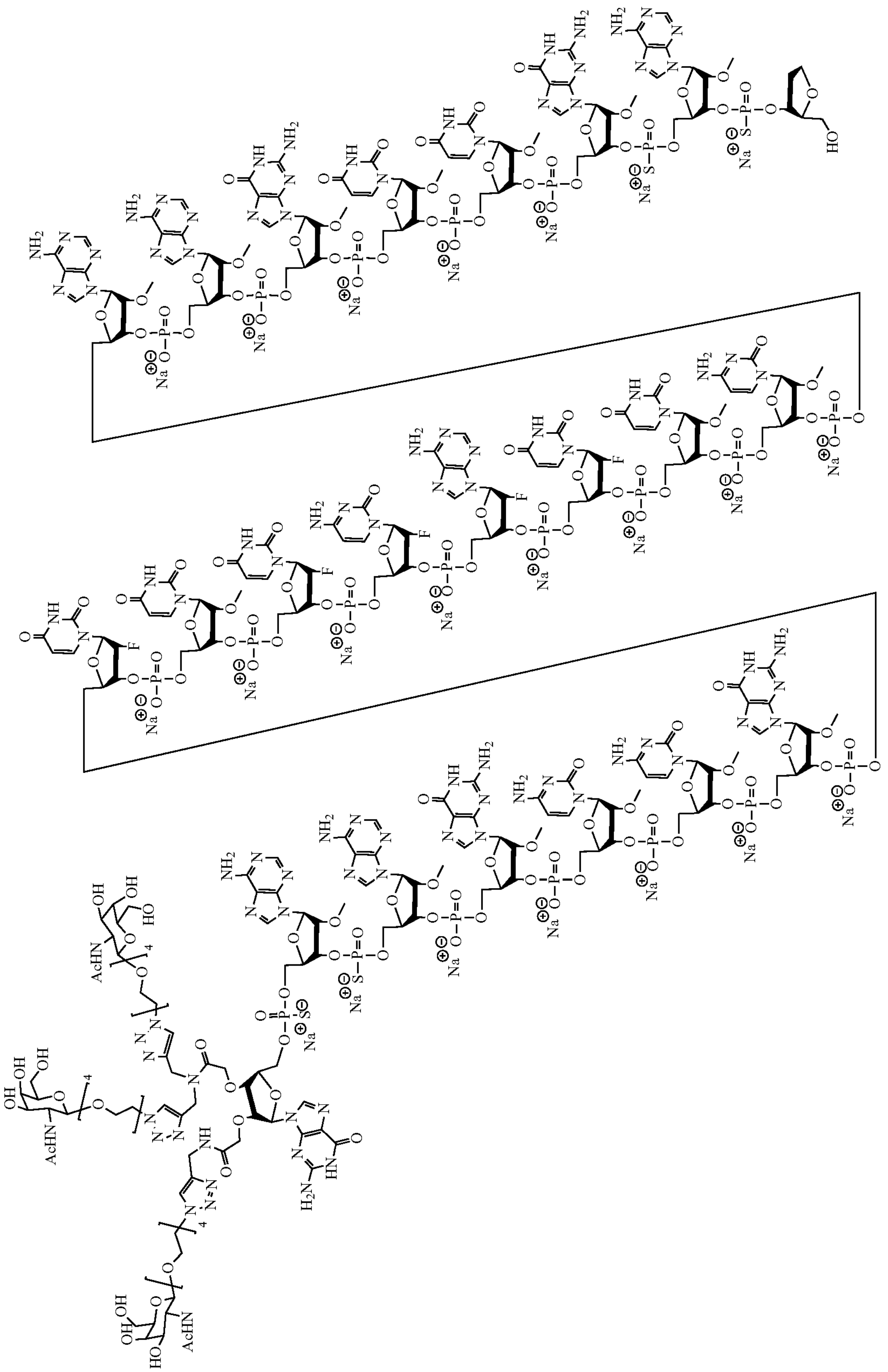

or a stereoisomer thereof. In certain embodiments, Ref ID NO: IS 1253 is a modified oligonucleotide, or a stereoisomer thereof, according to the preceding chemical structure.

In an aspect provided herein, is a sodium salt of a modified oligonucleotide according to the following chemical structure:

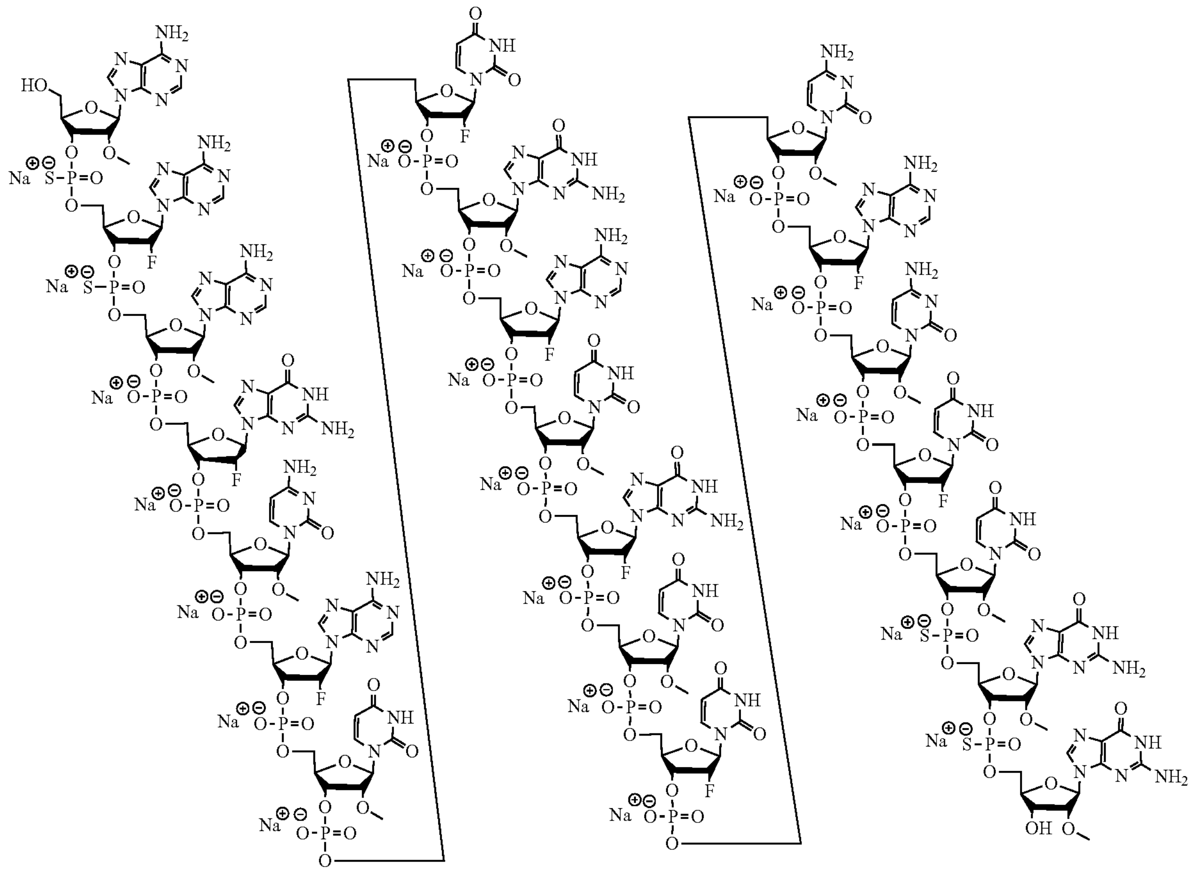

or a stereoisomer thereof. In certain embodiments, Ref ID NO: IA1010 is a modified oligonucleotide, or a stereoisomer thereof, according to the preceding chemical structure.

In an aspect provided herein, is a sodium salt of a modified oligonucleotide according to the following chemical structure:

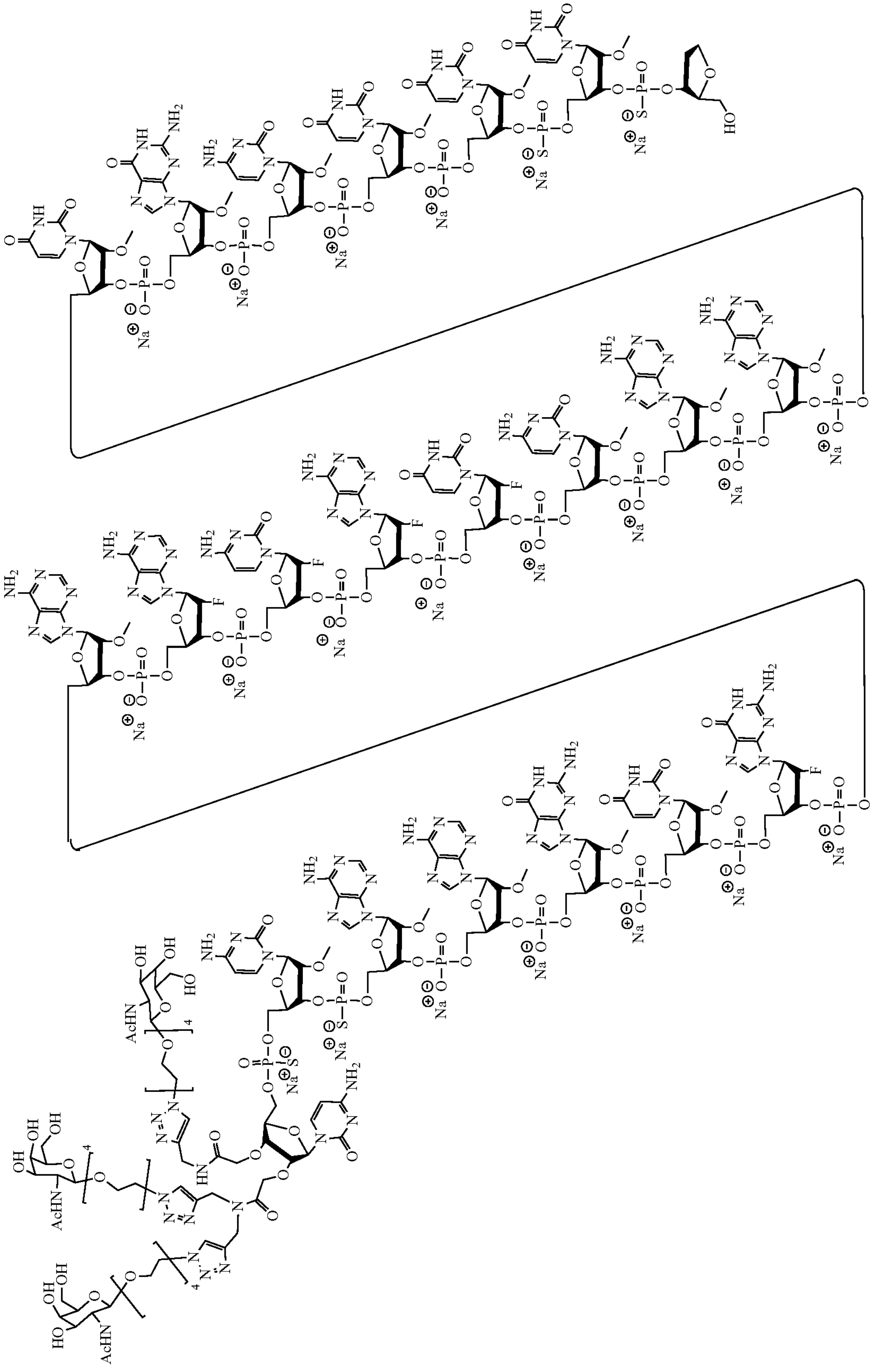

or a stereoisomer thereof. In certain embodiments, Ref ID NO: IS1109 is a modified oligonucleotide, or a stereoisomer thereof, according to the preceding chemical structure.

In an aspect provided herein, is a sodium salt of a modified oligonucleotide according to the following chemical structure:

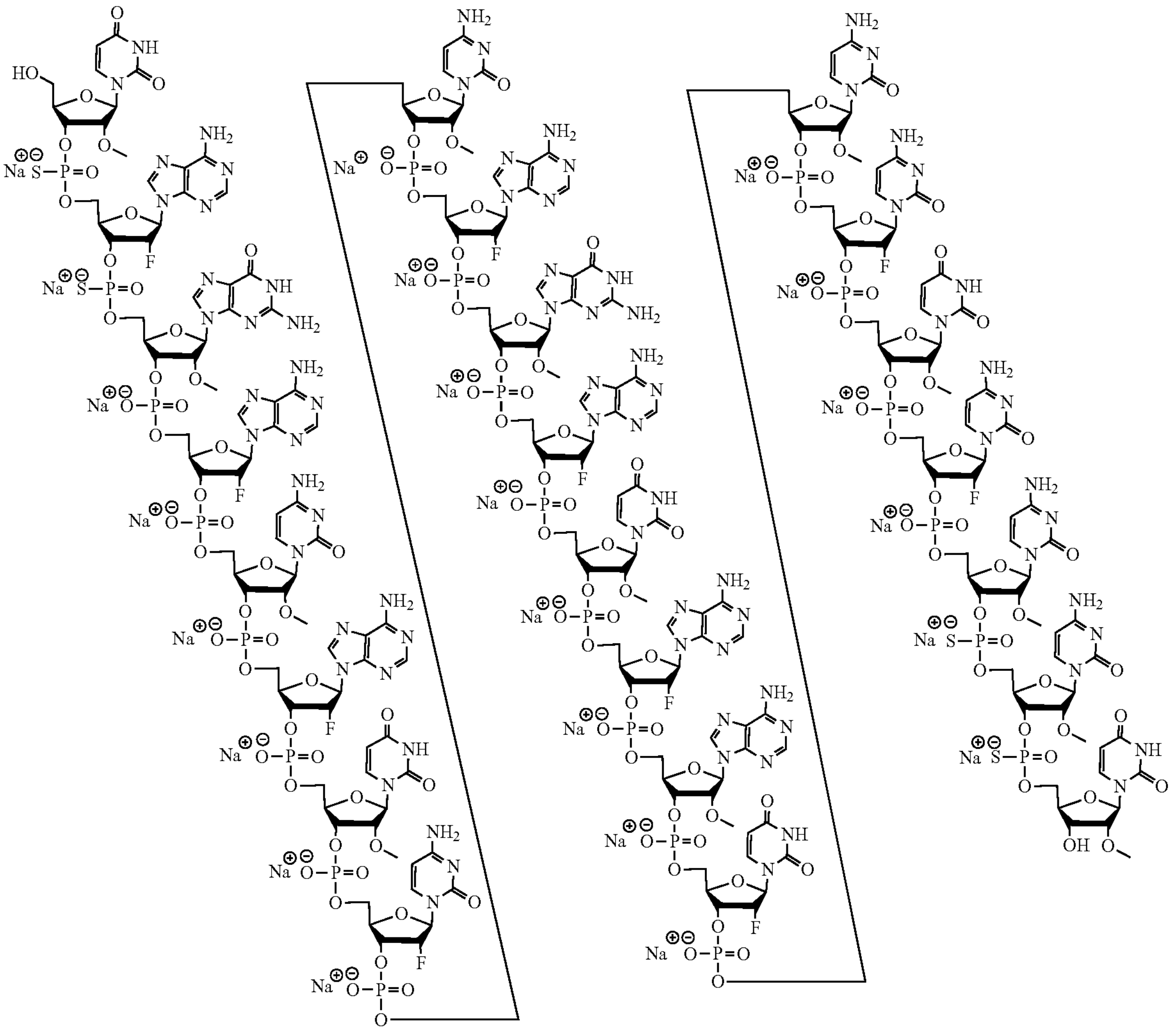

or a stereoisomer thereof. In certain embodiments, Ref ID NO: IA1011 is a modified oligonucleotide, or a stereoisomer thereof, according to the preceding chemical structure.

In an aspect provided herein, is a sodium salt of a modified oligonucleotide according to the following chemical structure:

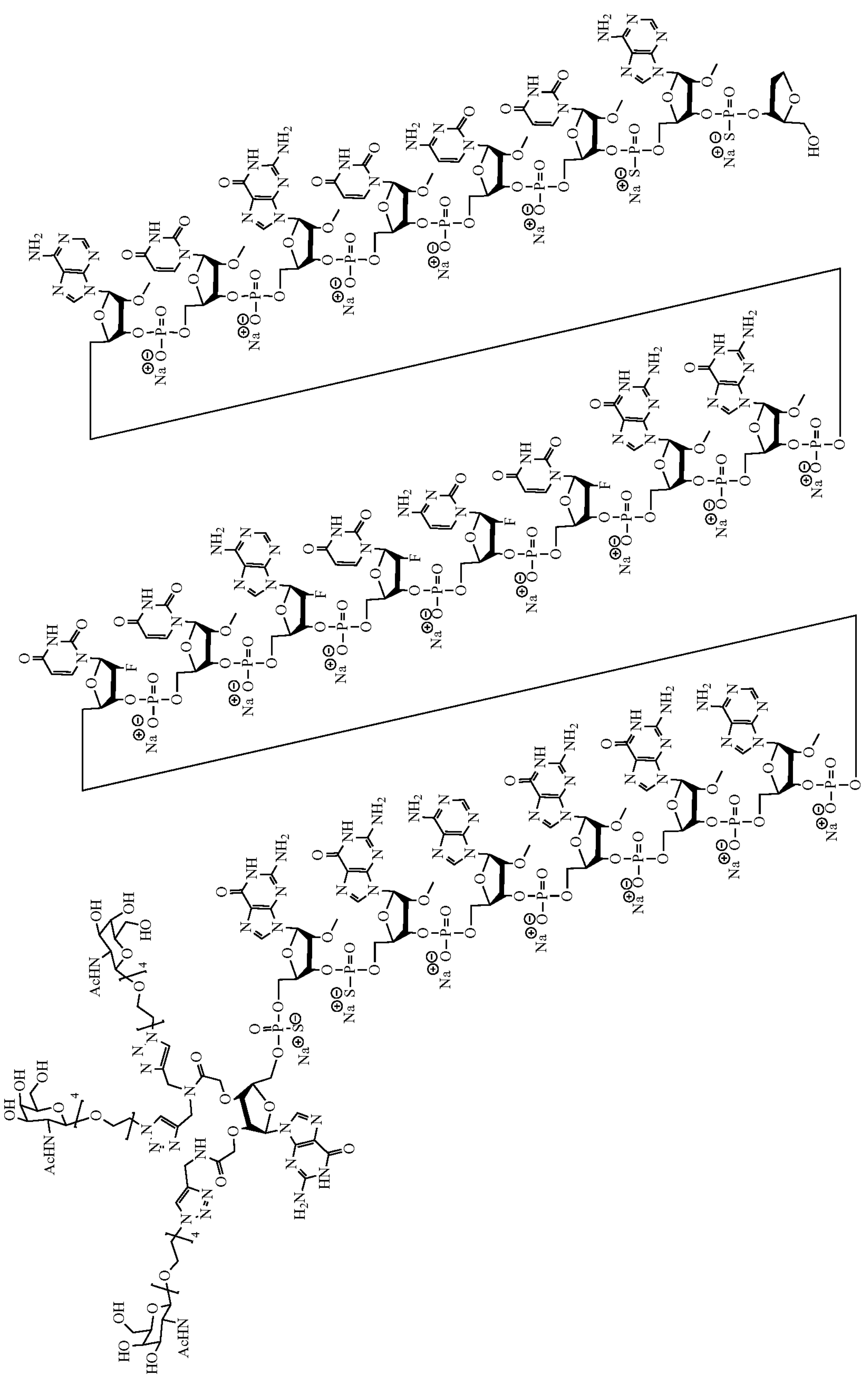

or a stereoisomer thereof. In certain embodiments, Ref ID NO: IS 1239 is a modified oligonucleotide, or a stereoisomer thereof, according to the preceding chemical structure.
In an aspect provided herein, is a compound according to the following chemical structure:
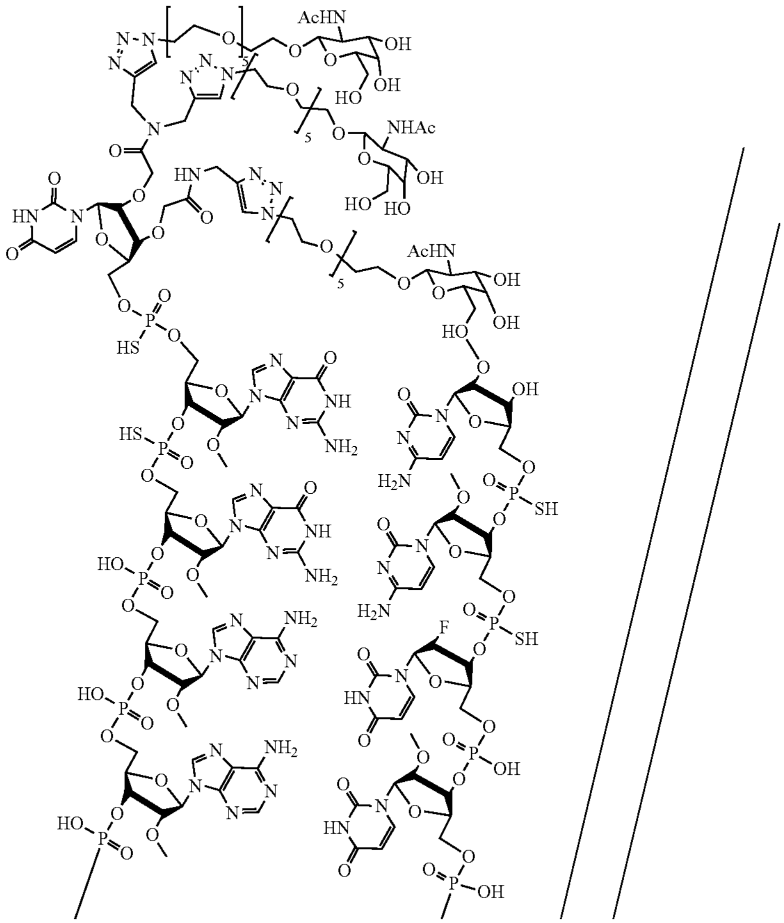

-continued
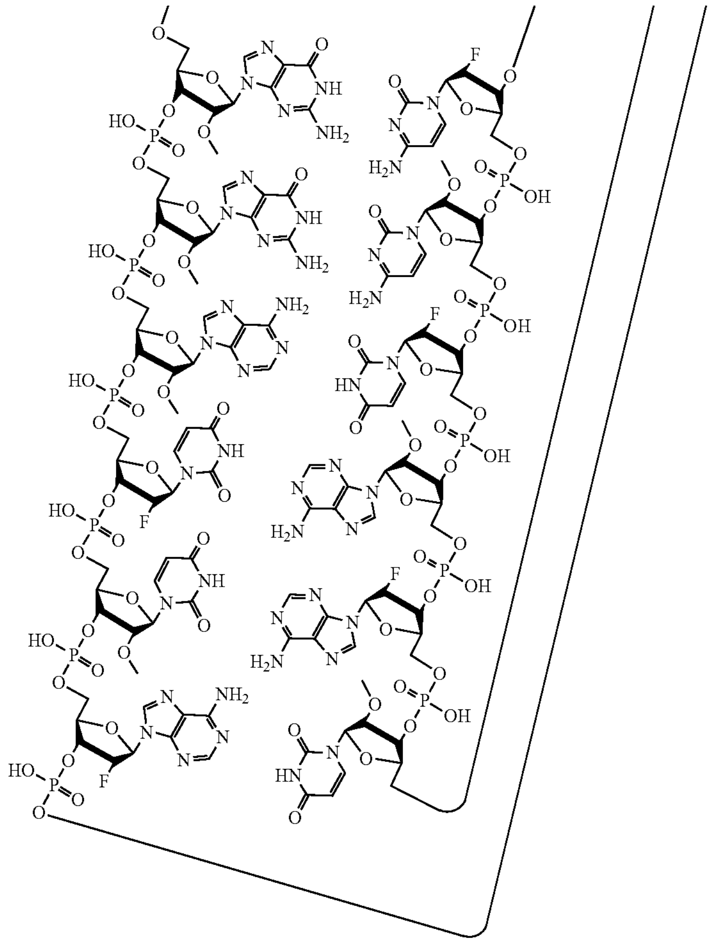

-continued
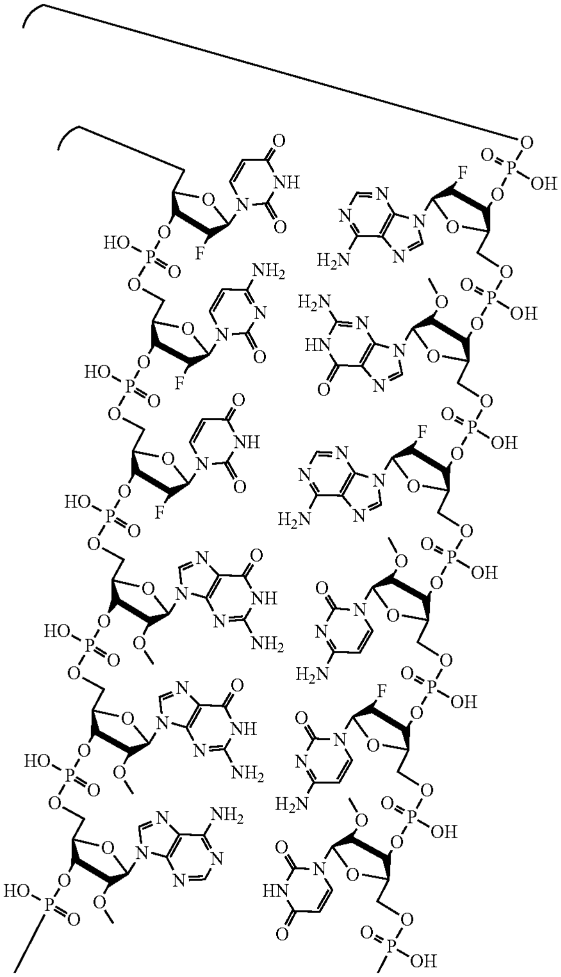

-continued
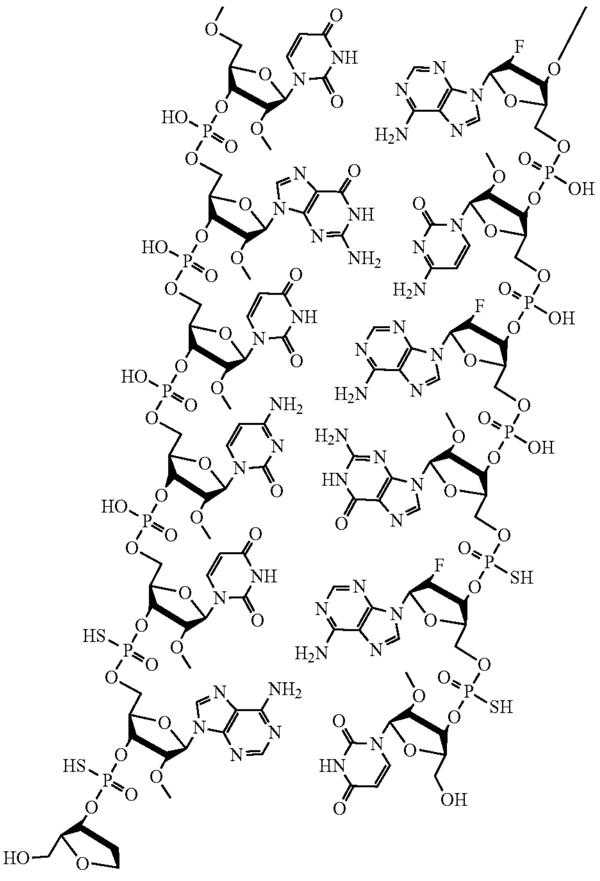
or a pharmaceutically acceptable salt or stereoisomer thereof. In certain embodiments, Compound Number RD2830 is a compound, or a pharmaceutically acceptable salt or stereoisomer thereof, according to the preceding chemical structure.
In an aspect provided herein, is a compound according to the following chemical structure:

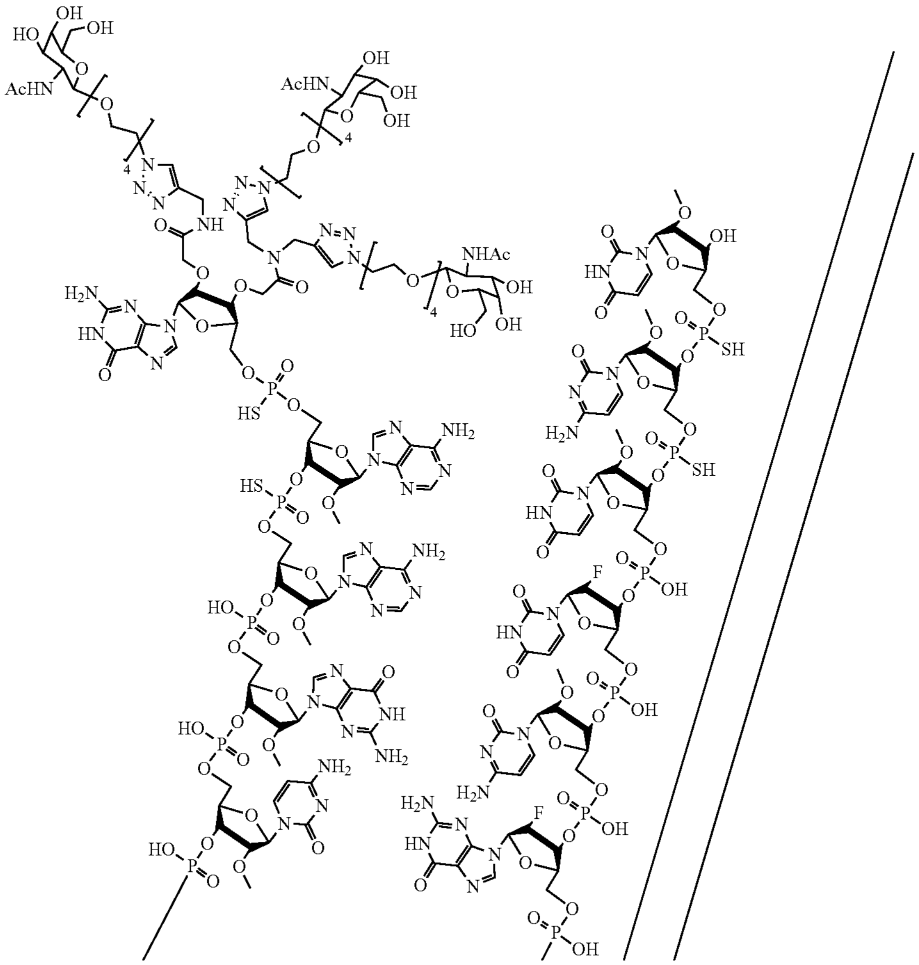

-continued
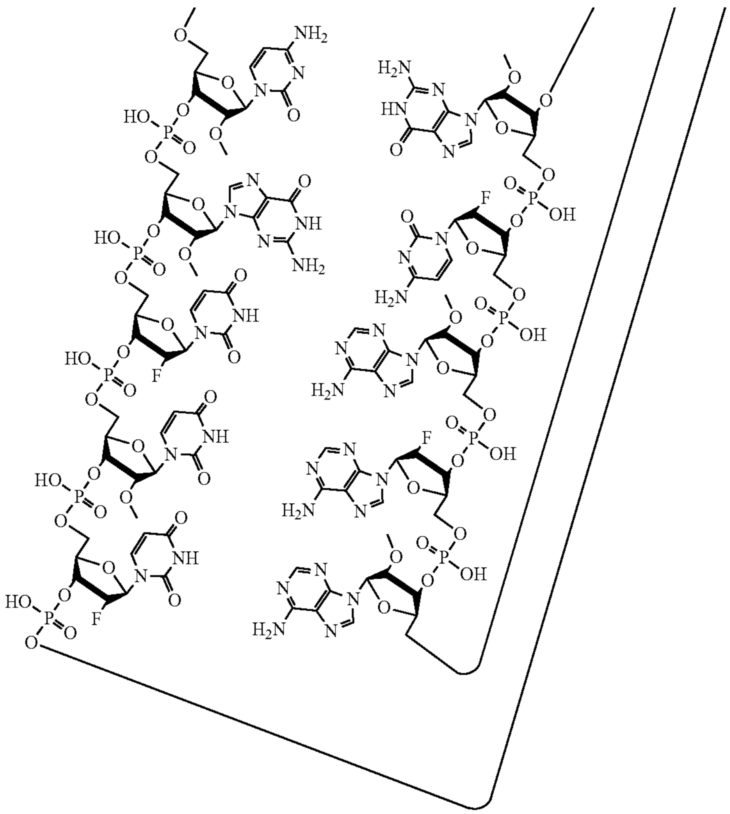

-continued
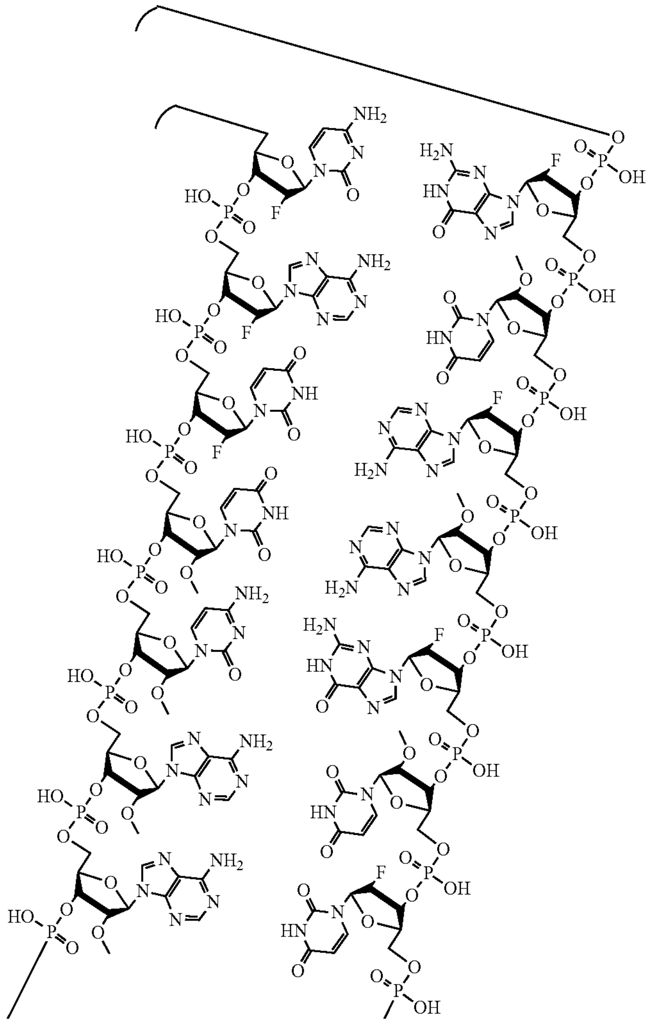

-continued
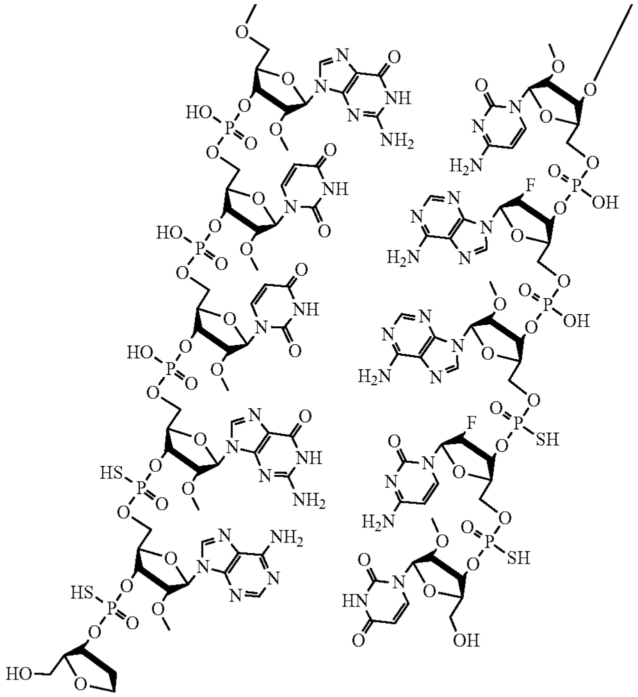
or a pharmaceutically acceptable salt or stereoisomer thereof. In certain embodiments, Compound Number RD2831 is a compound, or a pharmaceutically acceptable salt or stereoisomer thereof, according to the preceding chemical structure.
In an aspect provided herein, is a compound according to the following chemical structure:

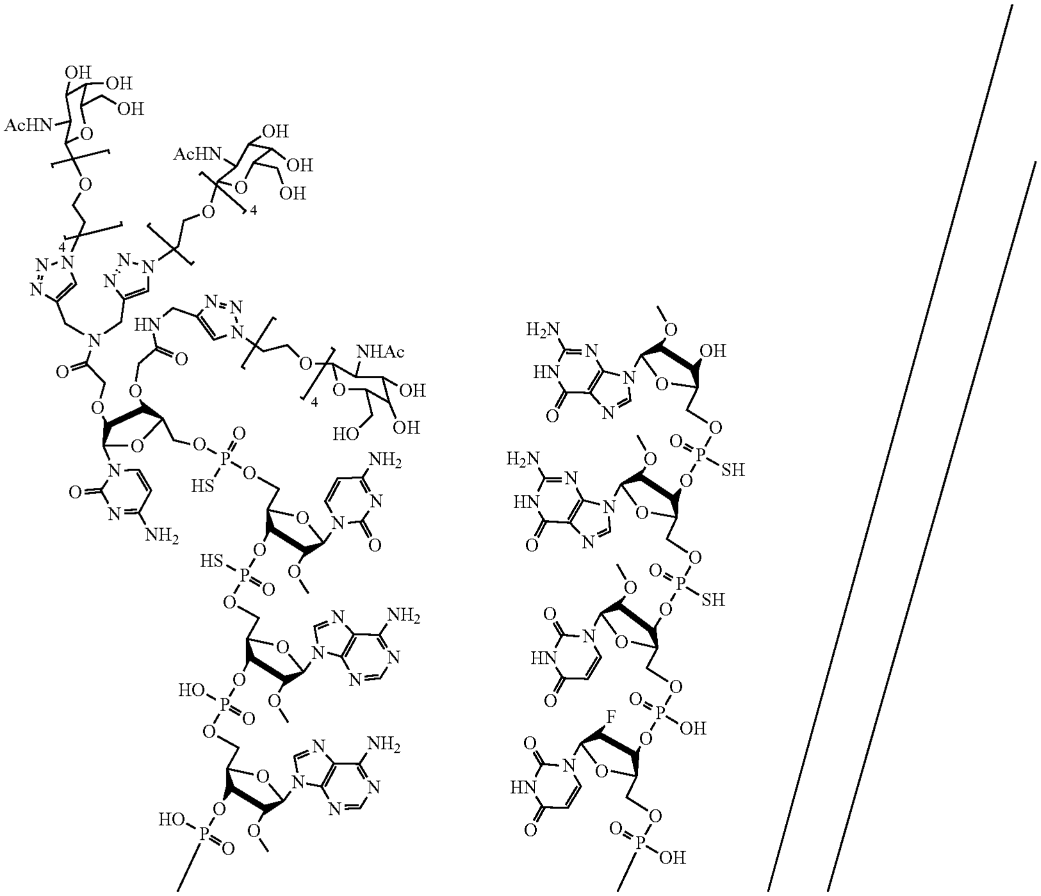

-continued
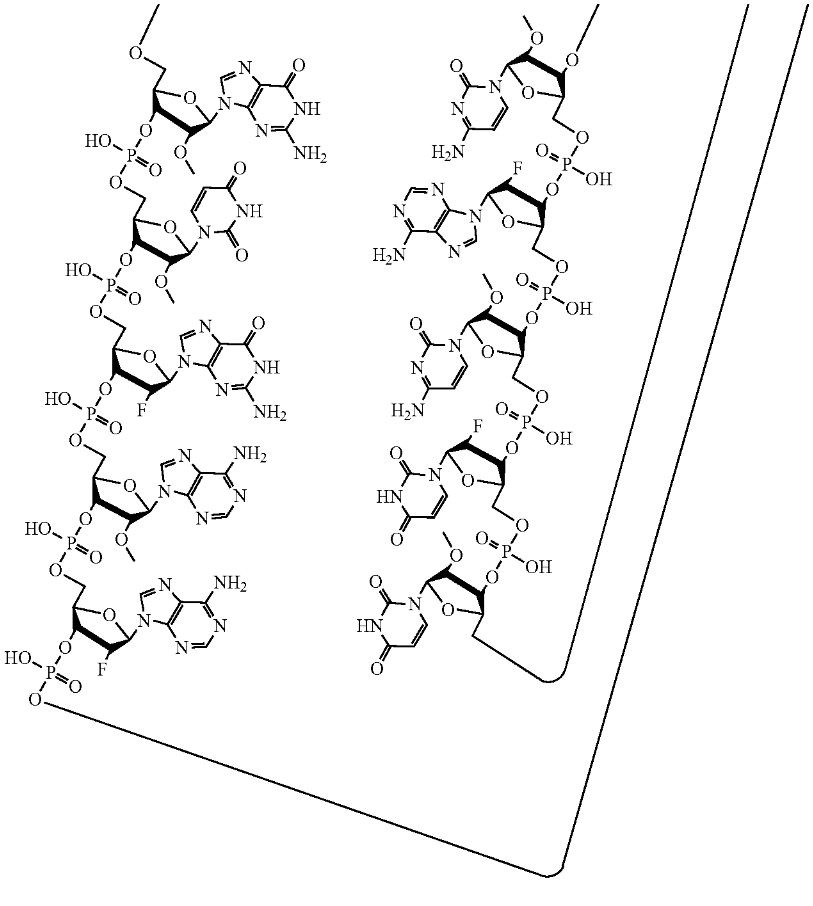

-continued
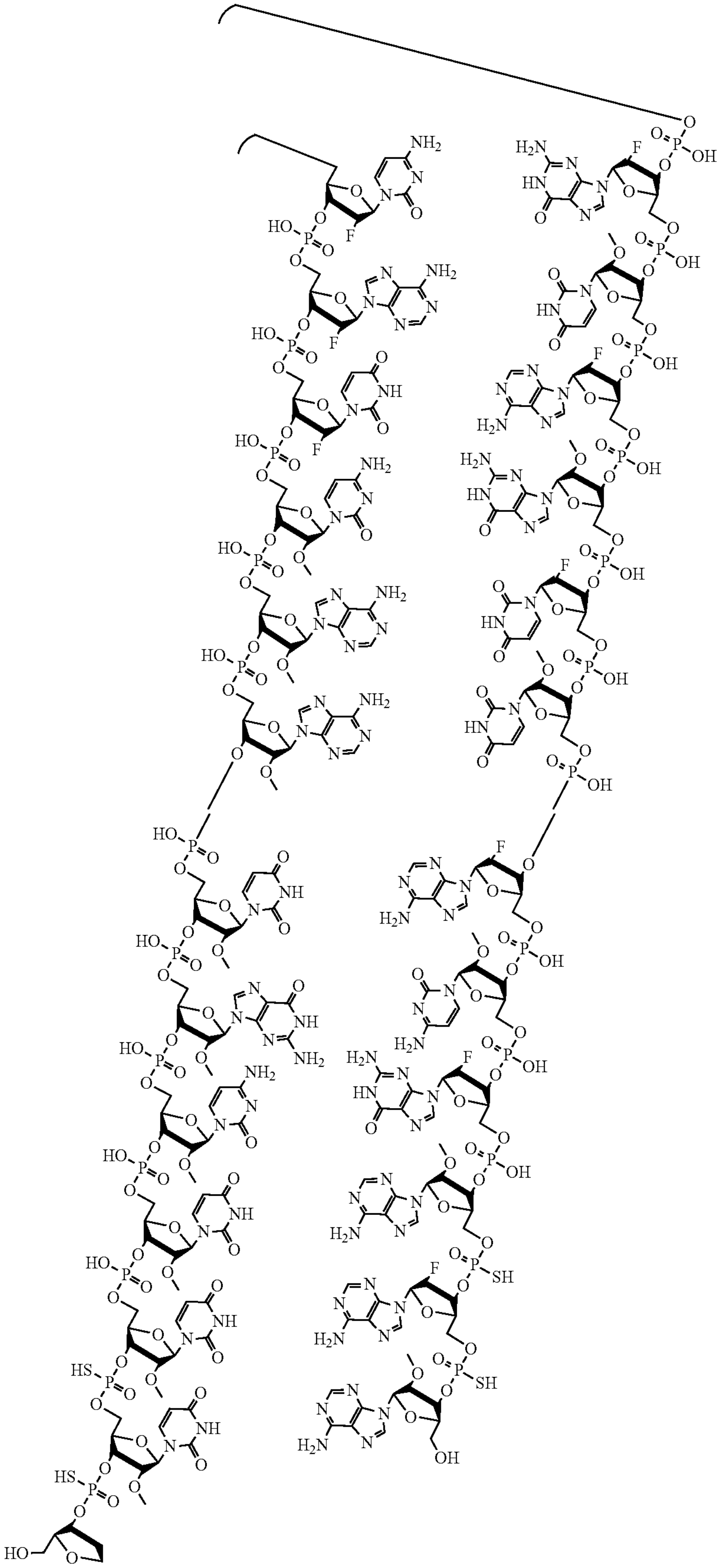

or a pharmaceutically acceptable salt or stereoisomer thereof. In certain embodiments, Compound Number RD2795 is a compound, or a pharmaceutically acceptable salt or stereoisomer thereof, according to the preceding chemical structure.
In an aspect provided herein, is a compound according to the following chemical structure:
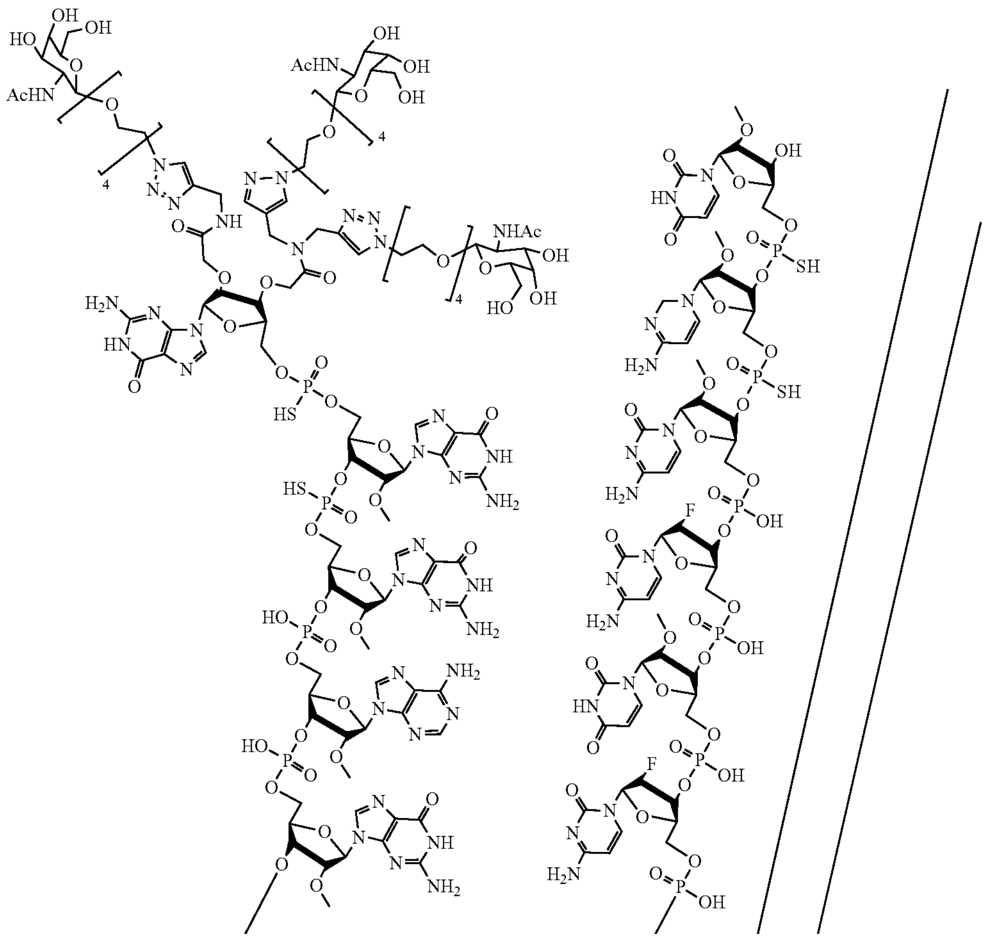

-continued
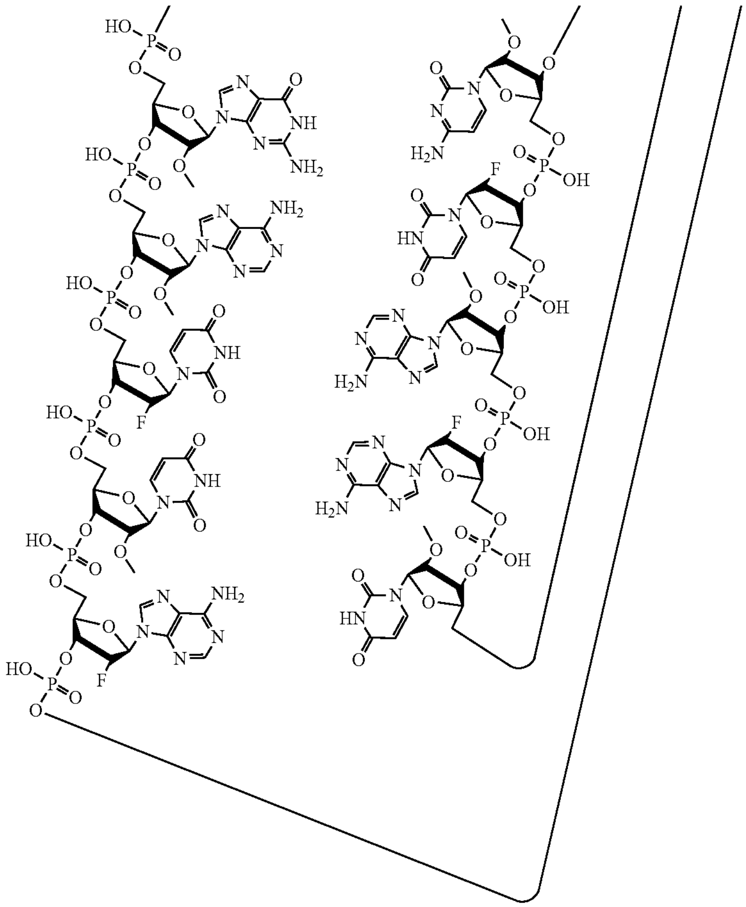

-continued
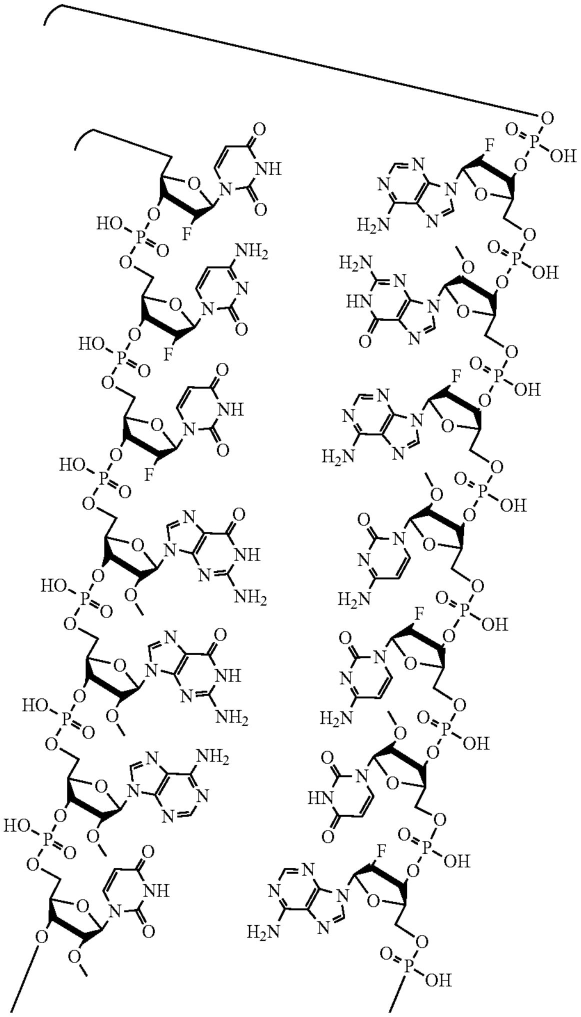

-continued
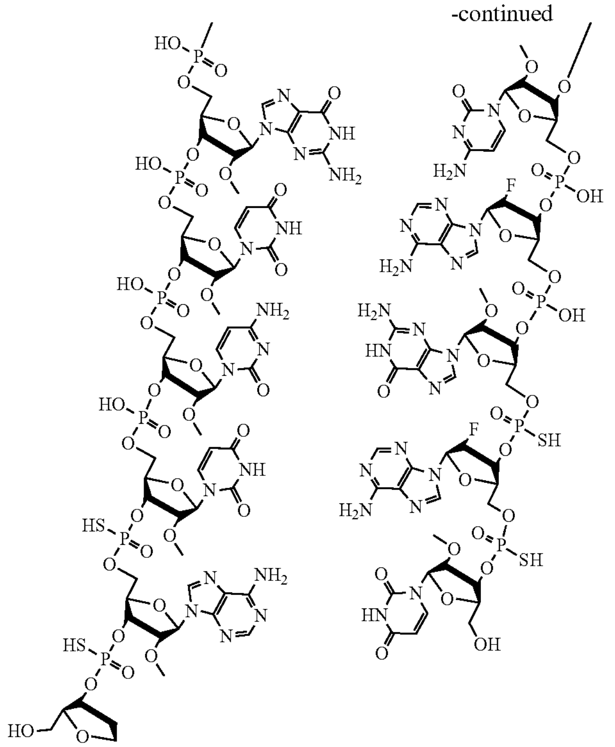
or a pharmaceutically acceptable salt or stereoisomer thereof. In certain embodiments, Compound Number RD2798 is a compound, or a pharmaceutically acceptable salt or stereoisomer thereof, according to the preceding chemical structure.
In an aspect provided herein, is a sodium salt of a compound according to the following chemical structure:
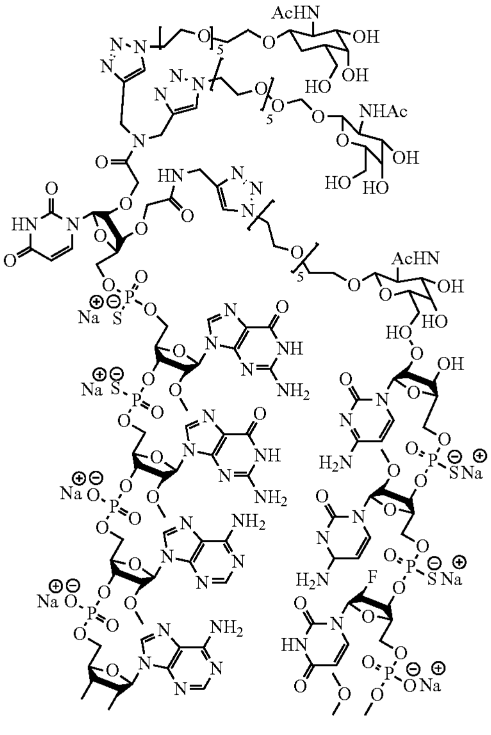

-continued
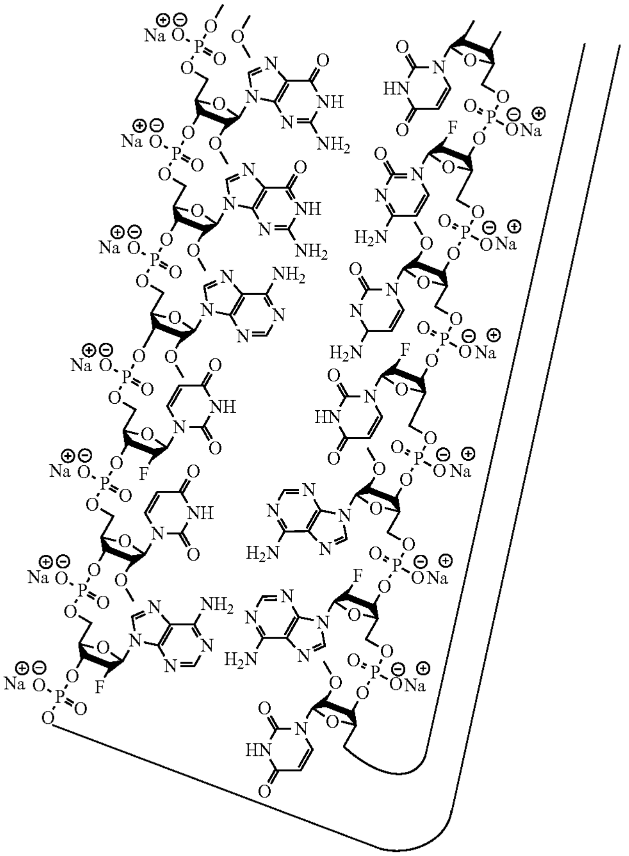
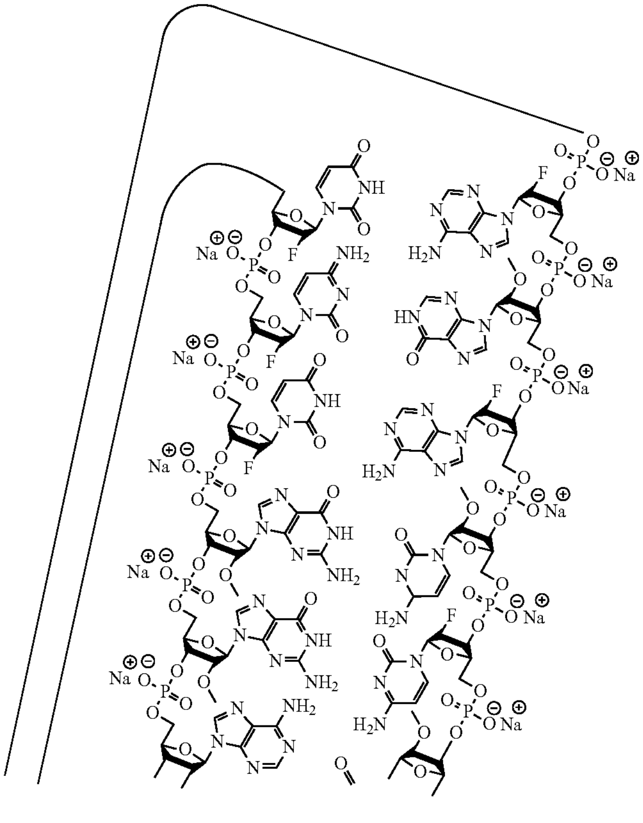

-continued
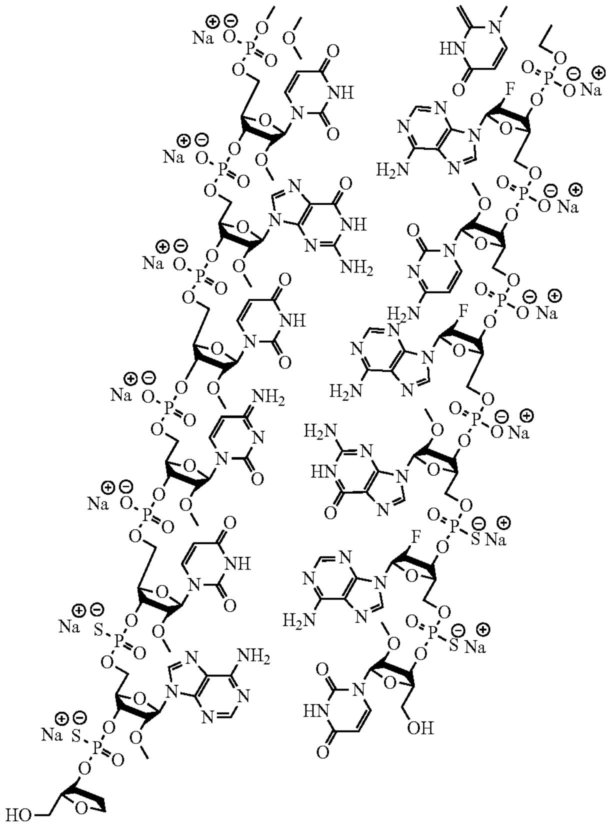
or a stereoisomer thereof. In certain embodiments, Compound Number RD2830 is a compound, or a pharmaceutically acceptable salt or stereoisomer thereof, according to the preceding chemical structure.
In an aspect provided herein, is a sodium salt of a compound according to the following chemical structure:

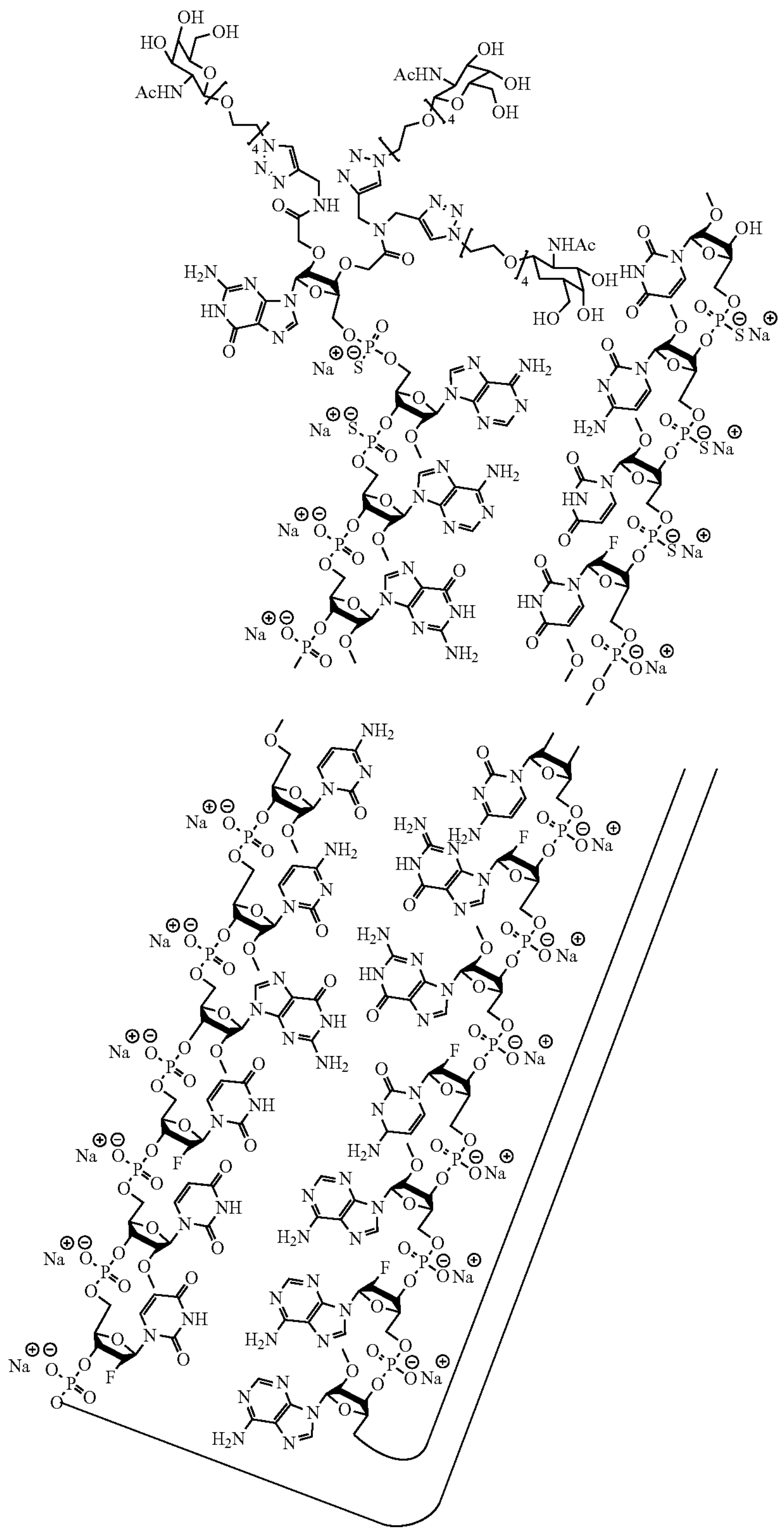

-continued
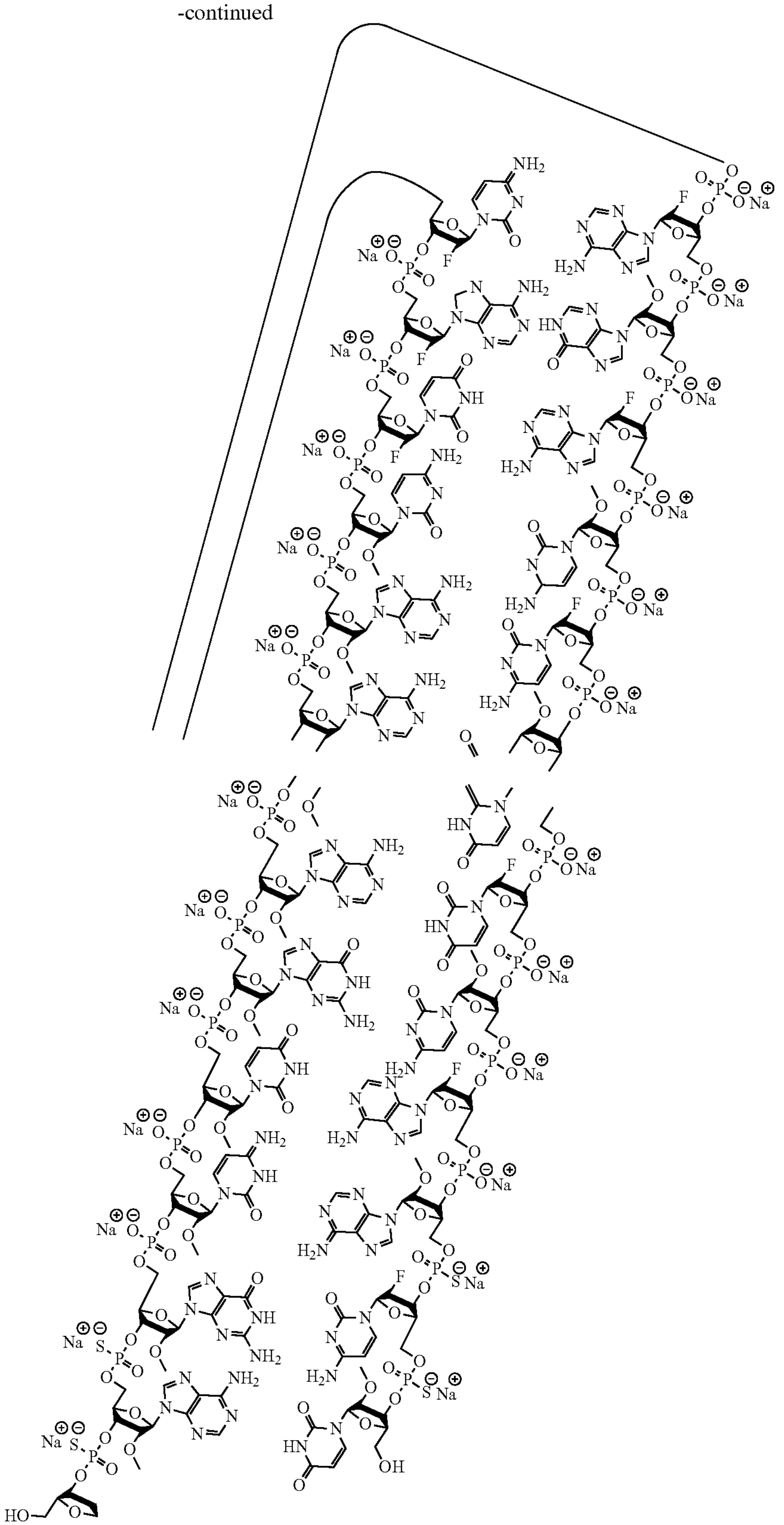
or a stereoisomer thereof. In certain embodiments, Compound Number RD2831 is a compound, or a pharmaceutically acceptable salt or stereoisomer thereof, according to the preceding chemical structure.

In an aspect provided herein, is a sodium salt of a compound according to the following chemical structure:
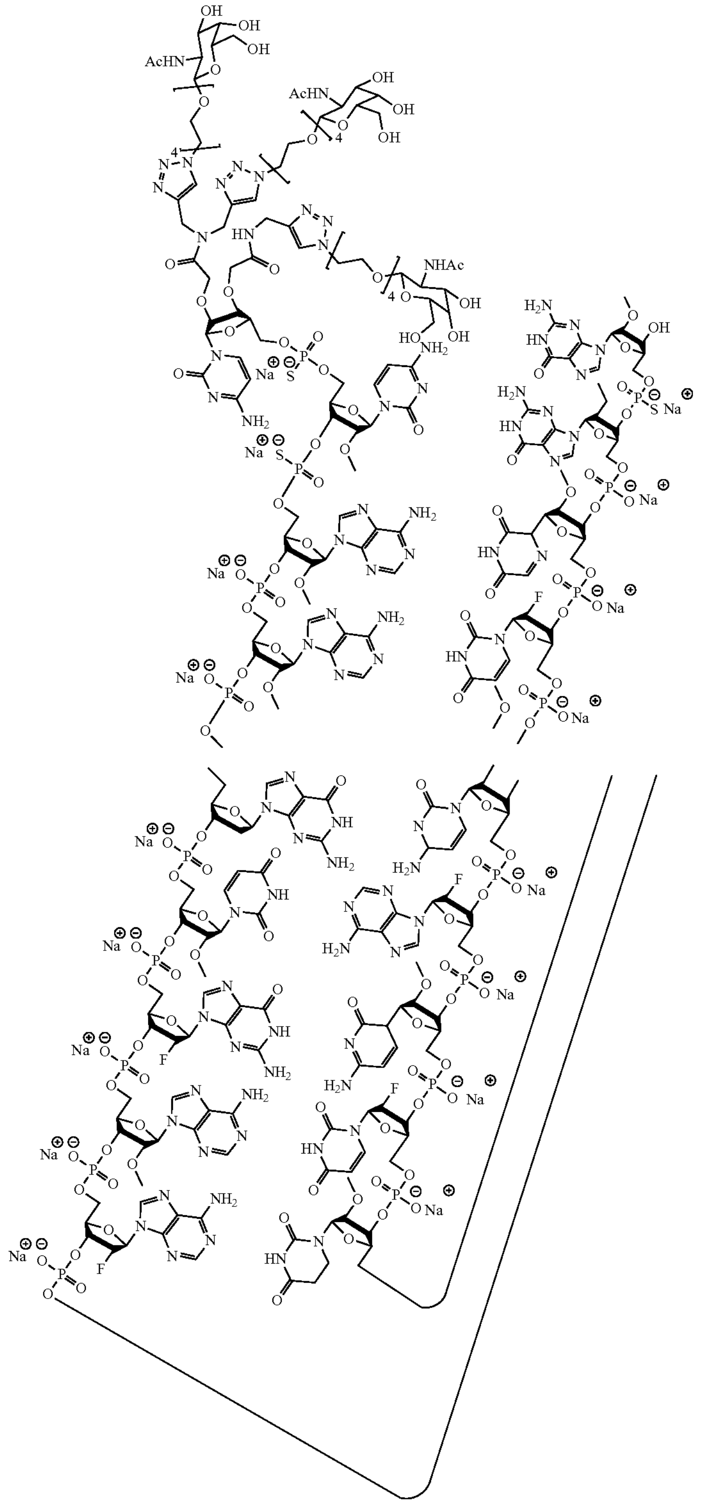

-continued
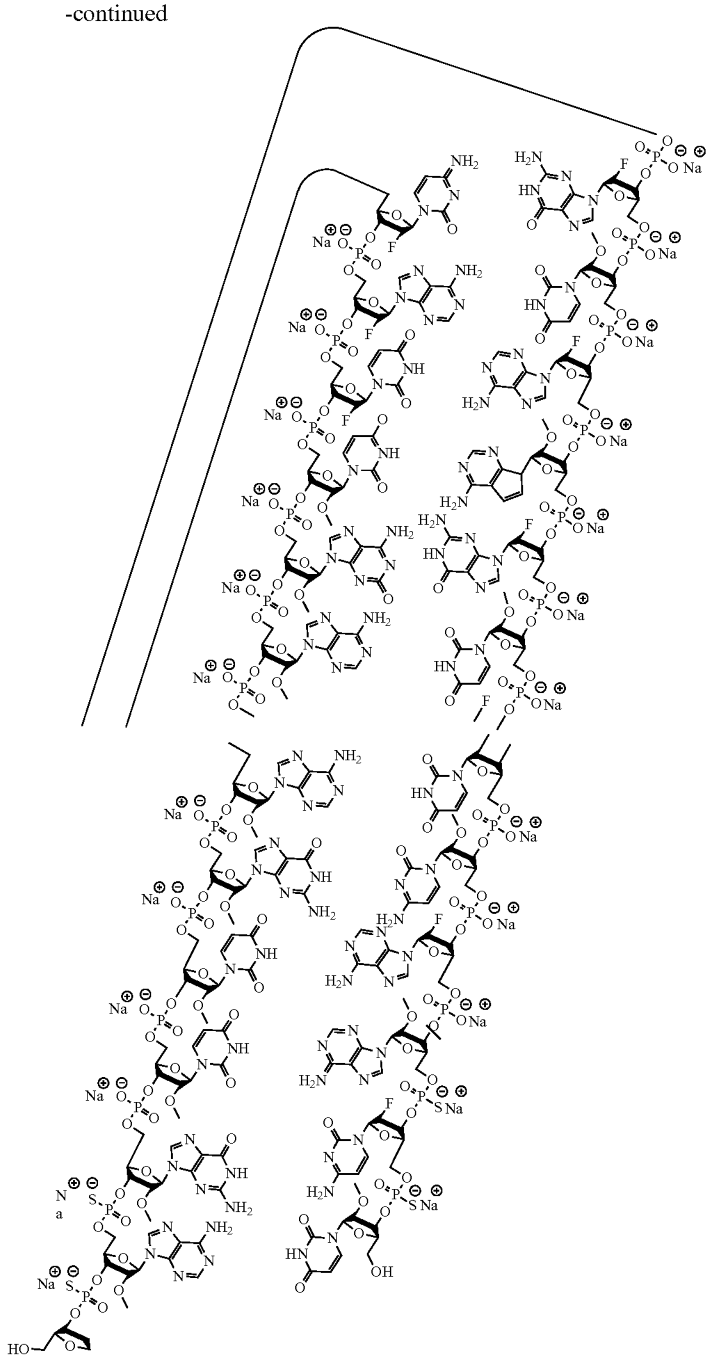
or a stereoisomer thereof. In certain embodiments, Compound Number RD2795 is a compound, or a pharmaceutically acceptable salt or stereoisomer thereof, according to the preceding chemical structure.
In an aspect provided herein, is a sodium salt of a compound according to the following chemical structure:

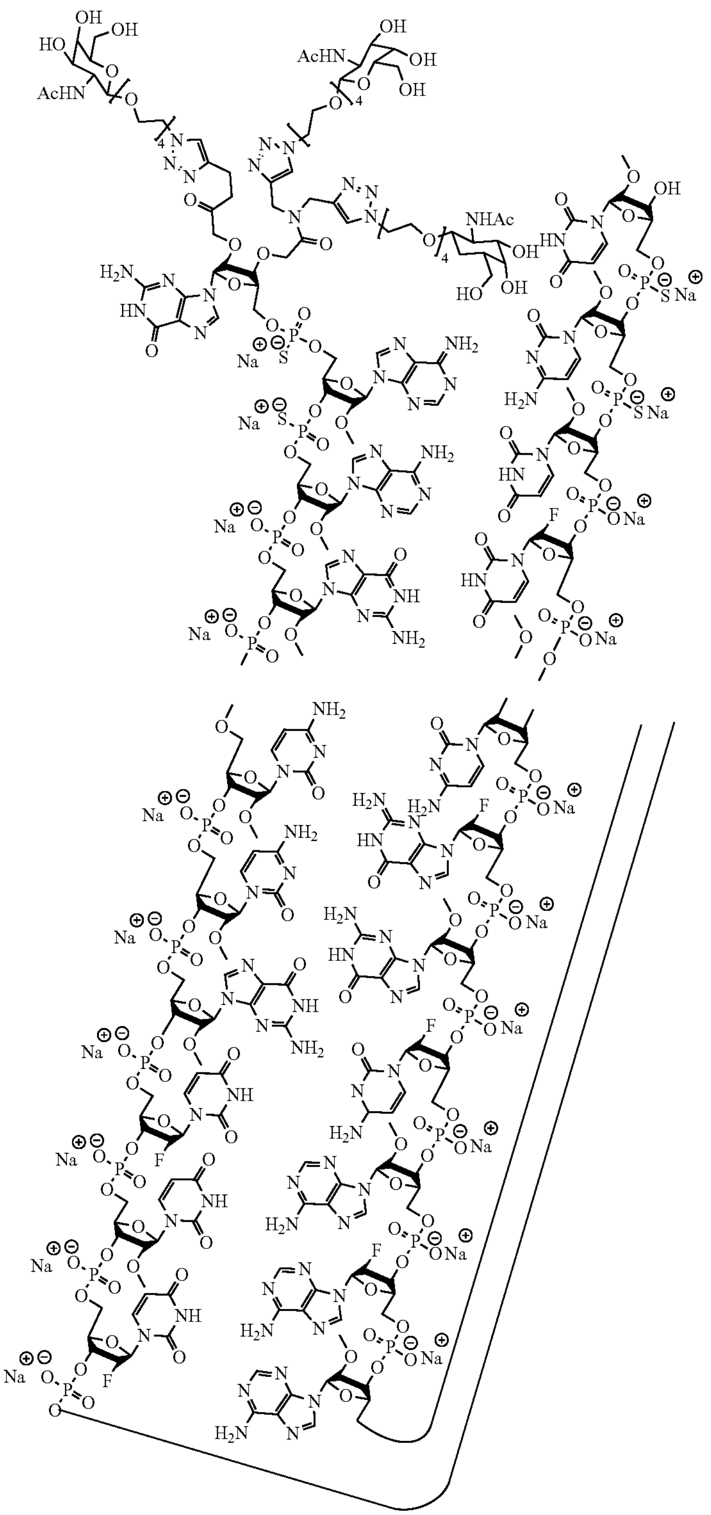

-continued
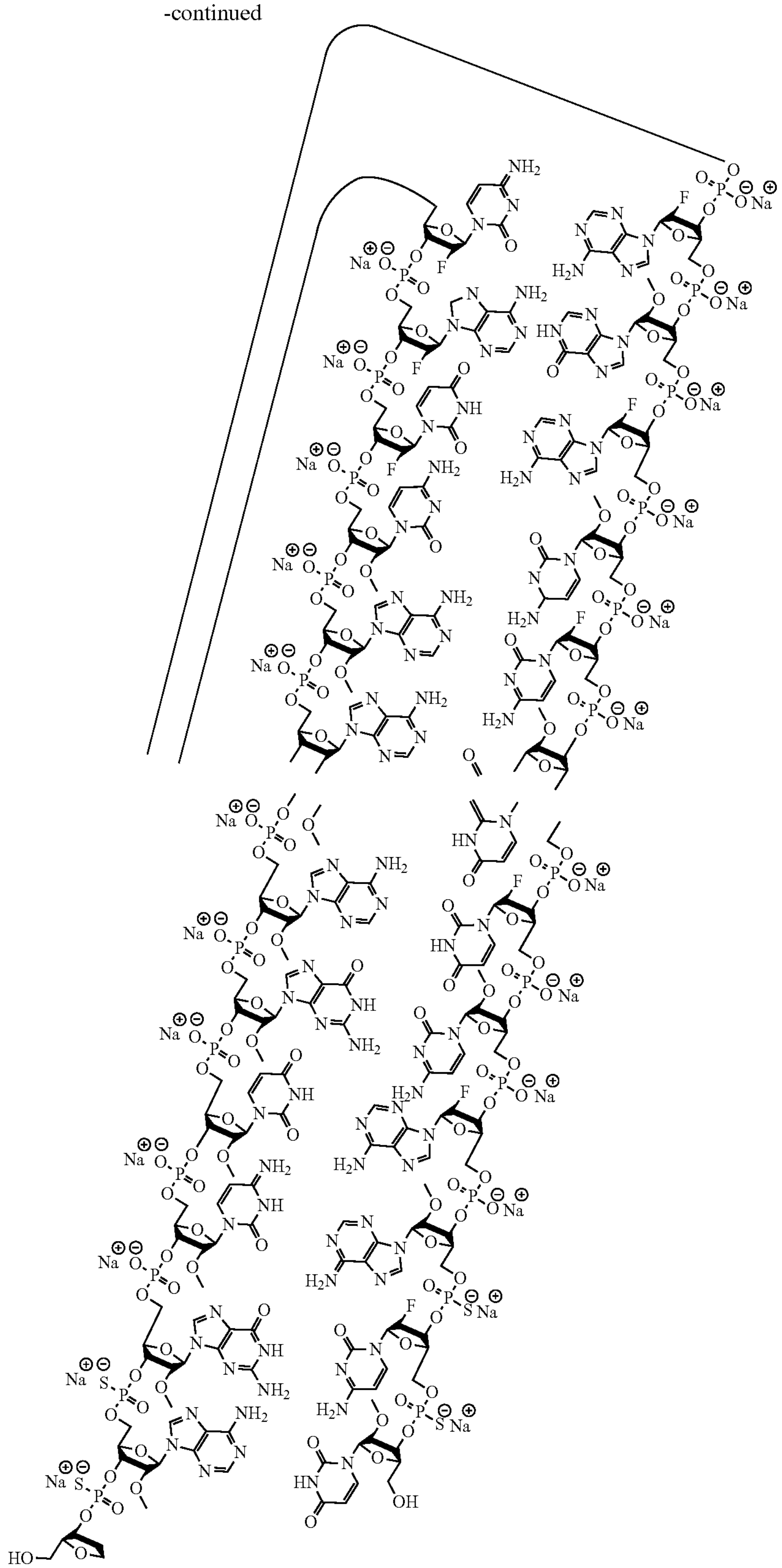
or a stereoisomer thereof. In certain embodiments, Compound Number RD2798 is a compound, or a pharmaceutically acceptable salt or stereoisomer thereof, according to the preceding chemical structure.

In certain embodiments, provided herein is a population of modified oligonucleotides, wherein all the phosphorothioate internucleoside linkages of the modified oligonucleotide are stereorandom. In certain embodiments, provided herein is a population of compounds, wherein all the phosphorothioate internucleoside linkages of the modified oligonucleotide are stereorandom.

Certain embodiments provide a composition comprising the compound of any preceding embodiment and a pharmaceutically acceptable carrier.

Certain embodiments provide a composition comprising a compound of any preceding embodiment, for use in therapy.

Certain embodiments provide a method of treating, preventing, or ameliorating a disease, disorder or condition associated with CFB in an individual comprising administering to the individual a compound targeted to CFB, thereby treating, preventing, or ameliorating the disease.

In certain embodiments, the compound or composition of any foregoing embodiment is administered to an individual. In certain embodiments, the disease, disorder, or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, administering the compound inhibits or reduces or improves atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom thereof.

In certain embodiments, a compound or composition comprising a compound of any preceding embodiment is administered to an individual in a therapeutically effective amount. In certain embodiments, a composition comprising a compound of any preceding embodiment is administered to an individual at a dosage level sufficient to deliver about 1 to 100 mg/kg of body weight of the individual. In certain embodiments, a compound or composition comprising a compound of any preceding embodiment is administered to an individual at a fixed dose of about 25 mg to about 1,000 mg. In certain embodiments, the compound or composition is administered to the individual one or more times in a day up to the dosage level or fixed dose.

In certain embodiments, a composition comprising a compound of any preceding embodiment is administered to an individual daily, weekly, monthly, quarterly, or yearly. In certain embodiments, a compound or composition comprising a compound of any preceding embodiment is administered to an individual about once per quarter (i.e., once every three months) to about once per year. In certain embodiments, a compound or composition comprising a compound of any preceding embodiment is administered to an individual about once per quarter, about once every six months or about once per year.

Certain embodiments provide a method of inhibiting expression of CFB in a cell comprising contacting the cell with a compound targeted to CFB, thereby inhibiting expression of CFB in the cell. In certain embodiments, the cell is in the liver of an individual. In certain embodiments, the individual has, or is at risk of having, atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA).

Certain embodiments provide a method of reducing or inhibiting atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof in an individual, comprising administering a compound targeted to CFB to the individual, thereby reducing or inhibiting atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof in the individual. In certain embodiments, the individual has, or is at risk of having, atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof. In certain embodiments, the compound is a compound targeted to CFB. In certain embodiments, the compound is any of the foregoing compounds. In certain embodiments, the compound or composition is administered parenterally.

Certain embodiments provide use of a compound targeted to CFB for treating, preventing, or ameliorating a disease, disorder or condition associated with CFB. In certain embodiments, the disease, disorder, or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound is a compound targeted to CFB. In certain embodiments, the compound is any of the foregoing compounds.

Certain embodiments provide use of a compound targeted to CFB in the manufacture of a medicament for treating, preventing, or ameliorating a disease, disorder or condition associated with CFB. In certain embodiments, the disease, disorder, or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound is a compound targeted to CFB. In certain embodiments, the compound is any of the foregoing compounds.

Certain Indications

In certain aspects, the disclosure relates to methods of inhibiting CFB expression, which can be useful for treating, preventing, or ameliorating a disease, disorder or condition associated with CFB in an individual, by administration of a compound that targets CFB. In certain embodiments, the compound can be a CFB specific inhibitor. In certain embodiments, the compound can be an antisense oligonucleotide, an oligomeric compound, or an oligonucleotide targeted to CFB.

In certain aspects, the disclosure relates to treating, preventing, or ameliorating a disease, disorder or condition associated with CFB. In certain embodiments, diseases, disorders or conditions associated with CFB treatable, preventable, and/or ameliorable with the methods provided herein include atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). Certain compounds provided herein are directed to compounds and compositions that reduce atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof in an animal.

In certain embodiments, a method of treating, preventing, or ameliorating a disease, disorder or condition associated with CFB in an individual comprises administering to the individual a compound comprising a CFB specific inhibitor, thereby treating, preventing, or ameliorating the disease, disorder, or condition. In certain embodiments, the individual is identified as having, or at risk of having, a disease, disorder or condition associated with CFB. In certain embodiments, the disease, disorder, or condition is a liver, kidney, or ocular disease. In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides) in length having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising any one of the nucleobase sequences of SEQ ID NOs: 24, 25, 42, 96, 97, 98, and 100. In certain embodiments, a compound comprises a modified oligonucleotide having a nucleobase sequence selected from any one of the nucleobase sequences of SEQ ID NOs: 24, 25, 42, 96, 97, 98, and 100. In any of the foregoing embodiments, the compound can be single-stranded or double-stranded. In certain embodiments, a single-stranded compound can be 14 to 30, 14 to 23, 14 to 20, 16 to 20, or 14 to 16, linked nucleosides in length. In certain embodiments, a single-stranded compound can be 14, 15, 16, 17, 18, 19, 20, 21, 22, 23, 24, 25, 26, 27, 28, 29, or 30, linked nucleosides in length. In certain embodiments, a double-stranded compound can comprise two oligonucleotides of the same or different lengths, as described elsewhere herein. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide. In certain embodiments, the compound is administered to the individual parenterally. In certain embodiments, administering the compound improves, preserves, or prevents atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof in an animal.

In certain embodiments, a method of treating, preventing, or ameliorating atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof in an animal comprises administering to the individual a compound comprising a CFB specific inhibitor, thereby treating, preventing, or ameliorating atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof. In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any one of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising any one of the nucleobase sequences of SEQ ID NOs: 24, 25, 42, 96, 97, 98, and 100. In certain embodiments, a compound comprises a modified oligonucleotide having a nucleobase sequence selected from the nucleobase sequences of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide. In certain embodiments, administering the compound improves, preserves, or prevents atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof in an animal. In certain embodiments, the individual is identified as having, or at risk of having, a disease, disorder or condition associated with CFB.

In certain embodiments, a method of inhibiting expression of CFB in an individual having, or at risk of having, a disease, disorder or condition associated with CFB comprises administering to the individual a compound comprising a CFB specific inhibitor, thereby inhibiting expression of CFB in the individual. In certain embodiments, administering the compound inhibits expression of CFB in the liver. In certain embodiments, the disease, disorder or condition is a complement pathway related disease, disorder or condition or is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the individual has, or is at risk of having, atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequence of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising any one of the nucleobase sequences of SEQ ID NOs: 24, 25, 42, 96, 97, 98, and 100. In certain embodiments, a compound comprises a modified oligonucleotide having a nucleobase sequence selected from the nucleobase sequences of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide. In certain embodiments, the compound is administered to the individual parenterally. In certain embodiments, administering the compound improves, preserves, or prevents atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, rheumatoid arthritis (RA) or a symptom of any thereof. In certain embodiments, a method of inhibiting expression of CFB in a cell comprises contacting the cell with a compound comprising a CFB specific inhibitor, thereby inhibiting expression of CFB in the cell. In certain embodiments, the cell is a hepatocyte. In certain embodiments, the cell is in the liver. In certain embodiments, the cell is in the liver of an individual who has, or is at risk of having, atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising any one of the nucleobase sequences of SEQ ID NOs: 24, 25, 42, 96, 97, 98, and 100. In certain embodiments, a compound comprises a modified oligonucleotide having a nucleobase sequence selected from the nucleobase sequences of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide.

In certain embodiments, a method of reducing or inhibiting a complement pathway related disease, disorder or condition or atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA) in an individual having, or at risk of having, a disease associated with CFB comprises administering to the individual a compound comprising a CFB specific inhibitor, thereby reducing or inhibiting a complement pathway related disease, disorder or condition or atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA) in the individual. In certain embodiments, the individual has, or is at risk of having, atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 24, 25, 42, 96, 97, 98, and 100. In certain embodiments, a compound comprises a modified oligonucleotide having a nucleobase sequence selected from the nucleobase sequences of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide. In certain embodiments, the compound is administered to the individual parenterally. In certain embodiments, the individual is identified as having, or at risk of having, a disease, disorder or condition associated with CFB.

Certain embodiments are drawn to a compound comprising a CFB specific inhibitor for use in treating a disease, disorder or condition associated with CFB. In certain embodiments, the disease, disorder, or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 24, 25, 42, 96, 97, 98, and 100. In certain embodiments, a compound comprises a modified oligonucleotide having a nucleobase sequence selected from the nucleobase sequences of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide. In certain embodiments, the compound is administered to the individual parenterally.

Certain embodiments are drawn to a compound comprising a CFB specific inhibitor for use in reducing or inhibiting a complement pathway related disease, disorder or condition or atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA) or a symptom of any thereof. In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 24, 25, 42, 96, 97, 98, and 100. In certain embodiments, a compound comprises a modified oligonucleotide having a nucleobase sequence selected from the nucleobase sequence of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide.

Certain embodiments are drawn to the use of a compound comprising a CFB specific inhibitor for the manufacture or preparation of a medicament for treating a disease, disorder or condition associated with CFB. Certain embodiments are drawn to the use of a compound comprising a CFB specific inhibitor for the preparation of a medicament for treating a disease, disorder or condition associated with CFB. In certain embodiments, the disease, disorder, or condition is a complement pathway related disease, disorder, or condition. In certain embodiments, the disease, disorder, or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 24, 25, 42, 96, 97, 98, and 100. In certain embodiments, a compound comprises a modified oligonucleotide having a nucleobase sequence selected from the nucleobase sequences of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide.

Certain embodiments are drawn to the use of a compound comprising a CFB specific inhibitor for the manufacture or preparation of a medicament for reducing or inhibiting a complement pathway related disease, disorder or condition or a symptom thereof in an individual having, or at risk of having, a complement pathway related disease. In certain embodiments, the complement pathway related disease is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). Certain embodiments are drawn to use of a compound comprising a CFB specific inhibitor for the preparation of a medicament for treating a disease, disorder or condition associated with CFB. In certain embodiments, the disease, disorder, or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), e.g., lupus nephritis, diabetic nephropathy, membranous nephropathy, polycystic kidney disease, age-related macular degeneration, thrombotic microangiopathy, myasthenia gravis, ischemia, reperfusion injury, or rheumatoid arthritis (RA). In certain embodiments, the compound comprises an antisense oligonucleotide targeted to CFB. In certain embodiments, the compound comprises an oligonucleotide targeted to CFB. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 11-44 and 96-102. In certain embodiments, a compound comprises a modified oligonucleotide having a nucleobase sequence selected from the nucleobase sequences of any one of SEQ ID NOs: 11-44 and 96-102. In certain embodiments, a compound comprises a modified oligonucleotide (e.g., of 14 to 30, for example, 14 to 23, linked nucleosides in length) having a nucleobase sequence comprising the nucleobase sequence of any one of SEQ ID NOs: 24, 25, 42, 96, 97, 98, and 100. In certain embodiments, a compound comprises a modified oligonucleotide having a nucleobase sequence selected from the nucleobase sequences of any one of SEQ ID NOs: 24, 25, 42, 96, 97, 98, and 100. In any of the foregoing embodiments, the compound can be single-stranded or double-stranded. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 96, 97, 100 or 101. In certain embodiments, a compound comprises a modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of the nucleobase sequence of SEQ ID NO: 93, 106, 109 or 110. In certain embodiments, a compound comprises a modified oligonucleotide having a nucleobase sequence selected from the nucleobase sequences of SEQ ID NO: 96, SEQ ID NO: 97, SEQ ID NO: 100 and SEQ ID NO: 101. In certain embodiments, a compound comprises a modified oligonucleotide having a nucleobase sequence selected from the nucleobase sequences of SEQ ID NO: 93, SEQ ID NO: 106, SEQ ID NO: 109 and SEQ ID NO: 110. In certain embodiments, the compound comprises a first modified oligonucleotide having a nucleobase sequence of SEQ ID NO: 96 and a second modified oligonucleotide having a nucleobase sequence of SEQ ID NO: 93. In certain embodiments, the compound comprises a first modified oligonucleotide having a nucleobase sequence of SEQ ID NO: 97 and a second modified oligonucleotide having a nucleobase sequence of SEQ ID NO: 106. In certain embodiments, the compound comprises a first modified oligonucleotide having a nucleobase sequence of SEQ ID NO: 100 and a second modified oligonucleotide having a nucleobase sequence of SEQ ID NO: 109. In certain embodiments, the compound comprises a first modified oligonucleotide having a nucleobase sequence of SEQ ID NO: 101 and a second modified oligonucleotide having a nucleobase sequence of SEQ ID NO: 110. In any of the foregoing embodiments, the compound can be an antisense oligonucleotide or oligomeric compound. In certain embodiments, a compound comprises a first modified oligonucleotide (e.g., of 14 to 30, for example, 14 to 23, linked nucleosides in length) having a nucleobase sequence comprising at least 14, at least 15, at least 16, at least 17, at least 18, at least 19, at least 20, at least 21, at least 22, or at least 23 contiguous nucleobases of any of the nucleobase sequences of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide (e.g., of 14 to 30, for example, 14 to 23, linked nucleosides in length) having a nucleobase sequence comprising the nucleobase sequence of any one of SEQ ID NOs: 11-110 and a second modified oligonucleotide (e.g., of 14 to 30, for example, 14 to 23, linked nucleosides in length) having a region of complementarity to the first modified oligonucleotide. In certain embodiments, a compound comprises a first modified oligonucleotide having a nucleobase sequence selected from any one of the nucleobase sequences of SEQ ID NOs: 11-110 and a second modified oligonucleotide 19 to 23 linked nucleosides in length having a region of complementarity to the first modified oligonucleotide.

In any of the foregoing methods or uses, the compound can be an oligomeric compound. In any of the foregoing methods or uses, the compound can be single-stranded or double-stranded. In any of the foregoing methods or uses, the compound can be targeted to CFB. In certain embodiments, the compound comprises or consists of a modified oligonucleotide. In certain embodiments, the compound comprises one or more modified oligonucleotides. In certain embodiments, the compound comprises a first modified oligonucleotide and a second modified oligonucleotide. In certain embodiments, a modified oligonucleotide is 8 to 80 linked nucleosides in length, 10 to 30 linked nucleosides in length, 14 to 30 linked nucleosides in length, 14 to 23 linked nucleosides in length, or 19 to 23 linked nucleosides in length. In certain embodiments, a modified oligonucleotide having a nucleobase sequence is at least 80%, at least 85%, at least 90%, at least 95% or 100% complementary to the nucleobase sequences recited in SEQ ID NO: 1 or 3 over its length. In certain embodiments, a modified oligonucleotide comprises at least one modified internucleoside linkage, at least one modified sugar and/or at least one modified nucleobase. In certain embodiments, the modified internucleoside linkage is a phosphorothioate internucleoside linkage. In certain embodiments, the modified sugar is a bicyclic sugar, 2'-MOE, 2'-F, or 2'-OMe. In certain embodiments, the modified nucleobase is a 5-methylcytosine. In any of the foregoing embodiments, each modified oligonucleotide is independently 12 to 30, 14 to 30, 14 to 25, 14 to 24, 14 to 23, 16 to 23, 17 to 23, 18 to 23, 19 to 23, 19 to 22, or 19 to 20 linked nucleosides in length. In certain embodiments, a modified oligonucleotide having a nucleobase sequence has at least 1, at least 2, or at least 3 mismatches to a region of the nucleobases of SEQ ID NO: 1 or 3.

In any of the forgoing methods or uses, the compound comprises a first and second modified oligonucleotide, wherein there is a region of complementarity between a first modified oligonucleotide and a second modified oligonucleotide. In certain embodiments, the region of complementarity between the first oligonucleotide and the second oligonucleotide is 14 to 23, 19 to 23, or 21 to 23 linked nucleosides in length. In certain embodiments, the first modified oligonucleotide is fully complementary to the second modified oligonucleotide. In certain embodiments, the first modified oligonucleotide comprises at least one modification selected from a modified internucleoside linkage, a modified sugar, and a modified nucleobase. In certain embodiments, the second modified oligonucleotide comprises at least one modification selected from a modified internucleoside linkage, a modified sugar, and a modified nucleobase. In certain embodiments, the modified internucleoside linkage is a phosphorothioate internucleoside linkage or a methylphosphonate internucleoside linkage. In certain embodiments, the modified internucleoside linkage is at the 3' terminus of the first or second modified oligonucleotide or at the 5' terminus of the first or second modified oligonucleotide. In certain embodiments, the first or second modified oligonucleotide comprises one or more modified sugars. In certain embodiments, each nucleoside of the first or second modified oligonucleotide comprises a modified sugar. In certain embodiments, the modified sugar comprises a modification selected from a halogen, an alkoxy group and a bicyclic sugar. In certain embodiments, the modified sugar comprises a modification selected from 2'-MOE, 2'-F, and 2'-OMe or a combination thereof. In certain embodiments, the first or second modified oligonucleotide comprises no more than ten 2'-F sugar modifications. In certain embodiments, the first or second modified oligonucleotide comprises no more than five 2'-F sugar modifications.

In any of the forgoing methods or uses, a compound comprises a conjugate group. In certain embodiments, the conjugate group is attached to the 5' end of a modified oligonucleotide. In certain embodiments, the conjugate group is a targeting moiety. In certain embodiments, the targeting moiety comprises one or more GalNAc. In certain embodiments, the one or more GalNAc is attached to the 2' or 3' position of the ribosyl ring. In certain embodiments, the one or more GalNAc is attached to the 5' nucleoside of the modified oligonucleotide. In certain embodiments, the 5' nucleoside of a modified oligonucleotide is selected from Formulae I-VIII and XII, or a salt, solvate, or hydrate thereof, wherein R is the modified oligonucleotide other than the 5' nucleoside. In certain embodiments, the 5' nucleoside of the modified oligonucleotide is Formula I and R' is O. In certain embodiments, the 5' nucleoside of the modified oligonucleotide is Formula I and R' is S. In certain embodiments, the 5' nucleoside of the modified oligonucleotide is Formula II and R' is O. In certain embodiments, the 5' nucleoside of the modified oligonucleotide is Formula II and R' is S. In certain embodiments, the 5' nucleoside of the modified oligonucleotide is Formula III and R' is O. In certain embodiments, the 5' nucleoside of the modified oligonucleotide is Formula III and R' is S. In certain embodiments, the 5' nucleoside of the modified oligonucleotide is Formula IV and R' is O. In certain embodiments, the 5' nucleoside of the modified oligonucleotide is Formula IV and R' is S. In certain embodiments, the 5' nucleoside of the modified oligonucleotide is Formula V and R' is O. In certain embodiments, the 5' nucleoside of the modified oligonucleotide is Formula V and R' is S. In certain embodiments, the 5' nucleoside of the modified oligonucleotide is Formula VI and R' is O. In certain embodiments, the 5' nucleoside of the modified oligonucleotide is Formula VI and R' is S. In certain embodiments, the 5' nucleoside of the modified oligonucleotide is Formula VII and R' is O. In certain embodiments, the 5' nucleoside of the modified oligonucleotide is Formula VII and R' is S. In certain embodiments, the 5' nucleoside of the modified oligonucleotide is Formula VIII and R' is O. In certain embodiments, the 5' nucleoside of the modified oligonucleotide is Formula VIII and R' is S. In certain embodiments, the 5' nucleoside of a modified oligonucleotide is Formula XII, or a salt, solvate, or hydrate thereof, wherein R is the modified oligonucleotide other than the 5' nucleoside. In certain embodiments, the 5' nucleoside of the modified oligonucleotide is Formula XII and R' is O. In certain embodiments, the 5' nucleoside of the modified oligonucleotide is Formula XII and R' is S.

In any of the foregoing methods or uses, the compound comprises a first modified oligonucleotide selected from any one of IA0478-490, IA0840, IA0842-846, IA0852-862, IA0872-882, IA0887-890, IA1010-1012, and IA1015-1018 and a second modified oligonucleotide 14 to 21 linked nucleosides in length fully complementary to the first modified oligonucleotide. In certain embodiments, the compound comprises a first modified oligonucleotide selected from IA0478-490, IA0840, IA0842-846, IA0852-862, IA0872-882, IA0887-890, IA1010-1012, and IA1015-1018 and a second modified oligonucleotide selected from IS0570-587, IS0969, IS0972-977, IS1023-1027, IS1029, IS1031-1037, IS1042-1046, IS1082, IS1085, IS1086, IS1091-1095, IS1108-1111, IS1236-1239, IS1242, IS1249, and IS1251-1254. Certain embodiments provide a compound comprising a first modified oligonucleotide which is IA0840 and a second modified oligonucleotide which is IS0972. Certain embodiments provide a compound comprising a first modified oligonucleotide which is IA0842 and a second modified oligonucleotide which is IS0974. Certain embodiments provide a compound comprising a first modified oligonucleotide which is IA0888 and a second modified oligonucleotide which is IS1109. Certain embodiments provide a compound comprising a first modified oligonucleotide which is IA0888 and a second modified oligonucleotide which is IS1236. Certain embodiments provide a compound comprising a first modified oligonucleotide which is IA1010 and a second modified oligonucleotide which is IS1109. Certain embodiments provide a compound comprising a first modified oligonucleotide which is IA1011 and a second modified oligonucleotide which is IS1239. Certain embodiments provide a compound comprising a first modified oligonucleotide which is IA1012 and a second modified oligonucleotide which is IS1242. Certain embodiments provide a compound comprising a first modified oligonucleotide which is IA1016 and a second modified oligonucleotide which is IS1252. Certain embodiments provide a compound comprising a first modified oligonucleotide which is IA1017 and a second modified oligonucleotide which is IS1253.

In certain embodiments, the compound is in a pharmaceutically acceptable salt form. In certain embodiments, the pharmaceutically acceptable salt is a sodium salt. In certain embodiments, the pharmaceutically acceptable salt is a potassium salt. In certain embodiments, a composition comprises the compound of any one of the foregoing embodiments and a pharmaceutically acceptable carrier.

In any of the foregoing methods or uses, a compound or composition comprising a compound of any preceding embodiment is administered to an individual in a therapeutically effective amount. In certain embodiments, a compound or composition comprising a compound of any preceding embodiment is administered to an individual at a dosage level sufficient to deliver about 1 to 100 mg/kg of body weight of the individual. In certain embodiments, a compound or composition comprising a compound of any preceding embodiment is administered to an individual at a fixed dose of about 25 mg to about 1,000 mg. In certain embodiments, the composition is administered to the individual one or more times in a day up to the dosage level or fixed dose.

In any of the foregoing methods or uses, a compound or composition comprising a compound of any preceding embodiment is administered to an individual daily, weekly, monthly, quarterly, or yearly. In certain embodiments, a compound or composition comprising a compound of any preceding embodiment is administered to an individual about once per quarter (i.e., once every three months) to about once per year. In certain embodiments, a compound or composition comprising a compound of any preceding embodiment is administered to an individual about once per quarter, about once every six months or about once per year.

Certain Compounds

In certain aspects, the disclosure relates to a compound that comprises or consists of an oligomeric compound. In certain embodiments, the oligomeric compound comprises a nucleobase sequence complementary to the nucleobase sequence or portion thereof of a target nucleic acid.

In certain aspects, the disclosure relates to a compound that comprises or consists of a modified oligonucleotide. In certain embodiments, the modified oligonucleotide has a nucleobase sequence complementary to the nucleobase sequence or portion thereof of a target nucleic acid.

In certain aspects, the disclosure relates to a compound that comprises or consists of an antisense oligonucleotide. In certain embodiments, the antisense oligonucleotide has a nucleobase sequence complementary to the nucleobase sequence or portion thereof of a target nucleic acid.

In certain aspects, the disclosure relates to a compound that is a single-stranded compound. In certain embodiments, the single-stranded compound comprises or consists of an oligomeric compound. In certain embodiments, such an oligomeric compound comprises or consists of an oligonucleotide and optionally a conjugate group. In certain embodiments, the oligonucleotide is a modified oligonucleotide. In certain embodiments, the oligonucleotide is an antisense oligonucleotide. In certain embodiments, the oligonucleotide or modified oligonucleotide of a single-stranded compound comprises a self-complementary nucleobase sequence. In certain aspects, the disclosure relates to a compound that is a double-stranded compound. In certain embodiments, the double-stranded compound comprises or consists of an oligomeric compound. In certain embodiments, the double-stranded compound comprises a first oligonucleotide and a second oligonucleotide. In certain embodiments, the first oligonucleotide has a region complementarity to a target nucleic acid and the second oligonucleotide has a region complementarity to the first modified oligonucleotide. In certain embodiments, the double-stranded compound comprises a modified oligonucleotide. In certain embodiments, the modified oligonucleotide has a region complementarity to a target nucleic acid. In certain embodiments, the double-stranded compound comprises a first modified oligonucleotide and a second modified oligonucleotide. In certain embodiments, the first modified oligonucleotide has a region complementarity to a target nucleic acid and the second modified oligonucleotide has a region complementarity to the first modified oligonucleotide. In certain embodiments, an oligonucleotide or modified oligonucleotide of a double-stranded compound is an RNA oligonucleotide. In such embodiments, the thymine nucleobase in the modified oligonucleotide is replaced by a uracil nucleobase.

In certain embodiments, a compound described herein comprises a conjugate group. In certain embodiments, the first oligonucleotide or first modified oligonucleotide of a double-stranded compound comprises a conjugate group. In certain embodiments, the second oligonucleotide or second modified oligonucleotide of a double-stranded compound comprises a conjugate group. In certain embodiments, a first oligonucleotide or first modified oligonucleotide and a second oligonucleotide or second modified oligonucleotide of a double-stranded compound each comprises a conjugate group.

In certain embodiments, a compound is 14-30 linked nucleosides in length. In certain embodiments, the first oligonucleotide or first modified oligonucleotide of a double-stranded compound is 14-30 linked nucleosides in length. In certain embodiments, the second oligonucleotide or second modified oligonucleotide is 14-30 linked nucleosides in length. In certain embodiments, the oligonucleotides or modified oligonucleotides of a double-stranded compound are blunt ended at one or both ends of the compound. In certain embodiments, the oligonucleotides or modified oligonucleotides of a double-stranded compound include non-complementary overhanging nucleosides at one or both ends of the compound.

In certain embodiments, a compound has a nucleobase sequence comprising at least 14 contiguous nucleobases of any of the nucleobase sequences of SEQ ID NOs: 11-44 and 96-102. In certain embodiments, one of the oligonucleotides or modified oligonucleotides of a double-stranded compound has a nucleobase sequence comprising at least 14 contiguous nucleobases of any of the nucleobase sequences of SEQ ID NOs: 11-44 and 96-102.

Examples of single-stranded and double-stranded compounds include, but are not limited to, oligonucleotides, antisense oligonucleotides, siRNAs, microRNA targeting oligonucleotides, occupancy-based compounds (e.g., mRNA processing or translation blocking compounds and splicing compounds), and single-stranded RNAi compounds (e.g., small hairpin RNAs (shRNAs), single stranded siRNAs (ssRNAs) and microRNA mimics).

In certain embodiments, a compound described herein has a nucleobase sequence that, when written in the 5' to 3' direction, comprises the reverse complement of the target region of a target nucleic acid to which it is targeted.

In certain embodiments, a compound described herein comprises an oligonucleotide 12 to 30 linked subunits in length. In certain embodiments, a compound described herein comprises an oligonucleotide 12 to 23 linked subunits in length. In certain embodiments, compound described herein comprises an oligonucleotide 14 to 30 linked subunits in length. In certain embodiments, compound described herein comprises an oligonucleotide 14 to 23 linked subunits in length. In certain embodiments, a compound described herein comprises an oligonucleotide 15 to 30 linked subunits in length. In certain embodiments, a compound described herein comprises an oligonucleotide 15 to 23 linked subunits in length. In certain embodiments, a compound described herein comprises an oligonucleotide 16 to 30 linked subunits in length. In certain embodiments, a compound described herein comprises an oligonucleotide 16 to 23 linked subunits in length. In certain embodiments, a compound described herein comprises an oligonucleotide 17 to 30 linked subunits in length. In certain embodiments, a compound described herein comprises an oligonucleotide 17 to 23 linked subunits in length. In certain embodiments, a compound described herein comprises an oligonucleotide 18 to 30 linked subunits in length. In certain embodiments, a compound described herein comprises an oligonucleotide 18 to 23 linked subunits in length. In certain embodiments, a compound described herein comprises an oligonucleotide 19 to 30 linked subunits in length. In certain embodiments, a compound described herein comprises an oligonucleotide 19 to 23 linked subunits in length. In other words, such oligonucleotides are 12 to 30 linked subunits, 12 to 23 linked subunits, 14 to 30 linked subunits, 14 to 23 linked subunits, 15 to 30 linked subunits, 15 to 23 linked subunits, 16 to 30 linked subunits, 16 to 23 linked subunits, 17 to 30 linked subunits, 17 to 23 linked subunits, 18 to 30 linked subunits, 18 to 23 linked subunits, 19 to 30 linked subunits or 19 to 23 linked subunits, respectively. In certain embodiments, a compound described herein comprises an oligonucleotide 14 linked subunits in length. In certain embodiments, a compound described herein comprises an oligonucleotide 16 linked subunits in length. In certain embodiments, a compound described herein comprises an oligonucleotide 17 linked subunits in length. In certain embodiments, compound described herein comprises an oligonucleotide 18 linked subunits in length. In certain embodiments, a compound described herein comprises an oligonucleotide 19 linked subunits in length. In certain embodiments, a compound described herein comprises an oligonucleotide 20 linked subunits in length. In certain embodiments, a compound described herein comprises an oligonucleotide 21 linked subunits in length. In certain embodiments, a compound described herein comprises an oligonucleotide 22 linked subunits in length. In certain embodiments, a compound described herein comprises an oligonucleotide 23 linked subunits in length. In other embodiments, a compound described herein comprises an oligonucleotide 8 to 80, 12 to 50, 13 to 30, 13 to 50, 14 to 30, 14 to 50, 15 to 30, 15 to 50, 16 to 30, 16 to 50, 17 to 30, 17 to 50, 18 to 23, 18 to 24, 18 to 25, 18 to 50, 19 to 23, 19 to 30, 19 to 50, 20 to 23 or 20 to 30 linked subunits. In certain such embodiments, the compound described herein comprises an oligonucleotide 8, 9, 10, 11, 12, 13, 14, 15, 16, 17, 18, 19, 20, 21, 22, 23, 24, 25, 26, 27, 28, 29, or 30 linked subunits in length, or a range defined by any two of the above values.

In certain embodiments, the compound may further comprise an additional moiety, such as a conjugate group or delivery moiety. In certain embodiments, such compounds are oligomeric compounds, and the additional moiety is attached to an oligonucleotide. In certain embodiments, a conjugate group is attached to a nucleoside of an oligonucleotide.

In certain embodiments, compounds may be shortened or truncated. For example, one or more subunits may be deleted from the 5' end (5' truncation), or alternatively from the 3' end (3' truncation) of an oligonucleotide.

In certain embodiments, compounds may be lengthened. For example, one or more subunits may be attached to the 3' end or 5' end of an oligonucleotide. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunits) is attached to the 5' end of an oligonucleotide. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunits) is attached to the 3' end of an oligonucleotide. In certain embodiments, at least one subunit may be attached to the 3' end or 5' end of an oligonucleotide of a double-stranded compound creating a 3' and/or 5' end overhang. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunits) is attached to the 5' end of both oligonucleotides of a double-stranded compound. In certain embodiments, at least one subunit (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more subunit) is attached to the 3' end of both oligonucleotides of a double-stranded compound. In certain embodiments, subunits are attached to both oligonucleotides of a double-stranded compound at the same end (e.g., that subunits are attached to the 3' end of one of the oligonucleotides and subunits are attached to the 5' end of the other oligonucleotide). In certain embodiments, when subunits are attached to both oligonucleotides of a double-stranded compound at the same end, the number of subunits attached to each oligonucleotide may be the same or may be different. In certain embodiments, when subunits are attached to both oligonucleotides of a double-stranded compound at the same end, the number of subunits attached to each oligonucleotide is the same. In certain embodiments, when subunits are attached to both oligonucleotides of a double-stranded compound at the same end, the number of subunits attached to each oligonucleotide is different. This scenario, where subunits are attached to both oligonucleotides of a double-stranded compound at the same end, may occur at one or both ends of a double-stranded compound. In certain embodiments, the subunits attached to the 3' and/or 5' end are modified.

In certain embodiments, compounds described herein are oligonucleotides. In certain embodiments, compounds described herein are modified oligonucleotides. In certain embodiments, compounds described herein are antisense oligonucleotides. In certain embodiments, compounds described herein are oligomeric compounds. In certain embodiments, compounds described herein are RNAi compounds. In certain embodiments, compounds described herein are siRNA compounds.

In certain embodiments, a compound described herein can comprise any of the oligonucleotide sequences targeted to CFB described herein. In certain embodiments, the compound can be double-stranded.

In certain embodiments, the compound comprises an oligonucleotide having a nucleobase sequence comprising at least an 8, 9, 10, 11, 12, 13, 14, 15, 16, 17, 18, 19, 20, 21, 22 or 23 contiguous nucleobase portion of any one of the nucleobase sequences of SEQ ID NOs: 11-44 or 96-102. In certain embodiments, the compound comprises an oligonucleotide comprising at least an 8, 9, 10, 11, 12, 13, 14, 15, 16, 17, 18, 19, 20, 21, 22 or 23 contiguous nucleobase portion of SEQ ID NO: 96, 97, 100 or 101. In certain embodiments, the compound comprises a second oligonucleotide. In certain embodiments, the compound comprises an oligonucleotide comprising at least an 8, 9, 10, 11, 12, 13, 14, 15, 16, 17, 18, 19, 20, 21, 22 or 23 contiguous nucleobase portion of SEQ ID NO: 93, 106, 109 or 110. In certain embodiments, the compound comprises a first oligonucleotide comprising at least an 8, 9, 10, 11, 12, 13, 14, 15, 16, 17, 18, 19, 20, 21, 22 or 23 contiguous nucleobase portion of SEQ ID NO: 96 and a second oligonucleotide comprising at least an 8, 9, 10, 11, 12, 13, 14, 15, 16, 17, 18, 19, 20, 21, 22 or 23 contiguous nucleobase portion of SEQ ID NO: 93. In certain embodiments, the compound comprises a first oligonucleotide comprising at least an 8, 9, 10, 11, 12, 13, 14, 15, 16, 17, 18, 19, 20, 21, 22 or 23 contiguous nucleobase portion of SEQ ID NO: 97 and a second oligonucleotide comprising at least an 8, 9, 10, 11, 12, 13, 14, 15, 16, 17, 18, 19, 20, 21, 22 or 23 contiguous nucleobase portion of SEQ ID NO: 106. In certain embodiments, the compound comprises a first oligonucleotide comprising at least an 8, 9, 10, 11, 12, 13, 14, 15, 16, 17, 18, 19, 20, 21, 22 or 23 contiguous nucleobase portion of SEQ ID NO: 100 and a second oligonucleotide comprising at least an 8, 9, 10, 11, 12, 13, 14, 15, 16, 17, 18, 19, 20, 21, 22 or 23 contiguous nucleobase portion of SEQ ID NO: 109. In certain embodiments, the compound comprises a first oligonucleotide comprising at least an 8, 9, 10, 11, 12, 13, 14, 15, 16, 17, 18, 19, 20, 21, 22 or 23 contiguous nucleobase portion of SEQ ID NO: 101 and a second oligonucleotide comprising at least an 8, 9, 10, 11, 12, 13, 14, 15, 16, 17, 18, 19, 20, 21, 22 or 23 contiguous nucleobase portion of SEQ ID NO: 110. In certain embodiments the oligonucleotide is a modified oligonucleotide.

In certain embodiments, the compound comprises ribonucleotides in which the oligonucleotide has uracil (U) in place of thymine (T) for any of the sequences provided here. In certain embodiments, the compound comprises deoxyribonucleotides in which the oligonucleotide has thymine (T) in place of uracil (U) for any of the sequences provided here.

Certain Mechanisms

In certain embodiments, compounds described herein comprise or consist of modified oligonucleotides. In certain embodiments, compounds described herein comprise or consist of antisense oligonucleotides. In certain embodiments, compounds comprise or consist of oligomeric compounds. In certain embodiments, compounds described herein are capable of hybridizing to a target nucleic acid. In certain embodiments, compounds described herein selectively affect one or more target nucleic acid. Such compounds comprise a nucleobase sequence that hybridizes to one or more target nucleic acid, resulting in one or more desired activity and does not hybridize to one or more non-target nucleic acid or does not hybridize to one or more non-target nucleic acid in such a way that results in a significant undesired activity.

In certain embodiments, hybridization of a compound described herein to a target nucleic acid results in recruitment of one or more proteins that cause the cleavage of the target nucleic acid. For example, certain compounds described herein, or a portion of the compounds, are loaded into an RNA-induced silencing complex (RISC), ultimately resulting in cleavage of the target nucleic acid. For example, certain compounds described herein result in cleavage of the target nucleic acid by Argonaute. Compounds that are loaded into RISC are RNAi compounds. RNAi compounds may be double-stranded (siRNA) or single-stranded (ssRNA).

In certain embodiments, hybridization of compounds described herein to a target nucleic acid does not result in recruitment of a protein that cleaves that target nucleic acid. In certain such embodiments, hybridization of the compound to the target nucleic acid results in the alteration of splicing of the target nucleic acid. In certain embodiments, hybridization of the compound to a target nucleic acid results in inhibition of a binding interaction between the target nucleic acid and a protein or other nucleic acid. In certain such embodiments, hybridization of the compound to the target nucleic acid results in the alteration of RNA processing. In certain such embodiments, hybridization of the compound to a target nucleic acid results in alteration of translation of the target nucleic acid.

Activities resulting from the hybridization of a compound to a target nucleic acid may be observed directly or indirectly. In certain embodiments, observation or detection of an activity involves observation or detection of a change in an amount of a target nucleic acid or protein encoded by such target nucleic acid, a change in the ratio of splice variants of a nucleic acid or protein, and/or a phenotypic change in a cell or animal.

Certain Modifications

In certain aspects, the disclosure relates to compounds that comprise or consist of oligonucleotides. Oligonucleotides consist of linked nucleosides. In certain embodiments, oligonucleotides may be unmodified RNA or DNA or may be modified. In certain embodiments, the oligonucleotides are modified oligonucleotides. In certain embodiments, the modified oligonucleotides comprise at least one modified sugar, modified nucleobase or modified internucleoside linkage relative to an unmodified RNA or DNA. In certain embodiments, an oligonucleotide has a modified nucleoside. A modified nucleoside may comprise a modified sugar, a modified nucleobase or both a modified sugar and a modified nucleobase. Modified oligonucleotides may also include end modifications, e.g., 5'-end modifications and 3'-end modifications.

Sugar Modifications and Motifs

In certain embodiments, a modified sugar is a substituted furanosyl sugar or non-bicyclic modified sugar. In certain embodiments, a modified sugar is a bicyclic or tricyclic modified sugar. In certain embodiments, a modified sugar is a sugar surrogate. A sugar surrogate may comprise one or more substitutions described herein.

In certain embodiments, a modified sugar is a substituted furanosyl or non-bicyclic modified sugar. In certain embodiments, the furanosyl sugar is a ribosyl sugar. In certain embodiments, the furanosyl sugar comprises one or more substituent groups, including, but not limited to, substituent groups at the 2', 3', 4', and 5' positions.

In certain embodiments, substituents at the 2' position include, but are not limited to, F and $OCH_3$ ("OMe", "O-methyl" or "methoxy"). In certain embodiments, substituent groups at the 2' position suitable for non-bicyclic modified sugars include, but are not limited to, halo, allyl, amino, azido, SH, CN, OCN, $CF_3$, $OCF_3$, F, Cl, Br, $SCH_3$, $SOCH_3$, $SO_2CH_3$, $ONO_2$, $NO_2$, $N_3$, and $NH_2$. In certain embodiments, substituent groups at the 2' position include, but are not limited to, O—($C_1$-$C_{10}$) alkoxy, alkoxyalkyl, O-alkyl, S-alkyl, N-alkyl, O-alkenyl, S-alkenyl, N-alkenyl, O-alkynyl, S-alkynyl, N-alkynyl, O-alkyl-O-alkyl, alkynyl, wherein the alkyl, alkenyl and alkynyl can be substituted or unsubstituted $C_1$ to $C_{10}$ alkyl or $C_2$ to $C_{10}$ alkenyl and alkynyl. In certain embodiments, substituent groups at the 2' position include, but are not limited to, alkaryl, aralkyl, O-alkaryl, and O-aralkyl. In certain embodiments, these 2' substituent groups can be further substituted with one or more substituent groups independently selected from hydroxyl, alkoxy, carboxy, benzyl, phenyl, nitro ($NO_2$), thiol, thioalkoxy, thioalkyl, halogen, alkyl, aryl, alkenyl, and alkynyl. In certain embodiments, substituent groups at the 2' position include, but are not limited to, $O[(CH_2)_nO]_mCH_3$, $O(CH_2)$, $OCH_3$, $O(CH_2)$, $CH_3$, $O(CH_2)_nONH_2$, $O(CH_2)_nNH_2$, $O(CH_2)_nSCH_3$, and $O(CH_2)_nON[(CH_2)_nCH_3)]_2$, where n and m are independently from 1 to about 10. In certain embodiments, substituent groups at the 2' position include, but are not limited to, $OCH_2CH_2OCH_3$ ("MOE"), $O(CH_2)_2ON(CH_3)_2$ ("DMAOE"), $O(CH_2)_2O(CH_2)_2N(CH_3)_2$ ("DMAEOE"), and $OCH_2C(=O)—N(H)CH_3$ ("NMA").

In certain embodiments, substituent groups at the 4' position suitable for non-bicyclic modified sugars include, but are not limited to, alkoxy (e.g., methoxy), alkyl, and those described in Manoharan et al., WO 2015/106128. In certain embodiments, substituent groups at the 5' position suitable for non-bicyclic modified sugars include, but are not limited to, methyl ("Me") (R or S), vinyl, and methoxy. In certain embodiments, substituents described herein for the 2', 4' and 5' position can be added to other specific positions on the sugar. In certain embodiments, such substituents may be added to the 3' position of the sugar on the 3' terminal nucleoside or the 5' position of the 5' terminal nucleoside. In certain embodiments, a non-bicyclic modified sugar may comprise more than one non-bridging sugar substituent. In certain such embodiments, non-bicyclic modified sugars substituents include, but are not limited to, 5'-Me-2'-F, 5'-Me-2'-OMe (including both R and S isomers). In certain embodiments, modified sugar substituents include those described in Migawa et al., WO 2008/101157 and Rajeev et al., US2013/0203836.

In certain embodiments, a modified sugar is a bicyclic sugar. A bicyclic sugar is a modified sugar comprising two rings, wherein the second ring is formed via a bridge connecting two of the atoms in the first ring thereby forming a bicyclic structure. In certain embodiments, a bicyclic sugar comprises a bridging substituent that bridges two atoms of the furanosyl ring to form a second ring. In certain embodiments, a bicyclic sugar does not comprise a furanosyl moiety. A "bicyclic nucleoside" ("BNA") is a nucleoside having a bicyclic sugar. In certain embodiments, the bicyclic sugar comprises a bridge between the 4' and 2' furanose ring atoms. In certain embodiments, the bicyclic sugar comprises a bridge between the 5' and 3' furanose ring atoms. In certain such embodiments, the furanose ring is a ribose ring. In certain embodiments, 4' to 2' bridging substituents include, but are not limited to, 4'-$CH_2$-2', 4'-$(CH_2)_2$-2', 4'-$(CH_2)_3$-2', 4'-$CH_2$—O-2' ("LNA"), 4'-$CH_2$—S-2', 4'-$(CH_2)_2$—O-2' ("ENA"), 4'-$CH(CH_3)$—O-2' ("constrained ethyl" or "cEt" when in the S configuration), 4'-$CH_2$—O—$CH_2$-2', 4'-$CH_2$—N(R)-2', 4'-$CH(CH_2OCH_3)$—O-2' ("constrained MOE" or "cMOE") and analogs thereof (e.g., U.S. Pat. No. 7,399,845), 4'-$C(CH_3)(CH_3)$—O-2' and analogs thereof (e.g., U.S. Pat. No. 8,278,283), 4'-$CH_2$—$N(OCH_3)$-2' and analogs thereof (e.g., U.S. Pat. No. 8,278,425), 4'-$CH_2$—O—$N(CH_3)$-2' (e.g., U.S. Patent Publication No. 2004/0171570), 4'-$CH_2$—N(R)—O-2', wherein R is H, $C_1$-$C_{12}$ alkyl, or a protecting group (e.g., U.S. Pat. No. 7,427,672), 4'-$CH_2$—$C(H)(CH_3)$-2' (e.g., Chattopadhyaya et al., J. Org. Chem., 2009, 74, 118-134), and 4'-$CH_2$—$C(=CH_2)$-2' and analogs thereof (e.g., U.S. Pat. No. 8,278,426). The entire contents of each of the foregoing are hereby incorporated herein by reference. Additional representative U.S. Patents and U.S. Patent Publications that teach the preparation of bicyclic nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, US 2013/0190383; and WO 2013/036868, the entire contents of each of which are hereby incorporated herein by reference. Any of the foregoing bicyclic nucleosides can be prepared having one or more stereochemical sugar configurations including for example α-L-ribofuranose and β-D-ribofuranose (see e.g., WO 99/14226). Specified bicyclic nucleosides herein are in the β-D configuration, unless otherwise specified.

In certain embodiments, a modified sugar is a sugar surrogate. In certain embodiments, a sugar surrogate has the oxygen atom replaced, e.g., with a sulfur, carbon, or nitrogen atom. In certain such embodiments, the sugar surrogate may also comprise bridging and/or non-bridging substituents as described herein. In certain embodiments, sugar surrogates comprise rings having other than 5 atoms. In certain such embodiments, the sugar surrogate comprises a cyclobutyl moiety in place of the pentofuranosyl sugar. In certain embodiments, the sugar surrogate comprises a six membered ring in place of the pentofuranosyl sugar. In certain embodiments, the sugar surrogate comprises a tetrahydropyran ("THP") in place of the pentofuranosyl sugar. In certain embodiments, the sugar surrogate comprises a morpholino in place of the pentofuranosyl sugar. Representative US patents that teach the preparation of such modified sugar structures include, but are not limited to, U.S. Pat. Nos. 4,981,957; 5,118,800; 5,166,315; 5,185,444; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,700,920; 7,875,733; 7,939,677, 8,088,904; 8,440,803; and 9,005,906, the entire contents of each of the foregoing are hereby incorporated herein by reference.

In some embodiments, sugar surrogates comprise acyclic moieties. In certain embodiments, the sugar surrogate is an unlocked nucleic acid ("UNA"). A UNA is unlocked acyclic nucleic acid, wherein any of the bonds of the sugar has been removed, forming an unlocked "sugar" residue. In one example, UNA also encompasses a monomer where the bonds between C1'-C4' have been removed (i.e., the covalent carbon-oxygen-carbon bond between the C1' and C4' carbons). In another example, the C2'-C3' bond (i.e., the covalent carbon-carbon bond between the C2' and C3' carbons) of the sugar has been removed. Representative U.S. publications that teach the preparation of UNA include, but are not limited to, U.S. Pat. No. 8,314,227; and U.S. Patent Publication Nos. 2013/0096289; 2013/0011922; and 2011/0313020, the entire contents of each of which are hereby incorporated herein by reference. In certain embodiments, sugar surrogates comprise peptide nucleic acid ("PNA"), acyclic butyl nucleic acid (see, e.g., Kumar et al., Org. Biomol. Chem., 2013, 11, 5853-5865), and nucleosides and oligonucleotides described in Manoharan et al., US2013/130378, the entire contents of which is hereby incorporated herein by reference. Many other bicyclic and tricyclic sugar and sugar surrogate ring systems are known in the art that can be used in modified nucleosides.

In certain aspects, the disclosure relates to compounds comprising at least one oligonucleotide wherein the nucleosides of such oligonucleotide comprise one or more types of modified sugars and/or unmodified sugars arranged along the oligonucleotide or region thereof in a defined pattern or "sugar motif". In certain instances, such sugar motifs include, but are not limited to, any of the patterns of sugar modifications described herein.

In certain embodiments, an oligonucleotide comprises a gapmer sugar motif. A gapmer oligonucleotide comprises or consists of a region having two external "wing" regions and a central or internal "gap" region. The gap and wing regions form a contiguous sequence of nucleosides, wherein the majority of nucleoside sugars of each of the wings differ from the majority of nucleoside sugars of the gap. In certain embodiments, the wing regions comprise a majority of modified sugars and the gap comprises a majority of unmodified sugars. In certain embodiments, the nucleosides of the gap are deoxynucleosides. Compounds with a gapmer sugar motif are described in, for example U.S. Pat. No. 8,790,919, the entire contents of which is hereby incorporated herein by reference.

In certain embodiments, one or both oligonucleotides of a double-stranded compound comprise a triplet sugar motif. An oligonucleotide with a triplet sugar motif comprises three identical sugar modifications on three consecutive nucleosides. In certain embodiments, the triplet is at or near the cleavage site of the oligonucleotide. In certain embodiments, an oligonucleotide of a double-stranded compound may contain more than one triplet sugar motif. In certain embodiments, the identical sugar modification of the triplet sugar motif is a 2'-F modification. Compounds with a triplet sugar motif are disclosed, for example, in U.S. Pat. No. 10,668,170, the entire contents of which is incorporated herein by reference.

In certain embodiments, one or both oligonucleotides of a double-stranded compound comprise a quadruplet sugar motif. An oligonucleotide with a quadruplet sugar motif comprises four identical sugar modifications on four consecutive nucleosides. In certain embodiments, the quadruplet is at or near the cleavage site. In certain embodiments, an oligonucleotide of a double-stranded compound may contain more than one quadruplet sugar motif. In certain embodiments, the identical sugar modification of the quadruplet sugar motif is a 2'-F modification. For a double-stranded compound having a duplex region of 19-23 nucleotides in length, the cleavage site of the antisense oligonucleotide is typically around the 10, 11, and 12 positions from the 5'-end. In certain embodiments, the quadruplet sugar motif is at the 8, 9, 10, 11 positions; the 9, 10, 11, 12 positions; the 10, 11, 12, 13 positions; the 11, 12, 13, 14 positions; or the 12, 13, 14, 15 positions of the sense oligonucleotide, counting from the first nucleoside of the 5'-end of the sense oligonucleotide, or, the count starting from the first paired nucleotide within the duplex region from the 5'-end of the sense oligonucleotide. In certain embodiments, the quadruplet sugar motif is at the 8, 9, 10, 11 positions; the 9, 10, 11, 12 positions; the 10, 11, 12, 13 positions; the 11, 12, 13, 14 positions; or the 12, 13, 14, 15 positions of the antisense oligonucleotide, counting from the first nucleoside of the 5'-end of the antisense oligonucleotide, or, the count starting from the first paired nucleotide within the duplex region from the 5'-end of the antisense oligonucleotide. The cleavage site may change according to the length of the duplex region of the double-stranded compound and may change the position of the quadruplet accordingly.

In certain embodiments, an oligonucleotide comprises an alternating sugar motif. In certain embodiments, one or both oligonucleotides of a double-stranded compound comprise an alternating sugar motif. An oligonucleotide with an alternating sugar motif comprises at least two different sugar modifications wherein one or more consecutive nucleosides comprising a first sugar modification alternates with one or more consecutive nucleosides comprising a second sugar modification and one or more consecutive nucleosides comprising a third sugar modification, etc. For example, if A, B and C each represent one type of modification to the nucleoside, the alternating motif can be "ABABABABABAB . . . ," "AABBAABBAABB . . . ," "AABAABAABAAB "AAABAAABAAAB . . . ," "AAABBBAAABBB . . . ," or "ABCABCABCABC . . . " etc. In certain embodiments, the alternating sugar motif is repeated for at least 2, 3, 4, 5, 6, 7, 8, 9, 10, 11, 12, 13, 14, 15, 16, 17, 18, 19, 20, 21, 22, or 23 contiguous nucleobases along an oligonucleotide. In certain embodiments, the alternating sugar motif is comprised of two different sugar modifications. In certain embodiments, the alternating sugar motif comprises 2'-OMe and 2'-F sugar modifications.

In certain embodiments, each nucleoside of an oligonucleotide is independently modified with one or more sugar modifications provided herein. In certain embodiments, each oligonucleotide of a double-stranded compound independently has one or more sugar motifs provided herein. In certain embodiments, an oligonucleotide containing a sugar motif, is fully modified in that each nucleoside other than the nucleosides comprising the sugar motif comprises a sugar modification.

Nucleobase Modifications and Motifs

In certain embodiments, compounds described herein comprise modified oligonucleotides. In certain embodiments, modified oligonucleotides comprise one or more nucleosides comprising a modified nucleobase. In certain embodiments, modified oligonucleotides comprise one or more nucleosides that do not comprise a nucleobase, referred to as an abasic nucleoside.

In certain embodiments, modified nucleobases are selected from: 5-substituted pyrimidines, 6-azapyrimidines, alkyl or alkynyl substituted pyrimidines, alkyl substituted purines, and N-2, N-6 and O-6 substituted purines. In certain embodiments, modified nucleobases are selected from: 2-aminopropyladenine, 5-hydroxymethyl cytosine, 5-methylcytosine, xanthine, hypoxanthine, 2-aminoadenine, 6-N-methylguanine, 6-N-methyladenine, 2-propyladenine, 2-thiouracil, 2-thiothymine and 2-thiocytosine, 5-propynyl ($C\equiv C-CH_3$) uracil, 5-propynylcytosine, 6-azouracil, 6-azocytosine, 6-azothymine, 5-ribosyluracil (pseudouracil), 4-thiouracil, 8-halo, 8-amino, 8-thiol, 8-thioalkyl, 8-hydroxyl, 8-aza and other 8-substituted purines, 5-halo, particularly, 5-bromo, 5-trifluoromethyl, 5-halouracil, and 5-halocytosine, 7-methylguanine, 7-methyladenine, 2-F-adenine, 2-aminoadenine, 7-deazaguanine, 7-deazaadenine, 3-deazaguanine, 3-deazaadenine, 6-N-benzoyladenine, 2-N-isobutyrylguanine, 4-N-benzoylcytosine, 4-N-benzoyluracil, 5-methyl 4-N-benzoylcytosine, 5-methyl 4-N-benzoyluracil, universal bases, hydrophobic bases, promiscuous bases, size expanded bases, and fluorinated bases. Further modified nucleobases include tricyclic pyrimidines, such as 1,3-diazaphenoxazine-2-one, 1,3-diazaphenothiazine-2-one, and 9-(2-aminoethoxy)-1,3-diazaphenoxazine-2-one (G-clamp). Modified nucleobases may also include those in which the purine or pyrimidine base is replaced with other heterocycles, for example, 7-deaza-adenine, 7-deazaguanosine, 2-aminopyridine and 2-pyridone.

Further nucleobases include those disclosed in U.S. Pat. No. 3,687,808; Modified Nucleosides in Biochemistry, Biotechnology and Medicine, Herdewijn, P. ed. Wiley-VCH, 2008; The Concise Encyclopedia Of Polymer Science And Engineering, pages 858-859; Kroschwitz, J. L., Ed., John Wiley & Sons, 1990, 858-859; Englisch et al., Angewandte Chemie, International Edition, 1991, 30, 613; Sanghvi, Y. S., Chapter 15, dsRNA Research and Applications, pages 289-302; Antisense Research and Applications, Crooke, S. T. and Lebleu, B., Eds., CRC Press, 1993, 273-288; Antisense Drug Technology, Crooke S. T., Ed., CRC Press, 2008, 163-166 and 442-443 (Chapters 6 and 15), each of which are hereby incorporated herein by reference.

Publications that teach the preparation of certain of the above noted modified nucleobases, as well as other modified nucleobases include without limitation, US Applications 2003/0158403 and 2003/0175906; U.S. Pat. Nos. 4,845,205; 5,130,302; 5,134,066; 5,175,273; 5,367,066; 5,432,272; 5,434,257; 5,457,187; 5,459,255; 5,484,908; 5,502,177; 5,525,711; 5,552,540; 5,587,469; 5,594,121; 5,596,091; 5,614,617; 5,645,985; 5,681,941; 5,811,534; 5,750,692; 5,948,903; 5,587,470; 5,457,191; 5,763,588; 5,830,653; 5,808,027; 6,005,096. 6,015,886; 6,147,200; 6,166,197; 6,166,199; 6,222,025; 6,235,887; 6,380,368; 6,528,640; 6,639,062; 6,617,438; 7,045,610; 7,427,672; and 7,495,088, the entire contents of each of which are hereby incorporated herein by reference.

In certain embodiments, compounds described herein comprise oligonucleotides. In certain embodiments, oligonucleotides comprise modified and/or unmodified nucleobases arranged along the oligonucleotide or region thereof in a defined pattern or motif. In certain embodiments, each nucleobase is modified. In certain embodiments, none of the nucleobases are modified. In certain embodiments, each purine or each pyrimidine is modified. In certain embodiments, each adenine is modified. In certain embodiments, each guanine is modified. In certain embodiments, each thymine is modified. In certain embodiments, each uracil is modified. In certain embodiments, each cytosine is modified. In certain embodiments, some or all of the cytosine nucleobases in a modified oligonucleotide are 5-methylcytosines.

In certain embodiments, modified oligonucleotides comprise a block of modified nucleobases. In certain such embodiments, the block is at the 3'-end of the oligonucleotide. In certain embodiments, the block is within 3 nucleosides of the 3'-end of the oligonucleotide. In certain embodiments, the block is at the 5'-end of the oligonucleotide. In certain embodiments, the block is within 3 nucleosides of the 5'-end of the oligonucleotide.

Internucleoside Linkage Modifications and Motifs

A 3' to 5' phosphodiester linkage is the naturally occurring internucleoside linkage of RNA and DNA. In certain embodiments, compounds described herein have one or more modified, i.e., non-naturally occurring, internucleoside linkages. Certain non-naturally occurring internucleoside linkages may impart desirable properties such as, for example, enhanced cellular uptake, enhanced affinity for target nucleic acids, and increased stability in the presence of nucleases. Representative phosphorus-containing modified internucleoside linkages include, but are not limited to, phosphotriesters, alkylphosphonates (e.g., methylphosphonates), phosphoramidates, and phosphorothioates ("P═S"), and phosphorodithioates ("HS-P═S"). Representative non-phosphorus containing internucleoside linking groups include, but are not limited to, methylenemethylimino (—$CH_2$—N($CH_3$)—O—$CH_2$), thiodiester, thionocarbamate (—O—C(═O)(NH)—S—); siloxane (—O—$SiH_2$—O—); and N,N'-dimethylhydrazine (—$CH_2$—N(($CH_3$)—N(($CH_3$)—). Methods of preparation of phosphorous-containing and non-phosphorous-containing internucleoside linkages are well known to those skilled in the art. Neutral internucleoside linkages include, without limitation, phosphotriesters, methylphosphonates, MMI (3'-$CH_2$—N($CH_3$)—O-5'), amide-3 (3'-$CH_2$—C(═O)—N(H)-5'), amide-4 (3'-$CH_2$—N(H)—C(═O)-5'), formacetal (3'-O—$CH_2$—O-5'), methoxypropyl, and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (see, for example: Carbohydrate Modifications in Antisense Research; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

In certain embodiments, compounds provided herein comprise at least one modified internucleoside linkage. A modified internucleoside linkage may be placed at any position of an oligonucleotide. For double-stranded compounds, a modified internucleoside linkage may be placed within the sense oligonucleotide, antisense oligonucleotide, or both oligonucleotides of the double-stranded compound.

In certain embodiments, the internucleoside linkage modification may occur on every nucleoside of an oligonucleotide. In certain embodiments, internucleoside linkage modifications may occur in an alternating pattern along an oligonucleotide. In certain embodiments, essentially each internucleoside linking group is a phosphate internucleoside linkage (P═O). In certain embodiments, each internucleoside linking group of a modified oligonucleotide is a phosphorothioate (P═S). In certain embodiments, each internucleoside linking group of a modified oligonucleotide is independently selected from a phosphorothioate and phosphate internucleoside linkage. In certain embodiments, the pattern of the internucleoside linkage modification on each oligonucleotide of a double-stranded compound is the same. In certain embodiments, the pattern of the internucleoside linkage modification on each oligonucleotide of a double-stranded compound is different. In certain embodiments, a double-stranded compound comprises 6-8 modified internucleoside linkages. In certain embodiments, the 6-8 modified internucleoside linkages are phosphorothioate internucleoside linkages or alkylphosphonate internucleoside linkages. In certain embodiments, the sense oligonucleotide comprises at least two modified internucleoside linkages at either or both the 5'-end and the 3'-end. In certain such embodiments, the modified internucleoside linkages are phosphorothioate internucleoside linkages or alkylphosphonate internucleoside linkages. In certain embodiments, the antisense oligonucleotide comprises at least two modified internucleoside linkages at either or both the 5'-end and the 3'-end. In certain such embodiments, the modified internucleoside linkages are phosphorothioate internucleoside linkages or alkylphosphonate internucleoside linkages.

In certain embodiments, a double-stranded compound comprises an overhang region. In certain embodiments, a double-stranded compound comprises a phosphorothioate or alkylphosphonate internucleoside linkage modification in the overhang region. In certain embodiments, a double-stranded compound comprises a phosphorothioate or alkylphosphonate internucleotide linkage linking the overhang nucleotide with a paired nucleotide that is next to the overhang nucleotide. For instance, there may be at least two phosphorothioate internucleoside linkages between the terminal three nucleosides, in which two of the three nucleosides are overhang nucleosides, and the third is a paired nucleoside next to the overhang nucleoside. These terminal three nucleosides may be at the 3'-end of the antisense oligonucleotide, the 3'-end of the sense oligonucleotide, the 5'-end of the antisense oligonucleotide, or the 5'-end of the antisense oligonucleotide.

In certain embodiments, modified oligonucleotides comprise one or more internucleoside linkages having chiral centers. Representative chiral internucleoside linkages include, but are not limited to, alkylphosphonates and phosphorothioates. Modified oligonucleotides comprising internucleoside linkages having chiral centers can be prepared as populations of modified oligonucleotides comprising stereorandom internucleoside linkages, or as populations of modified oligonucleotides comprising phosphorothioate linkages in particular stereochemical configurations. In certain embodiments, populations of modified oligonucleotides comprise phosphorothioate internucleoside linkages wherein all of the phosphorothioate internucleoside linkages are stereorandom. Such modified oligonucleotides can be generated using synthetic methods that result in random selection of the stereochemical configuration of each phosphorothioate linkage. As is well understood by those of skill in the art, each individual phosphorothioate of each individual oligonucleotide molecule has a defined stereoconfiguration. In certain embodiments, populations of modified oligonucleotides are enriched for modified oligonucleotides comprising one or more particular phosphorothioate internucleoside linkages in a particular, independently selected stereochemical configuration. In certain embodiments, the particular configuration of the particular phosphorothioate linkage is present in at least 65% of the molecules in the population. In certain embodiments, the particular configuration of the particular phosphorothioate linkage is present in at least 70% of the molecules in the population. In certain embodiments, the particular configuration of the particular phosphorothioate linkage is present in at least 80% of the molecules in the population. In certain embodiments, the particular configuration of the particular phosphorothioate linkage is present in at least 90% of the molecules in the population. In certain embodiments, the particular configuration of the particular phosphorothioate linkage is present in at least 99% of the molecules in the population. Such enriched populations of modified oligonucleotides can be generated using synthetic methods known in the art, e.g., methods described in Oka et al., JACS 125, 8307 (2003), Wan et al. Nuc. Acid. Res. 42, 13456 (2014), and WO 2017/015555. In certain embodiments, a population of modified oligonucleotides is enriched for modified oligonucleotides having at least one indicated phosphorothioate in the (Sp) configuration. In certain embodiments, a population of modified oligonucleotides is enriched for modified oligonucleotides having at least one phosphorothioate in the (Rp) configuration.

Conjugate Groups

In certain embodiments, the compounds described herein comprise or consist of one or more oligonucleotides and, optionally, one or more conjugate groups. Conjugate groups may be attached to either or both ends of an oligonucleotide and/or at any internal position. In certain embodiments, a conjugate group is attached at the 3' end of an oligonucleotide. In certain embodiments, a conjugate group is attached at the 5' end of an oligonucleotide. In certain embodiments, oligonucleotides are covalently attached to one or more conjugate groups.

In certain embodiments, conjugate groups are terminal groups attached to either or both ends of an oligonucleotide. In certain such embodiments, terminal groups are attached at the 3' end of an oligonucleotide. In certain such embodiments, terminal groups are attached at the 5' end of an oligonucleotide. In certain embodiments, terminal groups include, but are not limited to, capping groups, phosphate moieties, protecting groups, modified or unmodified nucleosides, and two or more nucleosides that are independently modified or unmodified, such as an overhang.

In certain embodiments, conjugate groups modify one or more properties of the attached oligonucleotide, including, but not limited to, pharmacodynamics, pharmacokinetics, stability, activity, half-life, binding, absorption, tissue distribution, cellular distribution, cellular uptake, charge and clearance. In certain embodiments, conjugate groups enhance the affinity of a compound for a selected target, e.g., molecule, cell or cell type, compartment, e.g., a cellular or organ compartment, tissue, organ, or region of the body, as, e.g., compared to a compound absent such a conjugate group. In certain embodiments, conjugate groups impart a new property on the attached oligonucleotide, e.g., fluorophores or reporter groups that enable detection of the oligonucleotide.

In certain embodiments, conjugate groups include, but are not limited to, intercalators, reporter molecules, polyamines, polyamides, peptides, carbohydrates, vitamin moieties, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins, fluorophores, and dyes.

In certain embodiments, conjugate groups include an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, fingolimod, flufenamic acid, folinic acid, a benzothiadiazide, chlorothiazide, a diazepine, indomethicin, a barbiturate, a cephalosporin, a sulfa drug, an antidiabetic, an antibacterial, or an antibiotic.

In certain embodiments, conjugate groups are targeting moieties. In certain embodiments, a targeting moiety includes, but is not limited to, a lectin, glycoprotein, lipid, protein, peptide, peptide mimetic, receptor ligand, antibody, thyrotropin, melanotropin, surfactant protein A, carbohydrate, carbohydrate derivative, modified carbohydrate, carbohydrate cluster, polysaccharide, modified polysaccharide, or polysaccharide derivative, mucin carbohydrate, multivalent lactose, multivalent galactose, N-acetyl-galactosamine (GalNAc), N-acetylglucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

In certain embodiments, conjugate groups may include, but are not limited to, the conjugate groups described in the following references such as cholesterol (e.g., Letsinger et al., Proc. Natl. Acid. Sci. USA, 1989, 86: 6553-6556), cholic acid (e.g., Manoharan et al., Biorg. Med. Chem. Let., 1994, 4:1053-1060), thioether, e.g., hexyl-S-tritylthiol (e.g., Manoharan et al., Ann. NY. Acad. Sci., 1992, 660:306-309;

Manoharan et al., Biorg. Med. Chem. Let., 1993, 3:2765-2770), thiocholesterol (e.g., Oberhauser et al., Nucl. Acids Res., 1992, 20:533-538), aliphatic chains, e.g., do-decan-diol or undecyl residues (e.g., Saison-Behmoaras et al., EMBO J, 1991, 10:1111-1118; Kabanov et al., FEBS Lett., 1990, 259:327-330; Svinarchuk et al., Biochimie, 1993, 75:49-54), phospholipids, e.g., di-hexadecyl-rac-glycerol or triethyl-ammonium 1,2-di-O-hexadecyl-rac-glycero-3-H-phosphonate (e.g., Manoharan et al., Tetrahedron Lett., 1995, 36:3651-3654; Shea et al., Nucl. Acids Res., 1990, 18:3777-3783), polyamines or a polyethylene glycol chains (e.g., Manoharan et al., Nucleosides & Nucleotides, 1995, 14:969-973), adamantane acetic acid (e.g., Manoharan et al., Tetrahedron Lett., 1995, 36:3651-3654), palmityl (e.g., Mishra et al., Biochim. Biophys. Acta, 1995, 1264:229-237), octadecylamine or hexylamino-carbonyloxychole sterol moiety (e.g., Crooke et al. J. Pharmacol. Exp. Ther., 1996, 277:923-937), tocopherol (e.g., Nishina et al., Molecular Therapy Nucleic Acids, 2015, 4, e220 and Nishina et al., Molecular Therapy, 2008, 16:734-740), GalNAc and other carbohydrates (e.g., Maier et al., Bioconjugate Chemistry, 2003, 14, 18-29; Rensen et al., J. Med. Chem. 2004, 47, 5798-5808; WO2009/073809 and U.S. Pat. Nos. 8,106,022; 8,450,467 and 8,828,957; and WO2014/179445; WO2014/179620 and U.S. Pat. Nos. 9,127,276; 9,181,549 and 10,844,379) each of which is incorporated herein by reference in its entirety.

Conjugate groups may be attached to oligonucleotides through conjugate linkers. In certain embodiments, a conjugate linker comprises a chain structure, such as a hydrocarbyl chain, or an oligomer of repeating units or combination of such repeating units. In certain embodiments, a conjugate linker comprises one or more groups selected from alkyl, amino, oxo, amide, disulfide, polyethylene glycol, ether, thioether, and hydroxylamino. In certain embodiments, a conjugate linker comprises at least one phosphorus group. In certain embodiments, a conjugate linker comprises at least one phosphate group. In certain embodiments, a conjugate linker includes at least one neutral linking group. In certain embodiments, conjugate linkers include, but are not limited to, pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other conjugate linkers include, but are not limited to, substituted or unsubstituted $C_1$-$C_{10}$ alkyl, substituted or unsubstituted $C_2$-$C_{10}$ alkenyl, or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl, and alkynyl. In certain embodiments, conjugate linkers comprise 1-10 linker-nucleosides. In certain embodiments, such linker-nucleosides may be modified or unmodified nucleosides. It is typically desirable for linker-nucleosides to be cleaved from the compound after it reaches a target tissue. Accordingly, linker-nucleosides herein can be linked to one another and to the remainder of the compound through cleavable bonds. Herein, linker-nucleosides are not considered to be part of the oligonucleotide. Accordingly, in embodiments in which a compound comprises an oligonucleotide including a specified number or range of linked nucleosides and/or a specified percent complementarity to a reference nucleic acid and the compound also comprises a conjugate group comprising a conjugate linker comprising linker-nucleosides, those linker-nucleosides are not counted toward the length of the oligonucleotide and are not used in determining the percent complementarity of the oligonucleotide for the reference nucleic acid.

In certain embodiments, conjugate groups and conjugate linkers as well as other modifications include, without limitation, those described in the following references: U.S. Pat. Nos. 5,994,517; 6,300,319; 6,660,720; 6,906,182; 7,262,177; 7,491,805; 8,106,022; 7,723,509; 9,127,276; US 2006/0148740; US 2011/0123520; WO2013/033230; WO2012/037254, Biessen et al., J. Med. Chem. 1995, 38, 1846-1852; Lee et al., Bioorganic & Medicinal Chemistry 2011,19, 2494-2500; Rensen et al., J. Biol. Chem. 2001, 276, 37577-37584; Rensen et al., J. Med. Chem. 2004, 47, 5798-5808; Sliedregt et al., J. Med. Chem. 1999, 42, 609-618; Valentijn et al., Tetrahedron, 1997, 53, 759-770; Lee, Carhohydr Res, 1978, 67, 509-514; Connolly et al., J Biol Chem, 1982, 257, 939-945; Pavia et al., Int J Pep Protein Res, 1983, 22, 539-548; Lee et al., Biochem, 1984, 23, 4255-4261; Lee et al., Glycoconjugate J, 1987, 4, 317-328; Toyokuni et al., Tetrahedron Lett, 1990, 31, 2673-2676; Biessen et al., J Med Chem, 1995, 38, 1538-1546; Valentijn et al., Tetrahedron, 1997, 53, 759-770; Kim et al., Tetrahedron Lett, 1997, 38, 3487-3490; Lee et al., Bioconjug Chem, 1997, 8, 762-765; Kato et al., Glycohiol, 2001, 11, 821-829; Rensen et al., J Biol Chem, 2001, 276, 37577-37584; Lee et al., Methods Enzymol, 2003, 362, 38-43; Westerlind et al., Glycoconj J, 2004, 21, 227-241; Lee et al., Bioorg Med Chem Lett, 2006, 16(19), 5132-5135; Maierhofer et al., Bioorg Med Chem, 2007, 15, 7661-7676; Khorev et al., Bioorg Med Chem, 2008, 16, 5216-5231; Lee et al., Bioorg Med Chem, 2011, 19, 2494-2500; Kornilova et al., Analyt Biochem, 2012, 425, 43-46; Pujol et al., Angew Chemie Int Ed Engl, 2012, 51, 7445-7448; Biessen et al., J Med Chem, 1995, 38, 1846-1852; Sliedregt et al., J Med Chem, 1999, 42, 609-618; Rensen et al., J Med Chem, 2004, 47, 5798-5808; Rensen et al., Arterioscler Thromh Vase Biol, 2006, 26, 169-175; van Rossenberg et al., Gene Ther, 2004, 11, 457-464; Sato et al., J Am Chem Soc, 2004, 126, 14013-14022; Lee et al., J Org Chem, 2012, 77, 7564-7571; Biessen et al., FASEB J, 2000, 14, 1784-1792; Rajur et al., Bioconjug Chem, 1997, 8, 935-940; Duff et al., Methods Enzymol, 2000, 313, 297-321; Maier et al., Bioconjug Chem, 2003, 14, 18-29; Jayaprakash et al., Org Lett, 2010, 12, 5410-5413; Manoharan, Antisense Nucleic Acid Drug Dev, 2002, 12, 103-128; Merwin et al., Bioconjug Chem, 1994, 5, 612-620; Tomiya et al., Bioorg Med Chem, 2013, 21, 5275-5281; International applications WO1998/013381; WO2011/038356; WO1997/046098; WO2008/098788; WO2004/101619; WO2012/037254; WO2011/120053; WO2011/100131; WO2011/163121; WO2012/177947; WO2013/033230; WO2013/075035; WO2012/083185; WO2012/083046; WO2009/082607; WO2009/134487; WO2010/144740; WO2010/148013; WO1997/020563; WO2010/088537; WO2002/043771; WO2010/129709; WO2012/068187; WO2009/126933; WO2004/024757; WO2010/054406; WO2012/089352; WO2012/089602; WO2013/

166121; WO2013/165816; U.S. Pat. Nos. 4,751,219; 7,582,744; 8,552,163; 8,137,695; 6,908,903; 6,383,812; 7,262,177; 6,525,031; 5,994,517; 6,660,720; 6,300,319; 7,723,509; 8,106,022; 7,491,805; 7,491,805; 8,541,548; 8,344,125; 8,313,772; 8,349,308; 8,450,467; 8,501,930; 8,158,601; 7,262,177; 6,906,182; 6,620,916; 8,435,491; 8,404,862; 7,851,615; Published U.S. Patent Application Publications US2011/0097264; US2011/0097265; US2013/0004427; US2003/0119724; US2011/0207799; US2012/0035115; US2012/0230938; US2005/0164235; US2006/0183886; US2012/0136042; US2012/0095075; US2013/0109817; US2006/0148740; US2008/0206869; US2012/0165393; US2012/0101148; US2013/0121954; US2011/0123520; US2003/0077829; US2008/0108801; and US2009/0203132; each of which is incorporated herein by reference in its entirety.

Certain Targeting Moieties

In certain embodiments, a compound provided herein comprises a conjugate group. In certain embodiments, an oligonucleotide or modified oligonucleotide provided herein comprises a conjugate group. In certain embodiments, the conjugate group is a targeting moiety. In certain embodiments, the targeting moiety comprises one or more GalNAc. In certain embodiments, the one or more GalNAc are attached to one or more positions on a furanose ring. In certain embodiments, the one or more GalNAc are attached to the 2' or 3' position on a furanose ring. In certain embodiments, the furanose ring is a subunit of the oligonucleotide or modified oligonucleotide. In certain embodiments, the furanose ring is the 5' nucleoside sugar of an oligonucleotide or modified oligonucleotide. In certain embodiments, the furanose ring is the 5' nucleoside sugar of a sense oligonucleotide or modified oligonucleotide. In certain embodiments, a compound, oligonucleotide, or modified oligonucleotide comprises one or more subunits with the following formula or a salt, solvate, or hydrate thereof:

Formula IX

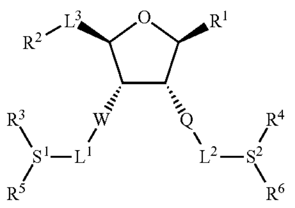

wherein:

- $R^1$ is H, adenine, guanine, thymine, cytosine, uracil, carbocyclyl, heterocyclyl, aryl, heteroaryl, or a nucleobase isostere;
- $R^2$ is an oligonucleotide sequence, modified oligonucleotide, or compound;
- $L^1$ is alkyl, or alkyl-C(=O)—NH-alkyl;
- $L^2$ is alkyl, or alkyl-C(=O)—NH-alkyl;
- $L^3$ is a bond, a phosphodiester bond, a phosphorothioate bond, a triazole, a tetrazole, an amide, a reverse-amide, a carbamate, a carbonate, urea, O, S, S(=O), $S(=O)_2$, NH, substituted N group, alkyl, alkenyl, dienyl, alkynyl, heteroalkyl, or phosphate;
- $R^3$ is H, —C=(O)—NH—$(CH_2CH_2O)_j$-GalNAc, or —C(=O)—NH-alkyl-NH—C(=O)-alkyl-O-GalNAc;
- $R^4$ is H, —C=(O)—NH—$(CH_2CH_2O)_k$-GalNAc, or —C(=O)—NH-alkyl-NH—C(=O)-alkyl-O-GalNAc;
- $R^5$ is —C=(O)—NH—$(CH_2CH_2O)_m$-GalNAc, or —C(=O)—NH-alkyl-NH—C(=O)-alkyl-O-GalNAc;
- $R^6$ is —C=(O)—NH—$(CH_2CH_2O)_n$-GalNAc, or —C(=O)—NH-alkyl-NH—C(=O)-alkyl-O-GalNAc;
- W and Q are each independently O, NH, $CH_2$, or $CH_2O$;
- $S^1$ and $S^2$ are each independently $C(R^7)$ or N, wherein each instance of $R^7$ is independently H, alkyl, heteroalkyl, or halogen;
- j is an integer 1-10, inclusive;
- k is an integer 1-10, inclusive;
- m is an integer 1-10, inclusive; and
- n is an integer 1-10, inclusive.

In certain embodiments, $R^3$, $R^4$, $R^5$, and $R^6$ are the same. In certain embodiments, $R^3$, $R^5$, and $R^6$ are the same. In certain embodiments, $R^3$ or $R^4$ is H.

In certain embodiments, $L^1$ and $L^2$ are the same.

In certain embodiments, $L^1$ and $L^2$ are each independently alkyl; $R^3$ is H, —C=(O)—NH—$(CH_2CH_2O)_j$-GalNAc, or —C(=O)—NH-alkyl-NH—C(=O)-alkyl-O-GalNAc; $R^4$ is H, —C=(O)—NH—$(CH_2CH_2O)_k$-GalNAc, or —C(=O)—NH-alkyl-NH—C(=O)-alkyl-O-GalNAc; $R^5$ is —C=(O)—NH—$(CH_2CH_2O)_m$-GalNAc, or —C(=O)—NH-alkyl-NH—C(=O)-alkyl-O-GalNAc; and $R^6$ is —C=(O)—NH—$(CH_2CH_2O)_n$-GalNAc, or —C(=O)—NH-alkyl-NH—C(=O)-alkyl-O-GalNAc.

In certain embodiments, $L^1$ and $L^2$ are each independently alkyl-C(=O)—NH-alkyl; $R^3$ is H, —C=(O)—NH—$(CH_2CH_2O)_j$-GalNAc, or —C(=O)—NH-alkyl-NH—C(=O)-alkyl-O-GalNAc; $R^4$ is H, —C=(O)—NH—$(CH_2CH_2O)_k$-GalNAc, or —C(=O)—NH-alkyl-NH—C(=O)-alkyl-O-GalNAc; $R^5$ is —C=(O)—NH—$(CH_2CH_2O)_m$-GalNAc, or —C(=O)—NH-alkyl-NH—C(=O)-alkyl-O-GalNAc; and $R^6$ is —C=(O)—NH—$(CH_2CH_2O)_n$-GalNAc, or —C(=O)—NH-alkyl-NH—C(=O)-alkyl-O-GalNAc.

In certain embodiments, $R^4$ is H.

In certain embodiments, $L^1$ and $L^2$ are each independently alkyl; $R^3$ is —C=(O)—NH—$(CH_2CH_2O)_j$-GalNAc, or —C(=O)—NH-alkyl-NH—C(=O)-alkyl-O-GalNAc; $R^4$ is H; $R^5$ is —C=(O)—NH—$(CH_2CH_2O)_m$-GalNAc, or —C(=O)—NH-alkyl-NH—C(=O)-alkyl-O-GalNAc; and $R^6$ is —C=(O)—NH—$(CH_2CH_2O)_n$-GalNAc, or —C(=O)—NH-alkyl-NH—C(=O)-alkyl-O-GalNAc.

In certain embodiments, $L^1$ and $L^2$ are each independently alkyl-C(=O)—NH-alkyl; $R^3$ is —C=(O)—NH—$(CH_2CH_2O)_j$-GalNAc, or —C(=O)—NH-alkyl-NH—C(=O)-alkyl-O-GalNAc; $R^4$ is H; $R^5$ is —C=(O)—NH—$(CH_2CH_2O)_m$-GalNAc, or —C(=O)—NH-alkyl-NH—C(=O)-alkyl-O-GalNAc; and $R^6$ is —C=(O)—NH—$(CH_2CH_2O)_n$-GalNAc, or —C(=O)—NH-alkyl-NH—C(=O)-alkyl-O-GalNAc.

In certain embodiments, $R^3$ is —C=(O)—NH—$(CH_2CH_2O)_j$-GalNAc; $R^4$ is H; $R^5$ is —C=(O)—NH—$(CH_2CH_2O)_m$-GalNAc; and $R^6$ is —C=(O)—NH—$(CH_2CH_2O)_n$-GalNAc.

In certain embodiments, $R^3$ is —C(=O)—NH-alkyl-NH—C(=O)-alkyl-O-GalNAc; $R^4$ is H; $R^5$ is —C(=O)—NH-alkyl-NH—C(=O)-alkyl-O-GalNAc; and $R^6$ is —C(=O)—NH-alkyl-NH—C(=O)-alkyl-O-GalNAc.

In certain embodiments, a compound, modified oligonucleotide, or oligonucleotide comprises one or more subunits with the following formula or a salt, solvate, or hydrate thereof:

Formula X

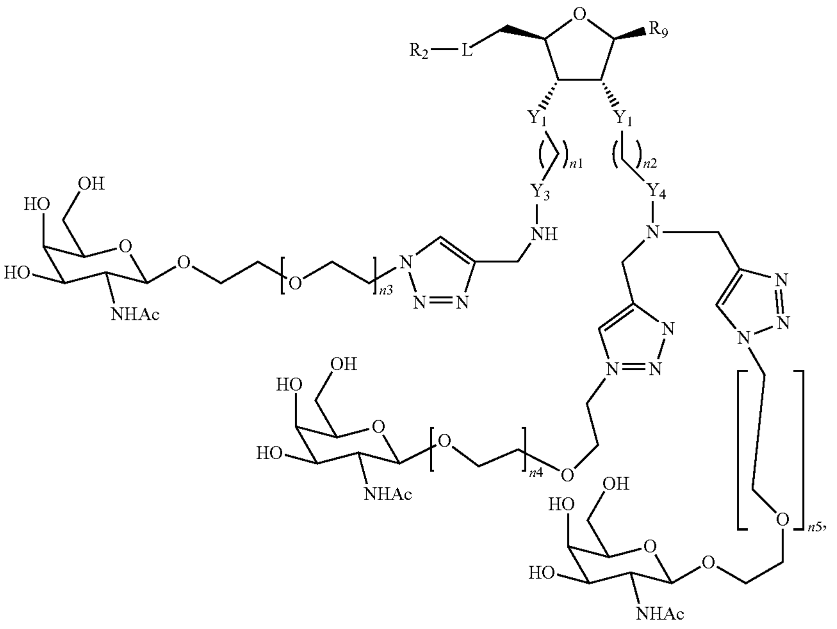

wherein:

$R^9$ is H, adenine, guanine, thymine, cytosine, or uracil, or adenine, guanine, thymine, cytosine, or uracil, each comprising a Protecting Group (PG), a modified nucleobase, optionally substituted alkyl, optionally substituted aryl, optionally substituted heteroaryl, optionally substituted carbocyclyl, optionally substituted heterocyclyl, or a nucleobase isostere;

L is a bond, a phosphodiester bond, a phosphorothioate bond, a triazole, a tetrazole, an amide, a reverse-amide, a carbamate, a carbonate, urea, alkyl, or heteroalkyl;

$R^2$ is an oligonucleotide sequence, modified oligonucleotide, or compound;

$Y_1$ is O, $CH_2$, $CH_2O$, or optionally substituted NH;

$Y_2$ is O, $CH_2$, $CH_2O$, or optionally substituted NH;

$Y_3$ is CO, $SO_2$, P(O)O, $CH_2$—O—C(O), $CH_2$—NH—C(O), $CH_2$—NH—$SO_2$, or $CH_2$;

$Y_4$ is CO, $SO_2$, P(O)O, $CH_2$—O—C(O), $CH_2$—NH—C(O), $CH_2$—NH—$SO_2$, or $CH_2$;

$n_2$ is 0, 1, 2, 3, 4, 5, or 6; and each $n_1$, $n_3$, $n_4$ and $n_5$ is independently 0, 1, 2, 3, 4, 5, 6, 7, 8, 9, or 10.

In certain embodiments, a compound, modified oligonucleotide, or oligonucleotide comprises one or more subunits with the following formula or a salt, solvate, or hydrate thereof:

Formula XI

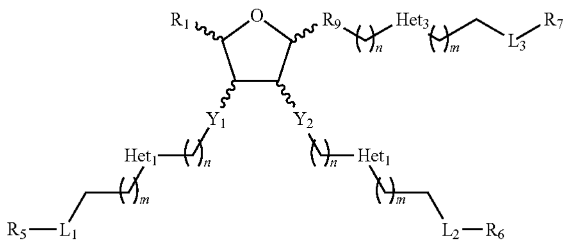

wherein:

each n is independently 1, 2, 3, 4, or 5;

each m is independently 0, 1, 2, 3, 4, 5, or 6;

each o is independently 0, 1, 2, 3, 4, 5, or 6;

each of $L_1$, $L_2$, and $L_3$ is independently absent, C(=O), or C(=O)NH;

each $Y_1$ is independently O, $CH(R^a)$, S, S(=O), $S(=O)_2$, NH, substituted N group, NHC(=O), C(=O)NH, $P(=O)_2$—O—, P(=O)(=S)—O, $P(=S)_2$—O, —O—$P(=O)_2$—O—, —O—P(=O)(=S)—O—, —O—$P(=S)_2$—O—, —O—$P(=O)_2$—, —O—P(=O)(=S)—, —O—$P(=S)_2$—;

each $Y_2$ is independently O, $CH(R^b)$, S, S(=O), $S(=O)_2$, NH, substituted N group, NHC(=O), C(=O)NH, $P(=O)_2$—O—, P(=O)(=S)—O, $P(=S)_2$—O, —O—$P(=O)_2$—O—, —O—P(=O)(=S)—O—, —O—$P(=S)_2$—O—, —O—$P(=O)_2$—, —O—P(=O)(=S)—, —O—$P(=S)_2$—;

each of $Het_1$, $Het_2$, and $Het_3$ is independently optionally substituted heteroaryl or optionally substituted heterocyclyl;

$R^1$ is an oligonucleotide sequence, modified oligonucleotide, or compound linked by a bond, a phosphodiester bond, a phosphorothioate bond, a triazole, a tetrazole, an amide, a reverse-amide, a carbamate, a carbonate, urea, alkyl, or heteroalkyl;

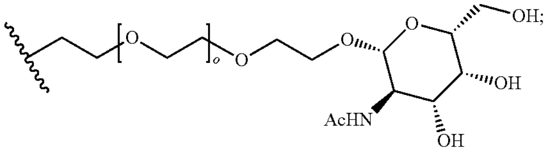

each $R_5$, $R_6$, and $R_7$ is independently $R_9$ is optionally substituted heterocyclyl;

each $R^a$ is independently H, alkyl, halo, $OR^c$, or $SR^c$;

each $R^b$ is independently H, alkyl, halo, $OR^c$, or $SR^c$; and each $R^c$ is independently H or alkyl.

In certain embodiments, R' is OH. In certain embodiments, R' is SH. In certain embodiments, the 5' nucleoside of the modified oligonucleotide is Formula I and R' is OH. In certain embodiments, the 5' nucleoside of the modified oligonucleotide is Formula I and R' is SH. In certain embodiments, the 5' nucleoside of the modified oligonucleotide is Formula II and R' is OH. In certain embodiments, the 5' nucleoside of the modified oligonucleotide is Formula II and R' is SH. In certain embodiments, the 5' nucleoside of the modified oligonucleotide is Formula III and R' is OH. In certain embodiments, the 5' nucleoside of the modified oligonucleotide is Formula III and R' is SH. In certain embodiments, the 5' nucleoside of the modified oligonucleotide is Formula IV and R' is OH. In certain embodiments, the 5' nucleoside of the modified oligonucleotide is Formula IV and R' is SH. In certain embodiments, the 5' nucleoside of the modified oligonucleotide is Formula V and R' is OH. In certain embodiments, the 5' nucleoside of the modified oligonucleotide is Formula V and R' is SH. In certain embodiments, the 5' nucleoside of the modified oligonucleotide is Formula VI and R' is OH. In certain embodiments, the 5' nucleoside of the modified oligonucleotide is Formula VI and R' is SH. In certain embodiments, the 5' nucleoside of the modified oligonucleotide is Formula VII and R' is OH. In certain embodiments, the 5' nucleoside of the modified oligonucleotide is Formula VII and R' is SH. In certain embodiments, the 5' nucleoside of the modified oligonucleotide is Formula VIII and R' is OH. In certain embodiments, the 5' nucleoside of the modified oligonucleotide is Formula VIII and R' is SH. In certain embodiments, the 5' nucleoside of the modified oligonucleotide is Formula XII and R' is OH. In certain embodiments, the 5' nucleoside of the modified oligonucleotide is Formula XII and R' is SH.

In certain embodiments, the subunit is selected from Formulae I-VIII and XII or a salt, solvate, or hydrate thereof, wherein R is the modified oligonucleotide other than the 5' nucleoside. In certain embodiments, the 5' nucleoside of the modified oligonucleotide is Formula I and R' is O. In certain embodiments, the 5' nucleoside of the modified oligonucleotide is Formula I and R' is S. In certain embodiments, the 5' nucleoside of the modified oligonucleotide is Formula II and R' is O. In certain embodiments, the 5' nucleoside of the modified oligonucleotide is Formula II and R' is S. In certain embodiments, the 5' nucleoside of the modified oligonucleotide is Formula III and R' is O. In certain embodiments, the 5' nucleoside of the modified oligonucleotide is Formula III and R' is S. In certain embodiments, the 5' nucleoside of the modified oligonucleotide is Formula IV and R' is O. In certain embodiments, the 5' nucleoside of the modified oligonucleotide is Formula IV and R' is S. In certain embodiments, the 5' nucleoside of the modified oligonucleotide is Formula V and R' is O. In certain embodiments, the 5' nucleoside of the modified oligonucleotide is Formula V and R' is S. In certain embodiments, the 5' nucleoside of the modified oligonucleotide is Formula VI and R' is O. In certain embodiments, the 5' nucleoside of the modified oligonucleotide is Formula VI and R' is S. In certain embodiments, the 5' nucleoside of the modified oligonucleotide is Formula VII and R' is O. In certain embodiments, the 5' nucleoside of the modified oligonucleotide is Formula VII and R' is S. In certain embodiments, the 5' nucleoside of the modified oligonucleotide is Formula VIII and R' is O. In certain embodiments, the 5' nucleoside of the modified oligonucleotide is Formula VIII and R' is S. In certain embodiments, the subunit is Formula XII or a salt, solvate, or hydrate thereof, wherein R is the modified oligonucleotide other than the 5' nucleoside. In certain embodiments, the 5' nucleoside of the modified oligonucleotide is Formula XII and R' is O. In certain embodiments, the 5' nucleoside of the modified oligonucleotide is Formula XII and R' is S.

Target Nucleic Acids and Target Regions

In certain embodiments, compounds described herein comprise or consist of an oligonucleotide comprising a region that is complementary to a target nucleic acid. In certain embodiments, the target nucleic acid is an endogenous RNA molecule. In certain embodiments, the target nucleic acid encodes a protein. In certain embodiments, the target nucleic acid is non-coding. In certain such embodiments, the target nucleic acid is selected from an mRNA and a pre-mRNA, including intronic, exonic and untranslated regions. In certain embodiments, the target RNA is an mRNA. In certain embodiments, the target nucleic acid is a pre-mRNA. In certain such embodiments, the target region is entirely within an exon. In certain such embodiments, the target region is entirely within an intron. In certain embodiments, the target region spans an intron/exon junction. In certain embodiments, the target region is at least 50% within an intron.

In certain embodiments, compounds disclosed herein hybridize with a CFB nucleic acid. The most common mechanism of hybridization involves hydrogen bonding between complementary nucleobases of the nucleic acid molecules. Hybridization can occur under varying conditions. Hybridization conditions are sequence-dependent and are determined by the nature and composition of the nucleic acid molecules to be hybridized. Methods of determining whether a sequence hybridizes specifically to a target nucleic acid are well known in the art. In certain embodiments, the compounds provided herein specifically hybridize with a CFB nucleic acid.

Nucleotide sequences that encode CFB include, without limitation, the following: GENBANK Accession Nos. NM_001710.6 (incorporated herein as SEQ ID NO: 1), nucleotides 31946095 to 31952084 of GenBank Accession No. NC_000006.12 (incorporated herein as SEQ ID NO: 2), GenBank Accession No. NM_001710.6 (incorporated herein as SEQ ID NO: 3), and nucleotides 3423522 to 3429511 of GenBank Accession No. NT_113891.3 (incorporated herein as SEQ ID NO: 4).

Complementarity

Oligonucleotides provided herein may have a defined percent complementarity to a particular nucleic acid, target region, oligonucleotide, or portion thereof. Non-complementary nucleobases may be tolerated provided that the oligonucleotide remains able to specifically hybridize to the nucleic acid, oligonucleotide, or portion thereof. In certain embodiments, the oligonucleotides provided herein, or a specified portion thereof are at least, or are up to 70%, 80%, 85%, 86%, 87%, 88%, 89%, 90%, 91%, 92%, 93%, 94%, 95%, 96%, 97%, 98%, 99%, or 100% complementary to a target nucleic acid, a target region, an oligonucleotide or specified portion thereof. In certain embodiments, the oligonucleotides provided herein, or a specified portion thereof, are 70% to 75%, 75% to 80%, 80% to 85%, 85% to 90%, 90% to 95%, 95% to 100%, or any number in between these ranges, complementary to a target nucleic acid, a target region, an oligonucleotide or specified portion thereof. Percent complementarity of an oligonucleotide with a target nucleic acid, a target region, an oligonucleotide or specified portion thereof can be determined using routine methods. For example, an oligonucleotide in which 18 of 20 nucleobases of the oligonucleotide are complementary to a target region, and would therefore specifically hybridize, would represent 90 percent complementarity. In this example, the remaining non-complementary nucleobases may be clustered or interspersed with complementary nucleobases and need not be contiguous to each other or to complementary nucleobases. As such, an oligonucleotide which is 18 nucleobases in length having four non-complementary nucleobases which are flanked by two regions of complete complementarity with the target nucleic acid would have 77.8% overall complementarity with the target nucleic acid. Percent complementarity of an oligonucleotide with a region of a target nucleic acid, a target region, an oligonucleotide or specified portion thereof can be determined routinely using BLAST programs (basic local alignment search tools) known in the art. In certain embodiments, oligonucleotides described herein, or specified portions thereof, are fully complementary (i.e., 100% complementary) to a target nucleic acid, a target region, an oligonucleotide or specified portion thereof. For example, an oligonucleotide may be fully complementary to a target nucleic acid, a target region, an oligonucleotide, or specified portion thereof. As used herein, "fully complementary" means each nucleobase of an oligonucleotide is complementary to the corresponding nucleobase of a target nucleic acid, a target region, an oligonucleotide, or a specified portion thereof. For example, a 20-nucleobase oligonucleotide is fully complementary to a target sequence that is 400 nucleobases long, so long as there is a corresponding 20 nucleobase portion of the target nucleic acid that is fully complementary to the compound. "Fully complementary" can also be used in reference to a specified portion of the first and/or the second nucleic acid. For example, a 20-nucleobase portion of a 30-nucleobase oligonucleotide can be "fully complementary" to a 20-nucleobase region of a target sequence that is 400 nucleobases long. The 20-nucleobase portion of the 30-nucleobase compound is fully complementary to the target sequence if the target sequence has a corresponding 20 nucleobase portion wherein each nucleobase is complementary to the 20-nucleobase portion of the compound. At the same time, the entire 30 nucleobase compound may or may not be fully complementary to the target sequence, depending on whether the remaining 10 nucleobases of the compound are also complementary to the target sequence.

In certain embodiments, oligonucleotides described herein comprise one or more mismatched nucleobases relative to a target nucleic acid, a target region, an oligonucleotide or a specified portion thereof. In certain embodiments, oligonucleotides described herein that are, or are up to 12, 13, 14, 15, 16, 17, 18, 19, 20, 21, 22, or 23 nucleobases in length comprise no more than 4, no more than 3, no more than 2, or no more than 1 non-complementary nucleobase(s) relative to a target nucleic acid, or specified portion thereof. In certain embodiments, oligonucleotides described herein that are, or are up to 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, a target region, an oligonucleotide, or specified portion thereof. In certain embodiments, the mismatch is at position 1, 2, 3, 4, 5, 6, 7, 8, 9, 10, 11, 12, 13 or 14 from the 5'-end of the oligonucleotide. In certain embodiments, the mismatch is at position 1, 2, 3, 4, 5, 6, 7, 8, 9, 10, 11, or 12, 13 or 14 from the 3'-end of the oligonucleotide. In certain embodiments, the mismatch forms a wobble base pair with a corresponding nucleobase on the target nucleic acid. For example, in certain embodiments, the mismatch forms a wobble base pair selected from hypoxanthine (nucleobase of inosine) and uracil (I:U base pair); guanine and uracil (G:U base pair); hypoxanthine and adenine (I:A base pair); and hypoxanthine and cytosine (I:C base pair). Accordingly, in certain embodiments, a mismatched nucleobase on an oligonucleotide comprises hypoxanthine, guanine, or uracil.

In certain embodiments, oligonucleotides described herein may be complementary to a portion of a nucleic acid. As used herein, "portion" refers to a defined number of contiguous nucleobases within a region of a nucleic acid. A "portion" can also refer to a defined number of contiguous nucleobases of an oligonucleotide. In certain embodiments, the oligonucleotides are complementary to at least an 8-nucleobase portion of a nucleic acid. In certain embodiments, the oligonucleotides are complementary to at least a 9-nucleobase portion of a nucleic acid. In certain embodiments, the oligonucleotides are complementary to at least a 10-nucleobase portion of a nucleic acid. In certain embodiments, the oligonucleotides are complementary to at least an 11-nucleobase portion of a nucleic acid. In certain embodiments, the oligonucleotides are complementary to at least a 12-nucleobase portion of a nucleic acid. In certain embodiments, the oligonucleotides are complementary to at least a 13-nucleobase portion of a nucleic acid. In certain embodiments, the oligonucleotides are complementary to at least a 14-nucleobase portion of a nucleic acid. In certain embodiments, the oligonucleotides are complementary to at least a 15-nucleobase portion of a nucleic acid. In certain embodiments, the oligonucleotides are complementary to at least a 16-nucleobase portion of a nucleic acid. Also contemplated are oligonucleotides that are complementary to at least a 9, 10, 17, 18, 19, 20, 21, 22, 23 or more nucleobase portion of a nucleic acid, or a range defined by any two of these values. In certain embodiments, the oligonucleotide is an antisense oligonucleotide. In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid. In certain embodiments, the oligonucleotide is a sense oligonucleotide. In certain embodiments, a portion of the sense oligonucleotide is compared to an equal length portion of an antisense oligonucleotide. In certain embodiments, an 8, 9, 10, 11, 12, 13, 14, 15, 16, 17, 18, 19, 20, 21, 22, 23, 24, or 25 nucleobase portion of a sense oligonucleotide is compared to an equal length portion of an antisense oligonucleotide.

Identity

The oligonucleotides provided herein may also have a defined percent identity to a particular nucleic acid, target region, oligonucleotide, or specified portion thereof. As used herein, an oligonucleotide is identical to a sequence disclosed herein if it has the same nucleobase pairing ability. For example, a DNA which contains thymidine in place of uracil in a disclosed RNA sequence would be considered identical to the RNA sequence since both uracil and thymidine pair with adenine. Shortened and lengthened versions of the compounds described herein as well as compounds having non-identical bases relative to the compounds provided herein also are contemplated. The non-identical bases may be adjacent to each other or dispersed throughout the compound. Percent identity of an oligonucleotide is calculated according to the number of bases that have identical base pairing relative to the sequence to which it is being compared. In certain embodiments, oligonucleotides described herein, or portions thereof, are, or are at least, 70%, 75%, 80%, 85%, 90%, 91%, 92%, 93%, 94%, 95%, 96%, 97%, 98%, 99% or 100% identical to one or more of the nucleic acids, oligonucleotides, or a portion thereof, disclosed herein. In certain embodiments, oligonucleotides described herein are about 70%, 75%, 80%, 85%, 90%, 91%, 92%, 93%, 94%, 95%, 96%, 97%, 98%, or 99% identical, or any percentage between such values, to a particular nucleic acid or oligonucleotide, or portion thereof.

In certain embodiments, an oligonucleotide may have one or more mismatched nucleobases. In certain such embodiments, the mismatch is at position 1, 2, 3, 4, 5, 6, 7, 8, 9, 10, 11, 12, 13 or 14 from the 5'-end of the oligonucleotide. In certain such embodiments, the mismatch is at position 1, 2, 3, 4, 5, 6, 7, 8, 9, 10, 11, or 12, 13 or 14 from the 3'-end of the oligonucleotide. In certain embodiments, a portion of the oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid. In certain embodiments, the oligonucleotide is a sense oligonucleotide. In certain embodiments, a portion of the sense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Pharmaceutical Compositions and Formulations

Compounds described herein may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered. Certain embodiments provide pharmaceutical compositions comprising one or more compounds or a salt thereof. In certain embodiments, the compounds are antisense oligonucleotides. In certain embodiments, the compounds are oligomeric compounds. In certain embodiments, the compounds comprise or consist of one or more modified oligonucleotides. In certain such embodiments, the pharmaceutical composition comprises one or more compound and a suitable pharmaceutically acceptable diluent or carrier. In certain embodiments, a pharmaceutical composition comprises one or more compound and a sterile saline solution. In certain embodiments, such pharmaceutical composition consists of one compound and a sterile saline solution. In certain embodiments, the sterile saline is pharmaceutical grade saline. In certain embodiments, a pharmaceutical composition comprises one or more compound and sterile water. In certain embodiments, a pharmaceutical composition consists of one compound and sterile water. In certain embodiments, the sterile water is pharmaceutical grade water. In certain embodiments, a pharmaceutical composition comprises one or more compounds and phosphate-buffered saline (PBS). In certain embodiments, a pharmaceutical composition consists of one compound and sterile PBS. In certain embodiments, the sterile PBS is pharmaceutical grade PBS.

A compound described herein targeted to CFB can be utilized in pharmaceutical compositions by combining the compound with a suitable pharmaceutically acceptable diluent or carrier. In certain embodiments, a pharmaceutically acceptable diluent is water, such as sterile water suitable for injection. Accordingly, in one embodiment, employed in the methods described herein is a pharmaceutical composition comprising a compound targeted to CFB and a pharmaceutically acceptable diluent. In certain embodiments, the pharmaceutically acceptable diluent is water. In certain embodiments, the compound comprises or consists of one or more modified oligonucleotide provided herein.

Pharmaceutical compositions comprising compounds provided herein encompass any pharmaceutically acceptable salts, esters, or salts of such esters, or any other oligonucleotide which, upon administration to an animal, including a human, is capable of providing (directly or indirectly) the biologically active metabolite or residue thereof. In certain embodiments, the compounds are antisense oligonucleotides. In certain embodiments, the compounds are oligomeric compounds. In certain embodiments, the compound comprises or consists of one or more modified oligonucleotide. Accordingly, for example, the disclosure is also drawn to pharmaceutically acceptable salts of compounds, prodrugs, pharmaceutically acceptable salts of such prodrugs, and other bioequivalents. Suitable pharmaceutically acceptable salts include, but are not limited to, sodium and potassium salts. A prodrug can include the incorporation of additional nucleosides at one or both ends of a compound which are cleaved by endogenous nucleases within the body, to form the active compound. In certain embodiments, the compounds or compositions further comprise a pharmaceutically acceptable carrier or diluent.

It is understood that the examples and embodiments described herein are for illustrative purposes and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

Additional Embodiments

Certain embodiments include embodiment 1 to embodiment 97 following.

Embodiment 1. A compound comprising a modified oligonucleotide 14 to 23 linked nucleosides in length having a nucleobase sequence comprising at least 14, at least 15, at least 16, at least 17, at least 18, at least 19, or at least 20 contiguous nucleobases of any one of the nucleobase sequences of SEQ ID NOs: 11-44 or 96-102.

Embodiment 2. A compound comprising a modified oligonucleotide 14 to 23 linked nucleosides in length having a nucleobase sequence comprising the nucleobase sequence of any one of SEQ ID NOs: 11-44 or 96-102.

Embodiment 3. A compound comprising a modified oligonucleotide having a nucleobase sequence selected from the nucleobase sequences of any one of SEQ ID NOs: 11-44 and 96-102.

Embodiment 4. The compound of any one of embodiments 1-3, wherein the nucleobase sequence of the modified oligonucleotide is at least 80%, at least 85%, at least 90%, or at least 95% complementary to the nucleobase sequence of SEQ ID NO: 1 or 3.

Embodiment 5. The compound of any one of embodiments 1-4, wherein the modified oligonucleotide comprises at least one modification selected from a modified internucleoside linkage, a modified sugar, and a modified nucleobase.

Embodiment 6. The compound of any one of embodiments 1-5, wherein the compound is double-stranded.

Embodiment 7. A compound comprising a first modified oligonucleotide 14 to 23 linked nucleosides in length having a nucleobase sequence comprising at least 14, at least 15, at least 16, at least 17, at least 18, at least 19, or at least 20 contiguous nucleobases of any of the nucleobase sequences of SEQ ID NOs: 11-110 and a second modified oligonucleotide 14 to 23 linked nucleosides in length having a region of complementarity to the first modified oligonucleotide.

Embodiment 8. A compound comprising a first modified oligonucleotide 14 to 23 linked nucleosides in length having a nucleobase sequence comprising the nucleobase sequence of any one of SEQ ID NOs: 11-110 and a second modified oligonucleotide 14 to 23 linked nucleosides in length having a region of complementarity to the first modified oligonucleotide.

Embodiment 9. A compound comprising a first modified oligonucleotide having a nucleobase sequence selected from the nucleobase sequences of any one of SEQ ID NOs: 11-110 and a second modified oligonucleotide 19 to 23 linked nucleosides in length having a region of complementarity to the first modified oligonucleotide.

Embodiment 10. The compound of any one of embodiments 7-9, wherein the nucleobase sequence of the first modified oligonucleotide has at least 80%, at least 85%, at least 90%, or at least 95% complementarity or identity to the nucleobase sequence of SEQ ID NO: 1 or 3 over its length.

Embodiment 11. The compound of any one of embodiments 7-10, wherein the nucleobase sequence of the first modified oligonucleotide has at least 1, at least 2, or at least 3 mismatches to a region of the nucleobase sequence of SEQ ID NO: 1 or 3 that is the same length as the first modified oligonucleotide.

Embodiment 12. The compound of any one of embodiments 7-11, wherein the region of complementarity between the first modified oligonucleotide and the second modified oligonucleotide is 14 to 23 linked nucleosides in length.

Embodiment 13. The compound of any one of embodiments 7-11, wherein the region of complementarity between the first modified oligonucleotide and the second modified oligonucleotide is 19 to 23 linked nucleosides in length.

Embodiment 14. The compound of any one of embodiments 7-11, wherein the region of complementarity between the first modified oligonucleotide and the second modified oligonucleotide is 21 to 23 linked nucleosides in length.

Embodiment 15. The compound of any one of embodiments 7-11, wherein the first modified oligonucleotide is fully complementary to the second modified oligonucleotide.

Embodiment 16. The compound of any one of embodiments 7-15, wherein the first modified oligonucleotide comprises at least one modification selected from a modified internucleoside linkage, a modified sugar, and a modified nucleobase.

Embodiment 17. The compound of any one of embodiments 7-16, wherein the second modified oligonucleotide comprises at least one modification selected from a modified internucleoside linkage, a modified sugar, and a modified nucleobase.

Embodiment 18. The compound of any one of embodiments 5, 16 or 17, wherein the modified internucleoside linkage is a phosphorothioate internucleoside linkage or a methylphosphonate internucleoside linkage.

Embodiment 19. The compound of embodiment 18, wherein the phosphorothioate internucleoside linkage or methylphosphonate internucleoside linkage is at the 3' terminus of the first or second modified oligonucleotide or at the 5' terminus of the first modified oligonucleotide.

Embodiment 20. The compound of any one of embodiments 5, 16 or 17, wherein the modified sugar comprises a modification selected from a halogen, an alkoxy group and a bicyclic sugar.

Embodiment 21. The compound of embodiment 20, wherein the modified sugar comprises a 2'-F modification.

Embodiment 22. The compound of embodiment 20, wherein the modified sugar comprises a 2'-OMe modification.

Embodiment 23. The compound of any one of embodiments 7-15, wherein each nucleoside of the first modified oligonucleotide comprises a modified sugar.

Embodiment 24. The compound of any one of embodiments 7-15, wherein each nucleoside of the second modified oligonucleotide comprises a modified sugar.

Embodiment 25. The compound of embodiment 23 or 24, wherein the modified sugar comprises a modification selected from a halogen, an alkoxy group and a bicyclic sugar or a combination thereof.

Embodiment 26. The compound of embodiment 25, wherein the modified sugar comprises a modification selected from LNA, cEt, 2'-MOE, 2'-F, 2'-OMe, and 2'-deoxy, or a combination thereof.

Embodiment 27. The compound of embodiment 23, wherein the first modified oligonucleotide comprises no more than ten 2'-F sugar modifications.

Embodiment 28. The compound of embodiment 24, wherein the second modified oligonucleotide comprises no more than five 2'-F sugar modifications.

Embodiment 29. The compound of any one of the preceding embodiments, comprising a conjugate group.

Embodiment 30. The compound of embodiment 29, wherein the conjugate group is attached to the 5' end of the modified oligonucleotide.

Embodiment 31. The compound of embodiment 29 or 30, wherein the conjugate group comprises a targeting moiety.

Embodiment 32. The compound of embodiment 31, wherein the targeting moiety comprises one or more GalNAc.

Embodiment 33. The compound of embodiment 32, wherein the modified oligonucleotide is the second modified oligonucleotide.

Embodiment 34. The compound of embodiment 32 or 33, wherein the one or more GalNAc are attached to the 2' or 3' position of the ribosyl ring of the 5' nucleoside of the modified oligonucleotide.

Embodiment 35. The compound of embodiment 34, wherein the 5' nucleoside is of the following formula:

Formula X

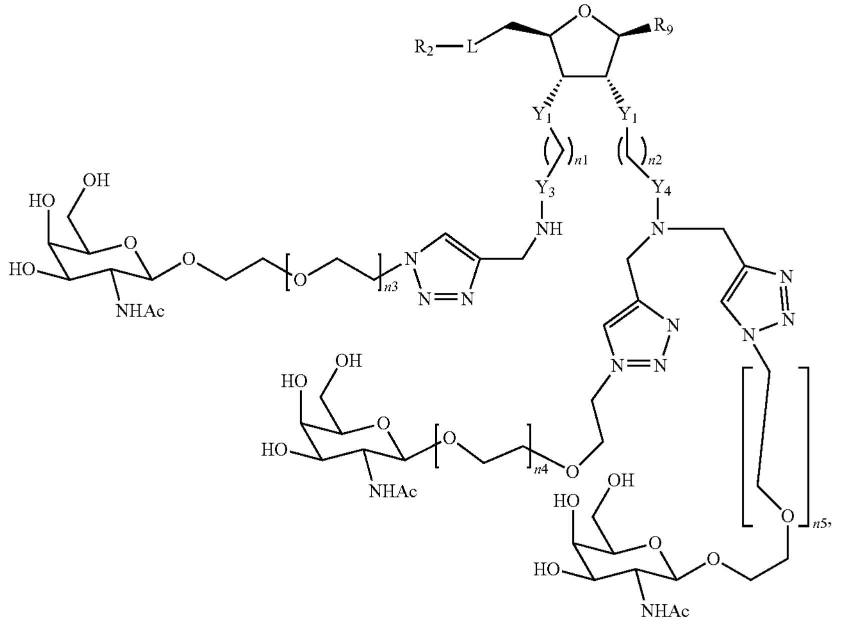

wherein:

$R^9$ is H, adenine, guanine, thymine, cytosine, or uracil, or adenine, guanine, thymine, cytosine, or uracil, each comprising a Protecting Group (PG), a modified nucleobase, optionally substituted alkyl, optionally substituted aryl, optionally substituted heteroaryl, optionally substituted carbocyclyl, optionally substituted heterocyclyl, or a nucleobase isostere;

L is a bond, a phosphodiester bond, a phosphorothioate bond, a triazole, a tetrazole, an amide, a reverse-amide, a carbamate, a carbonate, urea, alkyl, or heteroalkyl;

$R^2$ is an oligonucleotide sequence or modified oligonucleotide;

$Y_1$ is O, $CH_2$, $CH_2O$, or optionally substituted NH;

$Y_2$ is O, $CH_2$, $CH_2O$, or optionally substituted NH;

$Y_3$ is CO, $SO_2$, P(O)O, $CH_2$—O—C(O), $CH_2$—NH—C(O), $CH_2$—NH—$SO_2$, or $CH_2$;

$Y_4$ is CO, $SO_2$, P(O)O, $CH_2$—O—C(O), $CH_2$—NH—C(O), $CH_2$—NH—$SO_2$, or $CH_2$;

$n_2$ is 0, 1, 2, 3, 4, 5, or 6; and each $n_1$, $n_3$, $n_4$ and $n_5$ is independently 0, 1, 2, 3, 4, 5, 6, 7, 8, 9, or 10.

Embodiment 36. The compound of embodiment 34, wherein the 5' nucleoside is selected from any one of Formulae I-VIII and XII, and wherein R' is S or SH and R is the portion of the modified oligonucleotide other than the 5' nucleoside.

Embodiment 37. The compound of embodiment 34, wherein the 5' nucleoside is selected from any one of Formulae I-VIII and XII, and wherein R' is O or OH and R is the portion of the modified oligonucleotide other than the 5' nucleoside.

Embodiment 38. A compound comprising a first modified oligonucleotide having a nucleobase sequence selected from any one of the nucleobase sequences of SEQ ID NOs: 11-110 and a second modified oligonucleotide 14 to 21 linked nucleosides in length fully complementary to the first modified oligonucleotide.

Embodiment 39. A compound comprising a first modified oligonucleotide having a nucleobase sequence selected from any one of the nucleobase sequences of Ref ID NOs: IA0478-490, IA0840, IA0842-846, IA0852-862, IA0872-882, IA0887-890, IA1010-1012, and IA1015-1018 and a second modified oligonucleotide 14 to 21 linked nucleosides in length fully complementary to the first modified oligonucleotide.

Embodiment 40. A compound comprising a first modified oligonucleotide having a nucleobase sequence selected from any one of the nucleobase sequences of Ref ID NOs: IA0478-490, IA0840, IA0842-846, IA0852-862, IA0872-882, IA0887-890, IA1010-1012, and IA1015-1018 and a second modified oligonucleotide having a nucleobase sequence selected from any one of the nucleobase sequences of Ref ID NOs: IS0570-587, IS0969, IS0972-977, IS1023-1027, IS1029, IS1031-1037, IS1042-1046, IS1082, IS1085, IS1086, IS1091-1095, IS1108-1111, IS1236-1239, IS1242, IS1249, and IS1251-1254.

Embodiment 41. A compound comprising a first modified oligonucleotide having a nucleobase sequence selected from any one of the nucleobase sequences of Ref ID NOs: IA0840, IA0842, IA0888, IA1010-1012, and IA1016 and a second modified oligonucleotide having a nucleobase sequence selected from any one of the nucleobase sequences of Ref ID NOs: IS0972, IS0974, IS1109, IS1236, IS1239, IS1242 and IS1252.

Embodiment 42. A compound of any one of embodiments 1-41, wherein the compound is in a pharmaceutically acceptable salt form.

Embodiment 43. The compound of embodiment 42, wherein the pharmaceutically acceptable salt is a sodium salt.

Embodiment 44. The compound of embodiment 42, wherein the pharmaceutically acceptable salt is a potassium salt.

Embodiment 45. A modified oligonucleotide according to the following chemical structure:

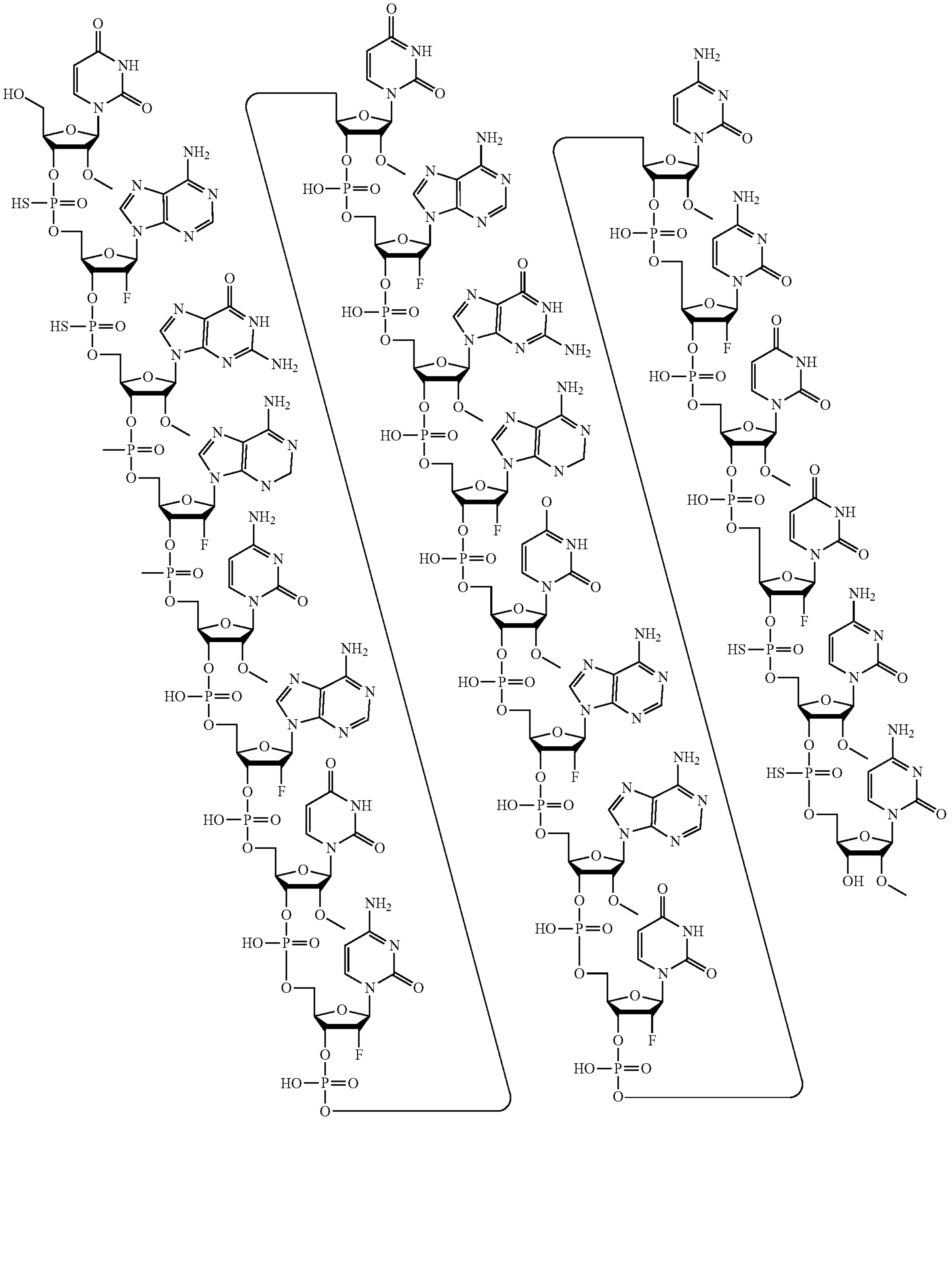
or a pharmaceutically acceptable salt or stereoisomer thereof.
Embodiment 46. A modified oligonucleotide according to the following chemical structure:

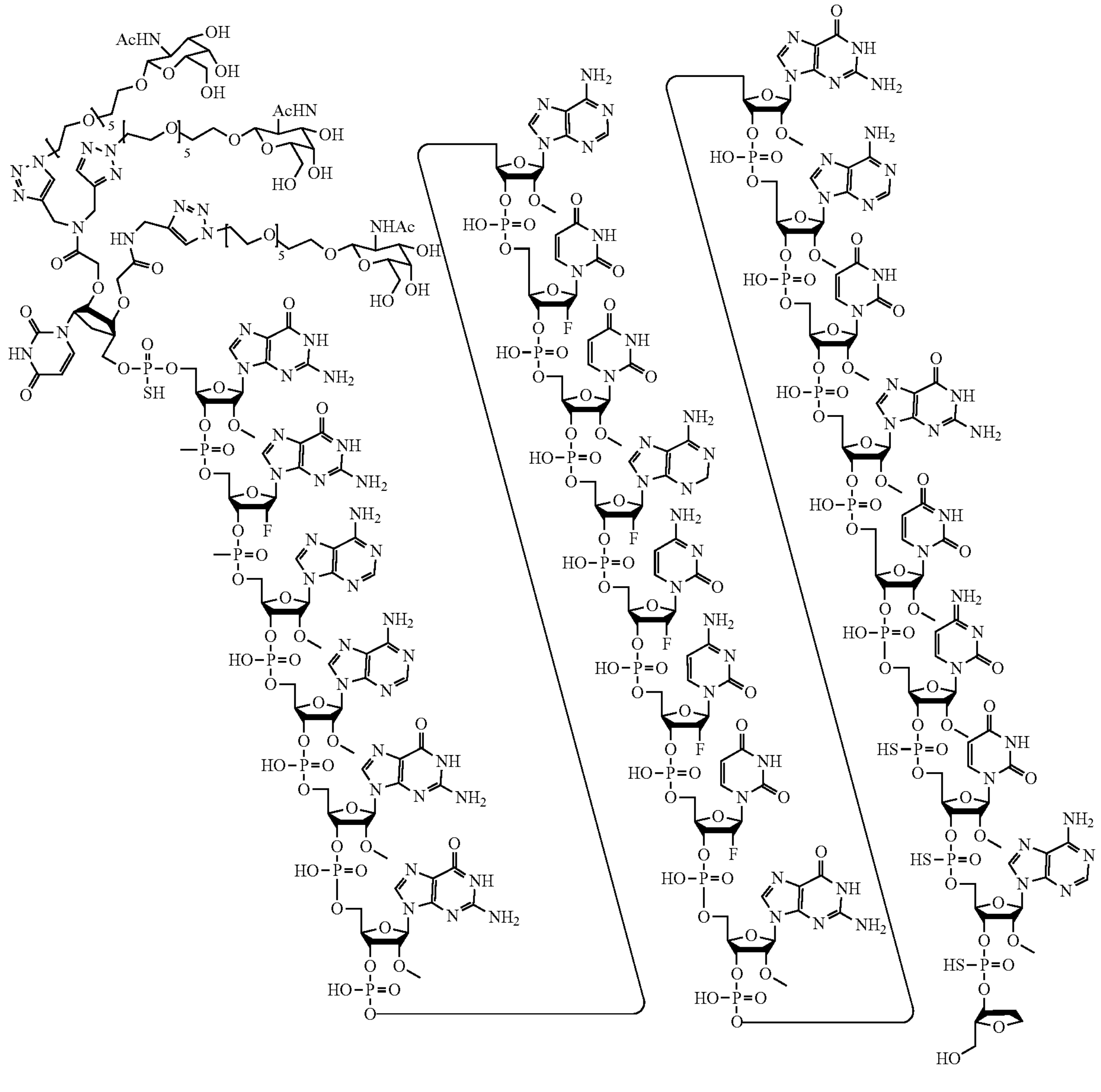
or a pharmaceutically acceptable salt or stereoisomer thereof.
Embodiment 47. A modified oligonucleotide according to the following chemical structure:

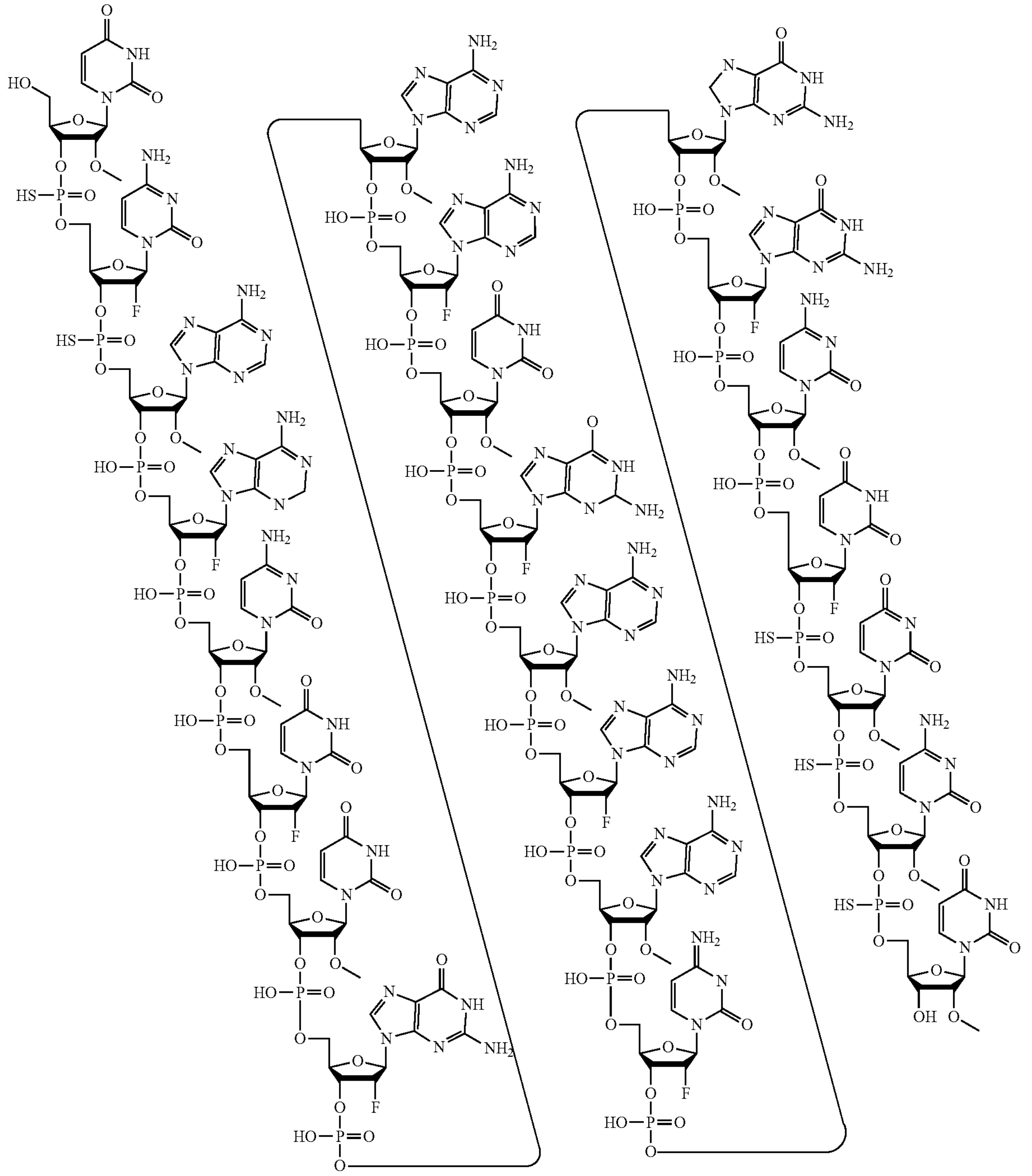
or a pharmaceutically acceptable salt or stereoisomer thereof.
Embodiment 48. A modified oligonucleotide according to the following chemical structure:

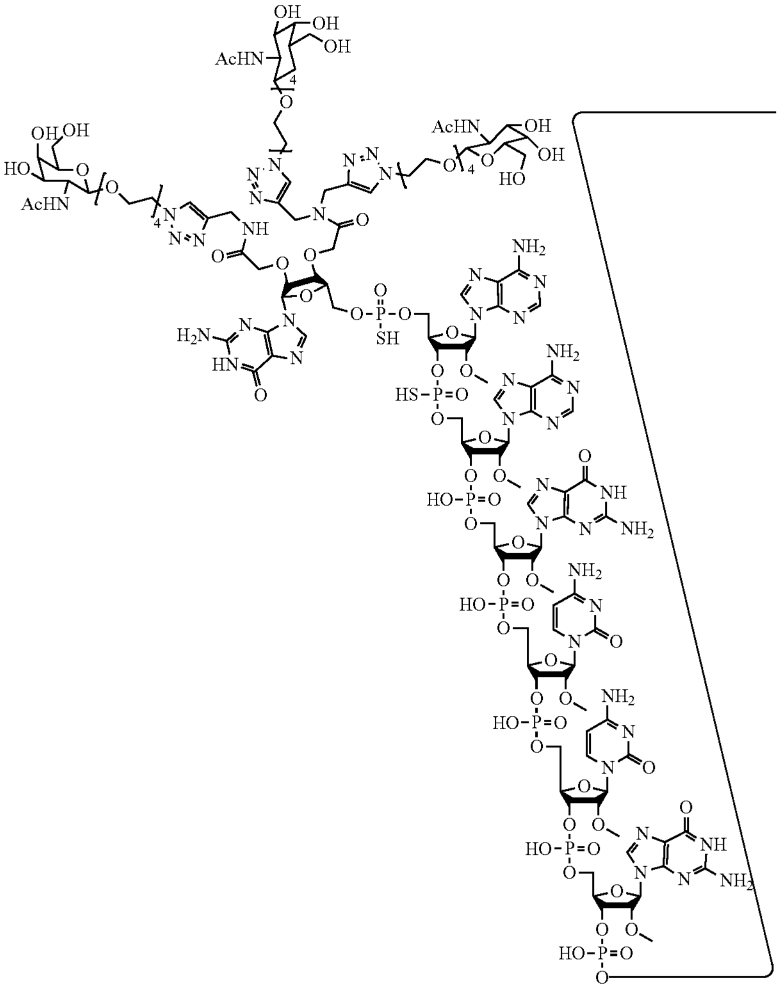

-continued
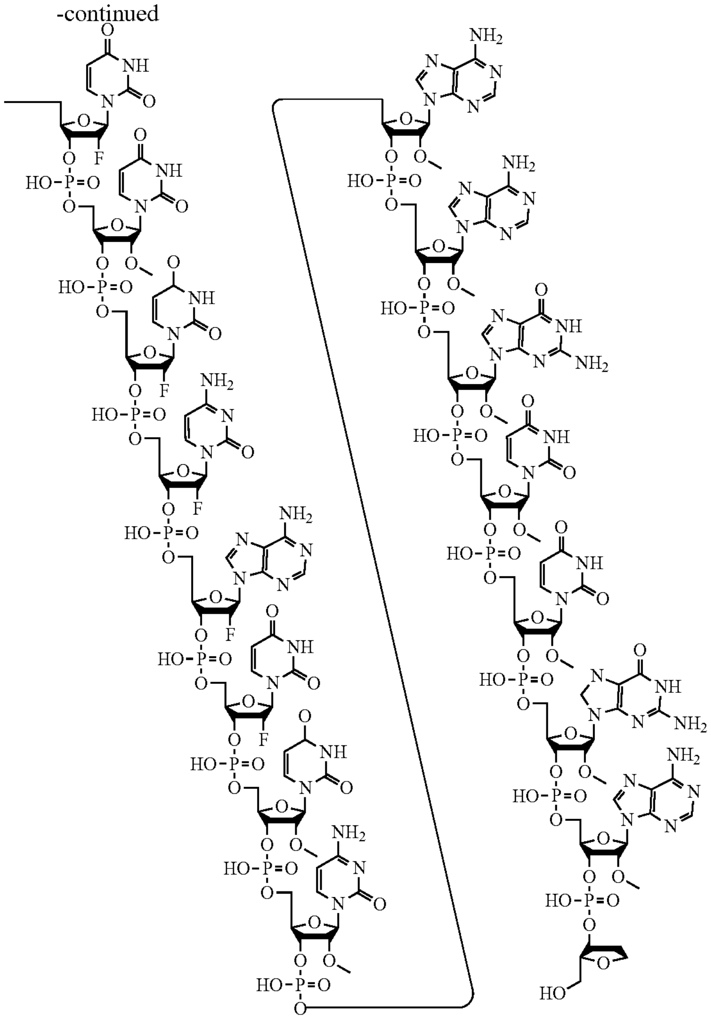
or a pharmaceutically acceptable salt or stereoisomer thereof.
Embodiment 49. A modified oligonucleotide according to the following chemical

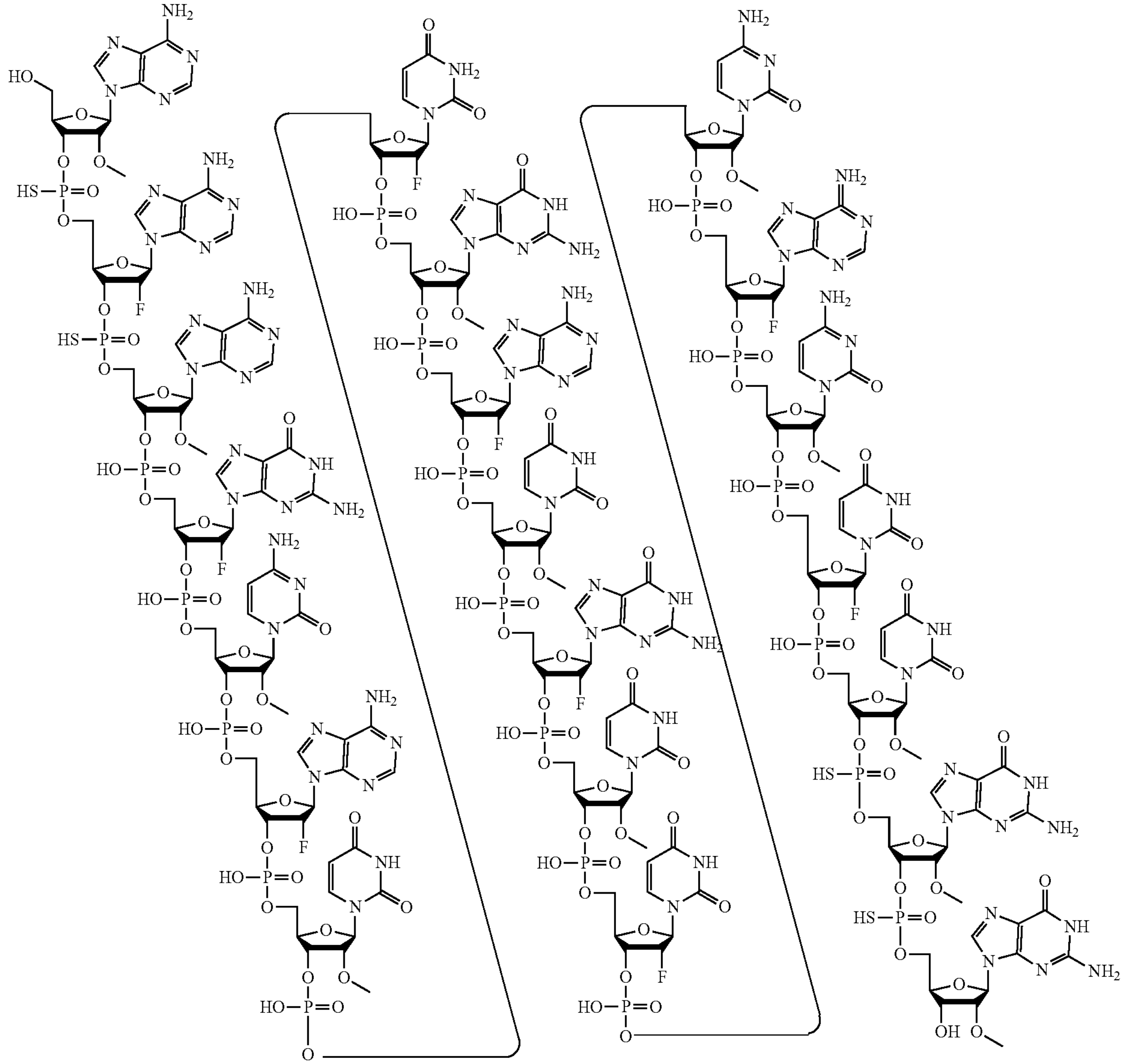
or a pharmaceutically acceptable salt or stereoisomer thereof.
Embodiment 50. A modified oligonucleotide according to the following chemical structure:

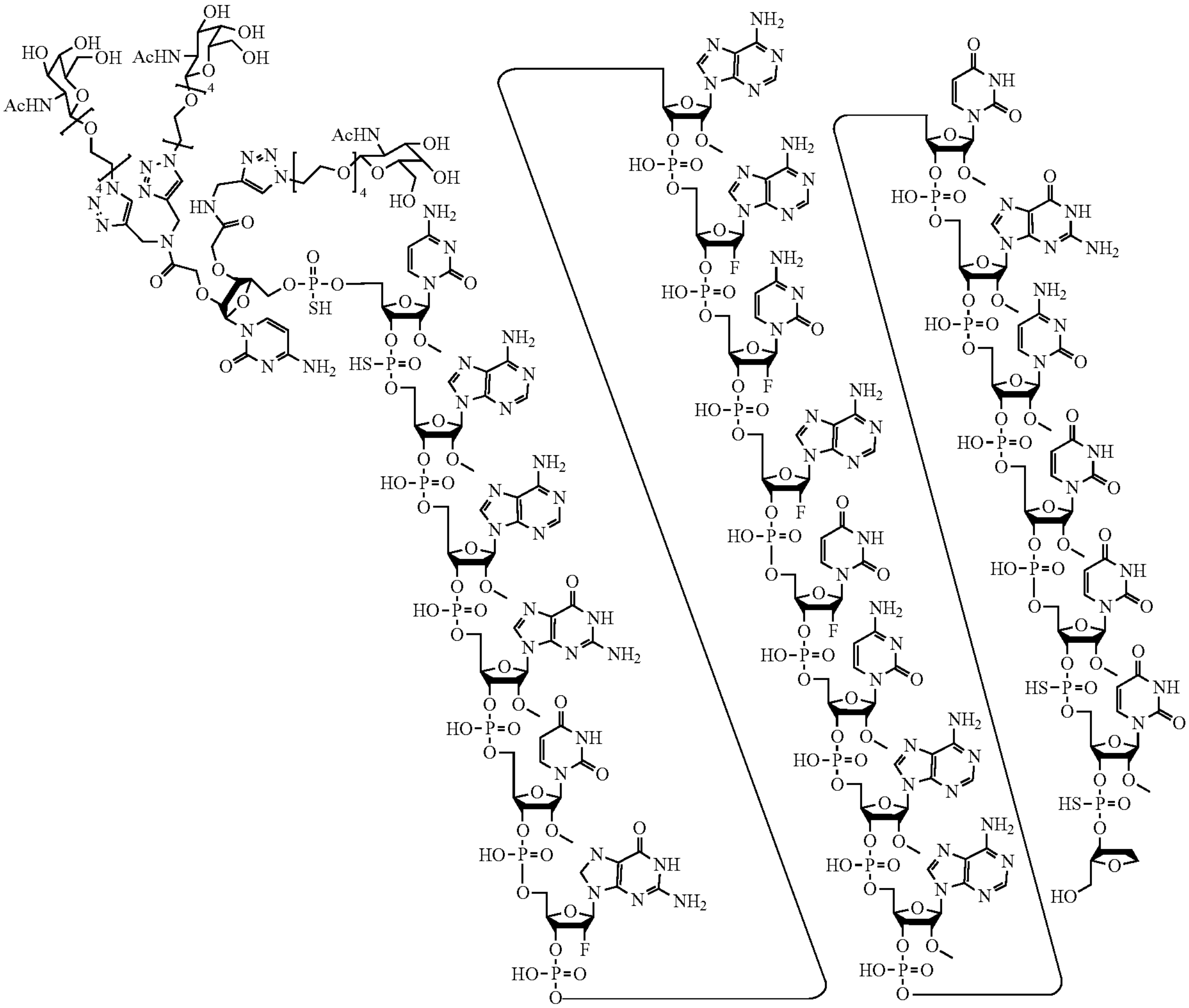
or a pharmaceutically acceptable salt or stereoisomer thereof.
Embodiment 51. A modified oligonucleotide according to the following chemical structure:

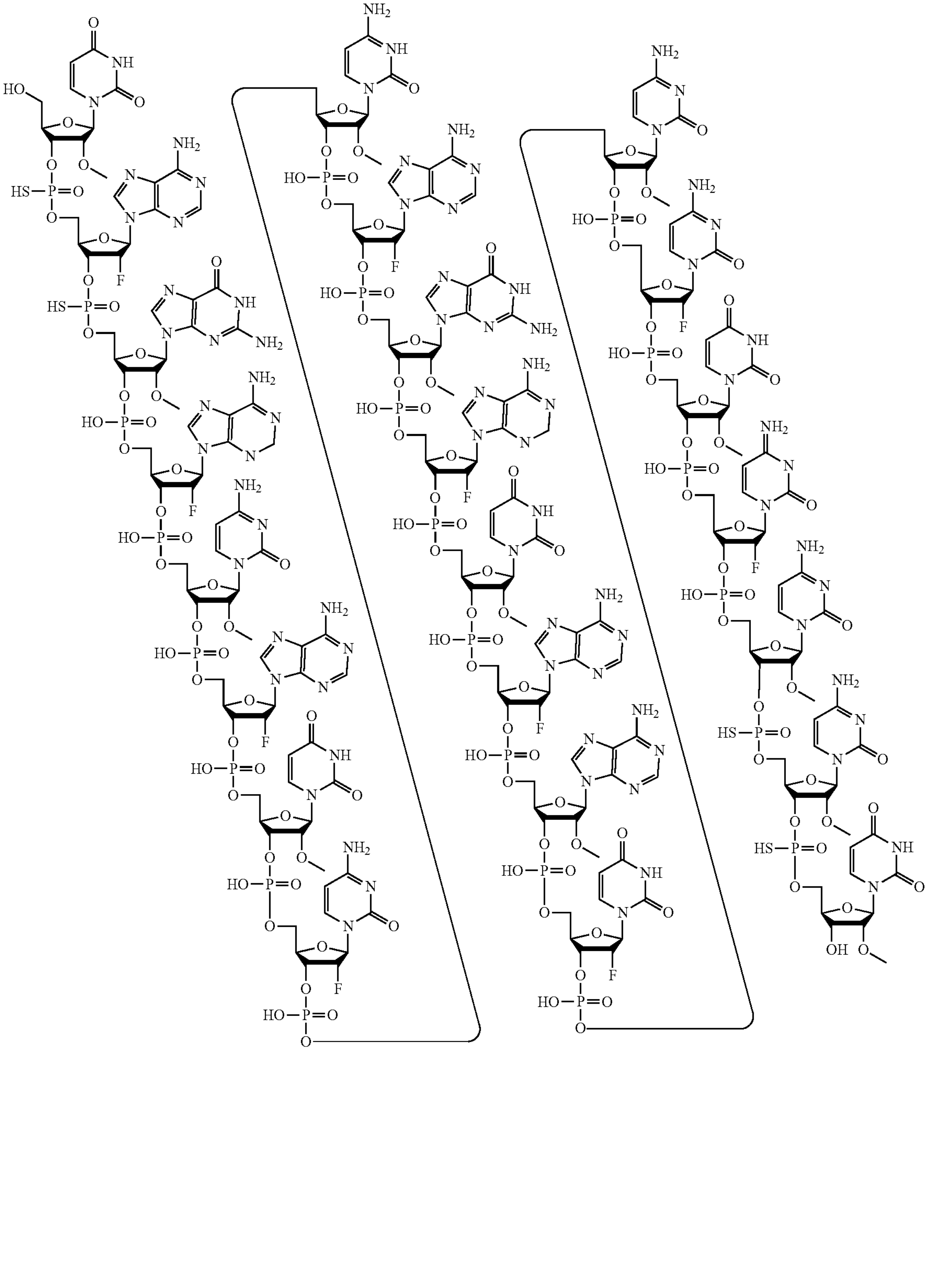
or a pharmaceutically acceptable salt or stereoisomer thereof.
Embodiment 52. A modified oligonucleotide according to the following chemical structure:

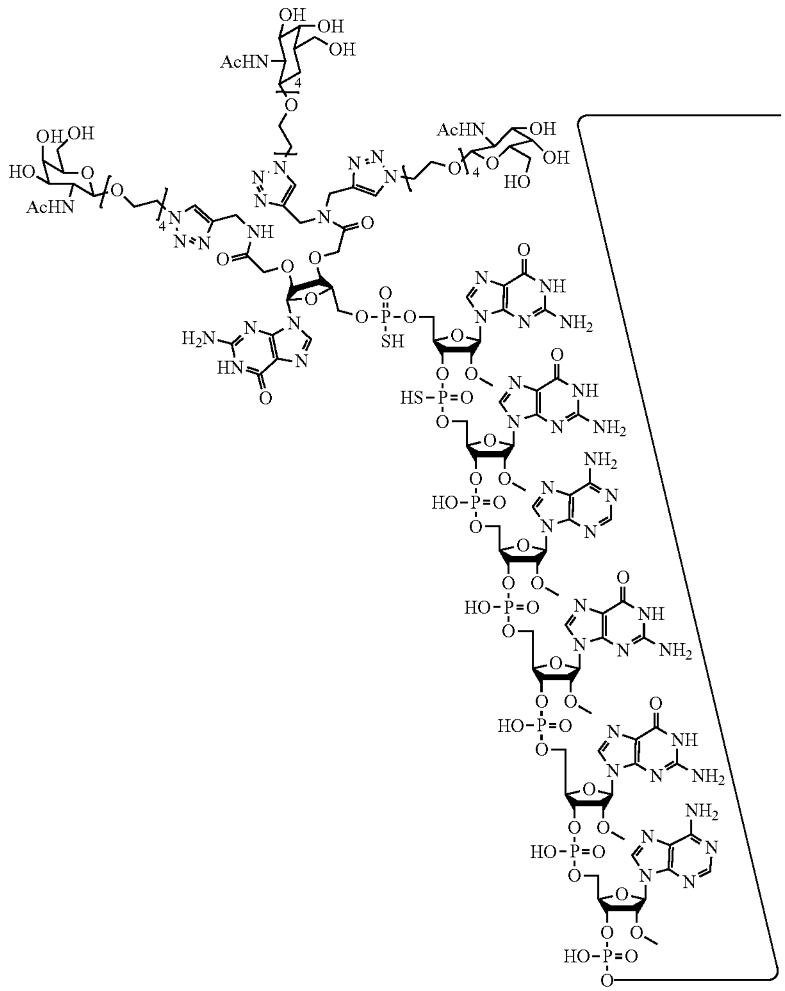

-continued
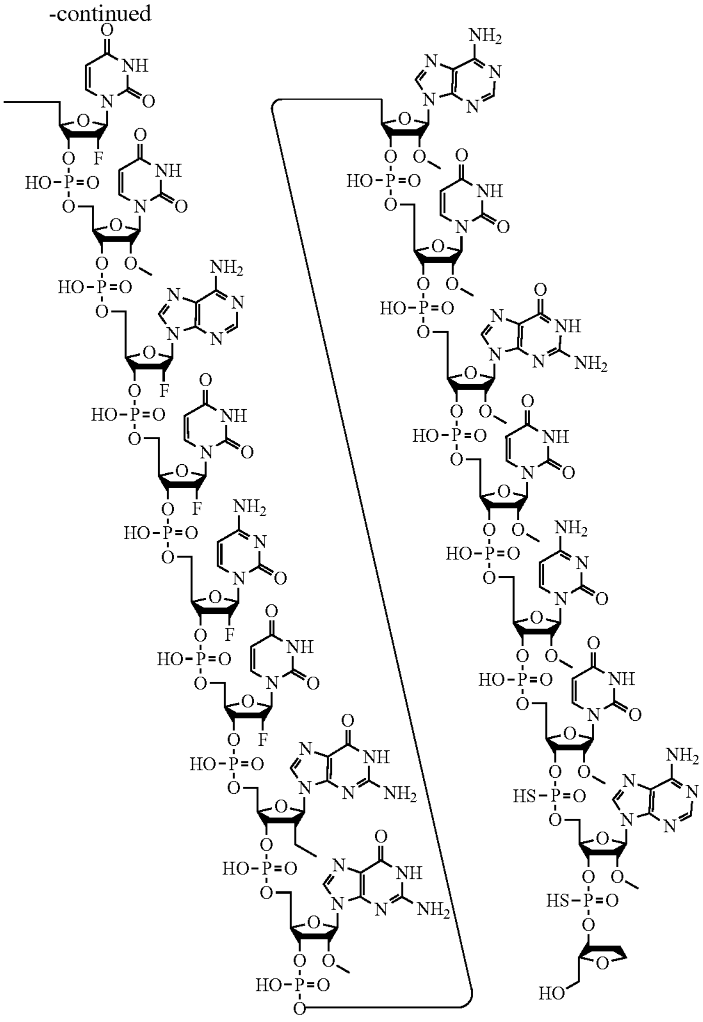
or a pharmaceutically acceptable salt or stereoisomer thereof.
Embodiment 53. The modified oligonucleotide of any one of embodiments 45-52, wherein the pharmaceutically acceptable salt is a sodium salt or a potassium salt.
Embodiment 54. The modified oligonucleotide of embodiment 53, which is a sodium salt according to the following chemical structure:

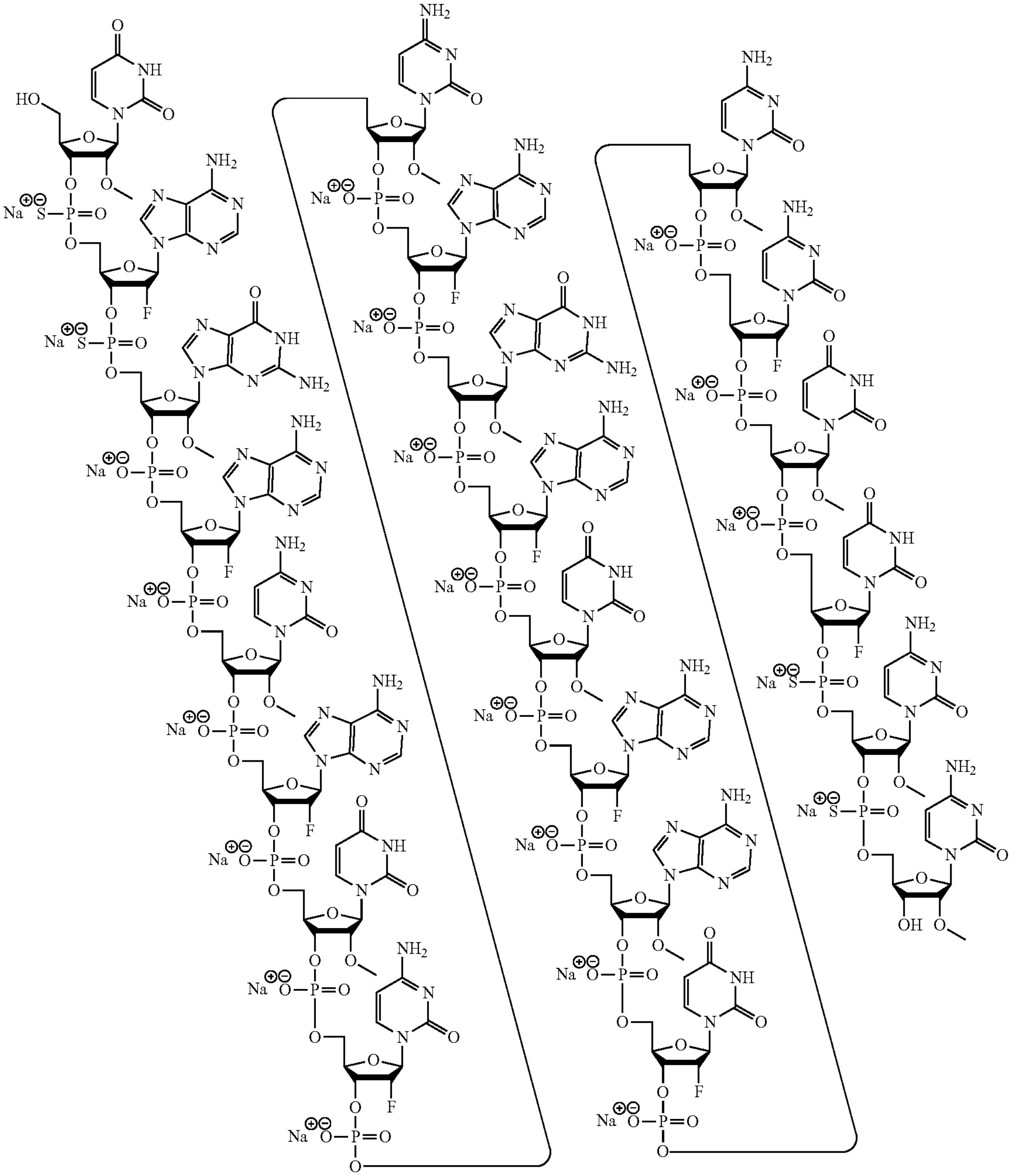
or a stereoisomer thereof.
Embodiment 55. The modified oligonucleotide of embodiment 53, which is a sodium salt according to the following chemical structure:

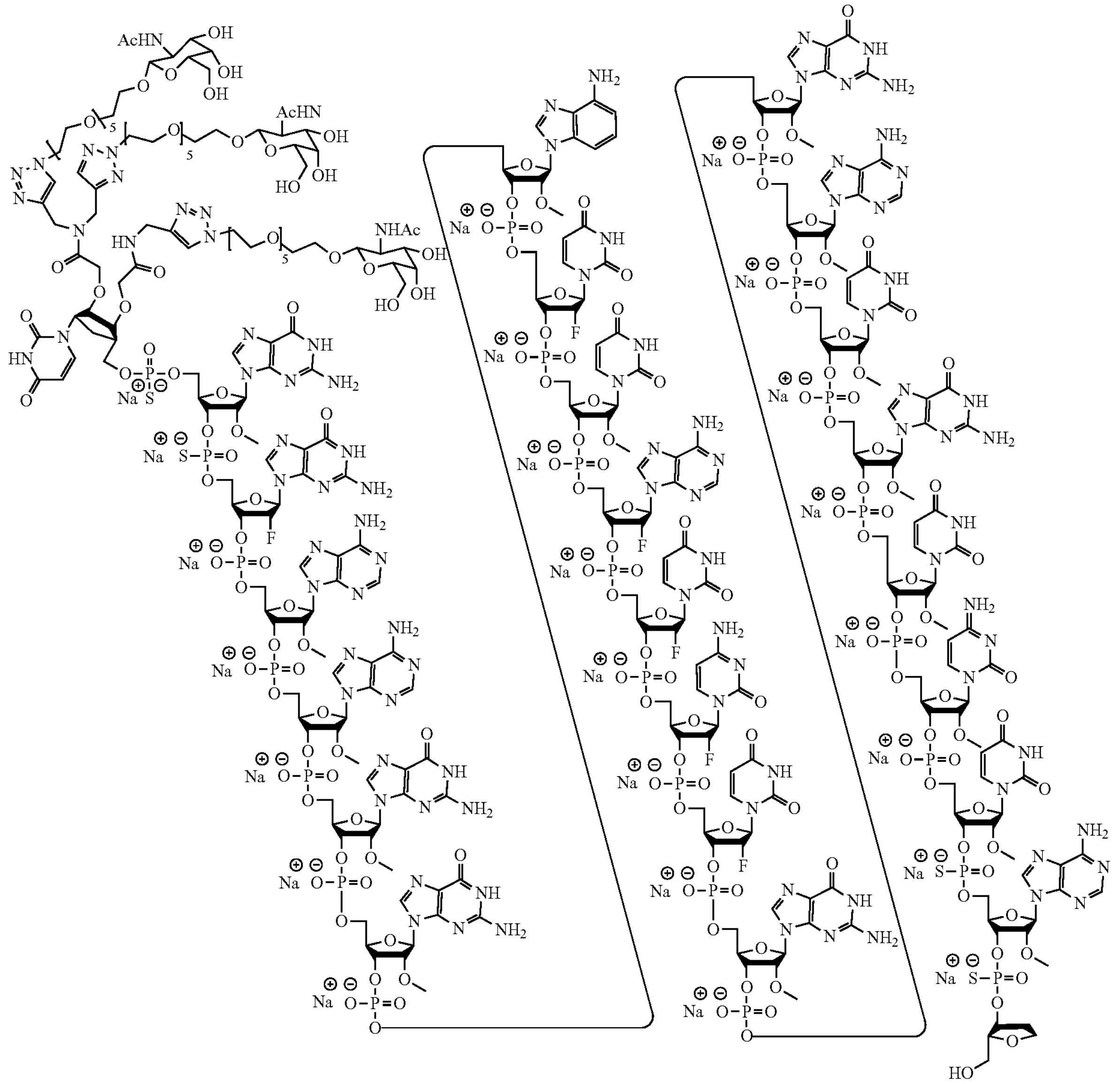
or a stereoisomer thereof.
Embodiment 56. The modified oligonucleotide of embodiment 53, which is a sodium salt according to the following chemical structure:

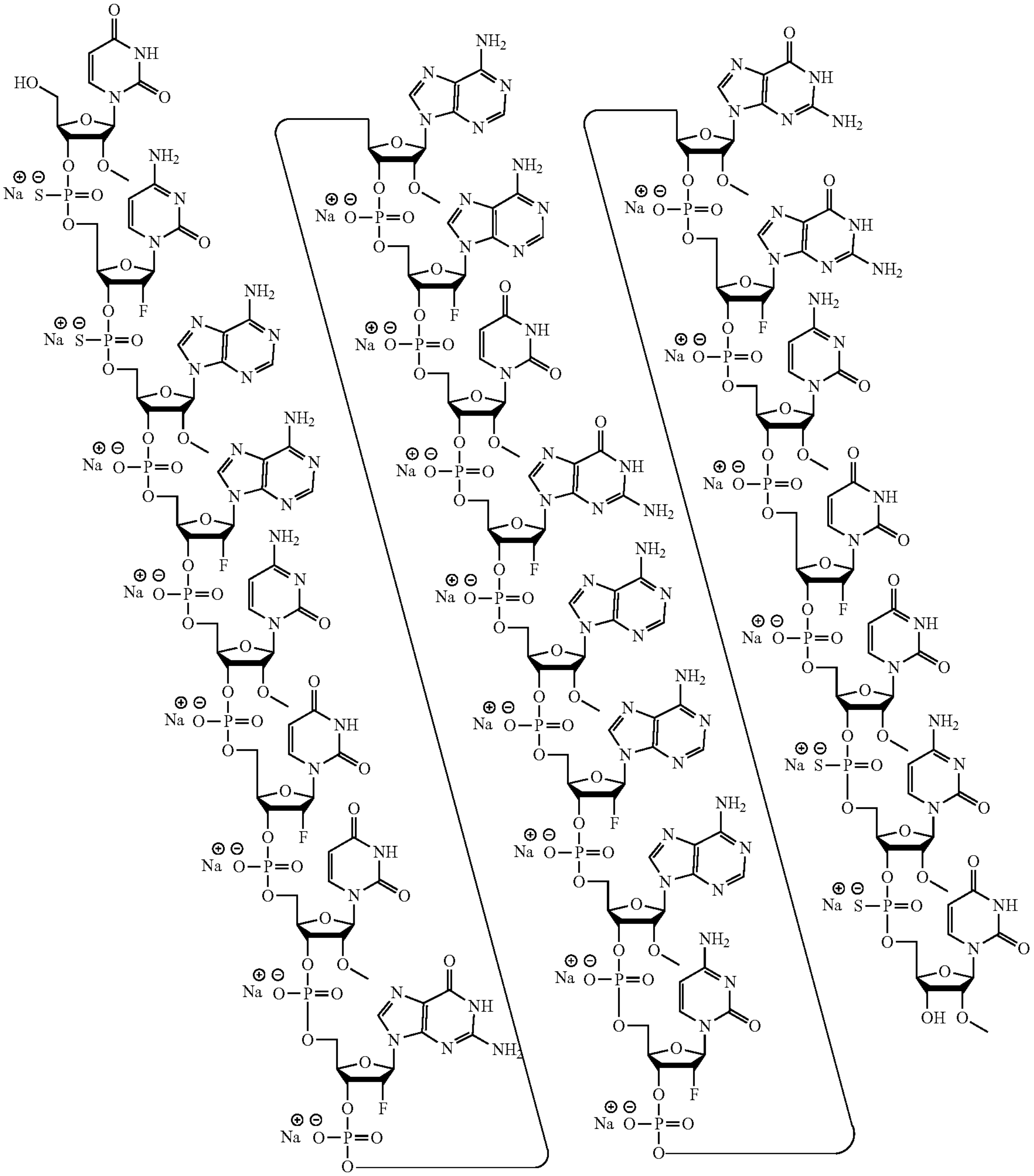
or a stereoisomer thereof.
Embodiment 57. The modified oligonucleotide of embodiment 53, which is a sodium salt according to the following chemical structure:

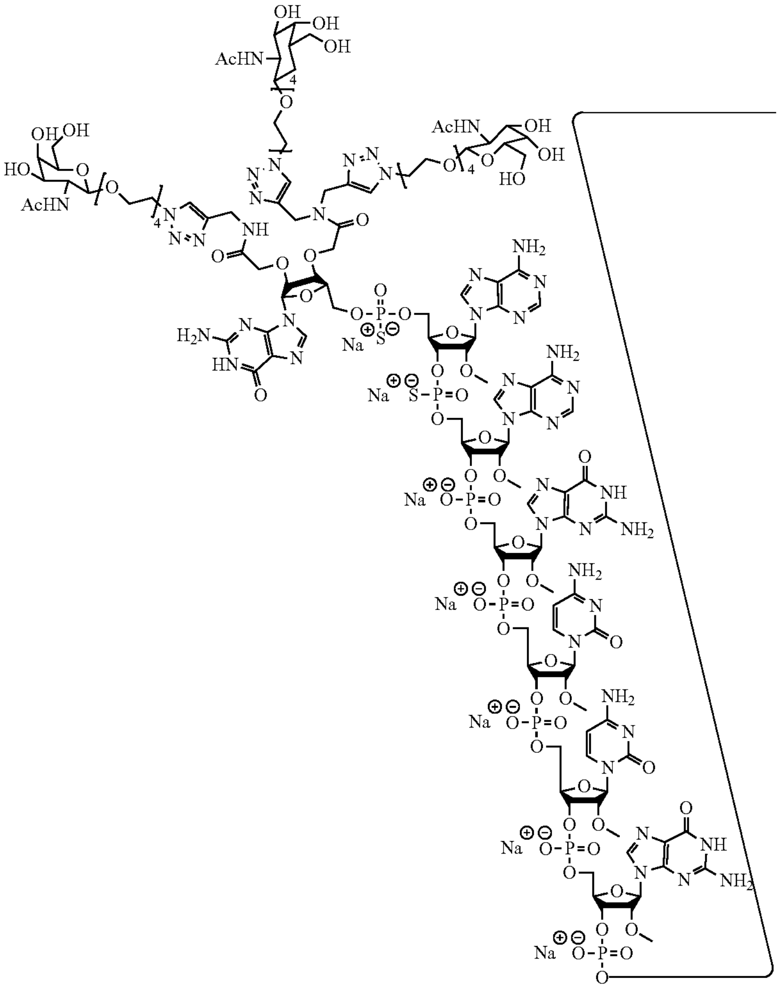

-continued
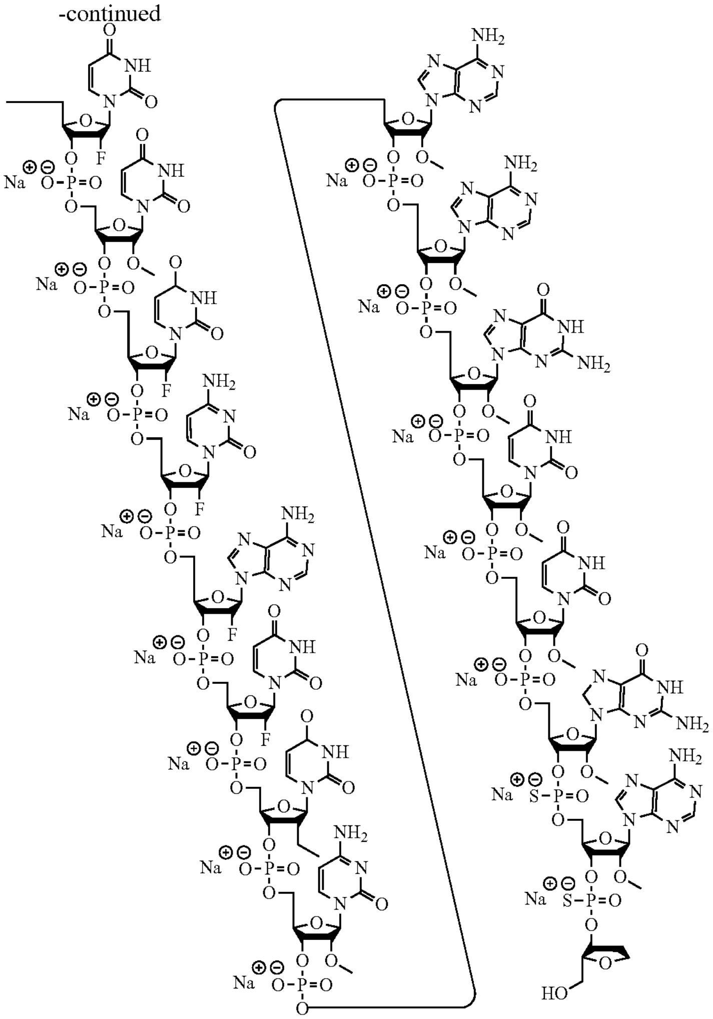
or a stereoisomer thereof.
Embodiment 58. The modified oligonucleotide of embodiment 53, which is a sodium salt according to the following chemical structure:

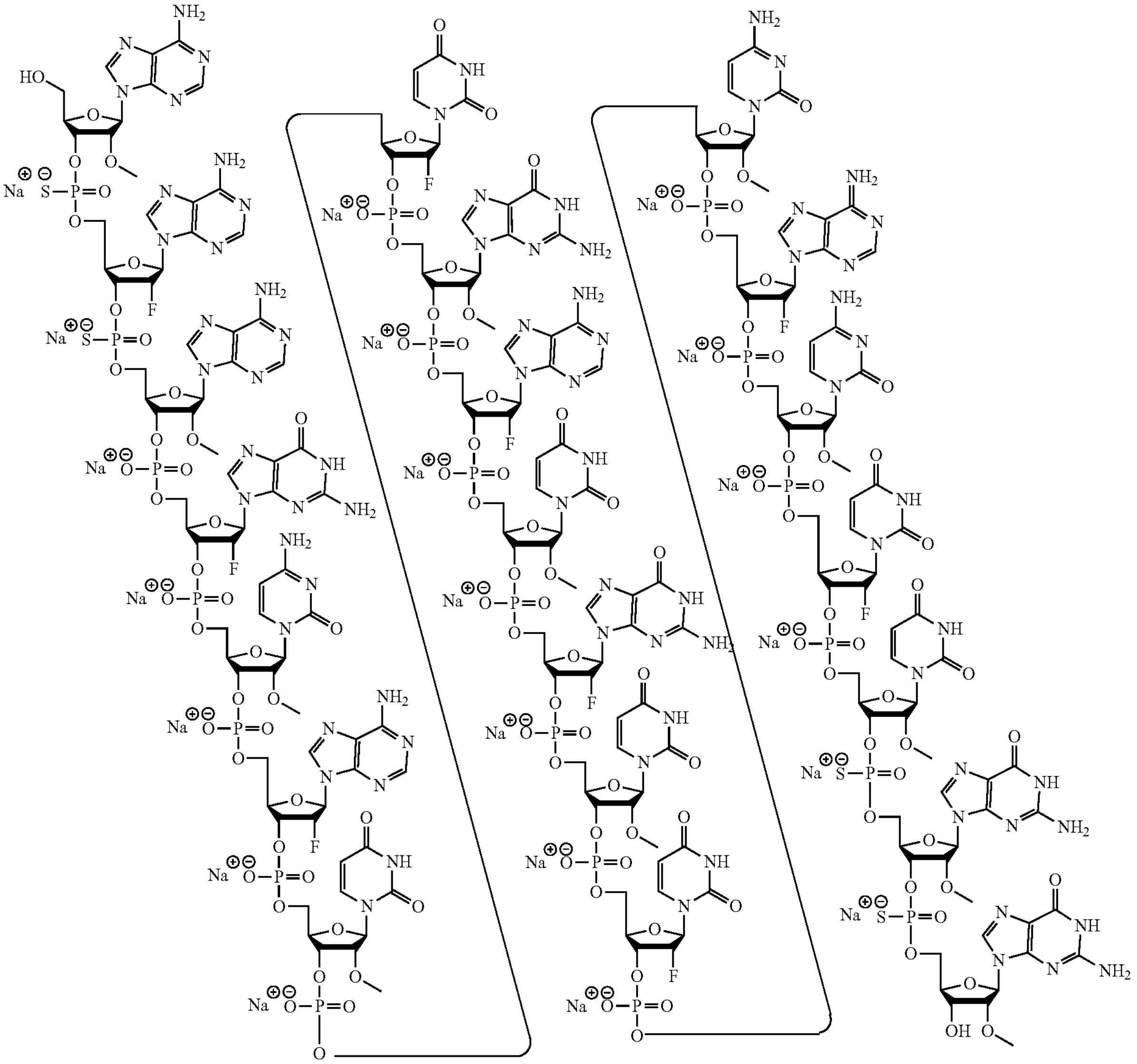
or a stereoisomer thereof.
Embodiment 59. The modified oligonucleotide of embodiment 53, which is a sodium salt according to the following chemical structure:

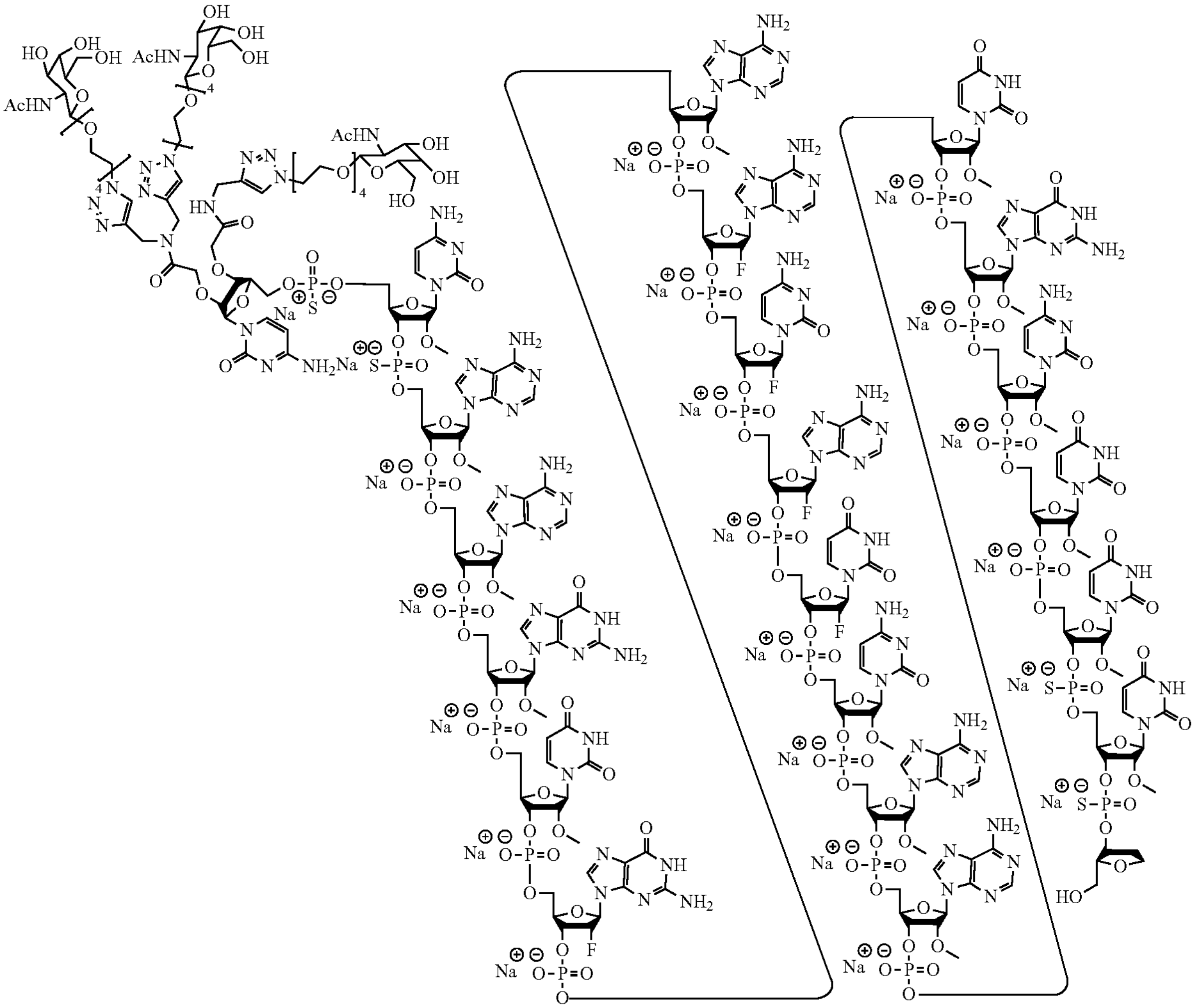
or a stereoisomer thereof.
Embodiment 60. The modified oligonucleotide of embodiment 53, which is a sodium salt according to the following chemical structure:

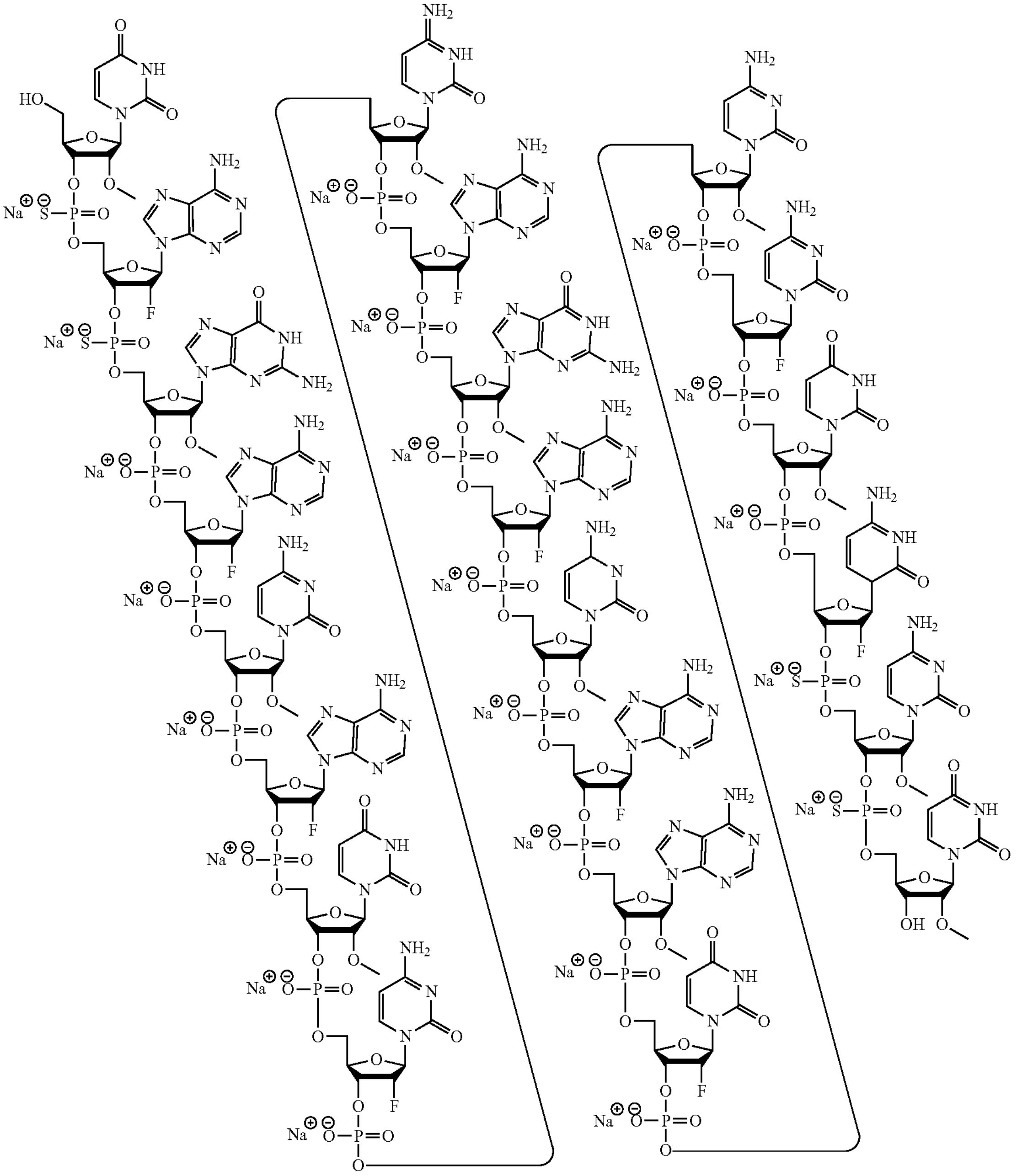
or a stereoisomer thereof.
Embodiment 61. The modified oligonucleotide of embodiment 53, which is a sodium salt according to the following chemical structure:

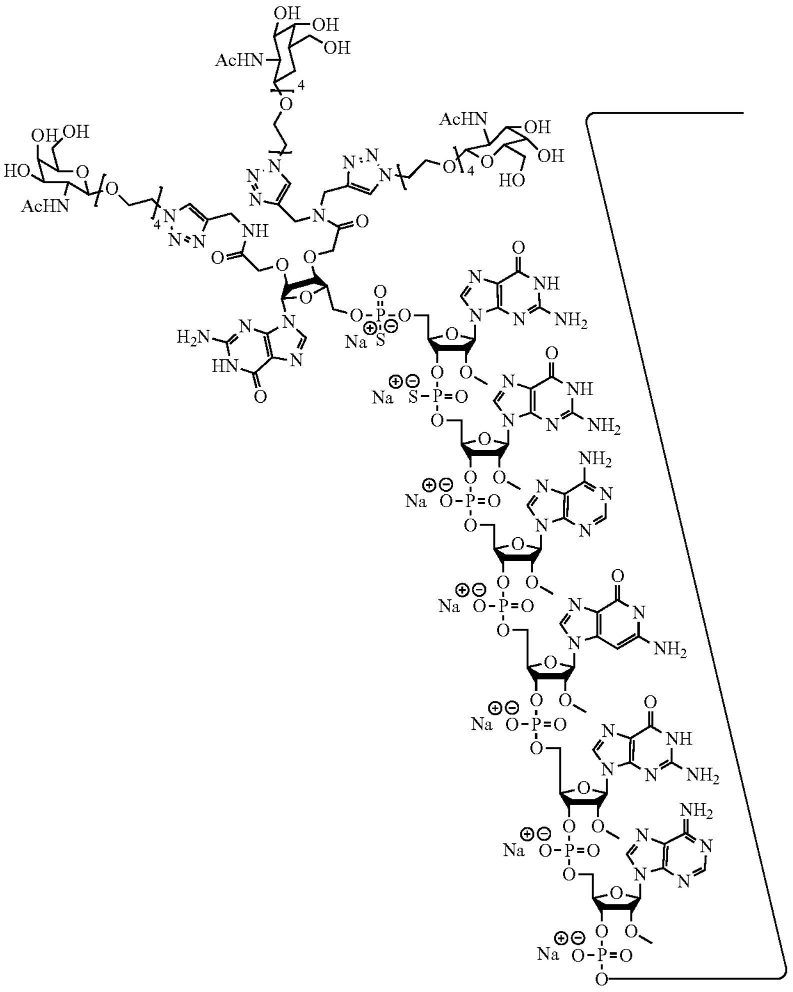

-continued
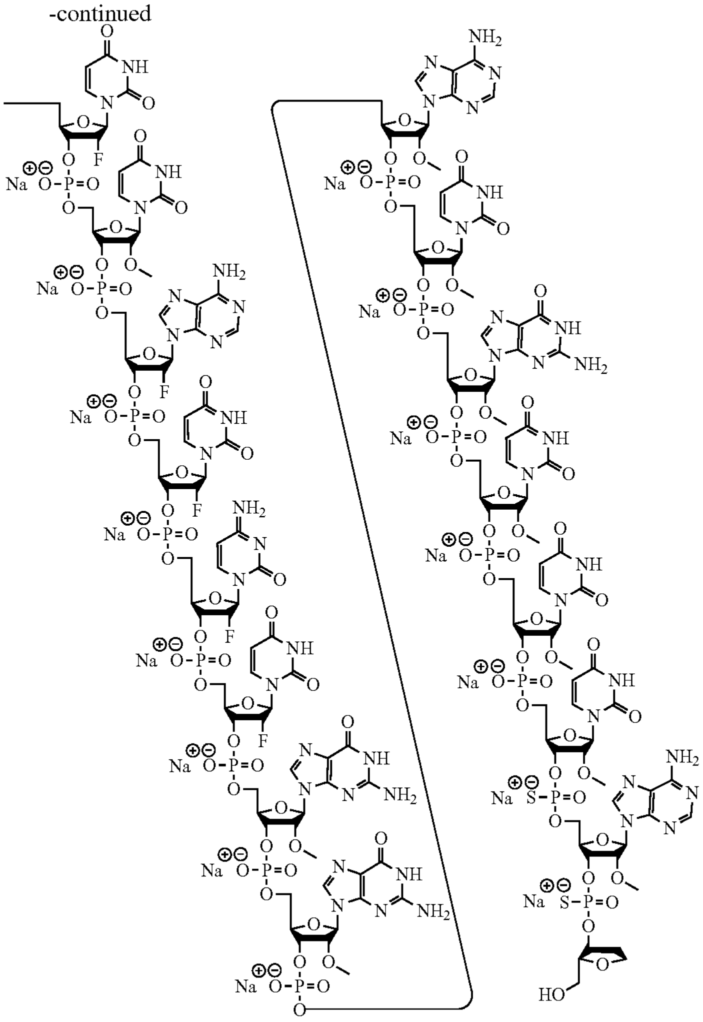
or a stereoisomer thereof.
Embodiment 62. A compound according to the following chemical structure:

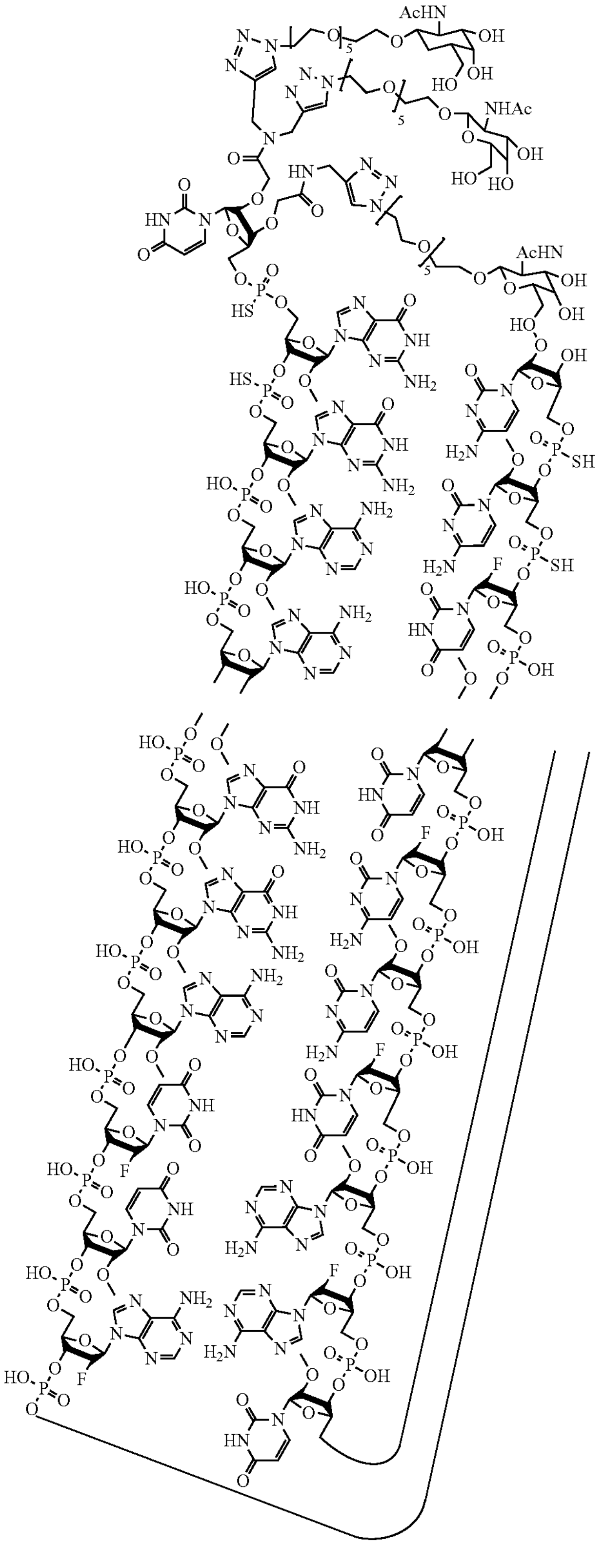

-continued
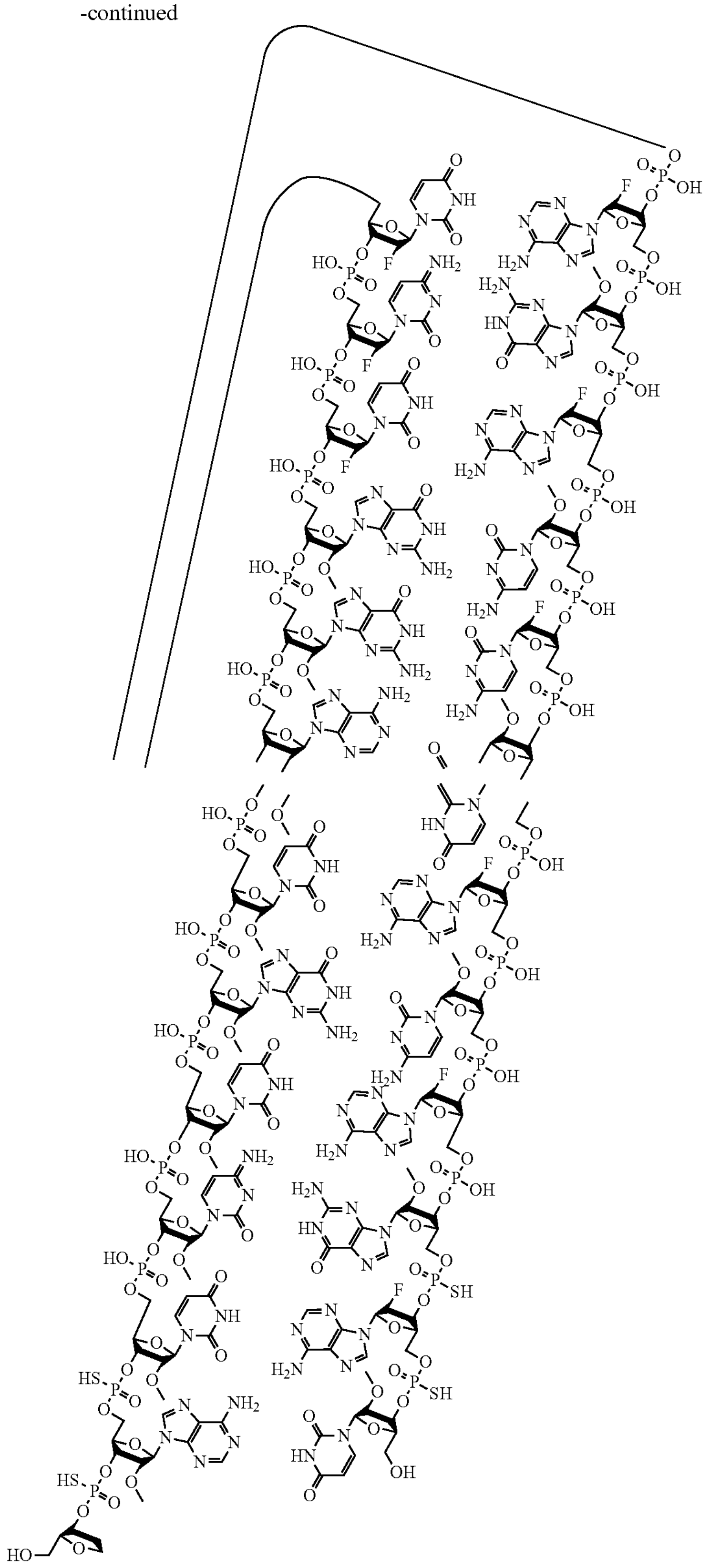
or a pharmaceutically acceptable salt or stereoisomer thereof.
Embodiment 63. A compound according to the following chemical structure:

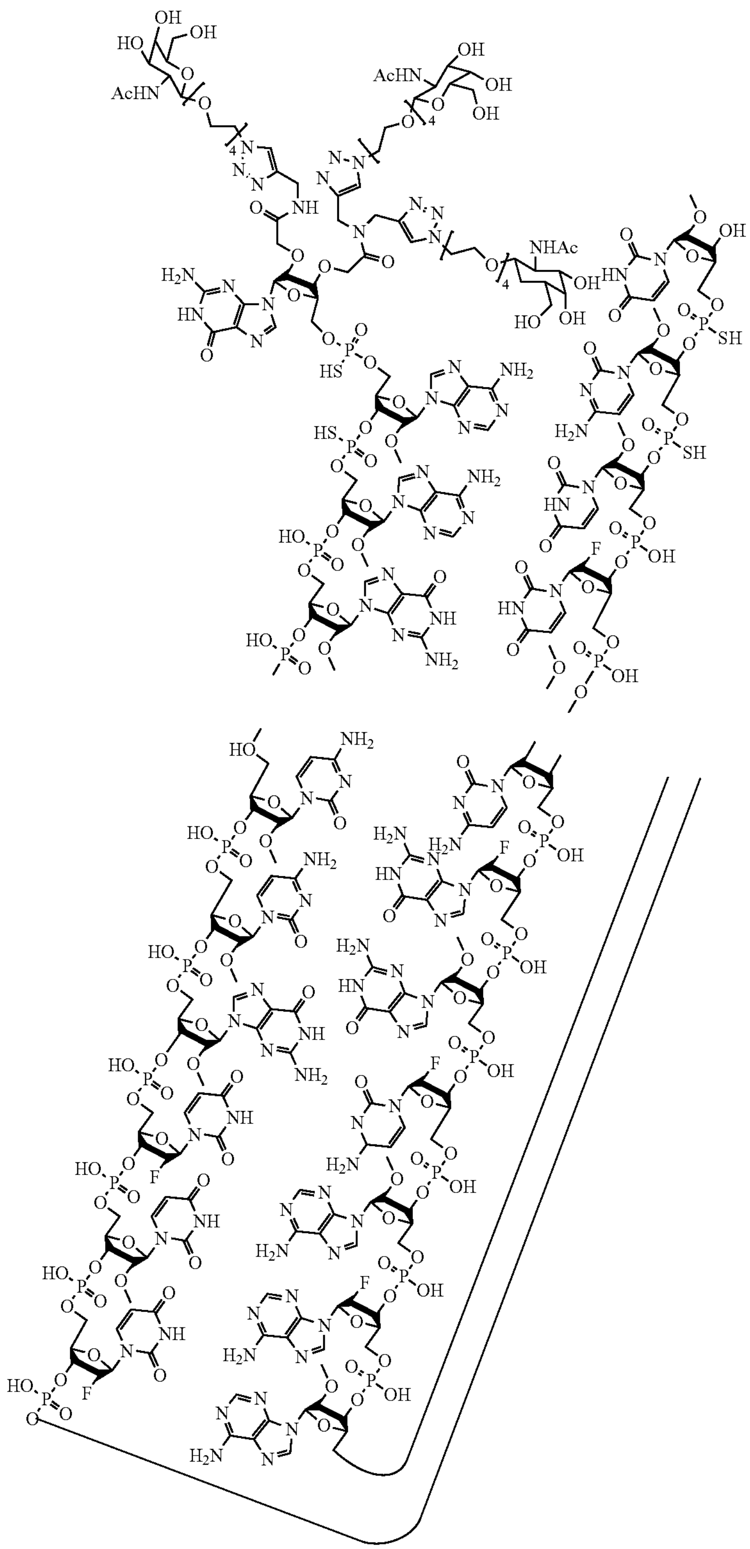

-continued
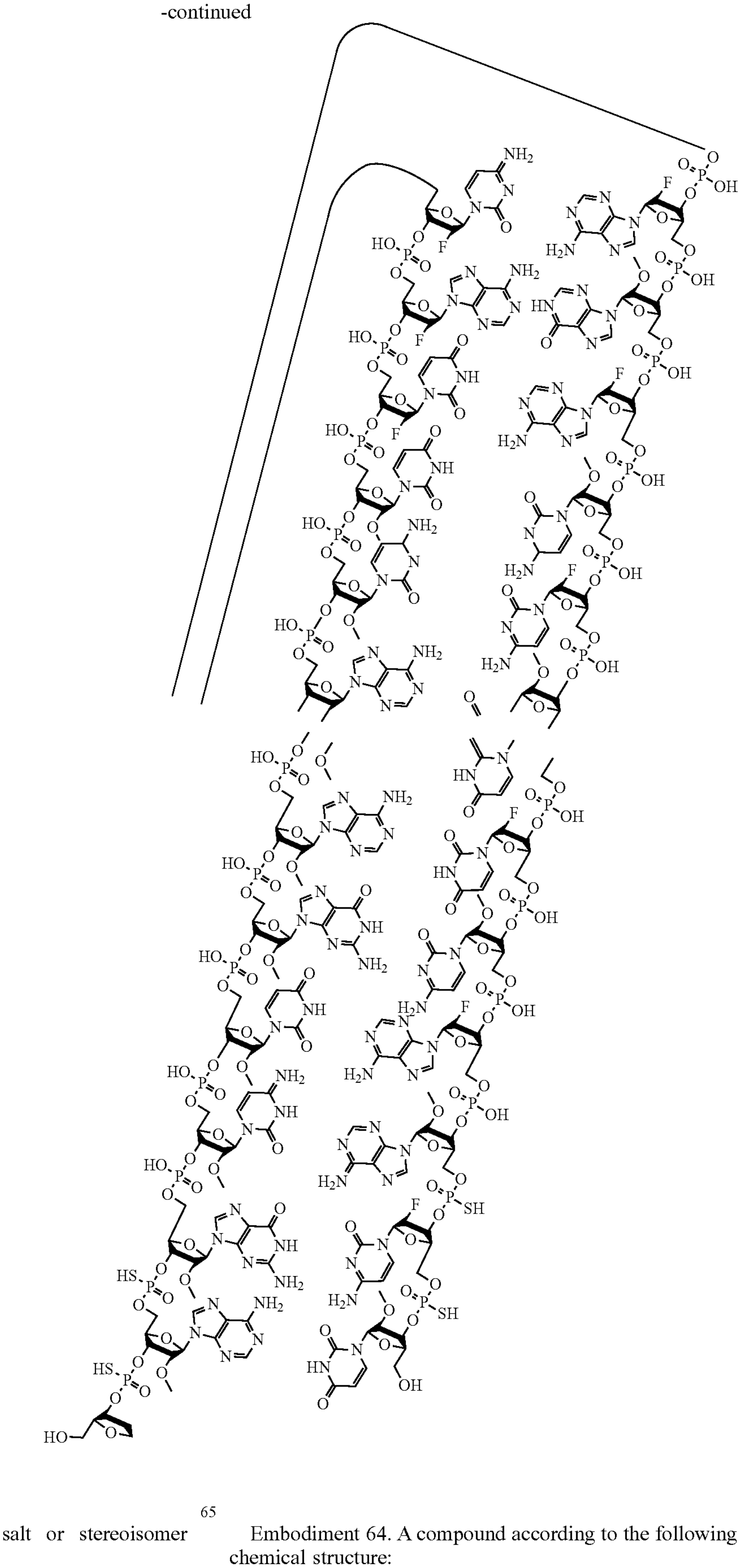
65
or a pharmaceutically acceptable salt or stereoisomer thereof.
Embodiment 64. A compound according to the following chemical structure:

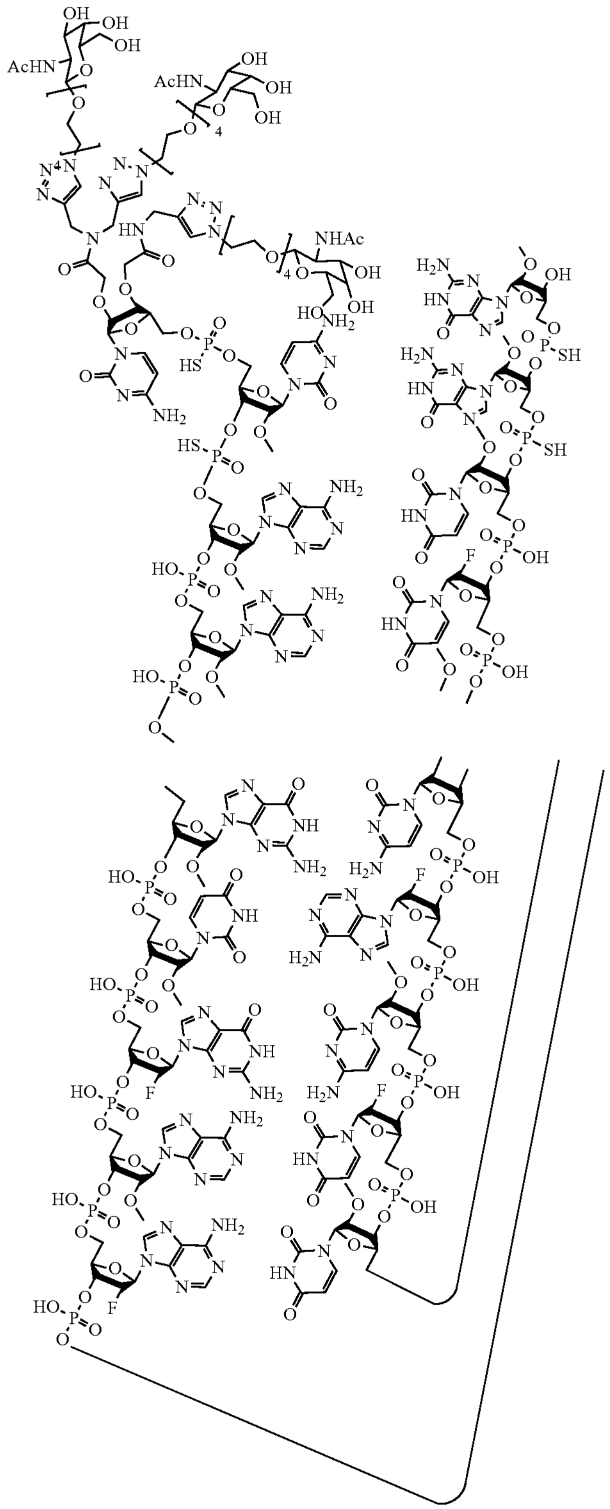

-continued
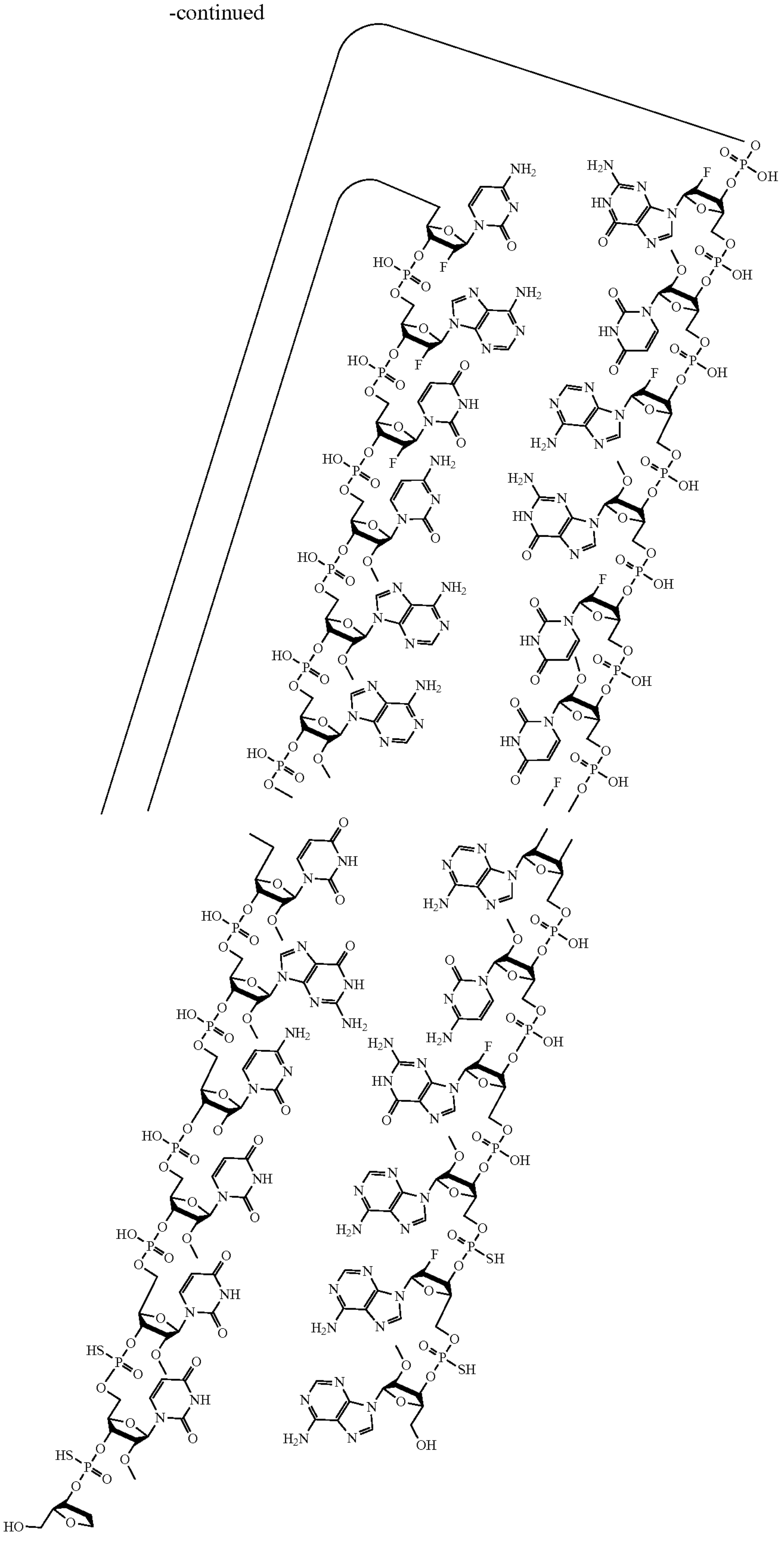
or a pharmaceutically acceptable salt or stereoisomer thereof.
Embodiment 65. A compound according to the following chemical structure:

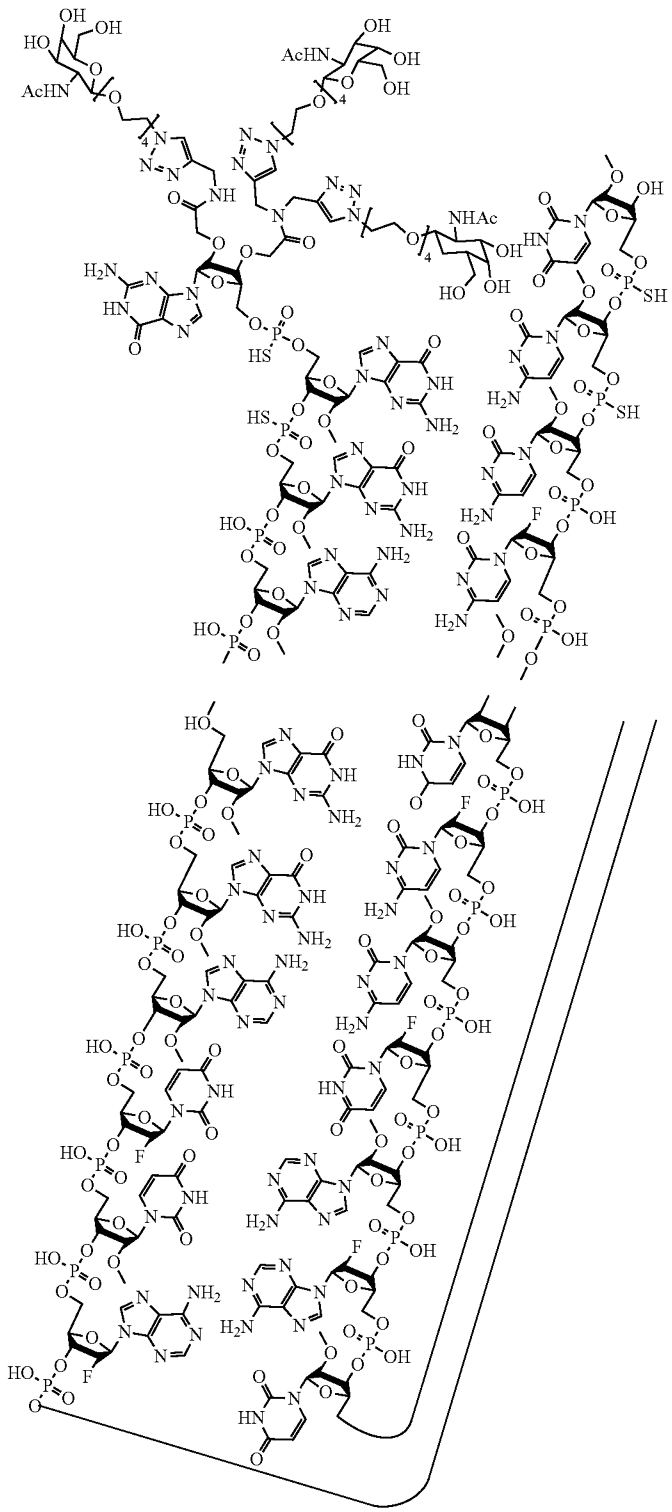

-continued
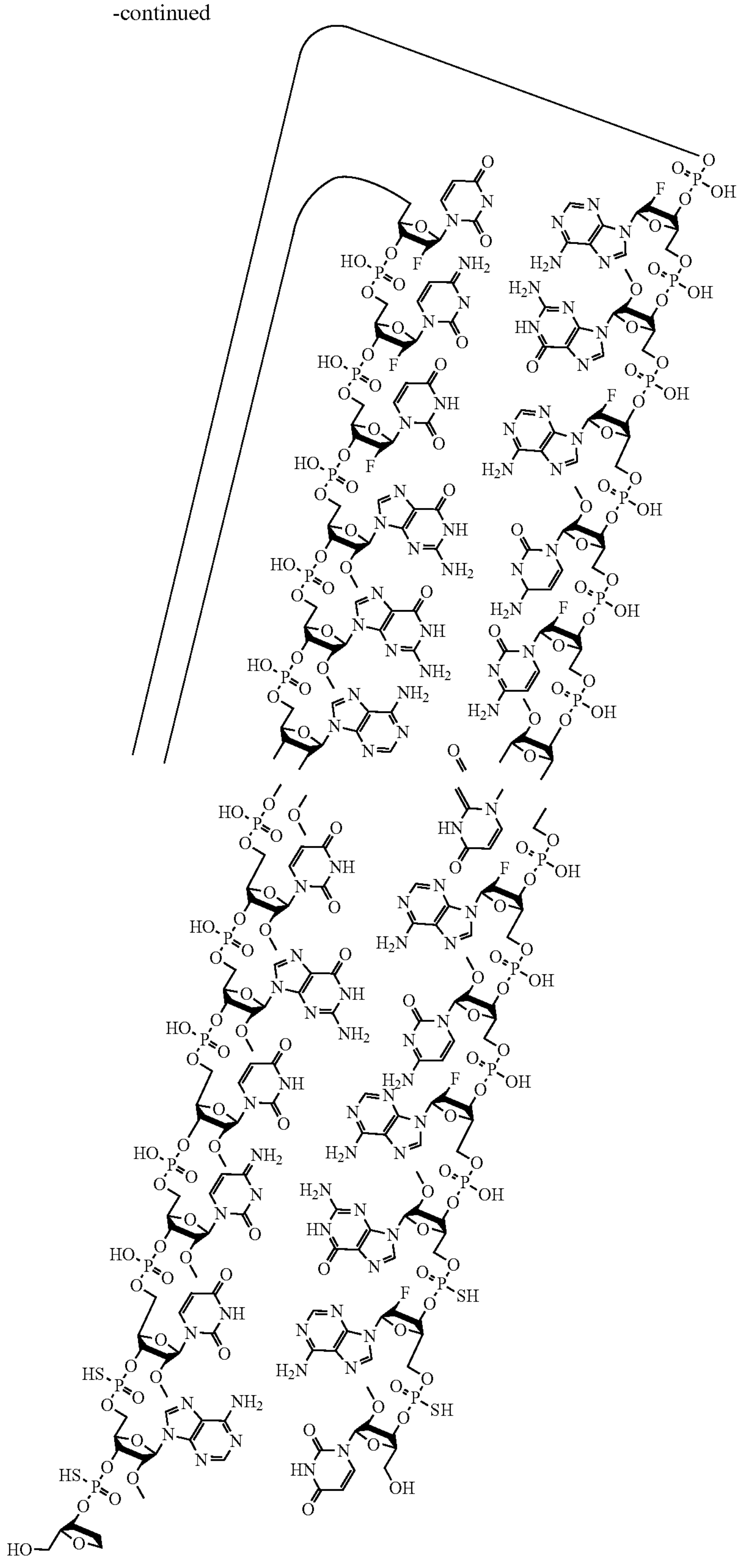
or a pharmaceutically acceptable salt or stereoisomer thereof.

Embodiment 66. The compound of any one of embodiments 62-65, wherein the pharmaceutically acceptable salt is a sodium salt or a potassium salt.
Embodiment 67. The compound of embodiment 66, which is a sodium salt according to the following chemical structure:
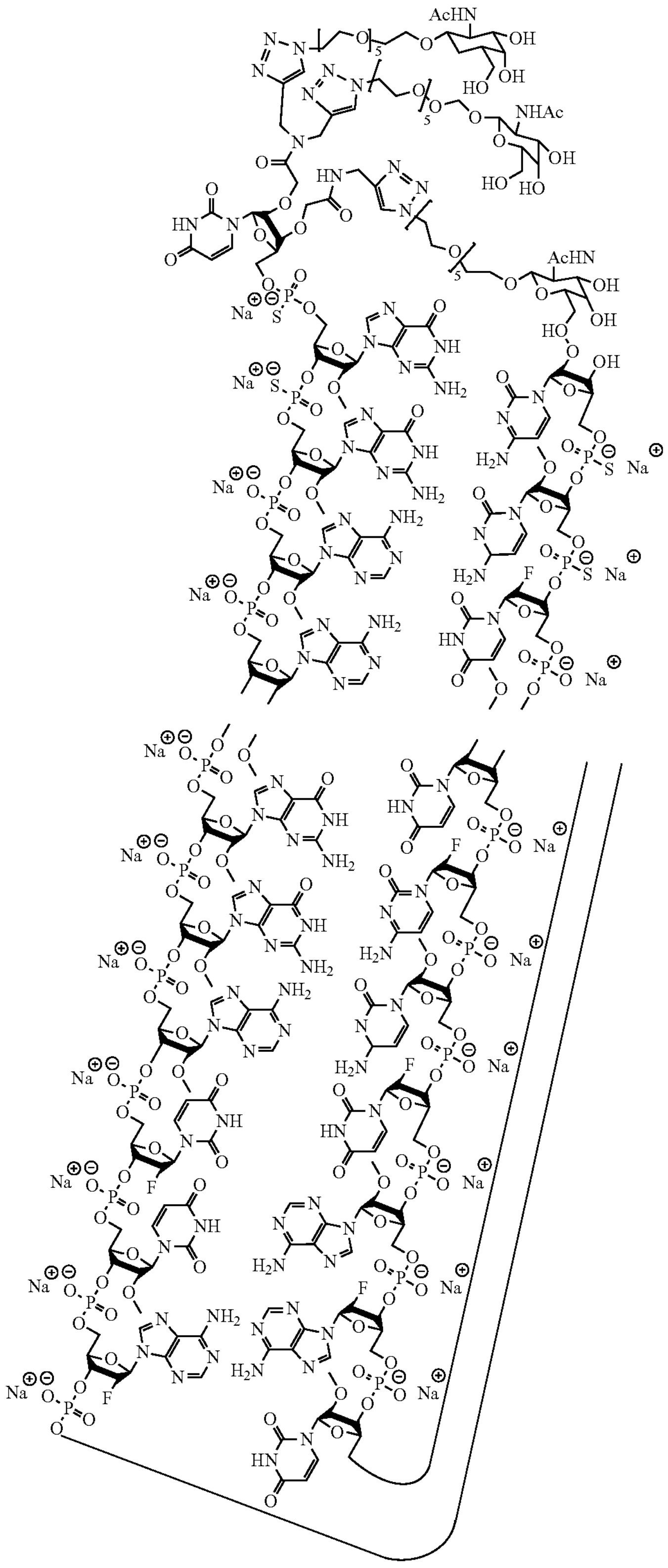

-continued
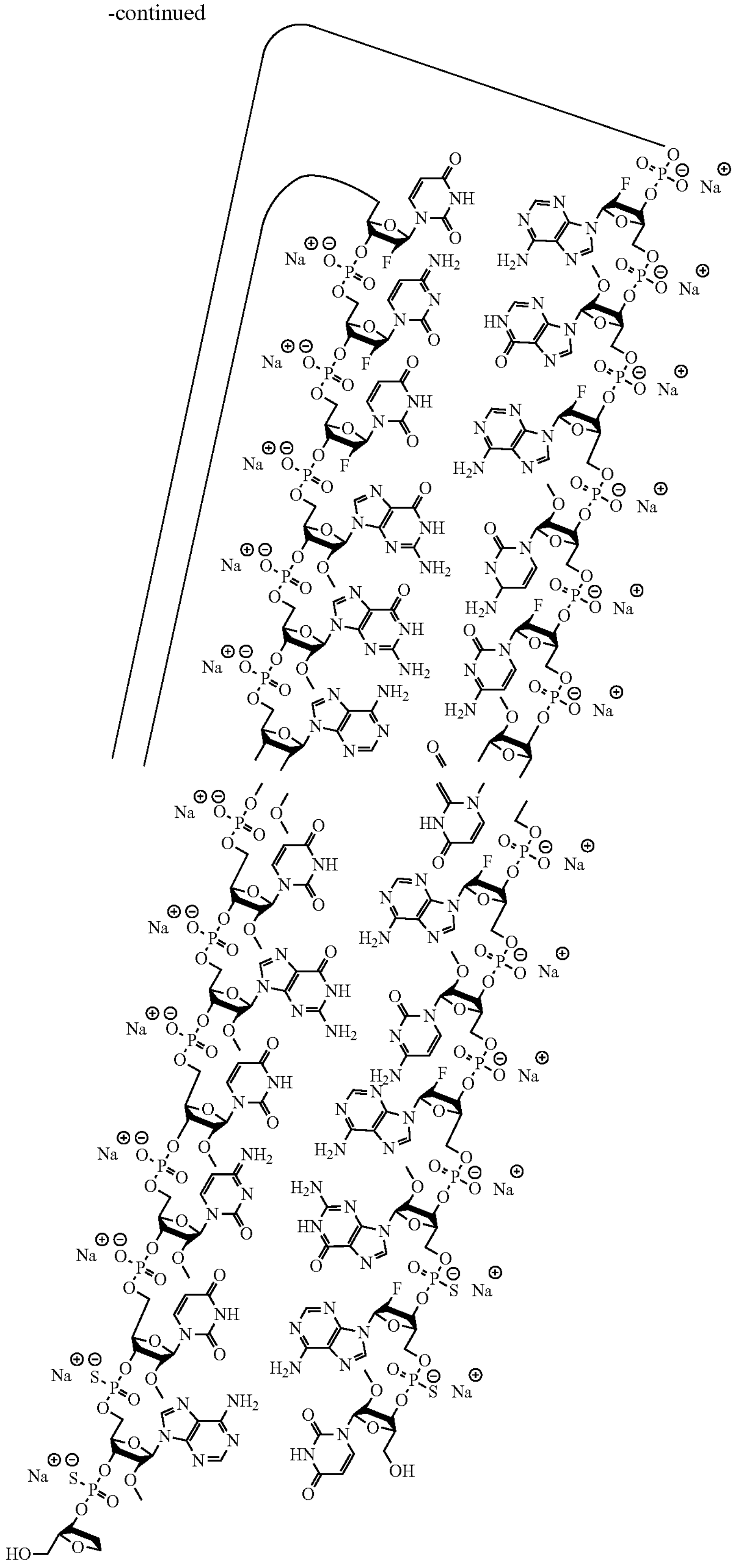
or a stereoisomer thereof.

Embodiment 68. The compound of embodiment 66, which is a sodium salt according to the following chemical structure:
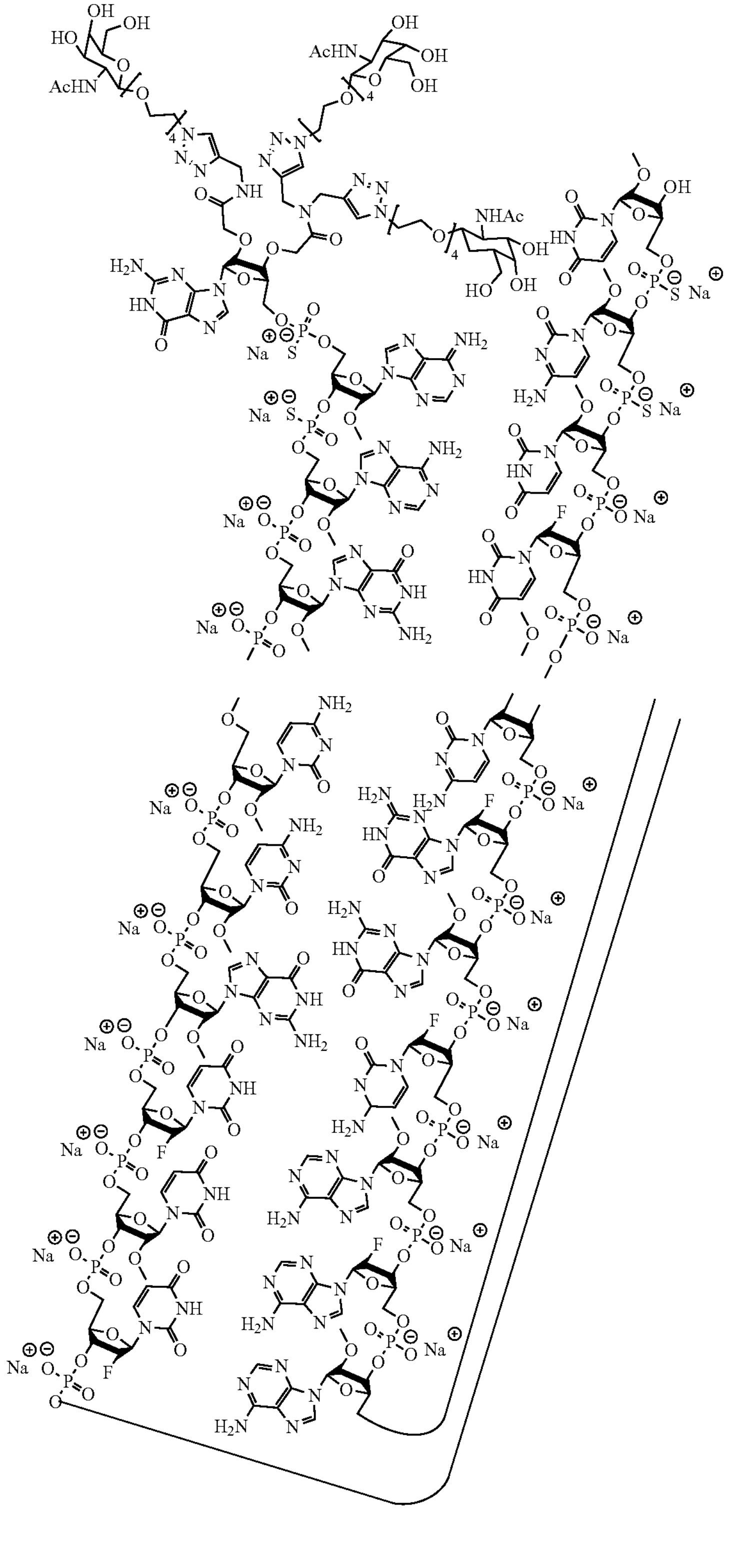

-continued
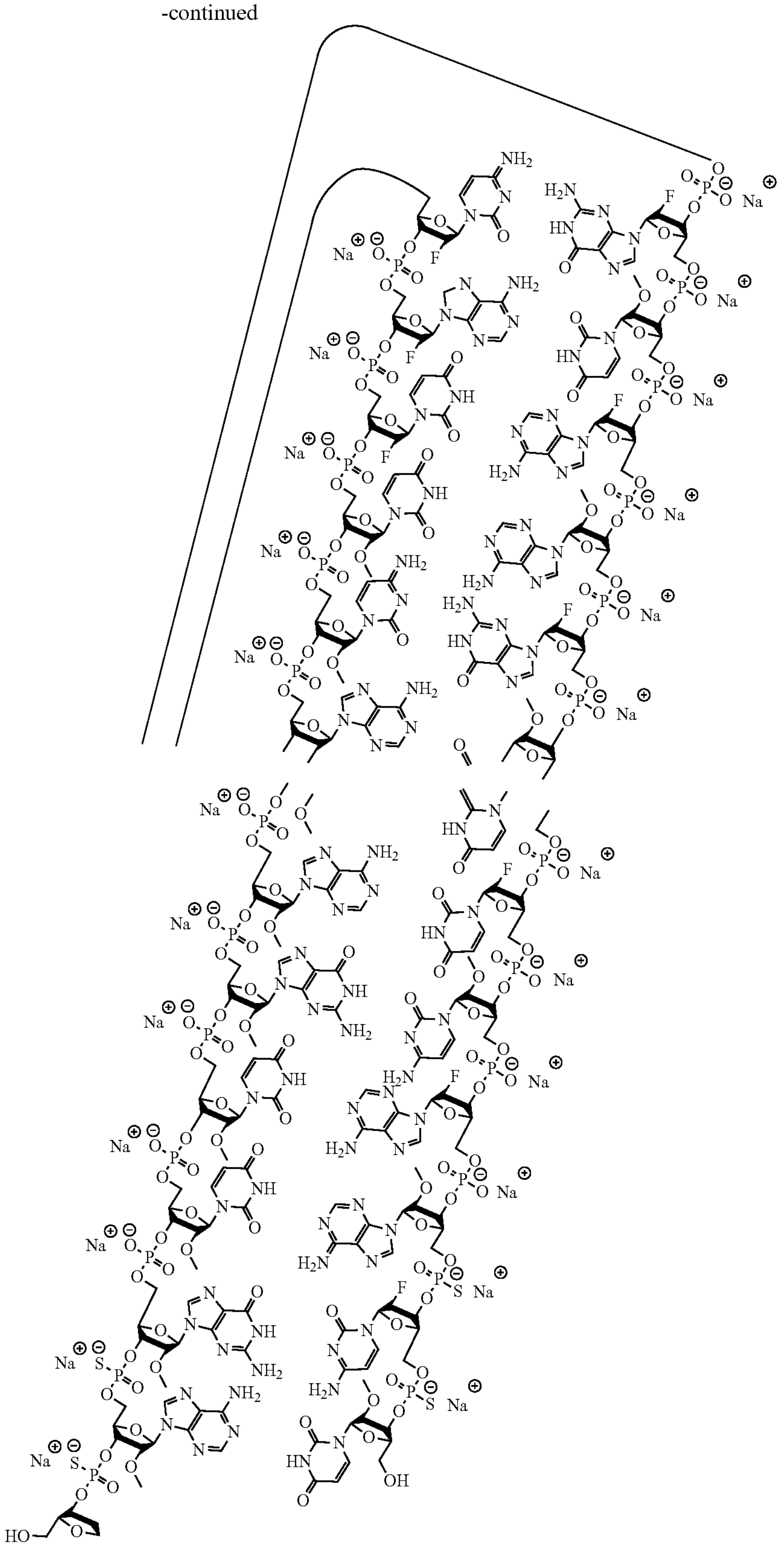
or a stereoisomer thereof.

Embodiment 69. The compound of embodiment 66, which is a sodium salt according to the following chemical structure:
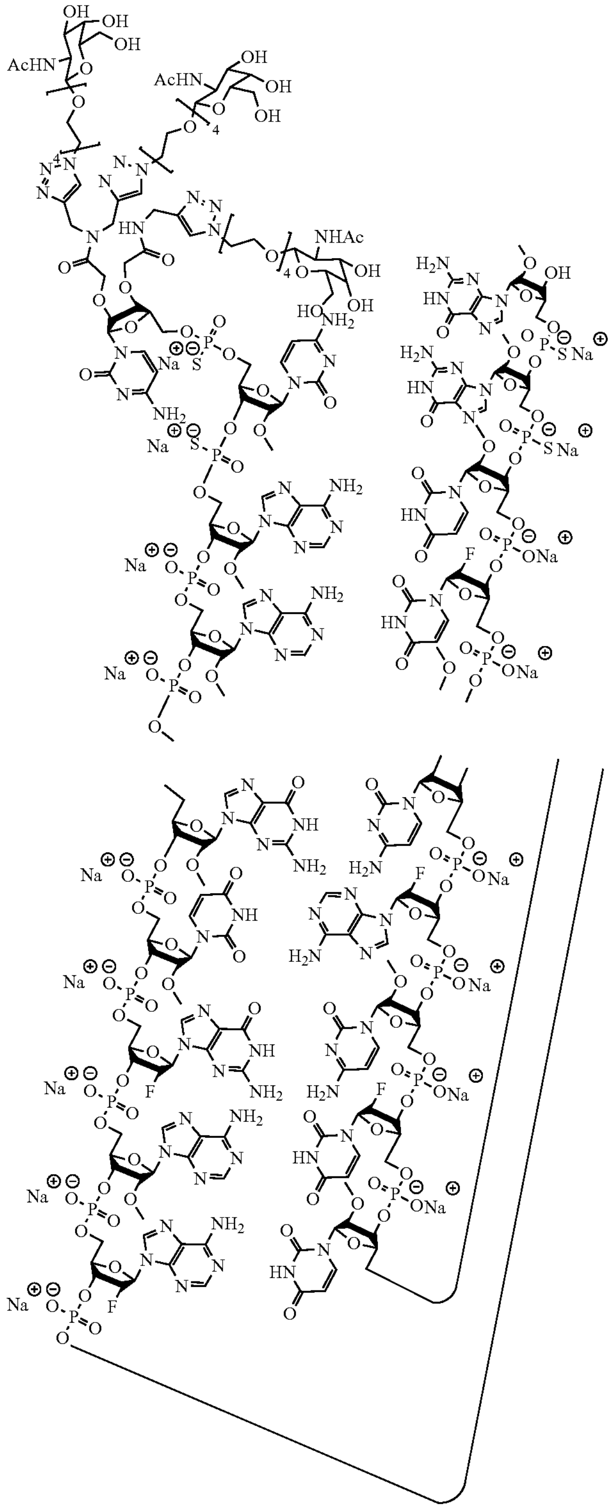

-continued
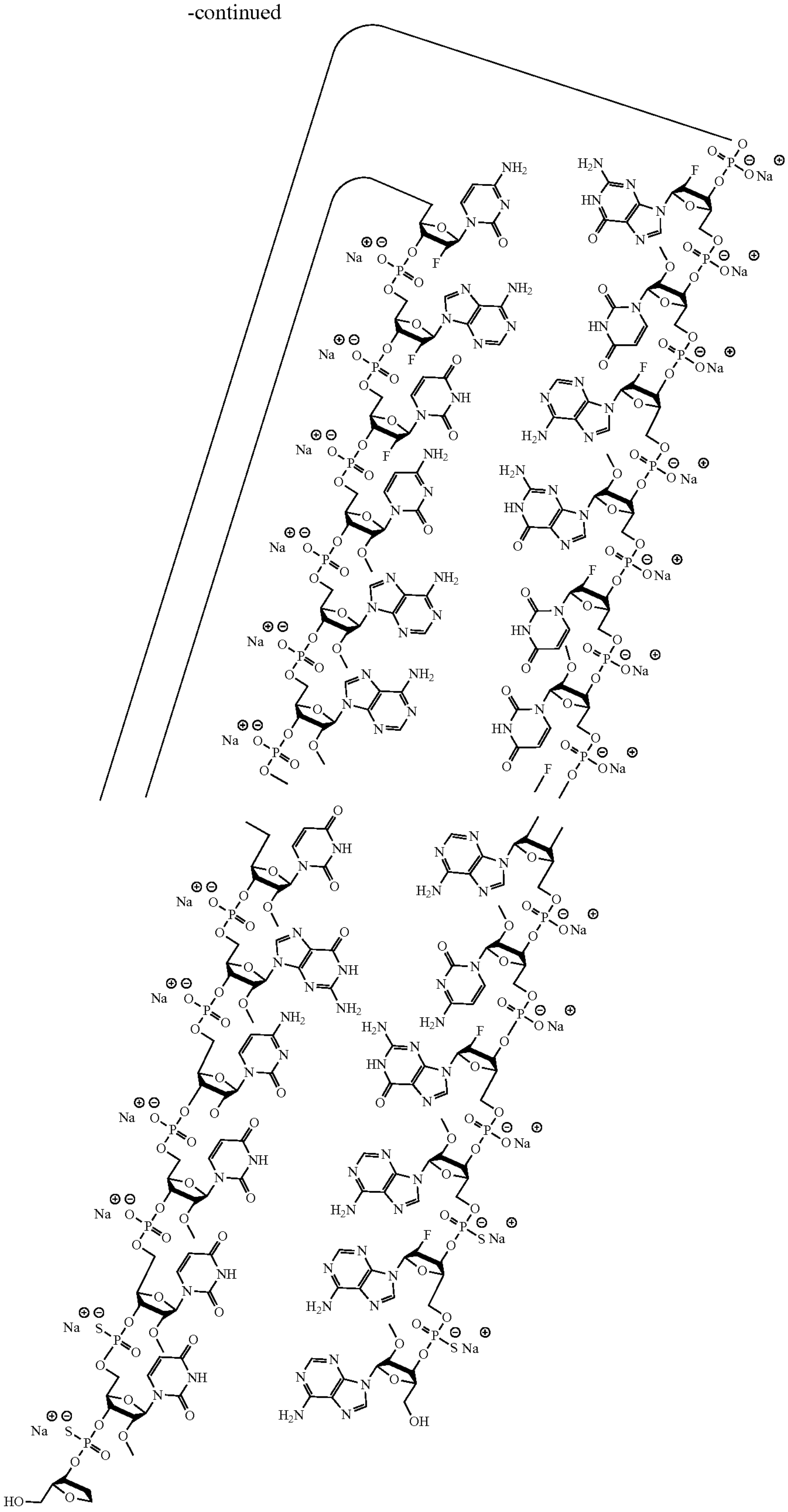
or a stereoisomer thereof.

Embodiment 70. The compound of embodiment 66, which is a sodium salt according to the following chemical structure:
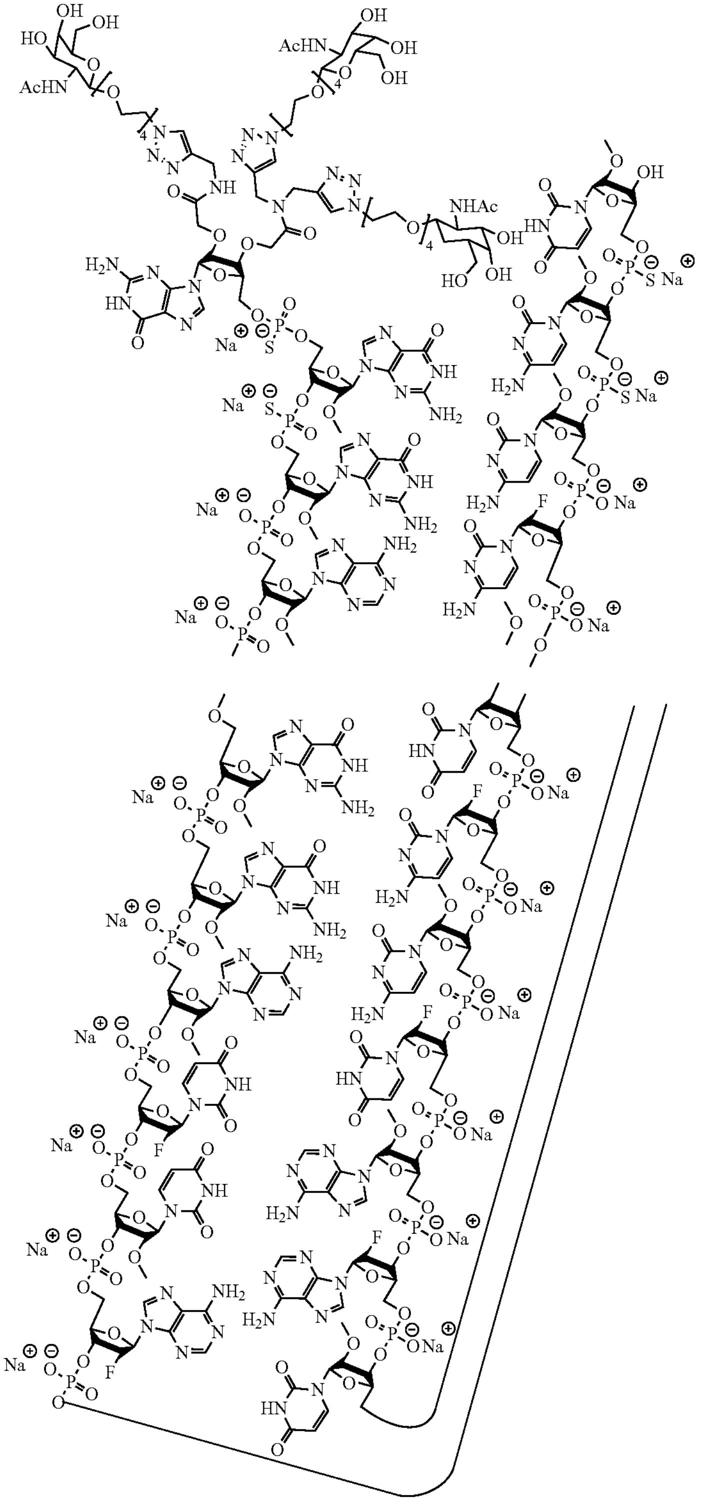

-continued
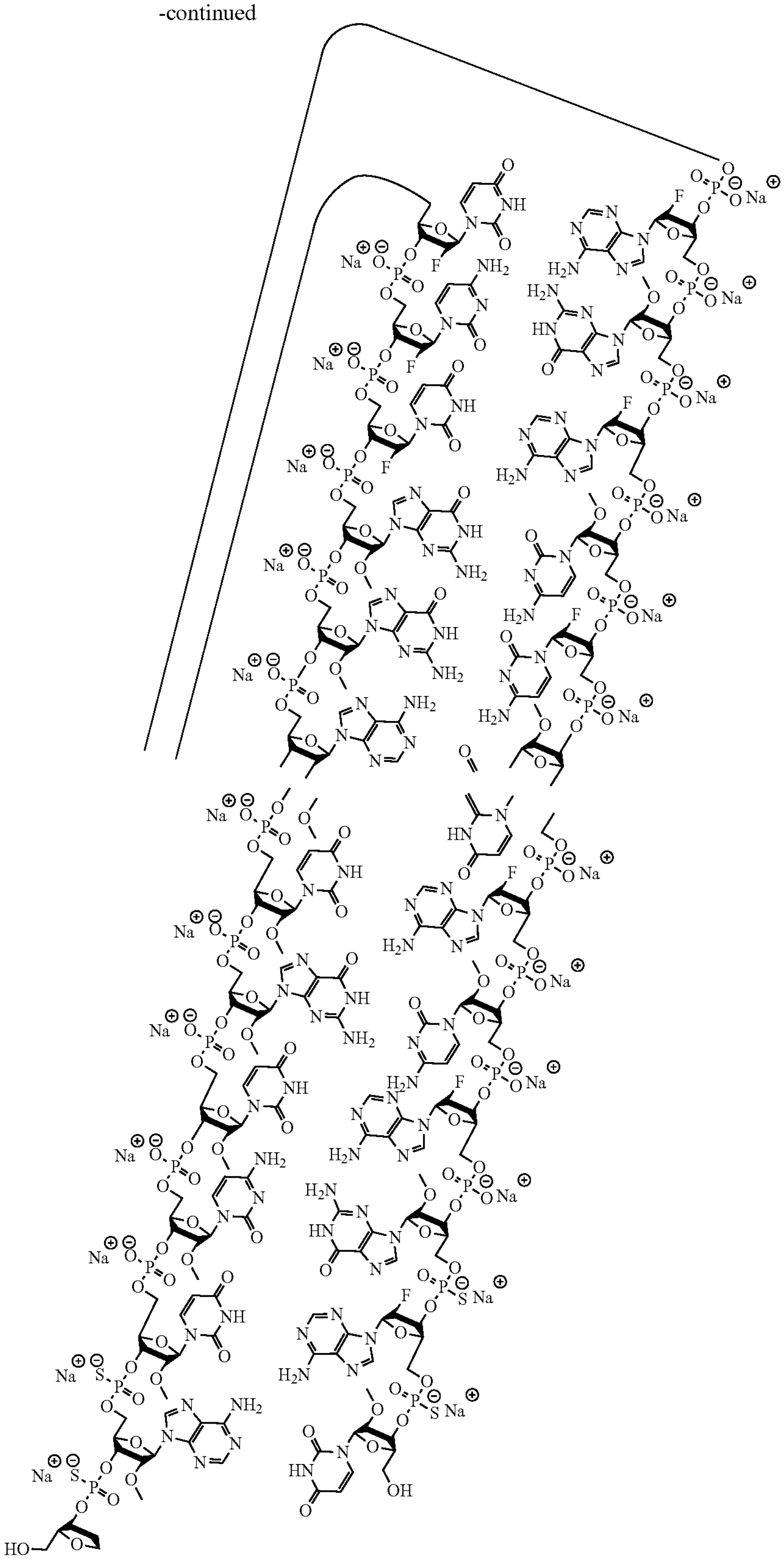
or a stereoisomer thereof.

Embodiment 71. A composition comprising the compound or modified oligonucleotide of any one of embodiments 1-70 and a pharmaceutically acceptable carrier.

Embodiment 72. A composition comprising a compound or modified oligonucleotide of any one of the preceding embodiments, for use in therapy.

Embodiment 73. A method of administering the compound or modified oligonucleotide of any one of embodiments 1-70 or the composition of embodiment 71 or 72 to a subject in need thereof.

Embodiment 74. A method of treating, preventing, or ameliorating a disease, disorder, or condition associated with Complement Factor B (CFB) comprising administering to a subject in need thereof a compound or modified oligonucleotide targeted to CFB, thereby treating, preventing, or ameliorating the disease, disorder, or condition.

Embodiment 75. The method of embodiment 74, wherein the disease, disorder, or condition is a complement pathway disease.

Embodiment 76. The method of any one of embodiments 73-75, wherein administering the compound inhibits, reduces, and/or improves the disease, disorder, condition or a symptom thereof.

Embodiment 77. A method of inhibiting expression of CFB in a cell comprising contacting the cell with a compound or modified oligonucleotide targeted to CFB, thereby inhibiting expression of CFB in the cell.

Embodiment 78. The method of embodiment 77, wherein the cell is in the liver of an individual.

Embodiment 79. The method of embodiment 78, wherein the subject has, or is at risk of having, a complement pathway disease, disorder, condition or a symptom thereof.

Embodiment 80. A method of reducing or inhibiting a complement pathway disease, disorder, condition or a symptom thereof comprising administering to a subject in need thereof a compound or modified oligonucleotide targeted to CFB.

Embodiment 81. The method of embodiment 80, wherein the subject has, or is at risk of having, a complement pathway disease, disorder or condition or a symptom thereof.

Embodiment 82. The method of any one of embodiments 74-81, wherein the disease, disorder or condition is atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), diabetic nephropathy, membranous nephropathy, polycystic kidney disease, age-related macular degeneration, thrombotic microangiopathy, myasthenia gravis, ischemia, reperfusion injury, or rheumatoid arthritis (RA).

Embodiment 83. The method of any one of embodiments 74-82, wherein the disease, disorder or condition is lupus nephritis.

Embodiment 84. The method of any one of embodiments 74-83, wherein the compound is a compound targeted to CFB.

Embodiment 85. The method of any one of embodiments 74-84, wherein the compound is the compound or modified oligonucleotide of any one of embodiments 1-70 or the composition of embodiment 71 or 72.

Embodiment 86. The method of embodiment 85, wherein the compound, modified oligonucleotide, or composition is administered parenterally.

Embodiment 87. Use of a compound targeted to CFB for treating, preventing, or ameliorating a disease, disorder or condition associated with CFB comprising administering to a subject in need thereof a compound or modified oligonucleotide targeted to CFB.

Embodiment 88. The use of embodiment 87, wherein the disease is a complement pathway disease, disorder, condition or a symptom thereof.

Embodiment 89. The use of embodiment 87 or 88, wherein the compound is a compound targeted to CFB.

Embodiment 90. The use of any one of embodiments 87-89, wherein the compound is the compound or modified oligonucleotide of any one of embodiments 1-70 or the composition of embodiment 71 or 72.

Embodiment 91. Use of a compound targeted to CFB in the manufacture of a medicament for treating, preventing, or ameliorating a disease, disorder or condition associated with CFB.

Embodiment 92. The use of any one of embodiments 87-91, wherein the disease is a complement pathway disease, disorder or condition or a symptom thereof, atypical hemolytic uremic syndrome (aHUS), paroxysmal nocturnal hemoglobinuria (PNH), C3 glomerulopathy (C3G), IgA nephropathy (IgAN), systemic lupus erythematosus (SLE), diabetic nephropathy, membranous nephropathy, polycystic kidney disease, age-related macular degeneration, thrombotic microangiopathy, myasthenia gravis, ischemia, reperfusion injury, or rheumatoid arthritis (RA).

Embodiment 93. The use of any one of embodiments 87-92, wherein the disease, disorder or condition is lupus nephritis.

Embodiment 94. The use of any one of embodiments 87-93, wherein the compound is a compound targeted to CFB.

Embodiment 95. The use of any one of embodiments 87-94, wherein the compound is the compound or modified oligonucleotide of any one of embodiments 1-70 or the composition of embodiment 71 or 72.

Embodiment 96. The method or use of any one of embodiments 73-95, wherein the compound or composition is administered to the subject about once every three months to about once every year.

Embodiment 97. The method or use of any one of embodiments 73-96, wherein the compound or composition is administered to the subject about once every three months, about once every six months, or about once every year.

EXAMPLES

The following examples describe the process to identify lead compounds targeted to CFB. Certain compounds are distinguished as having high potency and tolerability.

The following examples serve only to illustrate the compounds described herein and are not intended to limit the same. The following examples and related sequence listing accompanying this filing may identify sequence as either "RNA" or "DNA"; however, as disclosed herein, those sequences may be modified with any combination of chemical modifications. One of skill in the art will readily appreciate that the designation of a sequence as "RNA" or "DNA" is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (methylated uracil for natural uracil of RNA). Accordingly, nucleic acid sequences provided herein, including, but not limited to, those in the sequence listing, are intended to encompass nucleic acids containing any combination of natural or modified RNA and/or DNA, including, but not limited to, such nucleic acids having modified nucleobases.

Each of the references recited in the present application is incorporated herein by reference in its entirety.

TABLE 1

| Chemical Nomenclature | |
|---|---|
| Abbreviation | Structure |
| 'm' | 2'-O-methyl sugar modification (e.g., mA, mG, mC, mU) |
| 'f' | 2'-F sugar modification (e.g., fA, fG, fC, fU) |
| '*' | Phosphorothioate internucleoside linkage |
| '.' | Phosphate internucleoside linkage |
| 'dQ' | Inverted abasic deoxyribose |
| 'H1' | Formula I |
| 'H2' | Formula II |
| 'H4' | Formula III |
| 'H6' | Formula IV |
| 'H7' | Formula V |
| 'H9' | Formula VI |
| 'Hd' | Formula VII |
| 'HL' | Formula VIII |
| 'Hi' | Formula XII |

The newly designed double-stranded compounds in Tables 2 and 3 below were designed as unmodified (Table 2) and modified (Table 3) compounds. Abbreviations for chemical modifications used in Table 3 are provided in Table 1 above. IA and IS in a Ref ID NO:, identifies it as an antisense strand or sense strand of a compound, respectively. It is understood that the sequence set forth in each SEQ ID NO contained herein is independent of any modification to a sugar moiety, an internucleoside linkage, or a nucleobase even if shown in context with a modified compound. Oligomeric compounds referenced by Compound Number or Ref ID NO indicate a combination of nucleobase sequence and chemical modifications. "Start site" indicates the 5'-most nucleotide to which the compound is targeted in the human gene sequence (opposite to the 3'-most nucleoside of an antisense oligonucleotide). "Stop site" indicates the 3'-most nucleotide to which the compound is targeted in the human gene sequence opposite to the 5'-most nucleoside of an antisense oligonucleotide). Each compound listed in Tables 2 and 3 is targeted to the human CFB mRNA, designated herein as SEQ ID NO: 1 (GENBANK Accession No. NM_001710.6).

TABLE 2

Unmodified Antisense and Sense sequences of double-stranded compounds targeting CFB

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
|---|---|---|---|---|---|---|
| RD1705 | 940 | 960 | UAUCCAUCUAGCAUCAGGUAG | 11 | UCUACCUGAUGCUAGAUGGAUA | 45 |
| RD1706 | 943 | 963 | UCUGAUCCAUCUAICACCAGG | 12 | UCCUGGUGUUAGAUGGAUCAGA | 46 |
| RD1707 | 2398 | 2418 | AGAAAACCCAAAUUCUCAUCU | 13 | UAGAUGAGAAUUUGGGUUUUCU | 47 |
| RD1708 | 2398 | 2418 | AGAAAACCCAAAUUCUCAUCC | 14 | UGGAUGAGAAUUUGGGUUUUCU | 48 |
| RD1709 | 2281 | 2301 | UAGACAUCCACUAUUCCCCAG | 15 | UCUGGGGAAUAGUGGAUGUCUA | 49 |
| RD1710 | 2281 | 2301 | UAGACAUCCACUAUUCCCCAU | 16 | UAUGGGGAAUAGUGGAUGUCUA | 50 |
| RD1711 | 2284 | 2304 | UUGCAGACAUCCAUUACUCCC | 17 | UGGGAGUAAUGGAUGUCUGCAA | 51 |
| RD1712 | 2284 | 2304 | UUGCAGACAUCCAUUACUCCC | 17 | UGGGAGUAAUGGAUGUCUACAA | 52 |
| RD1713 | 2284 | 2304 | UUGCAGACAUCCAUUACUCCU | 18 | UAGGAGUAAUGGAUGUCUACAA | 53 |
| RD1714 | 241 | 261 | UUGAUCUCUACCCUCUCCAGA | 19 | UUCUGGAGAGGGUAGAGAUCAA | 54 |
| RD1715 | 1759 | 1779 | UCUAUCUCCAGGUUCCGCUUC | 20 | UGAAGCGGAACCUGGAGAUAGA | 55 |
| RD1716 | 2050 | 2070 | UUGAUGUAGACCUUCUUCCGA | 21 | UUCGGAAGAAGGUCUACAUCAA | 56 |
| RD1725 | 947 | 967 | UCUGUCUGAUCCAUCUAGCAC | 22 | UGUGCUAGAUGGAUCAGACAGA | 57 |
| RD1726 | 947 | 967 | UCUGUCUGAUCCAUCUAGCAC | 22 | UGUGCUAGAUGGAUCAGAUAGA | 58 |
| RD1727 | 947 | 967 | UCUGUCUGAUCCAUCUAGCAC | 22 | UGUGCUAGAUGGAUCAGAAAGA | 59 |
| RD1728 | 1988 | 2008 | AUCCUGUGCAGGGAGCAGCUC | 23 | GAGCUGCUCCCUGCACAGGAU | 60 |
| RD1729 | 1988 | 2008 | AUCCUGUGCAGGGAGCAGCUC | 23 | GAGCUGCUCCCUGCACAGAAU | 61 |
| RD1730 | 1988 | 2008 | AUCCUGUGCAGGGAGCAGCUC | 23 | GAGCUGCUCCCUGCACAAGAU | 62 |
| RD2262 | 2050 | 2070 | UUGAUGUAGACCUUCUUCCGA | 21 | UUCGGAAGAAGGUCUACAUCAA | 56 |
| RD2273 | 493 | 515 | UGAAAGAGAUCUCAUCACUCACA | 24 | UGUGAGUGAUGAGAUCUCUUUCA | 63 |
| RD2275 | 1383 | 1404 | UAGACAUCCAGAUAAUCCUCCC | 25 | UGGGAGGAUUAUCUGGAUGUCUA | 64 |

TABLE 2-continued

Unmodified Antisense and Sense sequences of double-stranded compounds targeting CFB

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
|---|---|---|---|---|---|---|
| RD2276 | 1452 | 1473 | UCAUUGUCUUUCUUGGAAGCCA | 26 | UGGCUUCCAAGAAAGACAAUGA | 65 |
| RD2277 | 1759 | 1779 | UCUAUCUCCAGGUCCCGCUUC | 27 | UGAAGCGGGACCUGGAGAUAGA | 66 |
| RD2278 | 2056 | 2076 | UCAUUCUUGAUGUAGACCUCC | 28 | UGGAGGUCUACAUCAAGAAUGA | 67 |
| RD2279 | 923 | 944 | UGUAGAUGUUCAUGGAGCCUGA | 29 | UCAGGCUCCAUGAACAUCUACA | 68 |
| RD2380 | 2284 | 2304 | UUGCAGACAUCCAUUACUCCC | 17 | UGGGAGUAAUGGAUGUCUGCAA | 51 |
| RD2381 | 2282 | 2304 | UUGCAGACAUCCAUUACUCCCCA | 30 | UGGGGAGUAAUGGAUGUCUGCAA | 69 |
| RD2382 | 2282 | 2304 | UUGCAGACAUCCAUUACUCCCCA | 30 | UGGGAGUAAUGGAUGUCUGCAA | 51 |
| RD2383 | 2283 | 2304 | UUGCAGACAUCCAUUACUCCCC | 31 | UGGGAGUAAUGGAUGUCUGCAAU | 70 |
| RD2384 | 2282 | 2304 | UUGCAGACAUCCAUUACUCCCCA | 30 | UGGGGAGUAAUGGAUGUCUGCAAU | 71 |
| RD2385 | 2282 | 2304 | UUGCAGACAUCCAUUACUCCCCA | 30 | UGGGAGUAAUGGAUGUCUGCAAU | 70 |
| RD2386 | 2281 | 2301 | UAGACAUCCACUAUUCCCCAG | 15 | UCUGGGGAAUAGUGGAUGUCUA | 49 |
| RD2388 | 2279 | 2301 | UAGACAUCCACUAUUCCCCAGCU | 32 | CUGGGGAAUAGUGGAUGUCUA | 72 |
| RD2390 | 2279 | 2301 | UAGACAUCCACUAUUCCCCAGCU | 32 | CUGGGGAAUAGUGGAUGUCUAU | 73 |
| RD2391 | 2280 | 2301 | UAGACAUCCACUAUUCCCCAGC | 33 | UGCUGGGGAAUAGUGGAUGUCUA | 74 |
| RD2392 | 2396 | 2418 | AGAAAACCCAAAUUCUCAUCUUG | 34 | CAAGAUGAGAAUUUGGGUUUUCU | 75 |
| RD2393 | 2396 | 2418 | AGAAAACCCAAAUUCUCAUCUGG | 35 | CCAGAUGAGAAUUUGGGUUUUCU | 76 |
| RD2394 | 2397 | 2418 | AGAAAACCCAAAUUCUCAUCUG | 36 | UCAGAUGAGAAUUUGGGUUUUCU | 77 |
| RD2395 | 2397 | 2418 | AGAAAACCCAAAUUCUCAUCUG | 36 | CAGAUGAGAAUUUGGGUUUUCU | 78 |
| RD2396 | 2397 | 2418 | AGAAAACCCAAAUUCUCAUCCG | 37 | CGGAUGAGAAUUUGGGUUUUCU | 79 |
| RD2401 | 940 | 960 | UAUCCAUCUAGCAUCAGGUAG | 11 | UCUACCUGAUGCUAGAUGGAUA | 45 |
| RD2402 | 938 | 960 | UAUCCAUCUAGCAUCAGGUAGAU | 38 | UCUACCUGAUGCUAGAUGGAUA | 45 |
| RD2403 | 939 | 960 | UAUCCAUCUAGCAUCAGGUAGA | 39 | UUCUACCUGAUGCUAGAUGGAUA | 80 |
| RD2404 | 939 | 960 | UAUCCAUCUAGCAUCAGGUAGG | 40 | UCCUACCUGAUGCUAGAUGGAUA | 81 |
| RD2405 | 939 | 960 | UAUCCAUCUAGCAUCAGGUAGA | 39 | UCUACCUGAUGCUAGAUGGAUA | 45 |
| RD2406 | 938 | 960 | UAUCCAUCUAGCAUCAGGUAGAU | 38 | UCUACCUGAUGCUAGAUGGAUAU | 82 |
| RD2407 | 940 | 960 | UAUCCAUCUAGCAUCAGGUAG | 11 | UCUACCUGAUGCUAGAUGGAUAU | 82 |
| RD2408 | 939 | 960 | UAUCCAUCUAGCAUCAGGUAGA | 39 | UCUACCUGAUGCUAGAUGGAUAU | 82 |
| RD2409 | 939 | 960 | UAUCCAUCUAGCAUCAGGUAGG | 40 | UCCUACCUGAUGCUAGAUGGAUAU | 83 |
| RD2501 | 2398 | 2418 | AGAAAACCCAAAUUCUCAUCU | 13 | UAAUUUGGGUUUUCU | 84 |
| RD2502 | 2398 | 2418 | AGAAAACCCAAAUUCUCAUCU | 13 | UAAUUUGGGUUUUCU | 84 |
| RD2503 | 2398 | 2418 | AGAAAACCCAAAUUCUCAUCU | 13 | UAAUUUGGGUUUUCU | 84 |
| RD2504 | 2398 | 2418 | AGAAAACCCAAAUUCUCAUCU | 13 | UAAUUUGGGUUUUCU | 84 |
| RD2505 | 2398 | 2418 | AGAAAACCCAAAUUCUCAUCU | 13 | UAAUUUGGGUUUUCU | 84 |
| RD2506 | 2398 | 2418 | AGAAAACCCAAAUUCUCAUCU | 13 | UAAUUUGGGUUUUCU | 84 |
| RD2507 | 2398 | 2418 | AGAAAACCCAAAUUCUCAUCU | 13 | UAAUUUGGGUUUUCU | 84 |

TABLE 2-continued

Unmodified Antisense and Sense sequences of double-stranded compounds targeting CFB

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
|---|---|---|---|---|---|---|
| RD2508 | 2398 | 2418 | AGAAAACCCAAAUUCUCAUCU | 13 | UAAUUUGGGUUUUCU | 84 |
| RD2509 | 2398 | 2418 | AGAAAACCCAAAUUCUCAUCU | 13 | UAAUUUGGGUUUUCU | 84 |
| RD2512 | 2398 | 2418 | AGAAAACCCAAAUUCUCAUCU | 13 | UUUGGGUUUUCU | 85 |
| RD2513 | 2279 | 2301 | UAGACAUCCACUAUUCCCCAGCU | 32 | AGCUGGGGAAUAGUGGAUGUCUAU | 86 |
| RD2518 | 2398 | 2418 | AGAAAACCCAAAUUCUCAUCU | 13 | AAUUUGGGUUUUCU | 87 |
| RD2519 | 2398 | 2418 | AGAAAACCCAAAUUCUCAUCU | 13 | AUUUGGGUUUUCU | 88 |
| RD2520 | 2279 | 2301 | UAGACAUCCACUAUUCCCCAGCU | 32 | AGCUGGGGAAUAGUGGAUGUCUA | 89 |
| RD2533 | 2396 | 2418 | AGAAAACCCAAAUUCUCAUCUUG | 34 | AAGAUGAGAAUUUGGGUUUUCU | 90 |
| RD2534 | 2282 | 2304 | UUGCAGACAUCCAUUACUCCCCA | 30 | UGGGAGUAAUGGAUGUUUGCAA | 91 |
| RD2557 | 1316 | 1338 | UCAUCAAUGACAGUAAUUGGGUC | 41 | CCCAAUUACUGUCAUUGAUGA | 92 |
| RD2558 | 1430 | 1452 | AAAGCAUUGAUGUUCACUUGGUU | 42 | CCAAGUGAACAUCAAUGCUUU | 93 |
| RD2559 | 1667 | 1689 | ACAAAGUACUCAGACACCACACG | 43 | UGUGGUGUCUGAGUACUUUGU | 94 |
| RD2560 | 2249 | 2271 | UCAACUUGAAUGAAACGACUUCU | 44 | AAGUCGUUUCAUUCAAGUUGA | 95 |

TABLE 3

Modified Antisense and Sense sequences of double-stranded compounds targeting CFB

| Compound | Modified Strands (5'-3') | Ref ID NO: | SEQ ID NO: |
|---|---|---|---|
| RD1705 | mU*fA*mU.fC.mC.fA.mU.fC.mU.fA.mG.fC.mA.fU.mC.fA.mG.fG.mU*fA*mG | IA0478 | 11 |
| | H2.mC*mU*mA.mC.mC.mU.fG.mA.fU.fG.fC.fU.mA.mG.mA.mU.mG.mG.mA.mU*mA*dQ | IS0570 | 45 |
| RD1706 | mU*fC*mU.fG.mA.fU.mC.fC.mA.fU.mC.fU.mA.f1.mC.fA.mC.fC.mA*fG*mG | IA0479 | 12 |
| | H2.mC*mC*mU.mG.mG.mU.fG.mU.fU.fA.fG.fA.mU.mG.mG.mA.mU.mC.mA.mG*mA*dQ | IS0571 | 46 |
| RD1707 | mA*fG*mA.fA.mA.fA.mC.fC.mC.fA.mA.fA.mU.fU.mC.fU.mC.fA.mU*fC*mU | IA0480 | 13 |
| | H2.mA*mG*mA.mU.mG.mA.fG.mA.fA.fU.fU.fU.mG.mG.mG.mU.mU.mU.mU.mC*mU*dQ | IS0572 | 47 |
| RD1708 | mA*fG*mA.fA.mA.fA.mC.fC.mC.fA.mA.fA.mU.fU.mC.fU.mC.fA.mU*fC*mC | IA0481 | 14 |
| | H2.mG*mG*mA.mU.mG.mA.fG.mA.fA.fU.fU.fU.mG.mG.mG.mU.mU.mU.mU.mC*mU*dQ | IS0573 | 48 |
| RD1709 | mU*fA*mG.fA.mC.fA.mU.fC.mC.fA.mC.fU.mA.fU.mU.fC.mC.fC.mC*fA*mG | IA0482 | 15 |
| | H2.mC*mU*mG.mG.mG.mG.fA.mA.fU.fA.fG.fU.mG.mG.mA.mU.mG.mU.mC.mU*mA*dQ | IS0574 | 49 |
| RD1710 | mU*fA*mG.fA.mC.fA.mU.fC.mC.fA.mC.fU.mA.fU.mU.fC.mC.fC.mC*fA*mU | IA0483 | 16 |
| | H2.mA*mU*mG.mG.mG.mG.fA.mA.fU.fA.fG.fU.mG.mG.mA.mU.mG.mU.mC.mU*mA*dQ | IS0575 | 50 |
| RD1711 | mU*fU*mG.fC.mA.fG.mA.fC.mA.fU.mC.fC.mA.fU.mU.fA.mC.fU.mC*fC*mC | IA0484 | 17 |
| | H2.mG*mG*mG.mA.mG.mU.fA.mA.fU.fG.fG.fA.mU.mG.mU.mC.mU.mG.mC.mA*mA*dQ | IS0576 | 51 |
| RD1712 | mU*fU*mG.fC.mA.fG.mA.fC.mA.fU.mC.fC.mA.fU.mU.fA.mC.fU.mC*fC*mC | IA0484 | 17 |
| | H2.mG*mG*mG.mA.mG.mU.fA.mA.fU.fG.fG.fA.mU.mG.mU.mC.mU.mA.mC.mA*mA*dQ | IS0577 | 52 |

TABLE 3-continued

Modified Antisense and Sense sequences of double-stranded compounds targeting CFB

| Compound | Modified Strands (5'-3') | Ref ID NO: | SEQ ID NO: |
|---|---|---|---|
| RD1713 | mU*fU*mG.fC.mA.fG.mA.fC.mA.fU.mC.fC.mA.fU.mU.fA.mC.fU.mC*fC*mU | IA0485 | 18 |
| | H2.mA*mG*mG.mA.mG.mU.fA.mA.fU.fG.fG.fA.mU.mG.mU.mC.mU.mA.mC.mA*mA*dQ | IS0578 | 53 |
| RD1714 | mU*fU*mG.fA.mU.fC.mU.fC.mU.fA.mC.fC.mC.fU.mC.fU.mC.fC.mA*fG*mA | IA0486 | 19 |
| | H2.mU*mC*mU.mG.mG.mA.fG.mA.fG.fG.fG.fU.mA.mG.mA.mG.mA.mU.mC.mA*mA*dQ | IS0579 | 54 |
| RD1715 | mU*fC*mU.fA.mU.fC.mU.fC.mC.fA.mG.fG.mU.fU.mC.fC.mG.fC.mU*fU*mC | IA0487 | 20 |
| | H2.mG*mA*mA.mG.mC.mG.fG.mA.fA.fC.fC.fU.mG.mG.mA.mG.mA.mU.mA.mG*mA*dQ | IS0580 | 55 |
| RD1716 | mU*fU*mG.fA.mU.fG.mU.fA.mG.fA.mC.fC.mU.fU.mC.fU.mU.fC.mC*fG*mA | IA0488 | 21 |
| | H2.mU*mC*mG.mG.mA.mA.fG.mA.fA.fG.fG.fU.mC.mU.mA.mC.mA.mU.mC.mA*mA*dQ | IS0581 | 56 |
| RD1725 | mU*fC*mU.fG.mU.fC.mU.fG.mA.fU.mC.fC.mA.fU.mC.fU.mA.fG.mC*fA*mC | IA0489 | 22 |
| | H2.mG*mU*mG.mC.mU.mA.fG.mA.fU.fG.fG.fA.mU.mC.mA.mG.mA.mC.mA.mG*mA*dQ | IS0582 | 57 |
| RD1726 | mU*fC*mU.fG.mU.fC.mU.fG.mA.fU.mC.fC.mA.fU.mC.fU.mA.fG.mC*fA*mC | IA0489 | 22 |
| | H2.mG*mU*mG.mC.mU.mA.fG.mA.fU.fG.fG.fA.mU.mC.mA.mG.mA.mU.mA.mG*mA*dQ | IS0583 | 58 |
| RD1727 | mU*fC*mU.fG.mU.fC.mU.fG.mA.fU.mC.fC.mA.fU.mC.fU.mA.fG.mC*fA*mC | IA0489 | 22 |
| | H2.mG*mU*mG.mC.mU.mA.fG.mA.fU.fG.fG.fA.mU.mC.mA.mG.mA.mA.mA.mG*mA*dQ | IS0584 | 59 |
| RD1728 | mA*fU*mC.fC.mU.fG.mU.fG.mC.fA.mG.fG.mG.fA.mG.fC.mA.fG.mC*fU*mC | IA0490 | 23 |
| | mG*mA*mG.mC.mU.mG.fC.mU.fC.fC.fC.fU.mG.mC.mA.mC.mA.mG.mG.mA*mU*dQ | IS0585 | 60 |
| RD1729 | mA*fU*mC.fC.mU.fG.mU.fG.mC.fA.mG.fG.mG.fA.mG.fC.mA.fG.mC*fU*mC | IA0490 | 23 |
| | mG*mA*mG.mC.mU.mG.fC.mU.fC.fC.fC.fU.mG.mC.mA.mC.mA.mG.mA.mA*mU*dQ | IS0586 | 61 |
| RD1730 | mA*fU*mC.fC.mU.fG.mU.fG.mC.fA.mG.fG.mG.fA.mG.fC.mA.fG.mC*fU*mC | IA0490 | 23 |
| | mG*mA*mG.mC.mU.mG.fC.mU.fC.fC.fC.fU.mG.mC.mA.mC.mA.mA.mG.mA*mU*dQ | IS0587 | 62 |
| RD2262 | mU*fU*mG.fA.mU.fG.mU.fA.mG.fA.mC.fC.mU.fU.mC.fU.mU.fC.mC*fG*mA | IA0488 | 21 |
| | H4.mU*mC*mG.mG.mA.mA.fG.mA.fA.fG.fG.fU.mC.mU.mA.mC.mA.mU.mC.mA*mA*dQ | IS0969 | 56 |
| RD2273 | mU*fG*mA.fA.mA.fG.mA.fG.mA.fU.mC.fU.mC.fA.mU.fC.mA.fC.mU.fC.mA*fC*mA | IA0840 | 24 |
| | H4.mG*mU*mG.mA.mG.mU.mG.fA.mU.fG.fA.fG.fA.mU.mC.mU.mC.mU.mU.mU.mC*mA*dQ | IS0972 | 63 |
| RD2275 | mU*fA*mG.fA.mC.fA.mU.fC.mC.fA.mG.fA.mU.fA.mA.fU.mC.fC.mU.fC*mC*mC | IA0842 | 25 |
| | H4.mG*mG*mG.mA.mG.mG.mA.fU.mU.fA.fU.fC.fU.mG.mG.mA.mU.mG.mU.mC.mU*mA*dQ | IS0974 | 64 |
| RD2276 | mU*fC*mA.fU.mU.fG.mU.fC.mU.fU.mU.fC.mU.fU.mG.fG.mA.fA.mG.fC*mC*mA | IA0843 | 26 |
| | H4.mG*mG*mC.mU.mU.mC.fC.mA.fA.fG.fA.fA.mA.mG.mA.mC.mA.mA.mU.mG*mA*dQ | IS0975 | 65 |
| RD2277 | mU*fC*mU.fA.mU.fC.mU.fC.mC.fA.mG.fG.mU.fC.mC.fC.mG.fC.mU*fU*mC | IA0844 | 27 |
| | H4.mG*mA*mA.mG.mC.mG.fG.mG.fA.fC.fC.fU.mG.mG.mA.mG.mA.mU.mA.mG*mA*dQ | IS0976 | 66 |
| RD2278 | mU*fC*mA.fU.mU.fC.mU.fU.mG.fA.mU.fG.mU.fA.mG.fA.mC.fC.mU*fC*mC | IA0845 | 28 |
| | H4.mG*mG*mA.mG.mG.mU.fC.mU.fA.fC.fA.fU.mC.mA.mA.mG.mA.mA.mU.mG*mA*dQ | IS0977 | 67 |
| RD2279 | mU*fG*mU.fA.mG.fA.mU.fG.mU.fU.mC.fA.mU.fG.mG.fA.mG.fC.mC.fU*mG*mA | IA0846 | 29 |
| | H4.mC*mA*mG.mG.mC.mU.fC.mC.fA.fU.fG.fA.mA.mC.mA.mU.mC.mU.mA.mC*mA*dQ | IS0973 | 68 |
| RD2380 | mU*fU*mG.fC.mA.fG.mA.fC.mA.fU.mC.fC.mA.fU.mU.fA.mC.fU.mC*fC*mC | IA0484 | 17 |
| | H4*mG*mG.mG.mA.mG.mU.fA.mA.fU.fG.fG.fA.mU.mG.mU.mC.mU.mG.mC.mA*mA*dQ | IS1023 | 51 |

TABLE 3-continued

Modified Antisense and Sense sequences of double-stranded compounds targeting CFB

| Com-pound | Modified Strands (5'-3') | Ref ID NO: | SEQ ID NO: |
|---|---|---|---|
| RD2381 | mU*fU*mG.fC.mA.fG.mA.fC.mA.fU.mC.fC.mA.fU.mU.fA.mC.fU.mC.fC.mC*mC*mA | IA0852 | 30 |
| | H4*mG*mG.mG.mG.mA.mG.mU.fA.mA.fU.fG.fG.fA.mU.mG.mU.mC.mU.mG.mC.mA*mA*dQ | IS1024 | 69 |
| RD2382 | mU*fU*mG.fC.mA.fG.mA.fC.mA.fU.mC.fC.mA.fU.mU.fA.mC.fU.mC.fC.mC*mC*mA | IA0852 | 30 |
| | H4*mG*mG.mG.mA.mG.mU.fA.mA.fU.fG.fG.fA.mU.mG.mU.mC.mU.mG.mC.mA*mA*dQ | IS1023 | 51 |
| RD2383 | mU*fU*mG.fC.mA.fG.mA.fC.mA.fU.mC.fC.mA.fU.mU.fA.mC.fU.mC.fC*mC*mC | IA0853 | 31 |
| | H4*mG*mG.mG.mA.mG.mU.fA.mA.fU.fG.fG.fA.mU.mG.mU.mC.mU.mG.mC.mA.mA*mU*dQ | IS1025 | 70 |
| RD2384 | mU*fU*mG.fC.mA.fG.mA.fC.mA.fU.mC.fC.mA.fU.mU.fA.mC.fU.mC.fC.mC*mC*mA | IA0852 | 30 |
| | H4.mG*mG*mG.mG.mA.mG.mU.fA.mA.fU.fG.fG.fA.mU.mG.mU.mC.mU.mG.mC.mA.mA*mU*dQ | IS1026 | 71 |
| RD2385 | mU*fU*mG.fC.mA.fG.mA.fC.mA.fU.mC.fC.mA.fU.mU.fA.mC.fU.mC.fC.mC*mC*mA | IA0852 | 30 |
| | H4*mG*mG.mG.mA.mG.mU.fA.mA.fU.fG.fG.fA.mU.mG.mU.mC.mU.mG.mC.mA.mA*mU*dQ | IS1025 | 70 |
| RD2386 | mU*fA*mG.fA.mC.fA.mU.fC.mC.fA.mC.fU.mA.fU.mU.fC.mC.fC.mC*fA*mG | IA0482 | 15 |
| | H4*mC*mU.mG.mG.mG.mG.fA.mA.fU.fA.fG.fU.mG.mG.mA.mU.mG.mU.mC.mU*mA*dQ | IS1027 | 49 |
| RD2388 | mU*fA*mG.fA.mC.fA.mU.fC.mC.fA.mC.fU.mA.fU.mU.fC.mC.fC.mC.fA.mG*mC*mU | IA0854 | 32 |
| | H9*mU*mG.mG.mG.mG.fA.mA.fU.fA.fG.fU.mG.mG.mA.mU.mG.mU.mC.mU*mA*dQ | IS1029 | 72 |
| RD2390 | mU*fA*mG.fA.mC.fA.mU.fC.mC.fA.mC.fU.mA.fU.mU.fC.mC.fC.mC.fA.mG*mC*mU | IA0854 | 32 |
| | H9*mU*mG.mG.mG.mG.fA.mA.fU.fA.fG.fU.mG.mG.mA.mU.mG.mU.mC.mU.mA*mU*dQ | IS1031 | 73 |
| RD2391 | mU*fA*mG.fA.mC.fA.mU.fC.mC.fA.mC.fU.mA.fU.mU.fC.mC.fC.mC.fA*mG*mC | IA0855 | 33 |
| | H4*mG*mC.mU.mG.mG.mG.mG.fA.mA.fU.fA.fG.fU.mG.mG.mA.mU.mG.mU.mC.mU*mA*dQ | IS1032 | 74 |
| RD2392 | mA*fG*mA.fA.mA.fA.mC.fC.mC.fA.mA.fA.mU.fU.mC.fU.mC.fA.mU.fC.mU*mU*mG | IA0856 | 34 |
| | H9*mA*mA.mG.mA.mU.mG.mA.fG.mA.fA.fU.fU.fU.mG.mG.mG.mU.mU.mU.mU.mC*mU*dQ | IS1033 | 75 |
| RD2393 | mA*fG*mA.fA.mA.fA.mC.fC.mC.fA.mA.fA.mU.fU.mC.fU.mC.fA.mU.fC.mU*mG*mG | IA0857 | 35 |
| | H9*mC*mA.mG.mA.mU.mG.mA.fG.mA.fA.fU.fU.fU.mG.mG.mG.mU.mU.mU.mU.mC*mU*dQ | IS1034 | 76 |
| RD2394 | mA*fG*mA.fA.mA.fA.mC.fC.mC.fA.mA.fA.mU.fU.mC.fU.mC.fA.mU.fC*mU*mG | IA0858 | 36 |
| | H4*mC*mA.mG.mA.mU.mG.mA.fG.mA.fA.fU.fU.fU.mG.mG.mG.mU.mU.mU.mU.mC*mU*dQ | IS1035 | 77 |
| RD2395 | mA*fG*mA.fA.mA.fA.mC.fC.mC.fA.mA.fA.mU.fU.mC.fU.mC.fA.mU.fC*mU*mG | IA0858 | 36 |
| | H9*mA*mG.mA.mU.mG.mA.fG.mA.fA.fU.fU.fU.mG.mG.mG.mU.mU.mU.mU.mC*mU*dQ | IS1036 | 78 |
| RD2396 | mA*fG*mA.fA.mA.fA.mC.fC.mC.fA.mA.fA.mU.fU.mC.fU.mC.fA.mU.fC*mC*mG | IA0859 | 37 |
| | H9*mG*mG.mA.mU.mG.mA.fG.mA.fA.fU.fU.fU.mG.mG.mG.mU.mU.mU.mU.mC*mU*dQ | IS1037 | 79 |
| RD2401 | mU*fA*mU.fC.mC.fA.mU.fC.mU.fA.mG.fC.mA.fU.mC.fA.mG.fG.mU*fA*mG | IA0478 | 11 |
| | H4*mC*mU.mA.mC.mC.mU.fG.mA.fU.fG.fC.fU.mA.mG.mA.mU.mG.mG.mA.mU*mA*dQ | IS1042 | 45 |
| RD2402 | mU*fA*mU.fC.mC.fA.mU.fC.mU.fA.mG.fC.mA.fU.mC.fA.mG.fG.mU.fA.mG*mA*mU | IA0860 | 38 |
| | H4*mC*mU.mA.mC.mC.mU.fG.mA.fU.fG.fC.fU.mA.mG.mA.mU.mG.mG.mA.mU*mA*dQ | IS1042 | 45 |
| RD2403 | mU*fA*mU.fC.mC.fA.mU.fC.mU.fA.mG.fC.mA.fU.mC.fA.mG.fG.mU.fA*mG*mA | IA0861 | 39 |
| | H4*mU*mC.mU.mA.mC.mC.mU.fG.mA.fU.fG.fC.fU.mA.mG.mA.mU.mG.mG.mA.mU*mA*dQ | IS1043 | 80 |
| RD2404 | mU*fA*mU.fC.mC.fA.mU.fC.mU.fA.mG.fC.mA.fU.mC.fA.mG.fG.mU.fA*mG*mG | IA0862 | 40 |
| | H4*mC*mC.mU.mA.mC.mC.mU.fG.mA.fU.fG.fC.fU.mA.mG.mA.mU.mG.mG.mA.mU*mA*dQ | IS1044 | 81 |

TABLE 3-continued

| Modified Antisense and Sense sequences of double-stranded compounds targeting CFB | | | |
|---|---|---|---|
| Com-pound | Modified Strands (5'-3') | Ref ID NO: | SEQ ID NO: |
| RD2405 | mU*fA*mU.fC.mC.fA.mU.fC.mU.fA.mG.fC.mA.fU.mC.fA.mG.fG.mU.fA*mG*mA | IA0861 | 39 |
| | H4*mC*mU.mA.mC.mC.mU.fG.mA.fU.fG.fC.fU.mA.mG.mA.mU.mG.mG.mA.mU*mA*dQ | IS1042 | 45 |
| RD2406 | mU*fA*mU.fC.mC.fA.mU.fC.mU.fA.mG.fC.mA.fU.mC.fA.mG.fG.mU.fA.mG*mA*mU | IA0860 | 38 |
| | H4*mC*mU.mA.mC.mC.mU.fG.mA.fU.fG.fC.fU.mA.mG.mA.mU.mG.mG.mA.mU.mA*mU*dQ | IS1045 | 82 |
| RD2407 | mU*fA*mU.fC.mC.fA.mU.fC.mU.fA.mG.fC.mA.fU.mC.fA.mG.fG.mU*fA*mG | IA0478 | 11 |
| | H4*mC*mU.mA.mC.mC.mU.fG.mA.fU.fG.fC.fU.mA.mG.mA.mU.mG.mG.mA.mU.mA*mU*dQ | IS1045 | 82 |
| RD2408 | mU*fA*mU.fC.mC.fA.mU.fC.mU.fA.mG.fC.mA.fU.mC.fA.mG.fG.mU.fA*mG*mA | IA0861 | 39 |
| | H4*mC*mU.mA.mC.mC.mU.fG.mA.fU.fG.fC.fU.mA.mG.mA.mU.mG.mG.mA.mU.mA*mU*dQ | IS1045 | 82 |
| RD2409 | mU*fA*mU.fC.mC.fA.mU.fC.mU.fA.mG.fC.mA.fU.mC.fA.mG.fG.mU.fA*mG*mG | IA0862 | 40 |
| | H4*mC*mC.mU.mA.mC.mC.mU.fG.mA.fU.fG.fC.fU.mA.mG.mA.mU.mG.mG.mA.mU.mA*mU*dQ | IS1046 | 83 |
| RD2501 | mA*fG*mA.fA.mA.fA.mC.fC.mC.fA.mA.fA.mU.fU.mC.fU.mC.fA.mU*fC*mU | IA0480 | 13 |
| | H2*mA*fA.fU.fU.fU.mG.mG.mG.mU.mU.mU.mU.mC*mU*dQ | IS1082 | 84 |
| RD2502 | mA*fG*mA.fA.mA.fA.mC.fC.mC.fA.mA.fA.mU.fU.mC.fU.mC.fA*mU*fC*mU | IA0872 | 13 |
| | H2*mA*fA.fU.fU.fU.mG.mG.mG.mU.mU.mU.mU.mC*mU*dQ | IS1082 | 84 |
| RD2503 | mA*fG*mA.fA.mA.fA.mC.fC.mC.fA.mA.fA.mU.fU.mC.fU.mC*fA*mU*fC*mU | IA0873 | 13 |
| | H2*mA*fA.fU.fU.fU.mG.mG.mG.mU.mU.mU.mU.mC*mU*dQ | IS1082 | 84 |
| RD2504 | mA*fG*mA.fA.mA.fA.mC.fC.mC.fA.mA.fA.mU.fU.mC.fU*mC*fA*mU*fC*mU | IA0874 | 13 |
| | H2*mA*fA.fU.fU.fU.mG.mG.mG.mU.mU.mU.mU.mC*mU*dQ | IS1082 | 84 |
| RD2505 | mA*fG*mA.fA.mA.fA.mC.fC.mC.fA.mA.fA.mU.fU.mC*fU*mC*fA*mU*fC*mU | IA0875 | 13 |
| | H2*mA*fA.fU.fU.fU.mG.mG.mG.mU.mU.mU.mU.mC*mU*dQ | IS1082 | 84 |
| RD2506 | mA*fG*mA.fA.mA.fA.mC.fC.mC.fA.mA.fA.mU.fU*mC*fU*mC*fA.mU*fC*mU | IA0876 | 13 |
| | H2*mA*fA.fU.fU.fU.mG.mG.mG.mU.mU.mU.mU.mC*mU*dQ | IS1082 | 84 |
| RD2507 | mA*fG*mA.fA.mA.fA.mC.fC.mC.fA.mA.fA.mU.fU*mC.fU*mC.fA*mU*fC*mU | IA0877 | 13 |
| | H2*mA*fA.fU.fU.fU.mG.mG.mG.mU.mU.mU.mU.mC*mU*dQ | IS1082 | 84 |
| RD2508 | mA*fG*mA.fA.mA.fA.mC.fC.mC.fA.mA.fA.mU.fU.mC*fU.mC*fA.mU*fC*mU | IA0878 | 13 |
| | H2*mA*fA.fU.fU.fU.mG.mG.mG.mU.mU.mU.mU.mC*mU*dQ | IS1082 | 84 |
| RD2509 | mA*fG*mA.fA.mA.fA.mC.fC.mC.fA.mA.fA.mU.fU.mC.fU.mC*fA*mUamC*mU | IA0879 | 13 |
| | H2*mA*fA.fU.fU.fU.mG.mG.mG.mU.mU.mU.mU.mC*mU*dQ | IS1082 | 84 |
| RD2512 | mA*fG*mA.fA.mA.fA.mC.fC.mC.fA.mA*fA*mU*fU*mC*fU*mC*fA*mU*fC*mU | IA0882 | 13 |
| | H2*fU*fU.mG.mG.mG.mU.mU.mU.mU.mC*mU*dQ | IS1085 | 85 |
| RD2513 | mU*fA*mG.fA.mC.fA.mU.fC.mC.fA.mC.fU.mA.fU.mU.fC.mC.fC.mC.fA.mG*mC*mU | IA0854 | 32 |
| | Hd*mG*mC.mU.mG.mG.mG.mG.fA.mA.fU.fA.fG.fU.mG.mG.mA.mU.mG.mU.mC.mU.mA*mU*dQ | IS1086 | 86 |
| RD2518 | mA*fG*mA.fA.mA.fA.mC.fC.mC.fA.mA.fA.mU*fU*mC*fU*mC*fA*mU*fC*mU | IA0880 | 13 |
| | Hd*A*fU.fU.fU.mG.mG.mG.mU.mU.mU.mU.mC*mU*dQ | IS1091 | 87 |
| RD2519 | mA*fG*mA.fA.mA.fA.mC.fC.mC.fA.mA.fA*mU*fU*mC*fU*mC*fA*mU*fC*mU | IA0881 | 13 |
| | Hd*fU*fU.fU.mG.mG.mG.mU.mU.mU.mU.mC*mU*dQ | IS1092 | 88 |

TABLE 3-continued

| Modified Antisense and Sense sequences of double-stranded compounds targeting CFB | | | |
|---|---|---|---|
| Compound | Modified Strands (5'-3') | Ref ID NO: | SEQ ID NO: |
| RD2520 | mU*fA*mG.fA.mC.fA.mU.fC.mC.fA.mC.fU.mA.fU.mU.fC.mC.fC.mC.fA.mG*mC*mU | IA0854 | 32 |
| | Hd*mG*mC.mU.mG.mG.mG.mG.fA.mA.fU.fA.fG.fU.mG.mG.mA.mU.mG.mU.mC.mU*mA*dQ | IS1093 | 89 |
| RD2533 | mA*fG*mA.fA.mA.fA.mC.fC.mC.fA.mA.fA.mU.fU.mC.fU.mC.fA.mU.fC.mU*mU*mG | IA0856 | 34 |
| | Hd*mA*mG.mA.mU.mG.mA.fG.mA.fA.fU.fU.fU.mG.mG.mG.mU.mU.mU.mU.mC*mU*dQ | IS1094 | 90 |
| RD2534 | mU*fU*mG.fC.mA.fG.mA.fC.mA.fU.mC.fC.mA.fU.mU.fA.mC.fU.mC.fC.mC*mC*mA | IA0852 | 30 |
| | H2*mG*mG.mG.mA.mG.mU.fA.mA.fU.fG.fG.fA.mU.mG.mU.mU.mU.mG.mC.mA*mA*dQ | IS1095 | 91 |
| RD2557 | mU*fC*mA.fU.mC.fA.mA.fU.mG.fA.mC.fA.mG.fU.mA.fA.mU.fU.mG.fG.mG*mU*mC | IA0887 | 41 |
| | H7*mC*mC.mA.mA.mU.fU.mA.fC.fU.fG.fU.mC.mA.mU.mU.mG.mA.mU.mG*mA*dQ | IS1108 | 92 |
| RD2558 | mA*fA*mA.fG.mC.fA.mU.fU.mG.fA.mU.fG.mU.fU.mC.fA.mC.fU.mU.fG.mG*mU*mU | IA0888 | 42 |
| | H7*mC*mA.mA.mG.mU.fG.mA.fA.fC.fA.fU.mC.mA.mA.mU.mG.mC.mU.mU*mU*dQ | IS1109 | 93 |
| RD2559 | mA*fC*mA.fA.mA.fG.mU.fA.mC.fU.mC.fA.mG.fA.mC.fA.mC.fC.mA.fC.mA*mC*mG | IA0889 | 43 |
| | H2*mG*mU.mG.mG.mU.fG.mU.fC.fU.fG.fA.mG.mU.mA.mC.mU.mU.mU.mG*mU*dQ | IS1110 | 94 |
| RD2560 | mU*fC*mA.fA.mC.fU.mU.fG.mA.fA.mU.fG.mA.fA.mA.fC.mG.fA.mC.fU.mU*mC*mU | IA0890 | 44 |
| | Hd*mA*mG.mU.mC.mG.fU.mU.fU.fC.fA.fU.mU.mC.mA.mA.mG.mU.mU.mG*mA*dQ | IS1111 | 95 |

Example 1: Inhibition of CFB in HepG2 Cells

HepG2 cells (ATCC Cat #HB-8065) or Hepa 1-6 cells (ATCC CRL-1830) were seeded in antibiotic-free media at 10,000 cells/well in a 96-well plate. The following day, test CFB compound was diluted to 1.0 μM (stock solution is 10 μM). Transfection mixes were prepared according to instructions for Dharmafect 4 transfection reagent (Dharmacon Cat #T-2004-0). Prepared transfection mixtures were incubated at room temperature for 20 minutes. During this incubation, the medium was replaced in the 96-well plates with 80 μl of antibiotic-free medium. 20 μl of the transfection mixture was then added to each well for a final concentration between 10 nM and 1 nM (tested in triplicate). CFB siRNA SMARTpool (Dharmacon Cat #L-005792-00-0005, 042586-00-0005) or Silencer Thermo Fisher (ID1966 or s533333) were used as a positive control. The cells were then incubated at 37° C. in 5% $CO_2$ for 24 hours.

Cell lysis was performed according to the Cells-To-CT 1 Step TaqMan Kit instructions. Following cell lysis, the 96-well plate was placed on ice while the qRT-PCR reaction was prepared. 2 μl of cell lysate was added to the reaction mixture containing 5 μl TaqMan 1-Step qRT-PCR Mix, 1 μl CFB(FAM) TaqMan Gene Expression Assay (Hs00156060_m1 or Mm00433909_m1), 1 μl GAPDH (VIC) TaqMan Gene Expression Assay (Hs02786624_g1 or Mm99999915_g1) and 11 μl RT-PCR grade nuclease-free water in a MicroAmp Optical 96-well plate (0.2 mL). qPCR was performed using a QuantStudio3 qPCR machine with the following cycles: 50° C. for 1 minute, 95° C. for 20 seconds and 40 cycles at 95° C. for 15 seconds and 60° C. for 1 minute. Results are presented in the tables below as percent inhibition of CFB, relative to untreated control cells (Table 4).

TABLE 4

| Inhibition of CFB mRNA by double-stranded compounds targeting SEQ ID NO: 1 | |
|---|---|
| Compound Number | % Inhibition |
| RD1709 | 77 |
| RD1710 | 83 |
| RD1711 | 86 |
| RD1712 | 87 |
| RD1713 | 85 |
| RD1714 | 65 |
| RD1715 | 84 |
| RD1716 | 80 |
| RD1725 | 74 |
| RD1726 | 61 |
| RD1727 | 80 |
| RD1728 | 62 |
| RD1729 | 61 |
| RD1730 | 51 |

Example 2: Effect of Compounds Targeting Human CFB in Mouse

Compounds RD1706, RD1707, RD1727, RD1708, RD1705, and RD1726 as modified in Table 3 were evaluated in C57Bl/6 mice. Prior to the study the mice were kept in a vivarium under IACUC approved housing. Mice were injected with a single 5 mg/kg subcutaneous dose of oligonucleotide on Day 0 of the study. During the study period, the mice were observed daily for signs of illness or distress. Animals were bled on day 0 and 8, 15, 22, 29, and 35.

Immunoblotting was used to evaluate the levels of Complement Factor B (CFB) in the serum of mice (C57Bl/6). Following serum collection, the serum was diluted in 1×PBS buffer and mixed with SDS-PAGE compatible loading buffer and a reducing reagent. Samples were heated to 70° C. for ten minutes and resolved by SDS-PAGE. Following the migration of the samples by PAGE, the proteins were transferred to nitrocellulose or other compatible membrane. The membranes were stained with Revert 700 and total protein for each sample was quantified using an Odyssey CLx detection system.

The membranes were blocked with Intercept® blocking buffer (P/N: 927-60001) and then probed with a primary antibody specific to CFB (Invitrogen #27924). The antibody was diluted in Intercept® antibody diluent (P/N: 927-75001. After incubating the membrane with the primary antibody, the membrane was washed and then probed with a secondary antibody (IgG P/N: 926-32211). The antibody was diluted in Intercept® antibody diluent (P/N: 927-75001). The membranes were then analyzed on an Odyssey CLx detection system to determine the levels of CFB in each sample. The data for each sample was normalized to the total protein loaded into each lane and the CFB levels were quantified using Image Studio Lite. CFB inhibition data in Table 5 are expressed as percent change from the predose level.

TABLE 5

| Average CFB Inhibition | | | | | |
|---|---|---|---|---|---|
| | Days | | | | |
| Compound | 8 | 15 | 22 | 29 | 35 |
| RD1706 | 76 | 67 | 54 | 25 | 27 |
| RD1707 | 68 | 59 | 46 | 31 | 30 |
| RD1727 | 50 | 46 | 32 | 32 | 46 |
| RD1708 | 83 | 81 | 78 | 62 | 39 |
| RD1705 | 74 | 68 | 58 | 44 | 41 |
| RD1726 | 70 | 64 | 54 | 39 | 37 |

Example 3: Effect of Compounds Targeting Human CFB in Mouse

Compounds RD2401, RD2402, RD2403, RD2404, RD2405, RD2406, RD2407, RD2408, and RD2409 as modified in Table 3 were evaluated in C57Bl/6 mice. Prior to the study the mice were kept in a vivarium under IACUC approved housing. Mice were injected with a single 5 mg/kg subcutaneous dose of oligonucleotide on Day 0 of the study. During the study period, the mice were observed daily for signs of illness or distress. Animals were bled on day 0, 8, 15, 22, 29 and 36. Immunoblotting was used to evaluate the levels of Complement Factor B (CFB) in the serum of mice (C57Bl/6) as described in Example 2. CFB inhibition data in Table 6 are expressed as percent change from the predose level.

TABLE 6

| Average CFB Inhibition | | | | | |
|---|---|---|---|---|---|
| | Days | | | | |
| Compound | 8 | 15 | 22 | 29 | 36 |
| RD2401 | 75 | 73 | 91 | 70 | 67 |
| RD2402 | 73 | 70 | 87 | 59 | 51 |
| RD2403 | 78 | 66 | 86 | 60 | 57 |
| RD2404 | 70 | 61 | 69 | 51 | 52 |
| RD2405 | 71 | 62 | 84 | 50 | 49 |

TABLE 6-continued

| Average CFB Inhibition | | | | | |
|---|---|---|---|---|---|
| | Days | | | | |
| Compound | 8 | 15 | 22 | 29 | 36 |
| RD2406 | 73 | 64 | 84 | 56 | 51 |
| RD2407 | 73 | 70 | 88 | 52 | 51 |
| RD2408 | 73 | 71 | 86 | 57 | 55 |
| RD2409 | 68 | 54 | 60 | 49 | 46 |

Example 4: Effect of Compounds Targeting Human CFB in Mouse

Compounds RD2392, RD2393, RD2394, RD2395, and RD2396 as modified in Table 3 were evaluated in C57Bl/6 mice. Prior to the study the mice were kept in a vivarium under IACUC approved housing. Mice were injected with a single 5 mg/kg subcutaneous dose of oligonucleotide on Day 0 of the study. During the study period, the mice were observed daily for signs of illness or distress. Animals were bled on day 0 and 7, 14, 21, 28, and 35. Immunoblotting was used to evaluate the levels of Complement Factor B (CFB) in the serum of mice (C57Bl/6) as described in Example 2. CFB inhibition data in Table 7 are expressed as percent change from the predose level.

TABLE 7

| Average CFB Inhibition | | | | | |
|---|---|---|---|---|---|
| | Days | | | | |
| Compound | 7 | 14 | 21 | 28 | 35 |
| RD2392 | 70 | 81 | 64 | 52 | 19 |
| RD2393 | 78 | 84 | 72 | 68 | 53 |
| RD2394 | 77 | 81 | 53 | 58 | 37 |
| RD2395 | 71 | 82 | 45 | 58 | 33 |
| RD2396 | 71 | 75 | 63 | 60 | 29 |

Example 5: Effect of Compounds Targeting Human CFB in Mouse

Compounds RD1701, RD2501, RD2502, RD2503, RD2504, RD2505, RD2506, RD2507, RD2508, RD2509, RD2512, RD2518, and RD2519 as modified in Table 3 were evaluated in C57Bl/6 mice. Prior to the study the mice were kept in a vivarium under IACUC approved housing. Mice were injected with a single 5 mg/kg subcutaneous dose of oligonucleotide on Day 0 of the study. During the study period, the mice were observed daily for signs of illness or distress. Animals were bled on day 0, 7, 15, 22, 28 and 35. Day 7, 15 and 22 data are shown below. Immunoblotting was used to evaluate the levels of Complement Factor B (CFB) in the serum of mice (C57Bl/6) as described in Example 2. CFB inhibition data in Table 8 are expressed as percent change from the predose level.

TABLE 8

| Average CFB Inhibition | | | |
|---|---|---|---|
| | Days | | |
| Compound | 7 | 15 | 22 |
| RD1701 | 30 | 37 | 36 |
| RD2501 | 2 | 3 | 10 |
| RD2502 | 23 | 0 | 16 |

TABLE 8-continued

| Average CFB Inhibition | | | |
|---|---|---|---|
| | Days | | |
| Compound | 7 | 15 | 22 |
| RD2503 | 32 | 14 | 6 |
| RD2504 | 28 | 6 | 26 |
| RD2505 | 38 | 18 | 24 |
| RD2506 | 28 | 10 | 17 |
| RD2507 | 55 | 25 | 28 |
| RD2508 | 47 | 20 | 3 |
| RD2509 | 14 | 0 | 0 |
| RD2512 | 3 | 3 | 0 |
| RD2518 | 29 | 15 | 5 |
| RD2519 | 18 | 17 | 11 |

Example 6: Effect of Compounds Targeting Human CFB in Rat

Compounds RD1709, RD1710, RD1711, RD1712, and RD1713 as modified in Table 3 were evaluated in Sprague-Dawley or Lewis rats. Prior to the study the rats were kept in a vivarium under IACUC approved housing. Rats were injected with a single 5 mg/kg subcutaneous dose of oligonucleotide on Day 0 of the study. During the study period, the rats were observed daily for signs of illness or distress. Animals were bled on day 0 and 8, 15, 22, 29, and 36. Day 8, 15 and 22 data are shown below.

Immunoblotting was used to evaluate the levels of Complement Factor B (CFB) in the serum of rats (Sprague-Dawley and Lewis). Following serum collection, the serum was diluted in 1×PBS buffer and mixed with SDS-PAGE compatible loading buffer and a reducing reagent. Samples were heated to 70° C. for ten minutes and resolved by SDS-PAGE. Following the migration of the samples by PAGE, the proteins were transferred to nitrocellulose or other compatible membrane. The membranes were stained with Revert 700 and total protein for each sample was quantified using an Odyssey CLx detection system.

The membranes were blocked with Intercept® blocking buffer (P/N: 927-60001) and then probed with a primary antibody specific to CFB (Invitrogen #27924). The antibody was diluted in Intercept® antibody diluent (P/N: 927-75001). After incubating the membrane with the primary antibody, the membrane was washed and then probed with a secondary antibody (IgG P/N: 926-32211). The antibody was diluted in Intercept® antibody diluent (P/N: 927-75001=. The membranes were then analyzed on an Odyssey CLx detection system to determine the levels of CFB in each sample. The data for each sample was normalized to the total protein loaded into each lane and the CFB levels were quantified using Image Studio Lite. CFB inhibition data in Table 9 are expressed as percent change from the predose level.

TABLE 9

| Average CFB Inhibition | | | |
|---|---|---|---|
| | Days | | |
| Compound | 8 | 15 | 22 |
| RD1709 | 75 | 71 | 51 |
| RD1710 | 79 | 75 | 55 |

TABLE 9-continued

| Average CFB Inhibition | | | |
|---|---|---|---|
| | Days | | |
| Compound | 8 | 15 | 22 |
| RD1711 | 64 | 65 | 58 |
| RD1712 | 71 | 72 | 58 |
| RD1713 | 67 | 62 | 51 |

Example 7: Effect of Compounds Targeting Human CFB in Rat

Compounds RD1709, RD1710, RD1711, and RD1712 as modified in Table 3 were evaluated in Sprague-Dawley or Lewis rats. Prior to the study the rats were kept in a vivarium under IACUC approved housing. Rats were injected with a single 5 mg/kg subcutaneous dose of oligonucleotide on Day 0 of the study. During the study period, the rats were observed daily for signs of illness or distress. Animals were bled on day 0 and 12. Data for day 12 is presented below. Immunoblotting was used to evaluate the levels of Complement Factor B (CFB) in the serum of rats (Sprague-Dawley and Lewis) as described in Example 6. CFB inhibition data in Table 10 are expressed as percent change from the predose level.

TABLE 10

| Average CFB Inhibition | |
|---|---|
| Compound | Days 12 |
| RD1709 | 71 |
| RD1710 | 62 |
| RD1711 | 55 |
| RD1712 | 60 |

Example 8: Effect of Compounds Targeting Human CFB in Rat

Compounds RD2380, RD2381, RD2382, RD2383, RD2384, and RD2385 as modified in Table 3 were evaluated in Sprague-Dawley or Lewis rats. Prior to the study the rats were kept in a vivarium under IACUC approved housing. Rats were injected with a single 5 mg/kg subcutaneous dose of oligonucleotide on Day 0 of the study. During the study period, the rats were observed daily for signs of illness or distress. Animals were bled on day 0, 4, 8, 15, 22, 29 and 36 in other groups. Immunoblotting was used to evaluate the levels of Complement Factor B (CFB) in the serum of rats (Sprague-Dawley and Lewis) as described in Example 6. CFB inhibition data in Table 11 are expressed as percent change from the predose level.

TABLE 11

| Average CFB Inhibition | | | | | | |
|---|---|---|---|---|---|---|
| | Days | | | | | |
| Compound | 4 | 8 | 15 | 22 | 29 | 36 |
| RD2380 | 29 | 50 | 48 | 45 | 0 | 0 |
| RD2381 | 19 | 37 | 28 | 15 | 4 | 1 |
| RD2382 | 38 | 51 | 38 | 36 | 4 | 1 |

TABLE 11-continued

| Average CFB Inhibition | | | | | | |
|---|---|---|---|---|---|---|
| | Days | | | | | |
| Compound | 4 | 8 | 15 | 22 | 29 | 36 |
| RD2383 | 28 | 42 | 36 | 32 | 0 | 0 |
| RD2384 | 18 | 27 | 32 | 19 | 10 | 6 |
| RD2385 | 28 | 41 | 42 | 32 | 0 | 0 |

Example 9: Effect of Compounds Targeting Human CFB in Rat

Compounds RD1709, RD1711, RD2386, RD2388, RD2390, RD2391, RD2513, and RD2520 as modified in Table 3 were evaluated in Sprague-Dawley or Lewis rats. Prior to the study the rats were kept in a vivarium under IACUC approved housing. Rats were injected with a single 5 mg/kg subcutaneous dose of oligonucleotide on Day 0 of the study. During the study period, the rats were observed daily for signs of illness or distress. Animals were bled on day 0, 4, 8, 15, 22, 29 and 36. Immunoblotting was used to evaluate the levels of Complement Factor B (CFB) in the serum of rats (Sprague-Dawley and Lewis) as described in Example 6. CFB inhibition data in Table 12 are expressed as percent change from the predose level.

TABLE 12

| Average CFB Inhibition | | | | | | |
|---|---|---|---|---|---|---|
| | Days | | | | | |
| Compound | 4 | 8 | 15 | 22 | 29 | 36 |
| RD1709 | 62 | 74 | 71 | 41 | 30 | 24 |
| RD1711 | 46 | 62 | 65 | 44 | 31 | 26 |
| RD2386 | 61 | 72 | 75 | 39 | 22 | 12 |
| RD2388 | 66 | 82 | 84 | 55 | 32 | 31 |
| RD2390 | 64 | 75 | 74 | 45 | 20 | 15 |
| RD2391 | 53 | 73 | 71 | 33 | 13 | 11 |
| RD2513 | 54 | 66 | 64 | 32 | 17 | 14 |
| RD2520 | 49 | 65 | 64 | 35 | 22 | 15 |

Example 10: Effect of Compounds Targeting Human CFB in Cynomolgus Monkeys

Compounds RD2273, RD2275, RD2276, RD2277, RD2278, RD2279, RD2533, and RD2534 as modified in Table 3 were evaluated in cynomolgus monkeys. Prior to the study the monkeys were kept in quarantine during which the animals were observed daily for general health. Eight groups of 2 cynomolgus monkey each were injected with a single 6 mg/kg subcutaneous dose of oligonucleotide on Day 1 of the study. During the study period, the monkeys were observed daily for signs of illness or distress. Animals are bled on day −6 and on days 1 (prior to dosing), 8, and 15, 22, 29, 36, 43, 50, 57 and 64.

CFB levels in the serum of cynomolgus monkeys was determined using the Abcam (ab137973) ELISA kit. The Abcam antibody has <5% cross reactivity with monkey CFB. The protocol used was that described by the manufacturer. All reagents, standards and samples were prepared as instructed by the manual. The standards or samples were added to the wells and incubated at room temperature. The wells were washed, and the biotin antibody was added to each well and incubated at room temperature. Following the incubation, the wells were washed, and a streptavidin-peroxidase conjugate was added to the wells and was incubated with the samples at room temperature. Chromogen substrate was added to each well and was incubated with the samples at room temperature. The stop solution was added to each well and the plate was immediately read using a Biotek® plate reader. CFB inhibition data are expressed as percent change from the predose level. Data for days 8, 15, 22, 29, 36 and 43 are provided below in Table 13.

TABLE 13

| Average CFB Inhibition (ELISA) | | | | | | |
|---|---|---|---|---|---|---|
| | Days | | | | | |
| Compound | 8 | 15 | 22 | 29 | 36 | 43 |
| RD2273 | 32 | 49 | 63 | 65 | 45 | 44 |
| RD2275 | 35 | 48 | 65 | 66 | 58 | 57 |
| RD2276 | 25 | 36 | 54 | 51 | 52 | 49 |
| RD2277 | 15 | 20 | 27 | | | |
| RD2278 | 8 | 18 | 25 | | | |
| RD2279 | 13 | 7 | 19 | | | |
| RD2533 | 27 | 44 | 56 | 46 | 54 | 40 |
| RD2534 | 14 | 21 | 27 | | | |

Immunoblotting was also used to evaluate the levels of Complement Factor B (CFB) in the serum of cynomolgus monkeys. Following serum collection, the serum was diluted in 1×PBS buffer and mixed with SDS-PAGE compatible loading buffer and a reducing reagent. Samples were heated to 70° C. for ten minutes and resolved by SDS-PAGE. Following the migration of the samples by PAGE, the proteins were transferred to nitrocellulose or other compatible membrane. The membranes were stained with Revert 700 and total protein for each sample was quantified using an Odyssey CLx detection system.

The membranes were blocked with Intercept® blocking buffer (P/N: 927-60001) and then probed with a primary antibody specific to CFB (ProteinTech, catalog no. 10170-1-AP). The antibody was diluted in Intercept® antibody diluent (P/N: 927-75001). After incubating the membrane with the primary antibody, the membrane was washed and then probed with a secondary antibody (IgG P/N: 926-32211). The antibody was diluted in Intercept® antibody diluent (P/N: 927-75001). The membranes were then analyzed on an Odyssey CLx detection system to determine the levels of CFB in each sample. The data for each sample was normalized to the total protein loaded into each lane and the CFB levels were quantified using Image Studio Lite. CFB inhibition data are expressed as percent change from the predose level. Data for days 8, 15, 22, 29, 36, 43, 50, 57, and 64 are provided below in Table 14. In a second set of experiments, certain animals were bled on day −6 and on days 1 (prior to dosing), 8, and 15, 22, 29, 36, 43, 50, 57, 64, 71, 78, 85 and 92 for serum collection and analysis and data are provided below in Table 15.

TABLE 14

| Average CFB Inhibition (Western) | | | | | | | | | |
|---|---|---|---|---|---|---|---|---|---|
| Compound | Day 8 | Day 15 | Day 22 | Day 29 | Day 36 | Day 43 | Day 50 | Day 57 | Day 64 |
| RD2273 | | 85 | 91 | 89 | 87 | 77 | 65 | 60 | 49 |
| RD2275 | | 86 | 91 | 92 | 91 | 90 | 86 | 77 | 71 |
| RD2276 | 45 | 70 | 79 | 81 | 77 | 80 | 80 | 82 | 80 |
| RD2533 | 47 | 72 | 80 | 75 | 79 | 75 | 71 | 73 | 68 |

TABLE 14-continued

| Average CFB Inhibition (Western) | | | | | | | | | |
|---|---|---|---|---|---|---|---|---|---|
| Compound | Day 8 | Day 15 | Day 22 | Day 29 | Day 36 | Day 43 | Day 50 | Day 57 | Day 64 |
| RD2277 | 12 | 36 | 44 | 34 | | | | | |
| RD2278 | 44 | 47 | 59 | 53 | | | | | |
| RD2279 | 18 | 22 | 25 | 21 | | | | | |
| RD2534 | 46 | 58 | 60 | 60 | | | | | |

TABLE 15

| Average CFB Inhibition (Western) | | | | | | | | | | | | | |
|---|---|---|---|---|---|---|---|---|---|---|---|---|---|
| Compound | Day 8 | Day 15 | Day 22 | Day 29 | Day 36 | Day 43 | Day 50 | Day 57 | Day 64 | Day 71 | Day 78 | Day 85 | Day 92 |
| RD2273 | 64 | 84 | 89 | 89 | 84 | 73 | 60 | 50 | 43 | 17 | 9 | 2 | 0 |
| RD2275 | 60 | 79 | 87 | 90 | 91 | 83 | 80 | 71 | 64 | 62 | 52 | 40 | 13 |
| RD2276 | 44 | 67 | 80 | 83 | 80 | 79 | 78 | 74 | 67 | | | | |
| RD2533 | 50 | 75 | 77 | 72 | 77 | 74 | 66 | 61 | 58 | | | | |

Example 11: Effect of Compounds Targeting Human CFB in Cynomolgus Monkeys

Compounds RD2557, RD2558, RD2559, and RD2560 as modified in Table 3 were evaluated in cynomolgus monkeys. Prior to the study the monkeys were kept in quarantine during which the animals were observed daily for general health. Each group of 2 cynomolgus monkey each were injected with a single 6 mg/kg subcutaneous dose of oligonucleotide on Day 1 of the study. During the study period, the monkeys were observed daily for signs of illness or distress. Animals are bled on day −6 and on days 1 (prior to dosing), 4, 8, and 15, 22, 29, 36, 43, 50, 57 and 64.

ELISA was used to evaluate the levels of Complement Factor B (CFB) in the serum of cynomolgus monkeys as described in Example 10. CFB inhibition data are expressed as percent change from the predose level. Data for days 8, 15, 22 and 29 are provided below in Table 16.

TABLE 16

| Average CFB Inhibition (ELISA) | | | | |
|---|---|---|---|---|
| | Days | | | |
| Compound | 8 | 15 | 22 | 29 |
| RD2557 | 3 | 27 | 29 | 48 |
| RD2558 | 46 | 63 | 63 | 57 |
| RD2559 | 11 | 0 | 18 | 3 |
| RD2560 | 28 | 44 | 57 | 44 |

Immunoblotting was also used to evaluate the levels of Complement Factor B (CFB) in the serum of cynomolgus monkeys as described in Example 10. CFB inhibition data are expressed as percent change from the predose level. Data for days 8, 15, 22, 29, 36, and 43 are provided below in Table 17. In a second set of experiments, certain animals were bled on day −6 and on days 1 (prior to dosing), 4, 8, and 15, 22, 29, 36, 43, 50, 57, 64, 71, 78, 85 and 92 for serum collection and analysis and data are provided below in Table 18.

TABLE 17

| Average CFB Inhibition (Western) | | | | | | |
|---|---|---|---|---|---|---|
| Compound | Day 8 | Day 15 | Day 22 | Day 29 | Day 36 | Day 43 |
| RD2557 | 51 | 68 | 72 | 80 | 80 | 61 |
| RD2558 | 83 | 92 | 89 | 88 | 87 | 81 |
| RD2559 | 0 | 5 | 22 | 18 | 13 | 0 |
| RD2560 | 55 | 84 | 89 | 85 | 84 | 76 |

TABLE 18

| Average CFB Inhibition (Western) | | | | | | | | | | | | | | |
|---|---|---|---|---|---|---|---|---|---|---|---|---|---|---|
| Compound | Day 4 | Day 8 | Day 15 | Day 22 | Day 29 | Day 36 | Day 43 | Day 50 | Day 57 | Day 64 | Day 71 | Day 78 | Day 85 | Day 92 |
| RD2557 | 22 | 43 | 61 | 71 | 82 | 69 | 57 | 52 | 54 | 37 | 8 | 7 | 1 | 3 |
| RD2558 | 32 | 75 | 90 | 88 | 84 | 77 | 67 | 44 | 29 | 20 | 11 | 0 | 0 | 0 |
| RD2559 | 6 | −2 | 11 | 29 | 34 | 32 | 18 | | | | | | | |
| RD2560 | 13 | 51 | 82 | 87 | 82 | 82 | 75 | 80 | 69 | 67 | 65 | 72 | 53 | 67 |

Example 12: Effect of Compounds Targeting Human CFB in Cynomolgus Monkeys

Compounds RD1714, RD1715, and RD2262 as modified in Table 3 were evaluated in cynomolgus monkeys. Prior to the study the monkeys were kept in quarantine during which the animals were observed daily for general health. Each group of 2 cynomolgus monkey each were injected with a single 3 mg/kg or 6 mg/kg subcutaneous dose of oligonucleotide on Day 1 of the study. During the study period, the monkeys were observed daily for signs of illness or distress. Animals are bled on day −6 and on days 1 (prior to dosing), 8, 15, 22, 29, 36, 43, 50, 57 and 64. ELISA was used to evaluate the levels of Complement Factor B (CFB) in the serum of cynomolgus monkeys as described in Example 10. CFB inhibition data are expressed as percent change from the predose level. Immunoblotting was also used to evaluate the levels of Complement Factor B (CFB) in the serum of cynomolgus monkeys as described in Example 10. ELISA Data for days 8, 15, 22, 29 and 36 are provided below in Table 19.

TABLE 19

| Average CFB Inhibition (ELISA) | | | | | |
|---|---|---|---|---|---|
| 6 mg/kg | Days | | | | |
| Compound | 8 | 15 | 22 | 29 | 36 |
| RD2262 | 18 | 28 | 33 | 40 | 40 |

Example 13: Effect of Compounds Targeting Human CFB in Complement Pathway Assay The level of active C5b-9 formation to assess alternative complement pathway activity and classical complement pathway activity was determined using the Wieslab Complement Alternative Pathway assay (COMPL AP330 RUO, SVAR) and Wieslab Complement Classical Pathway assay (COMPL CL310 RUO, SVAR) according to manufacturer's instructions. Serum from monkeys dosed with RD2273, RD2275, and RD2276 from Example 10 was tested and the data from the Wieslab Complement Alternative Pathway assay are presented below in Table 20. The Wieslab Complement Classical Pathway assay showed no effect as expected. Serum from monkeys dosed with RD2558 and RD2560 from Example 11 was also tested and the data from the Wieslab Complement Alternative Pathway assay are presented below in Table 21. The Wieslab Complement Classical Pathway assay showed no effect as expected. In a separate study, serum from monkeys dosed with RD2558 and RD2560 from Example 11 was tested and the data from the Wieslab Complement Alternative Pathway assay are presented below in Table 22. The Wieslab Complement Classical Pathway assay showed no effect as expected. Serum from monkeys dosed with RD2558 and RD2560 from Example 11 was also tested in hemolysis assays to determine alternative hemolytic activity and the data is presented in Table 23.

The alternative hemolytic activity was determined as follows. NHP serum (5.6%) was added to GVB° (Complement Technology, Tyler, Texas) and 5 mM EGTA with 25% rabbit erythrocytes (Er, Complement Technology, Tyler, Texas). Samples were incubated at 37° C. with intermittent shaking for 1 hour. Hemolysis was stopped by adding GVBE (Complement Technology, Tyler, Texas) at a 1:1 ratio to the samples. Samples were then centrifuged, and supernatants were transferred to a new 96-well plate. Absorbance was measured at 412 nm. Alternative hemolytic activity was measured by subtracting the OD value from the negative control sample (buffer and Er only) and normalizing each sample to the positive control sample (water and Er only). Individual timepoint samples were then normalized to their average pre-dose samples.

TABLE 20

| % Inhibition of Alternative Pathway | | | | | | | |
|---|---|---|---|---|---|---|---|
| Compound | Day 22 | Day 29 | Day 36 | Day 43 | Day 50 | Day 57 | Day 64 |
| RD2273 | 88 | 91 | 88 | 66 | 49 | 9 | 3 |
| RD2275 | 86 | 89 | 82 | 84 | 74 | 48 | 48 |
| RD2276 | 44 | 53 | 59 | 55 | 49 | 46 | |

TABLE 21

| % Inhibition of Alternative Pathway | | | | | |
|---|---|---|---|---|---|
| Compound | Day 8 | Day 15 | Day 22 | Day 36 | Day 43 |
| RD2558 | 80 | 96 | 93 | 88 | 32 |
| RD2560 | 30 | 72 | 80 | 64 | 26 |

TABLE 22

| % Inhibition of Alternative Pathway | | | | | | | | | | |
|---|---|---|---|---|---|---|---|---|---|---|
| Compound | Day 4 | Day 8 | Day 15 | Day 22 | Day 29 | Day 36 | Day 43 | Day 50 | Day 57 | Day 64 |
| RD2558 | 14 | 74 | 94 | 81 | 88 | 75 | 22 | 21 | 19 | 21 |
| RD2560 | 14 | 35 | 54 | 73 | 63 | 64 | 53 | 66 | 61 | 40 |

TABLE 23

| % Inhibition of Alternative Pathway Hemolysis | | | | | | | | | | |
|---|---|---|---|---|---|---|---|---|---|---|
| Compound | Day 4 | Day 8 | Day 15 | Day 22 | Day 29 | Day 36 | Day 43 | Day 50 | Day 57 | Day 64 |
| RD2558 | 28 | 75 | 94 | 85 | 76 | 65 | 74 | 62 | 53 | 51 |
| RD2560 | 14 | 35 | 54 | 73 | 63 | 64 | 53 | 66 | 61 | 40 |

Example 14: Effect of Compounds Targeting Human CFB in Cynomolgus Monkeys

Parent compound RD2558 was used as a starting point to design compounds RD2794, RD2795, and RD2796 as provided in Tables 24 and 25 below. The modified compounds provided in Table 25 are being evaluated in cynomolgus monkeys. Dosing of the monkeys will be carried out in accordance with the protocol in Example 10 with a 4 mg/kg subcutaneous dose of oligonucleotide on Day 1 of the study. ELISA will be used to evaluate the levels of Complement Factor B (CFB) in the serum of cynomolgus monkeys as described in Example 10. Immunoblotting will also be used to evaluate the levels of Complement Factor B (CFB) in the serum of cynomolgus monkeys as described in Example 10.

CFB inhibition data are expressed as percent change from the predose level. Data for days 4, 8, 15, 22, 29, and 36 are provided below in Table 26. In a second set of experiments, CFB inhibition data was collected for Days 4, 8, 15, 22, 29, 36, 43, 50, 57, and 64 for RD2795 and RD2796 and additionally Days 71, 78, 85 and 96 for RD2794 as provided below in Table 27. Inhibition of Alternative Complement Pathway Activity was evaluated using the WIESLAB assay (COMPL AP330) following manufacturer recommended protocol as described above. Data is provided below in Table 28. Inhibition of Alternative Hemolysis was evaluated using 5.6% serum, 25% Er (Complement Technologies, Inc.) and Buffer GVB°+MgEDTA as described above. Data is provided below in Table 29. Assays for the Classical Pathway showed no effect as expected (not shown).

TABLE 24

| Unmodified Antisense and Sense sequences of double-stranded compounds targeting CFB | | | | | | |
|---|---|---|---|---|---|---|
| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
| RD2794 | 1430 | 1452 | AAAGCAUUGAUGUUCACUUGGUU | 42 | ACCAAGUGAACAUCAAUGCUUU | 103 |
| RD2795 | 1432 | 1452 | AAAGCAUUGAUGUUCACUUGG | 96 | CCAAGUGAACAUCAAUGCUUU | 93 |
| RD2796 | 1432 | 1452 | AAAGCAUUGAUGUUCACUUGG | 96 | UCCAAGUGAACAUCAAUGCUUU | 104 |

TABLE 25

| Modified Antisense and Sense sequences of double-stranded compounds targeting CFB | | | |
|---|---|---|---|
| Compound | Modified Strands (5'-3') | Ref ID NO: | SEQ ID NO: |
| RD2794 | mA*fA*mA.fG.mC.fA.mU.fU.mG.fA.mU.fG.mU.fU.mC.fA.mC.fU.mU.fG.mG*mU*mU | IA0888 | 42 |
| | Hd*mC*mC.mA.mA.mG.mU.fG.mA.fA.fC.fA.fU.mC.mA.mA.mU.mG.mC.mU.mU*mU*dQ | IS1236 | 103 |
| RD2795 | mA*fA*mA.fG.mC.fA.mU.fU.mG.fA.mU.fG.mU.fU.mC.fA.mC.fU.mU*mG*mG | IA1010 | 96 |
| | H7*mC*mA.mA.mG.mU.fG.mA.fA.fC.fA.fU.mC.mA.mA.mU.mG.mC.mU.mU*mU*dQ | IS1109 | 93 |

TABLE 25-continued

| Modified Antisense and Sense sequences of double-stranded compounds targeting CFB | | | |
|---|---|---|---|
| Com-pound | Modified Strands (5'-3') | Ref ID NO: | SEQ ID NO: |
| RD2796 | mA*fA*mA.fG.mC.fA.mU.fU.mG.fA.mU.fG.mU.fU.mC.fA.mC.fU.mU*mG*mG | IA1010 | 96 |
| | H2*mC*mC.mA.mA.mG.mU.fG.mA.fA.fC.fA.fU.mC.mA.mA.mU.mG.mC.mU.mU*mU*dQ | IS1237 | 104 |

TABLE 26

| Average CFB Inhibition (Western) | | | | | | |
|---|---|---|---|---|---|---|
| Compound | Day 4 | Day 8 | Day 15 | Day 22 | Day 29 | Day 36 |
| RD2794 | 31 | 67 | 87 | 89 | 89 | 81 |
| RD2795 | 36 | 72 | 89 | 91 | 93 | 88 |
| RD2796 | 31 | 70 | 82 | 82 | 79 | 65 |

TABLE 27

| Average CFB Inhibition (Western) | | | | | | | | | | | | | | |
|---|---|---|---|---|---|---|---|---|---|---|---|---|---|---|
| Compound | Day 4 | Day 8 | Day 15 | Day 22 | Day 29 | Day 36 | Day 43 | Day 50 | Day 57 | Day 64 | Day 71 | Day 78 | Day 85 | Day 96 |
| RD2794 | 36 | 69 | 85 | 87 | 86 | 76 | 79 | 76 | 70 | 61 | 62 | 62 | 52 | 47 |
| RD2795 | 36 | 72 | 89 | 91 | 93 | 88 | 86 | 84 | 76 | 79 | | | | |
| RD2796 | 31 | 70 | 82 | 82 | 79 | 65 | 81 | 55 | 42 | 44 | | | | |

TABLE 28

| Average Alternative Pathway Inhibition (WIESLAB COMPL AP330) | | | | | | | | | | | | | | |
|---|---|---|---|---|---|---|---|---|---|---|---|---|---|---|
| Compound | Day 4 | Day 8 | Day 15 | Day 22 | Day 29 | Day 36 | Day 43 | Day 50 | Day 57 | Day 64 | Day 71 | \|Day 78 | Day 85 | Day 96 |
| RD2794 | 3 | 15 | 33 | 32 | 39 | 17 | 47 | 29 | 22 | 7 | 12 | 6 | 2 | 0 |
| RD2795 | 15 | 19 | 33 | 37 | 48 | 44 | 44 | 15 | | | | | | |

TABLE 29

| Average Alternative Hemolysis Inhibition | | | | | | | | | | | | | | |
|---|---|---|---|---|---|---|---|---|---|---|---|---|---|---|
| Compound | Day 4 | Day 8 | Day 15 | Day 22 | Day 29 | Day 36 | Day 43 | Day 50 | Day 57 | Day 64 | 71 Day | 78 Day | 85 Day | Day 96 |
| RD2794 | 10 | 29 | 46 | 54 | 48 | 40 | 42 | 36 | 34 | 26 | 27 | 22 | 12 | 17 |
| RD2795 | 4 | 43 | 60 | 63 | 63 | 60 | 59 | 32 | 30 | | | | | |
| RD2796 | 14 | 28 | 28 | 31 | 20 | 0 | 0 | | | | | | | |

Example 15: Effect of Compounds Targeting Human CFB in Cynomolgus Monkeys

Parent compounds RD2273, RD2275, RD2558, RD2560 and RD2276 were used as a starting point to design compounds RD2797, RD2829, RD2798, RD2801, RD2830, RD2821, RD2831, and RD2832 as provided in Tables 30 and 31 below. The modified compounds provided in Table 31 are being evaluated in cynomolgus monkeys. Dosing of the monkeys will be carried out in accordance with the protocol in Example 10 with a 4 mg/kg subcutaneous dose of oligonucleotide on Day 1 of the study. ELISA will be used to evaluate the levels of Complement Factor B (CFB) in the serum of cynomolgus monkeys as described in Example 10.

Immunoblotting will also be used to evaluate the levels of Complement Factor B (CFB) in the serum of cynomolgus monkeys as described in Example 10. CFB inhibition data are expressed as percent change from the predose level. Data for days 8, 15, 22, and 29 are provided below in Table 32 for RD2798, RD2801, RD2821, RD2830, and RD2832. In a second set of experiments, CFB inhibition data was collected for Days 8, 15, 22, 29, 36, 43, 50, 57, and 64 for RD2821 and RD2832 and additionally Days 71, 78, and 85 for RD2798 and RD2801 and additionally Day 96 for RD2830 as provided below in Table 33. In a third set of experiments, CFB inhibition data was collected for Days 8, 15, 22, 29, 36, 43, 50, 57, 64, and 71 for RD2797, RD2829 and RD2831 as provided below in Table 34. Inhibition of Alternative Complement Pathway Activity was evaluated using the WIESLAB assay (COMPL AP330) following manufacturer recommended protocol as described above. Data is provided below in Table 35. Inhibition of Alternative Hemolysis was evaluated using 5.6% serum, 25% Er (Complement Technologies, Inc.) and Buffer GVB°+ MgEDTA as provided above. Data is provided below in Table 36.

TABLE 30

Unmodified Antisense and Sense sequences of double-stranded compounds targeting CFB

| Compound Number | Seq ID NO: 1 Start Site | SEQ ID NO: 1 Stop Site | Antisense Sequence (5'-3') | SEQ ID NO: | Sense Sequence (5'-3') | SEQ ID NO: |
|---|---|---|---|---|---|---|
| RD2797 | 493 | 515 | UGAAAGAGAUCUCAUCACUCACA | 24 | GUGAGUGAUGAGAUCUCUUUCA | 105 |
| RD2829 | 1383 | 1404 | UAGACAUCCAGAUAAUCCUCCC | 25 | UGGGAGGAUUAUCUGGAUGUCUA | 64 |
| RD2798 | 1382 | 1404 | UAGACAUCCAGAUAAUCCUCCCU | 97 | GGGAGGAUUAUCUGGAUGUCUA | 106 |
| RD2801 | 1384 | 1404 | UAGACAUCCAGAUAAUCCUCC | 98 | UGGAGGAUUAUCUGGAUGUCUA | 107 |
| RD2821 | 1430 | 1452 | AAAGCAUUGAUGUUCGCUUGGUU | 99 | ACCAAGCGAACAUCAAUGCUUU | 108 |
| RD2830 | 1383 | 1404 | UAGACAUCCAGAUAAUCCUUCC | 100 | UGGAAGGAUUAUCUGGAUGUCUA | 109 |
| RD2831 | 2249 | 2271 | UCAACUUGAAUGAAACGGCUUCU | 101 | GAAGCCGUUUCAUUCAAGUUGA | 110 |
| RD2832 | 1451 | 1473 | UCAUUGUCUUUCUUGGAAGCCAA | 102 | UGGCUUCCAAGAAAGACAAUGA | 65 |

TABLE 31

Modified Antisense and Sense sequences of double-stranded compounds targeting CFB

| Compound | Modified Strands (5'-3') | Ref ID NO: | SEQ ID NO: |
|---|---|---|---|
| RD2797 | mU*fG*mA.fA.mA.fG.mA.fG.mA.fU.mC.fU.mC.fA.mU.fC.mA.fC.mU.fC.mA*fC*mA | IA0840 | 24 |
| | HL*mU*mG.mA.mG.mU.mG.fA.mU.fG.fA.fG.fA.mU.mC.mU.mC.mU.mU.mU.mC*mA*dQ | IS1238 | 105 |
| RD2829 | mU*fA*mG.fA.mC.fA.mU.fC.mC.fA.mG.fA.mU.fA.mA.fU.mC.fC.mU.fC*mC*mC | IA0842 | 25 |
| | H4*mG*mG.mG.mA.mG.mG.mA.fU.mU.fA.fU.fC.fU.mG.mG.mA.mU.mG.mU.mC.mU*mA*dQ | IS1251 | 64 |
| RD2798 | mU*fA*mG.fA.mC.fA.mU.fC.mC.fA.mG.fA.mU.fA.mA.fU.mC.fC.mU.fC.mC*mC*mU | IA1011 | 97 |
| | HL*mG*mG.mA.mG.mG.mA.fU.mU.fA.fU.fC.fU.mG.mG.mA.mU.mG.mU.mC.mU*mA*dQ | IS1239 | 106 |
| RD2801 | mU*fA*mG.fA.mC.fA.mU.fC.mC.fA.mG.fA.mU.fA.mA.fU.mC.fC.mU*fC*mC | IA1012 | 98 |
| | H4*mG*mG.mA.mG*mG.mA.fU.mU.fA.fU.fC.fU.mG.mG.mA.mU.mG.mU.mC.mU*mA*dQ | IS1242 | 107 |
| RD2821 | mA*fA*mA.fG.mC.fA.mU.fU.mG.fA.mU.fG.mU.fU.mC.fG.mC.fU.mU.fG.mG*mU*mU | IA1015 | 99 |
| | Hd*mC*mC.mA.mA.mG.mC.fG.mA.fA.fC.fA.fU.mC.mA.mA.mU.mG.mC.mU.mU*mU*dQ | IS1249 | 108 |
| RD2830 | mU*fA*mG.fA.mC.fA.mU.fC.mC.fA.mG.fA.mU.fA.mA.fU.mC.fC.mU.fU*mC*mC | IA1016 | 100 |
| | H4*mG*mG.mA.mA.mG.mG.mA.fU.mU.fA.fU.fC.fU.mG.mG.mA.mU.mG.mU.mC.mU*mA*dQ | IS1252 | 109 |
| RD2831 | mU*fC*mA.fA.mC.fU.mU.fG.mA.fA.mU.fG.mA.fA.mA.fC.mG.fG.mC.fU.mU*mC*mU | IA1017 | 101 |
| | HL*mA*mA.mG.mC.mC.mG.fU.mU.fU.fC.fA.fU.mU.mC.mA.mA.mG.mU.mU.mG*mA*dQ | IS1253 | 110 |
| RD2832 | mU*fC*mA.fU.mU.fG.mU.fC.mU.fU.mU.fC.mU.fU.mG.fG.mA.fA.mG.fC.mC*mA*mA | IA1018 | 102 |
| | H4*mG*mG.mC.mU.mU.mC.fC.mA.fA.fG.fA.fA.mA.mG.mA.mC.mA.mA.mU.mG*mA*dQ | IS1254 | 65 |

TABLE 32

Average CFB Inhibition (Western)

| Compound | Day 8 | Day 15 | Day 22 | Day 29 |
|---|---|---|---|---|
| RD2798 | 72 | 82 | 92 | 81 |
| RD2801 | 73 | 82 | 89 | 86 |
| RD2821 | 68 | 64 | 62 | 47 |

TABLE 32-continued

Average CFB Inhibition (Western)

| Compound | Day 8 | Day 15 | Day 22 | Day 29 |
|---|---|---|---|---|
| RD2830 | 64 | 81 | 89 | 85 |
| RD2832 | 40 | 48 | 71 | 60 |

TABLE 33

| Average CFB Inhibition (Western) | | | | | | | | | | | | | |
|---|---|---|---|---|---|---|---|---|---|---|---|---|---|
| Compound | Day 8 | Day 15 | Day 22 | Day 29 | Day 36 | Day 43 | Day 50 | Day 57 | Day 64 | Day 71 | Day 78 | Day 85 | Day 96 |
| RD2798 | 72 | 82 | 92 | 81 | 84 | 83 | 81 | 82 | 77 | 75 | 74 | 59 | |
| RD2801 | 73 | 82 | 89 | 86 | 87 | 83 | 77 | 78 | 76 | 64 | 55 | 49 | |
| RD2821 | 68 | 64 | 62 | 47 | 39 | 17 | 1 | 2 | 0 | | | | |
| RD2830 | 70 | 84 | 90 | 92 | 92 | 89 | 90 | 87 | 83 | 77 | 78 | 75 | 76 |
| RD2832 | 60 | 66 | 71 | 60 | 61 | 56 | 40 | 31 | 35 | | | | |

TABLE 34

| Average CFB Inhibition (Western) | | | | | | | | | | |
|---|---|---|---|---|---|---|---|---|---|---|
| Compound | Day 8 | Day 15 | Day 22 | Day 29 | Day 36 | Day 43 | Day 50 | Day 57 | Day 64 | Day 71 |
| RD2797 | 53 | 73 | 86 | 90 | 83 | 84 | 84 | 76 | 70 | 65 |
| RD2829 | 36 | 63 | 88 | 90 | 86 | 82 | 84 | 76 | 77 | 59 |
| RD2831 | 52 | 76 | 70 | 84 | 82 | 84 | 85 | 77 | 82 | 79 |

TABLE 35

| Average Alternative Pathway Inhibition (WIESLAB COMPL AP330) | | | | | | | | | | | | | |
|---|---|---|---|---|---|---|---|---|---|---|---|---|---|
| Compound | Day 8 | Day 15 | Day 22 | Day 29 | Day 36 | Day 43 | Day 50 | Day 57 | Day 64 | Day 71 | Day 78 | Day 85 | Day 96 |
| RD2798 | 55 | 71 | 85 | 75 | 59 | 69 | | | | | | | |
| RD2801 | 72 | 81 | 87 | 85 | 78 | 84 | | | | | | | |
| RD2830 | 60 | 87 | 95 | 95 | 98 | 97 | 94 | 93 | 89 | 83 | 75 | 75 | 74 |

TABLE 36

| Average Alternative Hemolysis Inhibition | | | | | | | | | | | | | |
|---|---|---|---|---|---|---|---|---|---|---|---|---|---|
| Compound | Day 8 | Day 15 | Day 22 | Day 29 | Day 36 | Day 43 | Day 50 | Day 57 | Day 64 | Day 71 | Day 78 | Day 85 | Day 96 |
| RD2798 | 42 | 55 | 57 | 54 | 48 | 48 | 53 | 47 | | | | | |
| RD2801 | 37 | 31 | 45 | 52 | 61 | 34 | 39 | 39 | | | | | |
| RD2821 | 44 | 0 | 13 | 0 | 0 | 0 | | | | | | | |
| RD2830 | 39 | 55 | 70 | 68 | 78 | 67 | 65 | 70 | 62 | 44 | 47 | 37 | 52 |
| RD2832 | 23 | 18 | 27 | 21 | 11 | 18 | | | | | | | |
| RD2797 | 41 | 33 | 57 | 64 | 58 | 46 | 67 | | | | | | |
| RD2829 | 23 | 25 | 34 | 41 | 34 | 29 | 34 | | | | | | |
| RD2831 | 2 | 18 | 30 | 29 | 28 | 42 | 40 | | | | | | |

Example 16: Effect of Compounds Targeting Human CFB in Sprague Dawley Rats

Sprague Dawley rats (3/sex/group main (Groups 1-5), 1/sex/group toxicokinetic (groups 6-9)), 8-9 weeks of age) were administered the vehicle control (Group 1) or 30, 60, 150, or 300 mg/kg/dose RD2830 (Groups 2 and 6, 3 and 7, 4 and 8, or 5 and 9, respectively) on Day 1 and Day 21 via SC injection at a dose volume of 5 mL/kg.

Observations included cage-side observations (general signs of toxicity including fecal and urine quality), physical examination (predose), body weight (Days 1, 5, 8, 12, 15, 19, 21 (toxicokinetic) and Day 26 (main) and quantitative food consumption (weekly). Blood samples were collected for clinical chemistry, hematology and coagulation on Day 26. Termination was on Day 26. Necropsy included visual examination for external abnormalities, abdominal, thoracic, and cranial cavities abnormalities. Organ weights (heart, kidney, liver, spleen and thymus) were recorded. Histology and microscopic pathology (heart, kidney, lesions, liver, lung, lymph nodes, injection sites, skin, spleen and thymus) were conducted.

RD2830, administered as single SC doses on Days 1 and 21 at 30, 60, 150 and 300 mg/kg/dose, was considered generally tolerated by male and female rats.

```
                                            SEQ ID NO: 1
1    gggaagggaa tgtgaccagg tctaggtctg gagtttcagc

     ttggacactg agccaagcag
```

-continued 61 acaagcaaag caagccagga cacaccatcc tgccccaggc ccagcttctc tcctgccttc
121 caacgccatg ggagcaatc tcagcccca actctgcctg atgccctttta tcttgggcct
181 cttgtctgga ggtgtgacca ccactccatg gtctttggcc cggccccagg gatcctgctc
241 tctggagggg gtagagatca aaggcggctc cttccgactt ctccaagagg gccaggcact
301 ggagtacgtg tgtccttctg gcttctaccc gtaccctgtg cagacacgta cctgcagatc
361 tacggggtcc tggagcaccc tgaagactca agaccaaaag actgtcagga aggcagagtg
421 cagagcaatc cactgtccaa gaccacacga cttcgagaac ggggaatact ggccccggtc
481 tccctactac aatgtgagtg atgagatctc tttccactgc tatgacggtt acactctccg
541 gggctctgcc aatcgcacct gccaagtgaa tggccgatgg agtgggcaga cagcgatctg
601 tgacaacgga gcggggtact gctccaaccc gggcatcccc attggcacaa ggaaggtggg
661 cagccagtac cgccttgaag acagcgtcac ctaccactgc agccgggggc ttaccctgcg
721 tggctcccag cggcgaacgt gtcaggaagg tggctcttgg agcgggacgg agccttcctg
781 ccaagactcc ttcatgtacg acacccctca agaggtggcc gaagctttcc tgtcttccct
841 gacagagacc atagaaggag tcgatgctga ggatgggcac ggcccagggg aacaacagaa
901 gcggaagatc gtcctggacc cttcaggctc catgaacatc tacctggtgc tagatggatc
961 agacagcatt ggggccagca acttcacagg agccaaaaag tgtctagtca acttaattga
1021 gaaggtggca agttatggtg tgaagccaag atatggtcta gtgacatatg ccacataccc
1081 caaaatttgg gtcaaagtgt ctgaagcaga cagcagtaat gcagactggg tcacgaagca
1141 gctcaatgaa atcaattatg aagaccacaa gttgaagtca gggactaaca ccaagaaggc
1201 cctccaggca gtgtacagca tgatgagctg gccagatgac gtccctcctg aaggctggaa -continued 1261 ccgcacccgc catgtcatca tcctcatgac tgatggattg cacaacatgg gcggggaccc
1321 aattactgtc attgatgaga tccgggactt gctatacatt ggcaaggatc gcaaaaaccc
1381 aagggaggat tatctggatg tctatgtgtt tggggtcggg cctttggtga accaagtgaa
1441 catcaatgct ttggcttcca agaaagacaa tgagcaacat gtgttcaaag tcaaggatat
1501 ggaaaacctg gaagatgttt tctaccaaat gatcgatgaa agccagtctc tgagtctctg
1561 tggcatggtt tgggaacaca ggaagggtac cgattaccac aagcaaccat ggcaggccaa
1621 gatctcagtc attcgccctt caaagggaca cgagagctgt atgggggctg tggtgtctga
1681 gtactttgtg ctgacagcag cacattgttt cactgtggat gacaaggaac actcaatcaa
1741 ggtcagcgta ggaggggaga agcgggacct ggagatagaa gtagtcctat ttcaccccaa
1801 ctacaacatt aatgggaaaa aagaagcagg aattcctgaa ttttatgact atgacgttgc
1861 cctgatcaag ctcaagaata agctgaaata tggccagact atcaggccca tttgtctccc
1921 ctgcaccgag ggaacaactc gagctttgag gcttcctcca actaccactt gccagcaaca
1981 aaaggaagag ctgctccctg cacaggatat caaagctctg tttgtgtctg aggaggagaa
2041 aaagctgact cggaaggagg tctacatcaa gaatggggat aagaaaggca gctgtgagag
2101 agatgctcaa tatgccccag gctatgacaa agtcaaggac atctcagagg tggtcacccc
2161 tcggttcctt tgtactggag gagtgagtcc ctatgctgac cccaatactt gcagaggtga
2221 ttctggcggc cccttgatag ttcacaagag aagtcgtttc attcaagttg gtgtaatcag -continued 2281 ctggggagta gtggatgtct gcaaaaacca gaagcggcaa aagcaggtac ctgctcacgc 2341 ccgagacttt cacatcaacc tctttcaagt gctgccctgg ctgaaggaga aactccaaga -continued 2401 tgaggatttg ggtttctat aaggggtttc ctgctggaca ggggcgtggg attgaattaa 2461 aacagctgcg acaaca Although the disclosure has been described with reference to the above examples, it will be understood that modifications and variations are encompassed within the spirit and scope of the disclosure and by the following claims.

What is claimed is:

1. A compound comprising a first modified oligonucleotide 14 to 23 linked nucleosides in length having a nucleobase sequence comprising at least 14, at least 15, at least 16, at least 17, at least 18, at least 19, or at least 20 contiguous nucleobases of the nucleobase sequence of SEQ ID NO: 109 and a second modified oligonucleotide 14 to 23 linked nucleosides in length having a region of complementarity to the first modified oligonucleotide, wherein one or more GalNAc are attached to the first modified oligonucleotide, wherein the 5' nucleoside of the first modified oligonucleotide is of the following formula:

Formula X

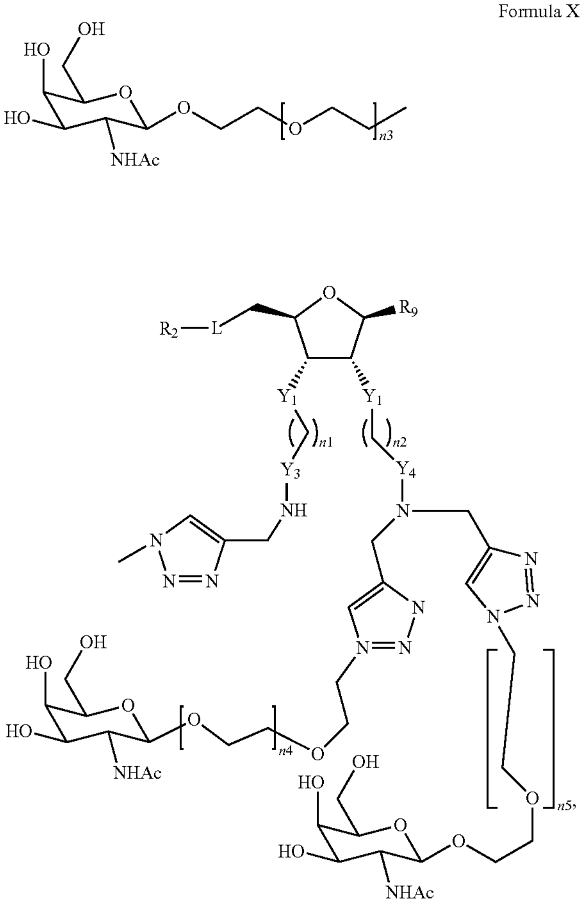

wherein:

$R^9$ is H, adenine, guanine, thymine, cytosine, uracil, adenine comprising a protecting group (PG), guanine comprising a PG, thymine comprising a PG, cytosine comprising a PG, uracil comprising a PG, a modified nucleobase, optionally substituted alkyl, optionally substituted aryl, optionally substituted heteroaryl, optionally substituted carbocyclyl, optionally substituted heterocyclyl, or a nucleobase isostere;

L is a bond, a phosphodiester bond, a phosphorothioate bond, a triazole, a tetrazole, an amide, a reverse-amide, a carbamate, a carbonate, urea, alkyl, or heteroalkyl;

$R^2$ is an oligonucleotide sequence or modified oligonucleotide;

$Y_1$ is O, $CH_2$, $CH_2O$, or optionally substituted NH;

$Y_2$ is O, $CH_2$, $CH_2O$, or optionally substituted NH;

$Y_3$ is CO, $SO_2$, P (O) O, $CH_2$—O—C(O), $CH_2$—NH—C(O), $CH_2$—NH—$SO_2$, or $CH_2$;

$Y_4$ is CO, $SO_2$, P (O) O, $CH_2$—O—C(O), $CH_2$—NH—C(O), $CH_2$—NH—$SO_2$, or $CH_2$;

$n_2$ is 0, 1, 2, 3, 4, 5, or 6; and each $n_1$, $n_3$, $n_4$ and $n_5$ is independently 0, 1, 2, 3, 4, 5, 6, 7, 8, 9, or 10.

2. The compound of claim 1, wherein the first modified oligonucleotide is 23 linked nucleosides in length having a nucleobase sequence comprising the nucleobase sequence of SEQ ID NO: 109.

3. The compound of claim 2, wherein the region of complementarity between the first modified oligonucleotide and the second modified oligonucleotide is 19 to 23 linked nucleosides in length.

4. The compound of claim 1, wherein at least one internucleoside linkage of the first or second modified oligonucleotide is a phosphorothioate internucleoside linkage or a methylphosphonate internucleoside linkage.

5. The compound of claim 4, wherein the phosphorothioate internucleoside linkage or methylphosphonate internucleoside linkage is at the 3' terminus of the first or second modified oligonucleotide or at the 5' terminus of the first or second modified oligonucleotide.

6. The compound of claim 1, wherein the first or second modified oligonucleotide comprises a modification selected from the group consisting of LNA, cEt, 2'-MOE, 2'-F, 2'-OMe, and 2'-deoxy, or a combination thereof.

7. The compound of claim 1, wherein the first modified oligonucleotide comprises no more than five 2'-F sugar modifications.

8. The compound of claim 1, wherein the second modified oligonucleotide is 14 to 22 linked nucleosides in length having a nucleobase sequence comprising at least 14 contiguous nucleobases of the nucleobase sequence of SEQ ID NO: 100.

9. The compound of claim 1, wherein the first modified oligonucleotide consists of Ref ID NO: IS1252 having the formula:

H4*mG*mG.mA.mA.mG.mG.mA.
fU.mU.fA.fU.fC.fU.mG.mG.mA.
mU.mG.mU.mC.mU*mA*dQ (SEQ ID NO: 109), wherein:

'A' is a nucleoside having an adenine nucleobase, 'G' is a nucleoside having a guanine nucleobase, 'C' is a nucleoside having a cytosine nucleobase, and 'U' is a nucleoside having a uracil nucleobase;

'm' is a 2'-O-methyl sugar modification;

'f' is a 2'-F sugar modification;

'*' is a phosphorothioate internucleoside linkage;

'.' is a phosphate internucleoside linkage;

'dQ' is an inverted abasic deoxyribose; and

'H4*' is of the formula:

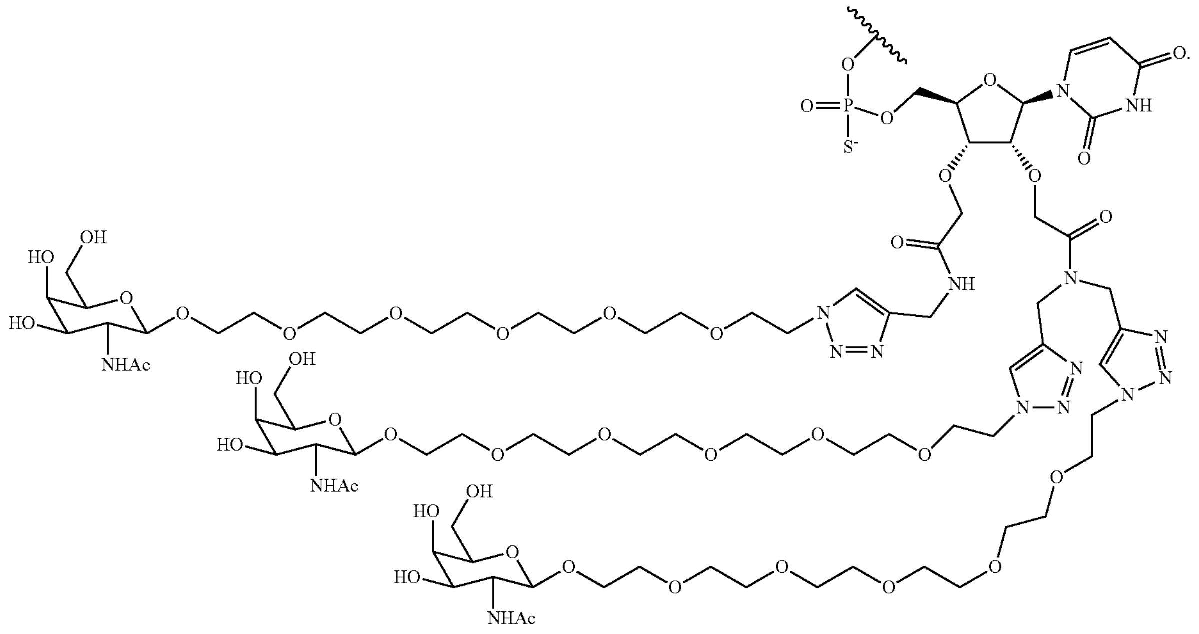 [SMILES: *OP(=O)([S-])OC[C@H]1O[C@@H](n2ccc(=O)[nH]c2=O)[C@H](OCC(=O)N(Cc2cn(CCOCCOCCOCCOCCOCCOC3OC(CO)C(O)C(O)C3NC(C)=O)nn2)Cc2cn(CCOCCOCCOCCOCCOCCOC3OC(CO)C(O)C(O)C3NC(C)=O)nn2)[C@@H]1OCC(=O)NCc1cn(CCOCCOCCOCCOCCOCCOC2OC(CO)C(O)C(O)C2NC(C)=O)nn1]

10. The compound of claim 1, wherein the second modified oligonucleotide consists of Ref ID NO: IA1016 having the formula:

mU*fA*mG.fA.mC.fA.mU.fC.mC.fA.mG.fA.mU.fA.mA.fU.mC.fC.mU.fU*mC*mC (SEQ ID NO: 100), wherein:

'A' is a nucleoside having an adenine nucleobase, 'G' is a nucleoside having a guanine nucleobase, 'C' is a nucleoside having a cytosine nucleobase, and 'U' is a nucleoside having a uracil nucleobase;

'm' is a 2'-O-methyl sugar modification;

'f' is a 2'-F sugar modification;

'*' is a phosphorothioate internucleoside linkage; and

'.' is a phosphate internucleoside linkage.

11. The compound of claim 8, wherein the compound is of the following chemical structure:

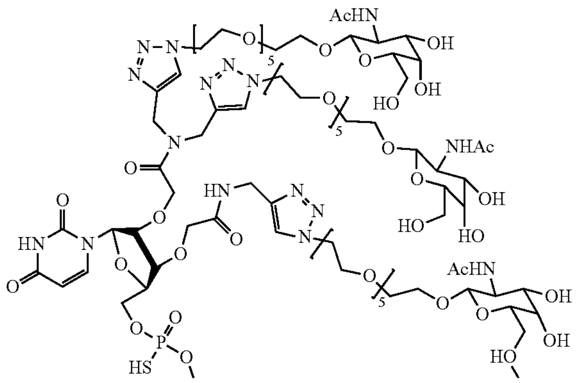

-continued
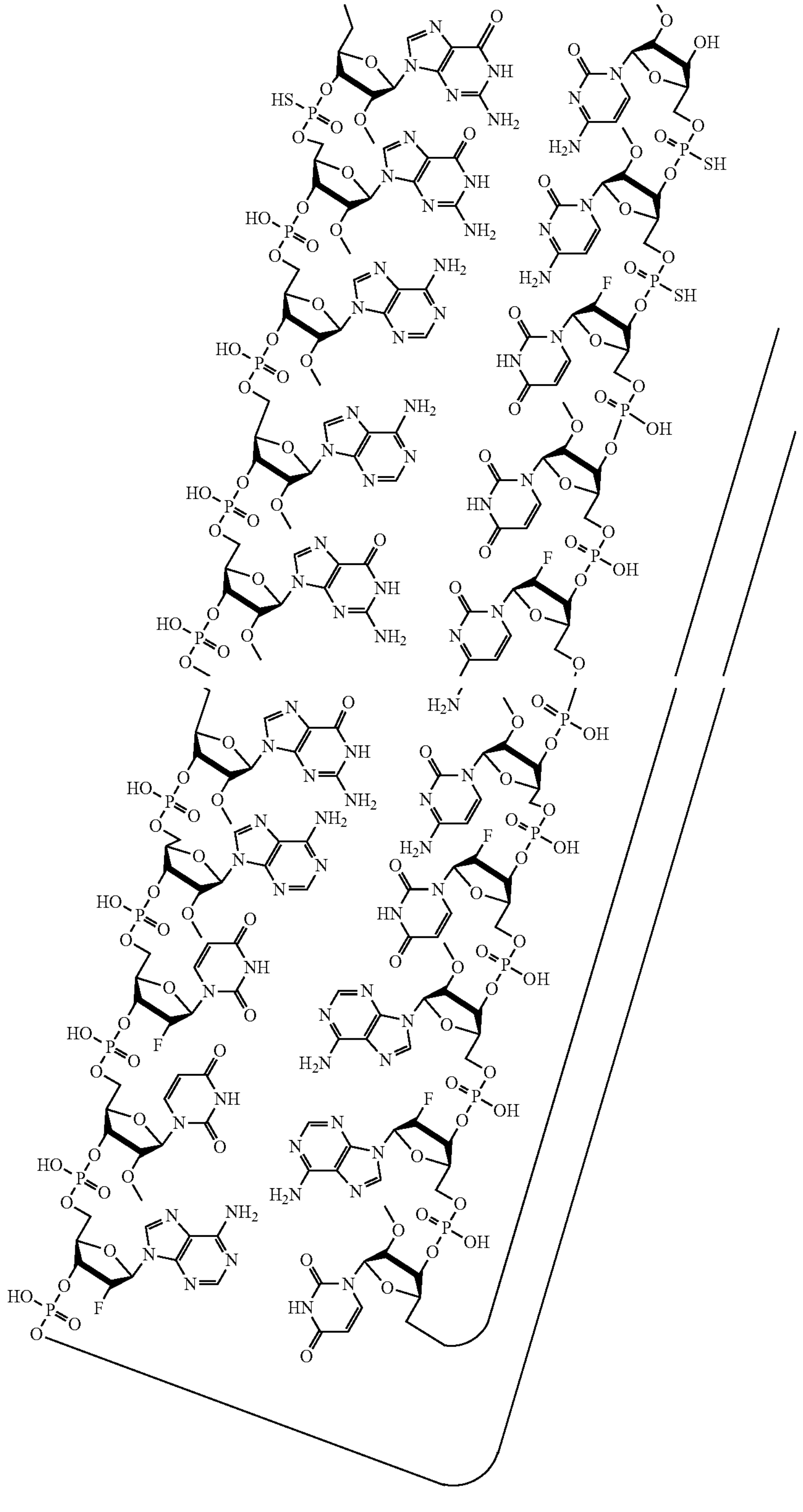

-continued
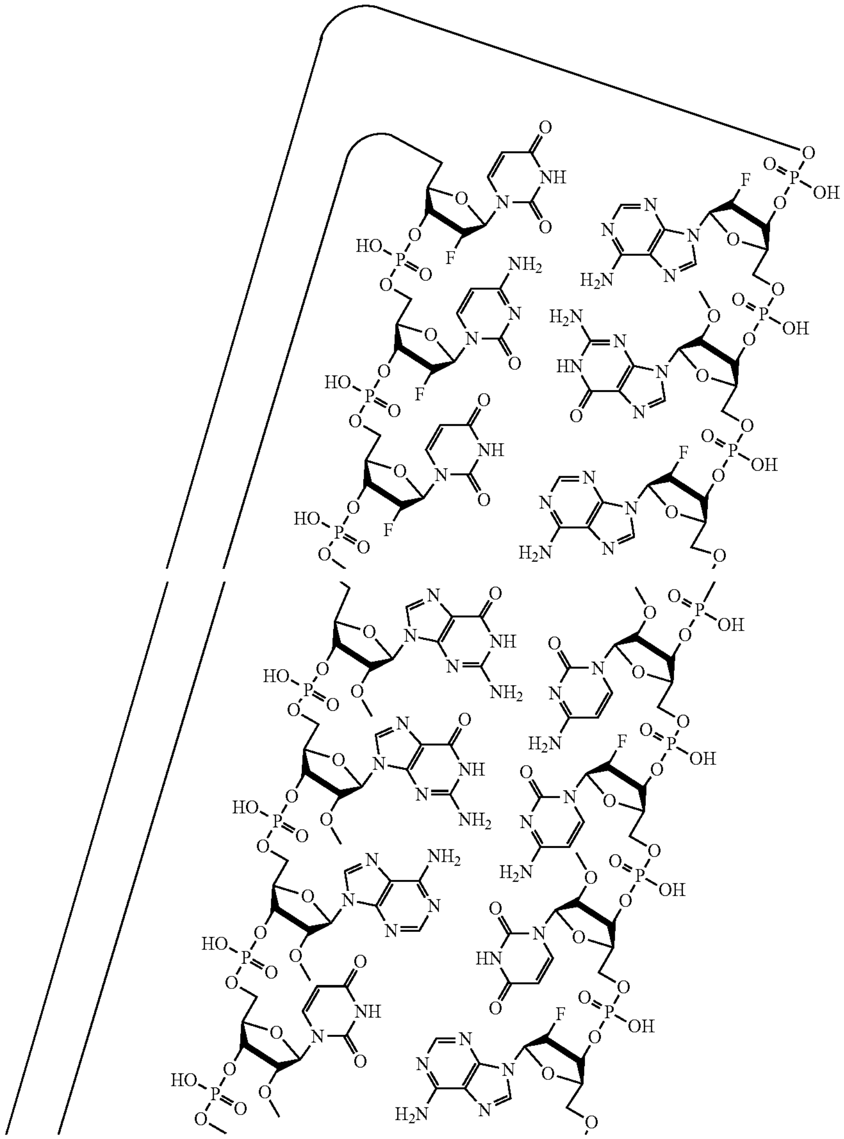

-continued
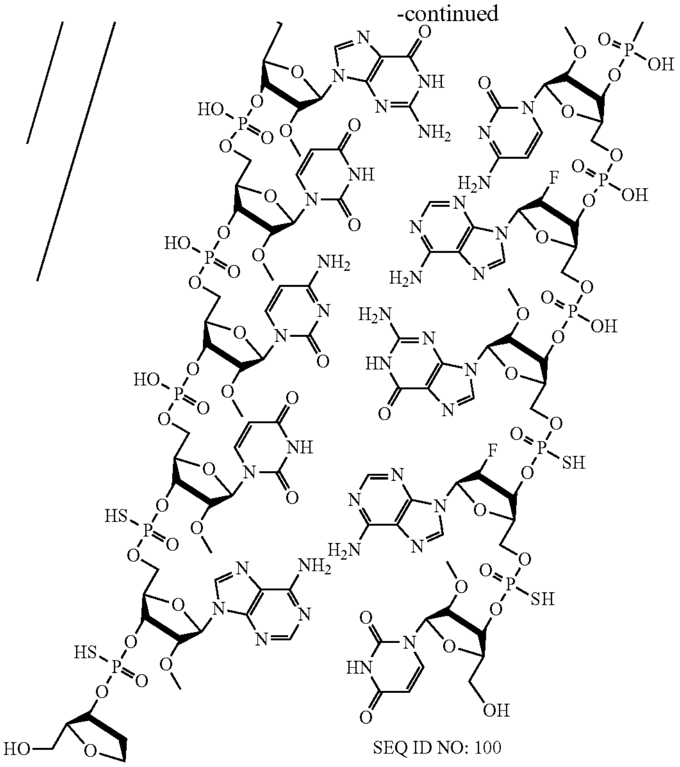
SEQ ID NO: 100
SEQ ID NO: 109
or a pharmaceutically acceptable salt or stereoisomer thereof.
12. The compound of claim 11, wherein the pharmaceutically acceptable salt is a sodium salt or a potassium salt.
13. The compound of claim 12, which is a sodium salt according to the following chemical structure:
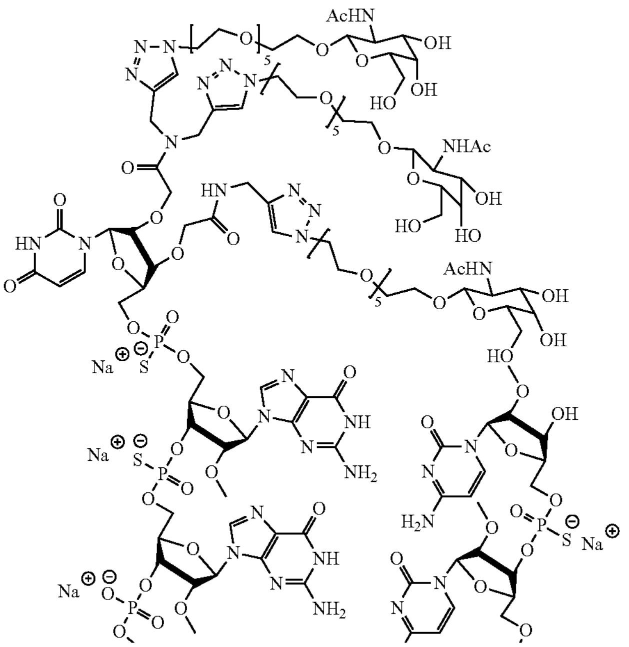

-continued
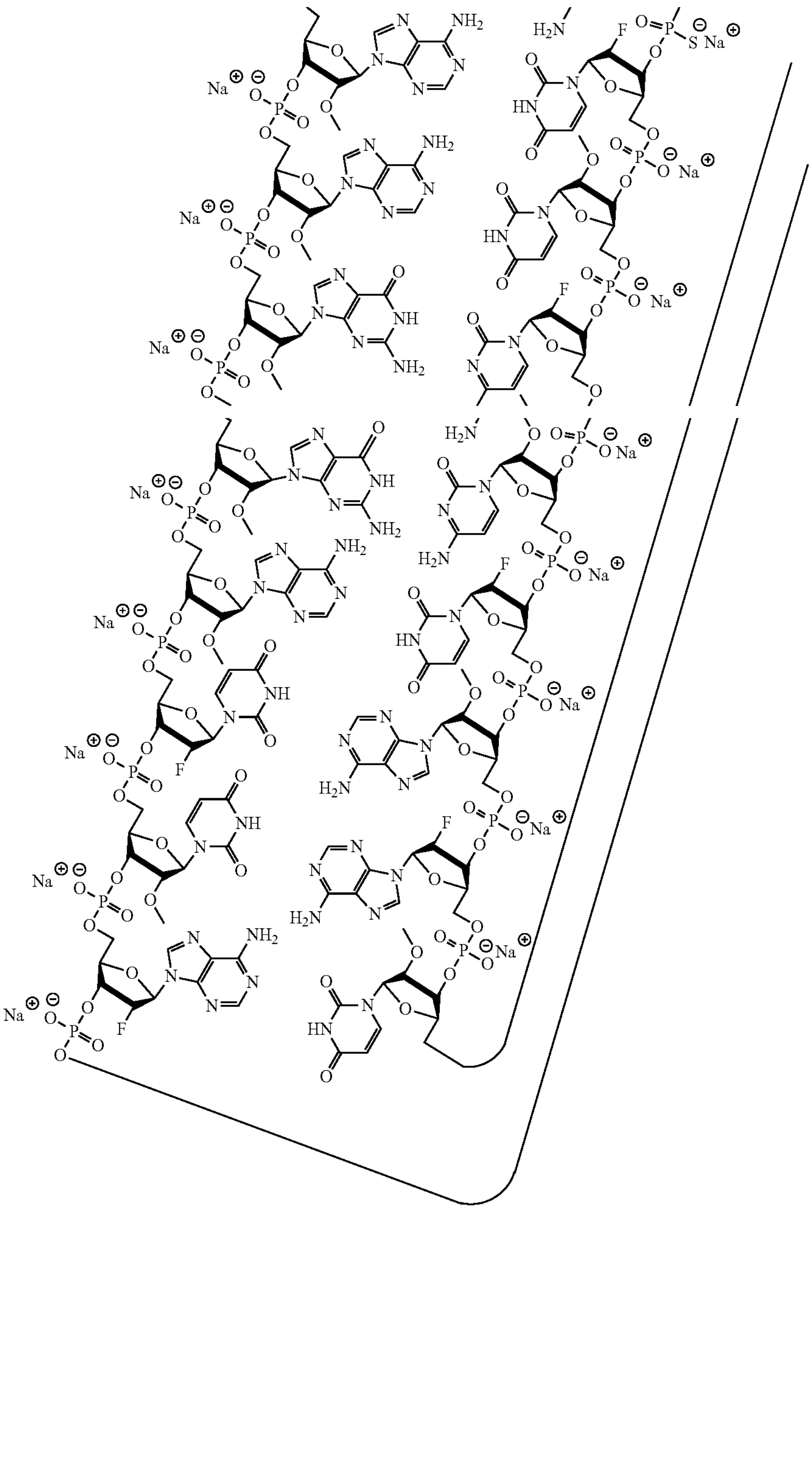

-continued
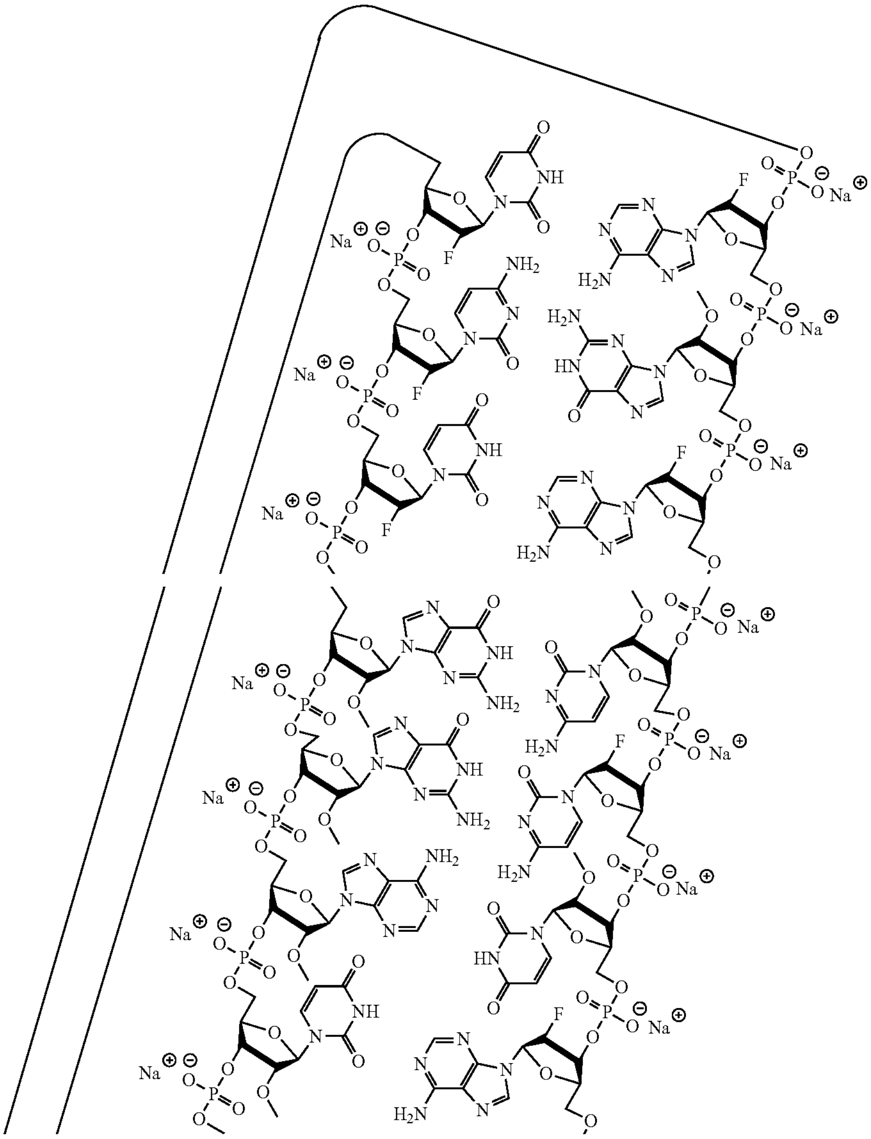

-continued

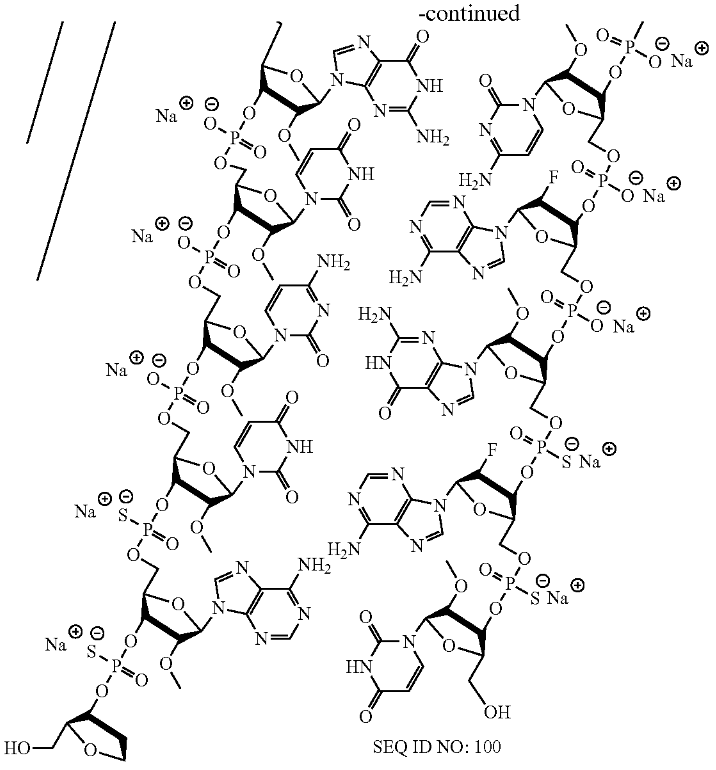

SEQ ID NO: 100

SEQ ID NO: 109 or a stereoisomer thereof.

14. A composition comprising the compound of claim 11 and a pharmaceutically acceptable carrier.

15. A composition comprising the compound of claim 1 and a pharmaceutically acceptable carrier.

16. A method comprising administering the compound of claim 1 to a subject in need thereof.

17. The method of claim 16, wherein administering the compound inhibits, reduces, and/or improves a disease, disorder, condition or a symptom thereof associated with Complement Factor B (CFB).

18. A method of inhibiting expression of CFB in a cell comprising contacting the cell with the compound of claim 1, thereby inhibiting expression of CFB in the cell.

19. The method of claim 18, wherein the cell is in the liver of an individual.

* * * * *

SEQUENCE LISTING

```
Sequence total quantity: 110
SEQ ID NO: 1            moltype = DNA  length = 2476
FEATURE                 Location/Qualifiers
source                  1..2476
                        mol_type = genomic DNA
                        organism = Homo sapiens
SEQUENCE: 1
gggaagggaa tgtgaccagg tctaggtctg gagtttcagc ttggacactg agccaagcag  60
acaagcaaag caagccagga cacaccatcc tgccccaggc ccagcttctc tcctgccttc  120
caacgccatg gggagcaatc tcagccccca actctgcctg atgcccttta tcttgggcct  180
cttgtctgga ggtgtgacca ccactccatg gtctttggcc cggccccagg gatcctgctc  240
tctggagggg gtagagatca aaggcggctc cttccgactt ctccaagagg gccaggcact  300
ggagtacgtg tgtccttctg gcttctaccc gtaccctgtg cagacacgta cctgcagatc  360
tacggggtcc tggagcaccc tgaagactca agaccaaaag actgtcagga aggcagagtg  420
cagagcaatc cactgtccaa gaccacacga cttcgagaac ggggaatact ggccccggtc  480
tccctactac aatgtgagtg atgagatctc tttccactgc tatgacggtt acactctccg  540
gggctctgcc aatcgcacct gccaagtgaa tggccgatgg agtgggcaga cagcgatctg  600
tgacaacgga gcggggtact gctccaaccc gggcatcccc attggcacaa ggaaggtggg  660
cagccagtac cgccttgaag acagcgtcac ctaccactgc agccgggggc ttaccctgcg  720
tggctcccag cggcgaacgt gtcaggaagg tggctcttgg agcgggacgg agccttcctg  780
ccaagactcc ttcatgtacg acacccctca agaggtggcc gaagctttcc tgtcttccct  840
gacagagacc atagaaggag tcgatgctga ggatgggcac ggcccagggg aacaacagaa  900
gcggaagatc gtcctggacc cttcaggctc catgaacatc tacctggtgc tagatggatc  960
agacagcatt ggggccagca acttcacagg agccaaaaag tgtctagtca acttaattga  1020
gaaggtggca agttatggtg tgaagccaag atatggtcta gtgacatatg ccacataccc  1080
caaaatttgg gtcaaagtgt ctgaagcaga cagcagtaat gcagactggg tcacgaagca  1140
gctcaatgaa atcaattatg aagaccacaa gttgaagtca gggactaaca ccaagaaggc  1200
cctccaggca gtgtacagca tgatgagctg gccagatgac gtccctcctg aaggctggaa  1260
ccgcacccgc catgtcatca tcctcatgac tgatggattg cacaacatgg gcggggaccc  1320
aattactgtc attgatgaga tccgggactt gctatacatt ggcaaggatc gcaaaaaccc  1380
aagggaggat tatctggatg tctatgtgtt tggggtcggg cctttggtga accaagtgaa  1440
catcaatgct ttggcttcca agaaagacaa tgagcaacat gtgttcaaag tcaaggatat  1500
ggaaaacctg gaagatgttt tctaccaaat gatcgatgaa agccagtctc tgagtctctg  1560
tggcatggtt tgggaacaca ggaagggtac cgattaccac aagcaaccat ggcaggccaa  1620
gatctcagtc attcgccctt caaagggaca cgagagctgt atgggggctg tggtgtctga  1680
gtactttgtg ctgacagcag cacattgttt cactgtggat gacaaggaac actcaatcaa  1740
ggtcagcgta ggaggggaga agcgggacct ggagatagaa gtagtcctat ttcaccccaa  1800
ctacaacatt aatgggaaaa aagaagcagg aattcctgaa ttttatgact atgacgttgc  1860
cctgatcaag ctcaagaata agctgaaata tggccagact atcaggccca tttgtctccc  1920
ctgcaccgag ggaacaactc gagctttgag gcttcctcca actaccactt gccagcaaca  1980
aaaggaagag ctgctccctg cacaggatat caaagctctg tttgtgtctg aggaggagaa  2040
aaagctgact cggaaggagg tctacatcaa gaatggggat aagaaaggca gctgtgagag  2100
agatgctcaa tatgccccag gctatgacaa agtcaaggac atctcagagg tggtcacccc  2160
tcggttcctt tgtactggag gagtgagtcc ctatgctgac cccaatactt gcagaggtga  2220
ttctggcggc cccttgatag ttcacaagag aagtcgtttc attcaagttg gtgtaatcag  2280
ctggggagta gtggatgtct gcaaaaacca gaagcggcaa aagcaggtac ctgctcacgc  2340
ccgagacttt cacatcaacc tctttcaagt gctgccctgg ctgaaggaga aactccaaga  2400
tgaggatttg ggttttctat aaggggtttc ctgctggaca ggggcgtggg attgaattaa  2460
aacagctgcg acaaca                                                  2476

SEQ ID NO: 2            moltype = DNA  length = 5990
FEATURE                 Location/Qualifiers
source                  1..5990
                        mol_type = genomic DNA
                        organism = Homo sapiens
SEQUENCE: 2
gggaagggaa tgtgaccagg tctaggtctg gagtttcagc ttggacactg agccaagcag  60
acaagcaaag caagccagga cacaccatcc tgccccaggc ccagcttctc tcctgccttc  120
caacgccatg gggagcaatc tcagccccca actctgcctg atgcccttta tcttgggcct  180
cttgtctgga ggtaagcgag ggtaaccttc ccttcctgct gtctccagca tccctccttg  240
gccttttggg gccaggcttc atcagccttt ctcttcaggt gtgaccacca ctccatggtc  300
tttggcccgg ccccagggat cctgctctct ggagggggta gagatcaaag gcggctcctt  360
ccgacttctc caagagggcc aggcactgga gtacgtgtgt ccttctggct tctacccgta  420
ccctgtgcag acacgtacct gcagatctac ggggtcctgg agcaccctga agactcaaga  480
ccaaaagact gtcaggaagg cagagtgcag aggtttgagg gcaatgagtg tgggcagtgg  540
```

-continued

```
cctaaggcag aaacagggca ggcggcagca aggtcaggac taggatgaga ctaggcaggg  600
tgacaaggtg ggctgaccgg gagtaggagc agttttaggg tggcaggcgg aaagggggca  660
agaaaaagcg gagttaaccc ttactaagca tttaccctgg gcttccaggc agccctggaa  720
gtcaagagaa cactcagaaa tggggaggga gaagcagtgg aaatccatat gggttgagga  780
gtaggtaaga tgctgcttct gcgggactgg gaatgcgctg tttctcagtg acatggtctc  840
cgagaccagg agggatacac ctaaggcagc ctttccctct tgatgacttc tacttgtccc  900
cccttctcaa agcaatccac tgtccaagac cacacgactt cgagaacggg gaatactggc  960
cccggtctcc ctactacaat gtgagtgatg agatctcttt ccactgctat gacggttaca  1020
ctctccgggg ctctgccaat cgcacctgcc aagtgaatgg ccgatggagt gggcagacag  1080
cgatctgtga caacggaggt gagaagcatc ccctccccct acattgctgt ctccctgacg  1140
gcgcccagcc cgaggagtgg gcactcggct ccggacactg taactcttgc tctctacctt  1200
gctcacgggg cctcaggctt cagtgcttac ctcgatgtct catacctctg cagcggggta  1260
ctgctccaac ccgggcatcc ccattggcac aaggaaggtg ggcagccagt accgccttga  1320
agacagcgtc acctaccact gcagccgggg gcttaccctg cgtggctccc agcggcgaac  1380
gtgtcaggaa ggtggctctt ggagcgggac ggagccttcc tgccaaggtg acctttgacc  1440
tgtacccccca ggtcagatcc tggtcttcca tcctactgtc ttctctcccc acctcaaccc  1500
tgctctttcc tcactttgtt taaacctccc tgtacaacta tctcacttct gagcctttta  1560
taccctggaa acccatgatc ccccgtctct ttggtcactg tatccctgac actcccagac  1620
atttgacctc atttctgact ctcccagact ccttcatgta cgacacccct caagaggtgg  1680
ccgaagcttt cctgtcttcc ctgacagaga ccatagaagg agtcgatgct gaggatgggc  1740
acggcccagg tttgaagaca gagaagggag gcagggcagg gaactggggg aaaatggaga  1800
agggacagaa ctgttaatgc tggagcctga gccactctcc tggcacccag gggaacaaca  1860
gaagcggaag atcgtcctgg acccttcagg ctccatgaac atctacctgg tgctagatgg  1920
atcagacagc attggggcca gcaacttcac aggagccaaa aagtgtctag tcaacttaat  1980
tgagaaggtg gaatcctcct atccctgaac tcggggggaat ggaatctcgc tgatcttcca  2040
ggactagctc cctgatcatt ccagcccctc tgaacaacag ggccccagga aaatctccag  2100
gtcctattct gtcctccttc ccttttactt gaagcagttt cttgactggt aattcctcca  2160
tgaacctcag cccttgagcc tcttactgag agcctccctg tcccagcaaa gtcgctgaaa  2220
tctcccaatc acagtattct attttcaatg ccatggcgcc ttgttctcct cacccacagg  2280
tggcaagtta tggtgtgaag ccaagatatg gtctagtgac atatgccaca taccccaaaa  2340
tttgggtcaa agtgtctgaa gcagacagca gtaatgcaga ctgggtcacg aagcagctca  2400
atgaaatcaa ttatgaaggt cagaggttag ggaatggtgg gaggttcact ttggggtcag  2460
gaggttcagg gtggaggggg tcatgagact accttgaggg cgacagggag gaccactttg  2520
tagtcaaaag ttgaacagca ggatcgttgg gcaatggagg ttagtgggaa cctgttgggg  2580
gctggaaggg ccactttgtg gtcaaaggga agtccgtgta atgatgatta acttaaaaag  2640
ttgaaagatg tgggatttca gttgcagatt ggtctctggg gttaaaagat ggcttggaag  2700
accaggtgag gtgatggtct cttccctctc cacagaccac aagttgaagt cagggactaa  2760
caccaagaag gccctccagg cagtgtacag catgatgagc tggccagatg acgtccctcc  2820
tgaaggctgg aaccgcaccc gccatgtcat catcctcatg actgatggtc agaagggacc  2880
tctctcctgt cccagcctcc ccaccttctc agaccagcat gtggccctta agtccacttg  2940
taacactata cccatggttg gggccctgaa tgtgactcat agctggctgt tcatctctcc  3000
tgtgaccctt cataaggaat tcttcctaag ccctgtgatc aactatctct aacccttcct  3060
caacttgctc accctgccat gtgtatccct gcctttagcc agtttatctt ccttatctcc  3120
taccctcatg gtcctgtctc ttctgcagga ttgcacaaca tgggcgggga cccaattact  3180
gtcattgatg agatccggga cttgctatac attggcaagg atcgcaaaaa cccaagggag  3240
gattatctgg gtgagtaacc tgcctaggac ccagcacccc acttcctcag ggcttggacc  3300
ctcatccttc ctttttatcc ctcagatgtc tatgtgtttg gggtcgggcc tttggtgaac  3360
caagtgaaca tcaatgcttt ggcttccaag aaagacaatg agcaacatgt gttcaaagtc  3420
aaggatatgg aaaacctgga agatgttttc taccaaatga tcggtaggga gatacaaggg  3480
aataaagaac acaactctcc tcaggttccc ctgaagtaat tcattcttcc tctacacctg  3540
aagctctagt tgcctggaaa gccttcttca ttcctccttc tctacctcag tgtcactatt  3600
cttgtttcct ggcactgttc acttaacctt agaatcacag agctctgagc acttcagaga  3660
tctttctata gtcctacatt tgacacgtgg aaacagaagc caaaggaggt caagggacag  3720
caagttagca acaagggtgg gcttgaaaac agccaggcct ctgacagctt gatcccaagt  3780
tctttccctt ttcagtccac catagcagtt ttctcctaac acgaggaaac aaatacccgt  3840
ggtctttccc tttctccttt tgggcctttg ctccccatag actcctaccc aaaaggctgc  3900
tgccatttgg gaatgaagtg ttccgagttt tcagcacatt ctccttctct gccagatgaa  3960
agccagtctc tgagtctctg tggcatggtt tgggaacaca ggaagggtac cgattaccac  4020
aagcaaccat ggcaggccaa gatctcagtc attgtaagca cagaatccca gtagtgggga  4080
cttgggggag gtgaggtcaa ggtgaaatgg gagtagggga aggaaaaaat ggccataaga  4140
gatggtggtt tgtgaaagtt gagctttccc tctctactgt tgtgtcccca gcgcccttca  4200
aagggacacg agagctgtat gggggctgtg gtgtctgagt actttgtgct gacagcagca  4260
cattgtttca ctgtggatga caaggaacac tcaatcaagg tcagcgtagg taaggatgca  4320
actgaaggtc ctgggctgca cctatgctct ccaggcaaca cctcccactt tctacagatc  4380
ctacactcca cccatcctca atgcagcccc attccttgca ccccagacca gtcagggatg  4440
ggggaagacg tgaagttagg aatgacacgg ggccagaggc aggaagctgc ccacaaagag  4500
gtggtaccta ctctcctact tcaggagggg agaagcggga cctggagata gaagtagtcc  4560
tatttcaccc caactacaac attaatggga aaaaagaagc aggaattcct gaattttatg  4620
actatgacgt tgccctgatc aagctcaaga ataagctgaa atatggccag actatcaggt  4680
gagagcgtcc agatccctga ggaaaggctg ggaaaggctg gaggactggg gtgaggagca  4740
ggcctggttt gctgttctcc ttgtccttta taggcccatt tgtctcccct gcaccgaggg  4800
aacaactcga gctttgaggc ttcctccaac taccacttgc cagcaacaaa gtaagacata  4860
cttggcaaga ggataaggat gagatcccaa gagacaagtg gggcatgaga gggaggtgca  4920
ataggaagag atgatgcctg gcccagaacc tagctctaga agggcttagg ggacatctac  4980
tgagtgacaa aggcaatggg gagatgacag tggtgggagc agctgaagtg acgcagtcta  5040
ttcgtccaga ggaagagctg ctccctgcac aggatatcaa agctctgttt gtgtctgagg  5100
aggagaaaaa gctgactcgg aaggaggtct acatcaagaa tggggataag gtgagaaacg  5160
ggcatcctaa ggaggcactc taggccccaa tccttcctaa gccacttctg ttcattactt  5220
ctccatgctt cccacctccc ctacagaaag gcagctgtga gagagatgct caatatgccc  5280
```

-continued caggctatga caaagtcaag gacatctcag aggtggtcac ccctcggttc ctttgtactg 5340
gaggagtgag tccctatgct gaccccaata cttgcagagg tgagagaatg ctctttggtt 5400
gtgctacaag tgcccaaggc ccaacagtcc ttttctctac agcttctcct ctccttgcag 5460
gtgattctgg cggccccttg atagttcaca agagaagtcg tttcattcaa gtgagtcctc 5520
cctttcctat ctggggagat gccaagtggt cagcatgggc cccaaagcag gaaagctcaa 5580
tgcatgtggc tagtaattcg aggtaggcag agcctgcctc accttaggac cgcatgtctt 5640
gcctgcgtgt gtcaagaacg aggctgagct gggtccctag tctgattcct ttaggtcagc 5700
taagacacaa gcaggaacag ccatgcttcc aggattagga attctactga atgatccatg 5760
gcaccccact gcctctgcag gttggtgtaa tcagctgggg agtagtggat gtctgcaaaa 5820
accagaagcg gcaaaagcag gtacctgctc acgcccgaga ctttcacatc aacctctttc 5880
aagtgctgcc ctggctgaag gagaaactcc aagatgagga tttgggtttt ctataagggg 5940
tttcctgctg gacaggggcg tgggattgaa ttaaaacagc tgcgacaaca 5990

SEQ ID NO: 3 moltype = DNA length = 2476
FEATURE Location/Qualifiers
source 1..2476
mol_type = genomic DNA
organism = Homo sapiens
SEQUENCE: 3
gggaagggaa tgtgaccagg tctaggtctg gagtttcagc ttggacactg agccaagcag 60
acaagcaaag caagccagga cacaccatcc tgccccaggc ccagcttctc tcctgccttc 120
caacgccatg gggagcaatc tcagccccca actctgcctg atgcccttta tcttgggcct 180
cttgtctgga ggtgtgacca ccactccatg gtctttggcc cggccccagg gatcctgctc 240
tctggagggg gtagagatca aaggcggctc cttccgactt ctccaagagg gccaggcact 300
ggagtacgtg tgtccttctg gcttctaccc gtaccctgtg cagacacgta cctgcagatc 360
tacggggtcc tggagcaccc tgaagactca agaccaaaag actgtcagga aggcagagtg 420
cagagcaatc cactgtccaa gaccacacga cttcgagaac ggggaatact ggccccggtc 480
tccctactac aatgtgagtg atgagatctc tttccactgc tatgacggtt acactctccg 540
gggctctgcc aatcgcacct gccaagtgaa tggccgatgg agtgggcaga cagcgatctg 600
tgacaacgga gcggggtact gctccaaccc gggcatcccc attggcacaa ggaaggtggg 660
cagccagtac cgccttgaag acagcgtcac ctaccactgc agccgggggc ttaccctgcg 720
tggctcccag cggcgaacgt gtcaggaagg tggctcttgg agcgggacgg agccttcctg 780
ccaagactcc ttcatgtacg acacccctca agaggtggcc gaagctttcc tgtcttccct 840
gacagagacc atagaaggag tcgatgctga ggatgggcac ggcccagggg aacaacagaa 900
gcggaagatc gtcctggacc cttcaggctc catgaacatc tacctggtgc tagatggatc 960
agacagcatt ggggccagca acttcacagg agccaaaaag tgtctagtca acttaattga 1020
gaaggtggca agttatggtg tgaagccaag atatggtcta gtgacatatg ccacataccc 1080
caaaatttgg gtcaaagtgt ctgaagcaga cagcagtaat gcagactggg tcacgaagca 1140
gctcaatgaa atcaattatg aagaccacaa gttgaagtca gggactaaca ccaagaaggc 1200
cctccaggca gtgtacagca tgatgagctg gccagatgac gtccctcctg aaggctggaa 1260
ccgcacccgc catgtcatca tcctcatgac tgatggattg cacaacatgg gcggggaccc 1320
aattactgtc attgatgaga tccgggactt gctatacatt ggcaaggatc gcaaaaaccc 1380
aagggaggat tatctggatg tctatgtgtt tggggtcggg cctttggtga accaagtgaa 1440
catcaatgct ttggcttcca agaaagacaa tgagcaacat gtgttcaaag tcaaggatat 1500
ggaaaacctg gaagatgttt tctaccaaat gatcgatgaa agccagtctc tgagtctctg 1560
tggcatggtt tgggaacaca ggaagggtac cgattaccac aagcaaccat ggcaggccaa 1620
gatctcagtc attcgccctt caaagggaca cgagagctgt atgggggctg tggtgtctga 1680
gtactttgtg ctgacagcag cacattgttt cactgtggat gacaaggaac actcaatcaa 1740
ggtcagcgta ggaggggaga agcgggacct ggagatagaa gtagtcctat ttcaccccaa 1800
ctacaacatt aatgggaaaa aagaagcagg aattcctgaa ttttatgact atgacgttgc 1860
cctgatcaag ctcaagaata agctgaaata tggccagact atcaggccca tttgtctccc 1920
ctgcaccgag ggaacaactc gagctttgag gcttcctcca actaccactt gccagcaaca 1980
aaaggaagag ctgctccctg cacaggatat caaagctctg tttgtgtctg aggaggagaa 2040
aaagctgact cggaaggagg tctacatcaa gaatggggat aagaaaggca gctgtgagag 2100
agatgctcaa tatgccccag gctatgacaa agtcaaggac atctcagagg tggtcacccc 2160
tcggttcctt tgtactggag gagtgagtcc ctatgctgac cccaatactt gcagaggtga 2220
ttctggcggc cccttgatag ttcacaagag aagtcgtttc attcaagttg gtgtaatcag 2280
ctggggagta gtggatgtct gcaaaaacca gaagcggcaa aagcaggtac ctgctcacgc 2340
ccgagacttt cacatcaacc tctttcaagt gctgccctgg ctgaaggaga aactccaaga 2400
tgaggatttg ggttttctat aaggggtttc ctgctggaca ggggcgtggg attgaattaa 2460
aacagctgcg acaaca 2476

SEQ ID NO: 4 moltype = DNA length = 5990
FEATURE Location/Qualifiers
source 1..5990
mol_type = genomic DNA
organism = Homo sapiens
SEQUENCE: 4
gggaagggaa tgtgaccagg tctaggtctg gagtttcagc ttggacactg agccaagcag 60
acaagcaaag caagccagga cacaccatcc tgccccaggc ccagcttctc tcctgccttc 120
caacgccatg gggagcaatc tcagccccca actctgcctg atgcccttta tcttgggcct 180
cttgtctgga ggtaagcgag ggtaaccttc ccttcctgct gtctccagca tccctccttg 240
gccttttggg gccaggcttc atcagccttt ctcttcaggt gtgaccacca ctccatggtc 300
tttggcccgg ccccagggat cctgctctct ggagggggta gagatcaaag gcggctcctt 360
ccgacttctc caagagggcc aggcactgga gtacgtgtgt ccttctggct tctacccgta 420
ccctgtgcag acacgtacct gcagatctac ggggtcctgg agcaccctga agactcaaga 480
ccaaaagact gtcaggaagg cagagtgcag aggtttgagg gcaatgagtg tgggcagtgg 540
cctaaggcag aaacagggca ggcggcagca aggtcaggac taggatgaga ctaggcaggg 600
tgacaaggtg ggctgaccgg gagtaggagc agttttaggg tggcaggcgg aaagggggca 660

-continued

```
agaaaaagcg gagttaaccc ttactaagca tttaccctgg gcttccaggc agccctggaa  720
gtcaagagaa cactcagaaa tggggaggga gaagcagtgg aaatccatat gggttgagga  780
gtaggtaaga tgctgcttct gcgggactgg gaatgcgctg tttctcagtg acatggtctc  840
cgagaccagg agggatacac ctaaggcagc ctttccctct tgatgacttc tacttgtccc  900
cccttctcaa agcaatccac tgtccaagac cacacgactt cgagaacggg gaatactggc  960
cccggtctcc ctactacaat gtgagtgatg agatctcttt ccactgctat gacggttaca  1020
ctctccgggg ctctgccaat cgcacctgcc aagtgaatgg ccggtggagt gggcagacag  1080
cgatctgtga caacggaggt gagaagcatc ccctccccct acattgctgt ctccctgacg  1140
gcgcccagcc cgaggagtgg gcactcggct ccggacactg taactcttgc tctctacctt  1200
gctcacgggg cctcaggctt cagtgcttac ctcgatgtct catacctctg cagcggggta  1260
ctgctccaac ccgggcatcc ccattggcac aaggaaggtg ggcagccagt accgccttga  1320
agacagcgtc acctaccact gcagccgggg gcttaccctg cgtggctccc agcggcgaac  1380
gtgtcaggaa ggtggctctt ggagcgggac ggagccttcc tgccaaggtg acctttgacc  1440
tgtacccccca ggtcagatcc tggtcttcca tcctactgtc ttctctcccc acctcaaccc  1500
tgctctttcc tcactttgtt taaacctccc tgtacaacta tctcacttct gagcctttta  1560
taccctggaa acccatgatc ccccgtctct ttggtcactg tatccctgac actcccagac  1620
atttgacctc atttctgact ctcccagact ccttcatgta cgacacccct caagaggtgg  1680
ccgaagcttt cctgtcttcc ctgacagaga ccatagaagg agtcgatgct gaggatgggc  1740
acggcccagg tttgaagaca gagaagggag gcagggcagg gaactggggg aaaatggaga  1800
agggacagaa ctgttaatgc tggagcctga gccactctcc tggcacccag gggaacaaca  1860
gaagcggaag atcgtcctgg acccttcagg ctccatgaac atctacctgg tgctagatgg  1920
atcagacagc attggggcca gcaacttcac aggagccaaa aagtgtctag tcaacttaat  1980
tgagaaggtg gaatcctcct atccctgaac tcggggggaat ggaatctcgc tgatcttcca  2040
ggactagctc cctgatcatt ccagcccctc tgaacaacag ggccccagga aaatctccag  2100
gtcctattct gtcctccttc ccttttactt gaagcagttt cttgactggt aattcctcca  2160
tgaacctcag cccttgagcc tcttactgag agcctccctg tcccagcaaa gtcgctgaaa  2220
tctcccaatc acagtattct attttcaatg ccatggcgcc ttgttctcct cacccacagg  2280
tggcaagtta tggtgtgaag ccaagatatg gtctagtgac atatgccaca taccccaaaa  2340
tttgggtcaa agtgtctgaa gcagacagca gtaatgcaga ctgggtcacg aagcagctca  2400
atgaaatcaa ttatgaaggt cagaggttag ggaatggtgg gaggttcact ttggggtcag  2460
gaggttcagg gtggaggggg tcatgagact accttgaggg cgacagggag gaccactttg  2520
tagtcaaaag ttgaacagca ggatcgttgg gcaatggagg ttagtgggaa cctgttgggg  2580
gctggaaggg ccactttgtg gtcaaaggga agtccgtgta atgatgatta acttaaaaag  2640
ttgaaagatg tgggatttca gttgcagatt ggtctctggg gttaaaagat ggcttggaag  2700
accaggtgag gtgatggtct cttccctctc cacagaccac aagttgaagt cagggactaa  2760
caccaagaag gccctccagg cagtgtacag catgatgagc tggccagatg acgtccctcc  2820
tgaaggctgg aaccgcaccc gccatgtcat catcctcatg actgatggtc agaagggacc  2880
tctctcctgt cccagcctcc ccaccttctc agaccagcat gtggccctta agtccacttg  2940
taacactata cccatggttg ggccctgaa tgtgactcat agctggctgt tcatctctcc  3000
tgtgaccctt cataaggaat tcttcctaag ccctgtgatc aactatctct aaccccttcct  3060
caacttgctc accctgccat gtgtatccct gcctttagcc agtttatctt ccttatctcc  3120
taccctcatg gtcctgtctc ttctgcagga ttgcacaaca tgggcgggga cccaattact  3180
gtcattgatg agatccggga cttgctatac attggcaagg atcgcaaaaa cccaagggag  3240
gattatctgg gtgagtaacc tgcctaggac ccagcacccc acttcctcag ggcttggacc  3300
ctcatccttc cttttatcc ctcagatgtc tatgtgtttg gggtcgggcc tttggtgaac  3360
caagtgaaca tcaatgcttt ggcttccaag aaagacaatg agcaacatgt gttcaaagtc  3420
aaggatatgg aaaacctgga agatgttttc taccaaatga tcggtaggga gatacaaggg  3480
aataaagaac acaactctcc tcaggttccc ctgaagtaat tcattcttcc tctacacctg  3540
aagctctagt tgcctggaaa gccttcttca ttcctccttc tctacctcag tgtcactatt  3600
cttgtttcct ggcactgttc acttaacctt agaatcacag agctctgagc acttcagaga  3660
tctttctata gtcctacatt tgacacgtgg aaacagaagc caaaggaggt caagggacag  3720
caagttagca acaagggtgg gcttgaaaac agccaggcct ctgacagctt gatcccaagt  3780
tctttccctt ttcagtccac catagcagtt ttctcctaac acgaggaaac aaatacccgt  3840
ggtctttccc tttctccttt tgggcctttg ctcccccatag actcctaccc aaaaggctgc  3900
tgccatttgg gaatgaagtg ttccgagttt tcagcacatt ctccttctct gccagatgaa  3960
agccagtctc tgagtctctg tggcatggtt tgggaacaca ggaagggtac cgattaccac  4020
aagcaaccat ggcaggccaa gatctcagtc attgtaagca cagaatccca gtagtgggga  4080
cttgggggag gtgaggtcaa ggtgaaatgg gagtagggga aggaaaaaat ggccataaga  4140
gatggtggtt tgtgaaagtt gagctttccc tctctactgt tgtgtcccca gcgcccttca  4200
aagggacacg agagctgtat gggggctgtg gtgtctgagt actttgtgct gacagcagca  4260
cattgtttca ctgtggatga caaggaacac tcaatcaagg tcagcgtagg taaggatgca  4320
actgaaggtc ctgggctgca cctatgctct ccaggcaaca cctcccactt tctacagatc  4380
ctacactcca cccatcctca atgcagcccc attccttgca ccccagacca gtcagggatg  4440
ggggaagacg tgaagttagg aatgacacgg ggccagaggc aggaagctgc ccacaaagag  4500
gtggtaccta ctctcctact tcaggagggg agaagcggga cctggagata gaagtagtcc  4560
tatttcaccc caactacaac attaatggga aaaaagaagc aggaattcct gaattttatg  4620
actatgacgt tgccctgatc aagctcaaga ataagctgaa atatggccag actatcaggt  4680
gagagcgtcc agatccctga ggaaaggctg ggaaaggctg gaggactggg gtgaggagca  4740
ggcctggttt gctgttctcc ttgtccttta taggcccatt tgtctcccct gcaccgaggg  4800
aacaactcga gctttgaggc ttcctccaac taccacttgc cagcaacaaa gtaagacata  4860
cttggcaaga ggataaggat gagatcccaa gagacaagtg gggcatgaga gggaggtgca  4920
ataggaagag atgatgcctg gcccagaacc tagctctaga agggcttagg ggacatctac  4980
tgagtgacga aggcaatggg gagatgacag tggtgggagc agctgaagtg acgcagtcta  5040
ttcgtccaga ggaagagctg ctccctgcac aggatatcaa agctctgttt gtgtctgagg  5100
aggagaaaaa gctgactcgg aaggaggtct acatcaagaa tggggataag gtgagaaacg  5160
ggcatcctaa ggaggcactc taggccccaa tccttcctaa gccacttctg ttcattactt  5220
ctccatgctt cccacctccc ctacagaaag gcagctgtga gagagatgct caatatgccc  5280
caggctatga caaagtcaag gacatctcag aggtggtcac ccctcggttc ctttgtactg  5340
gaggagtgag tccctatgct gaccccaata cttgcagagg tgagagaatg ctctttggtt  5400
```

```
gtgctacaag tgcccaaggc ccaacagtcc ttttctctac agcttctcct ctccttgcag  5460
gtgattctgg cggccccttg atagttcaca agagaagtcg tttcattcaa gtgagtcctc  5520
cctttcctat ctggggagat gccaagtggt cagcatgggc cccaaagcag gaaagctcaa  5580
tgcatgtggc tagtaattcg aggtaggcag agcctgcctc accttaggac cgcatgtctt  5640
gcctgcgtgt gtcaagaacg aggctgagct gggtccctag tctgattcct ttaggtcagc  5700
taagacacaa gcaggaacag ccatgcttcc aggattagga attctactga atgatccatg  5760
gcaccccact gcctctgcag gttggtgtaa tcagctgggg agtagtggat gtctgcaaaa  5820
accagaagcg gcaaaagcag gtacctgctc acgcccgaga ctttcacatc aacctctttc  5880
aagtgctgcc ctggctgaag gagaaactcc aagatgagga tttgggtttt ctataagggg  5940
tttcctgctg gacaggggcg tgggattgaa ttaaaacagc tgcgacaaca             5990

SEQ ID NO: 5           moltype =   length =
SEQUENCE: 5
000

SEQ ID NO: 6           moltype =   length =
SEQUENCE: 6
000

SEQ ID NO: 7           moltype =   length =
SEQUENCE: 7
000

SEQ ID NO: 8           moltype =   length =
SEQUENCE: 8
000

SEQ ID NO: 9           moltype =   length =
SEQUENCE: 9
000

SEQ ID NO: 10          moltype =   length =
SEQUENCE: 10
000

SEQ ID NO: 11          moltype = RNA  length = 21
FEATURE                Location/Qualifiers
source                 1..21
                       mol_type = other RNA
                       organism = synthetic construct
SEQUENCE: 11
tatccatcta gcatcaggta g                                           21

SEQ ID NO: 12          moltype = RNA  length = 21
FEATURE                Location/Qualifiers
source                 1..21
                       mol_type = other RNA
                       organism = synthetic construct
modified_base          14
                       mod_base = i
SEQUENCE: 12
tctgatccat ctancaccag g                                           21

SEQ ID NO: 13          moltype = RNA  length = 21
FEATURE                Location/Qualifiers
source                 1..21
                       mol_type = other RNA
                       organism = synthetic construct
SEQUENCE: 13
agaaaaccca aattctcatc t                                           21

SEQ ID NO: 14          moltype = RNA  length = 21
FEATURE                Location/Qualifiers
source                 1..21
                       mol_type = other RNA
                       organism = synthetic construct
SEQUENCE: 14
agaaaaccca aattctcatc c                                           21

SEQ ID NO: 15          moltype = RNA  length = 21
FEATURE                Location/Qualifiers
source                 1..21
                       mol_type = other RNA
                       organism = synthetic construct
SEQUENCE: 15
tagacatcca ctattcccca g                                           21

SEQ ID NO: 16          moltype = RNA  length = 21
FEATURE                Location/Qualifiers
```

-continued

```
source                 1..21
                       mol_type = other RNA
                       organism = synthetic construct
SEQUENCE: 16
tagacatcca ctattcccca t                                                     21

SEQ ID NO: 17          moltype = RNA  length = 21
FEATURE                Location/Qualifiers
source                 1..21
                       mol_type = other RNA
                       organism = synthetic construct
SEQUENCE: 17
ttgcagacat ccattactcc c                                                     21

SEQ ID NO: 18          moltype = RNA  length = 21
FEATURE                Location/Qualifiers
source                 1..21
                       mol_type = other RNA
                       organism = synthetic construct
SEQUENCE: 18
ttgcagacat ccattactcc t                                                     21

SEQ ID NO: 19          moltype = RNA  length = 21
FEATURE                Location/Qualifiers
source                 1..21
                       mol_type = other RNA
                       organism = synthetic construct
SEQUENCE: 19
ttgatctcta ccctctccag a                                                     21

SEQ ID NO: 20          moltype = RNA  length = 21
FEATURE                Location/Qualifiers
source                 1..21
                       mol_type = other RNA
                       organism = synthetic construct
SEQUENCE: 20
tctatctcca ggttccgctt c                                                     21

SEQ ID NO: 21          moltype = RNA  length = 21
FEATURE                Location/Qualifiers
source                 1..21
                       mol_type = other RNA
                       organism = synthetic construct
SEQUENCE: 21
ttgatgtaga ccttcttccg a                                                     21

SEQ ID NO: 22          moltype = RNA  length = 21
FEATURE                Location/Qualifiers
source                 1..21
                       mol_type = other RNA
                       organism = synthetic construct
SEQUENCE: 22
tctgtctgat ccatctagca c                                                     21

SEQ ID NO: 23          moltype = RNA  length = 21
FEATURE                Location/Qualifiers
source                 1..21
                       mol_type = other RNA
                       organism = synthetic construct
SEQUENCE: 23
atcctgtgca gggagcagct c                                                     21

SEQ ID NO: 24          moltype = RNA  length = 23
FEATURE                Location/Qualifiers
source                 1..23
                       mol_type = other RNA
                       organism = synthetic construct
SEQUENCE: 24
tgaaagagat ctcatcactc aca                                                   23

SEQ ID NO: 25          moltype = RNA  length = 22
FEATURE                Location/Qualifiers
source                 1..22
                       mol_type = other RNA
                       organism = synthetic construct
SEQUENCE: 25
tagacatcca gataatcctc cc                                                    22

SEQ ID NO: 26          moltype = RNA  length = 22
```

```
FEATURE                Location/Qualifiers
source                 1..22
                       mol_type = other RNA
                       organism = synthetic construct
SEQUENCE: 26
tcattgtctt tcttggaagc ca                                          22

SEQ ID NO: 27          moltype = RNA  length = 21
FEATURE                Location/Qualifiers
source                 1..21
                       mol_type = other RNA
                       organism = synthetic construct
SEQUENCE: 27
tctatctcca ggtcccgctt c                                           21

SEQ ID NO: 28          moltype = RNA  length = 21
FEATURE                Location/Qualifiers
source                 1..21
                       mol_type = other RNA
                       organism = synthetic construct
SEQUENCE: 28
tcattcttga tgtagacctc c                                           21

SEQ ID NO: 29          moltype = RNA  length = 22
FEATURE                Location/Qualifiers
source                 1..22
                       mol_type = other RNA
                       organism = synthetic construct
SEQUENCE: 29
tgtagatgtt catggagcct ga                                          22

SEQ ID NO: 30          moltype = RNA  length = 23
FEATURE                Location/Qualifiers
source                 1..23
                       mol_type = other RNA
                       organism = synthetic construct
SEQUENCE: 30
ttgcagacat ccattactcc cca                                         23

SEQ ID NO: 31          moltype = RNA  length = 22
FEATURE                Location/Qualifiers
source                 1..22
                       mol_type = other RNA
                       organism = synthetic construct
SEQUENCE: 31
ttgcagacat ccattactcc cc                                          22

SEQ ID NO: 32          moltype = RNA  length = 23
FEATURE                Location/Qualifiers
source                 1..23
                       mol_type = other RNA
                       organism = synthetic construct
SEQUENCE: 32
tagacatcca ctattcccca gct                                         23

SEQ ID NO: 33          moltype = RNA  length = 22
FEATURE                Location/Qualifiers
source                 1..22
                       mol_type = other RNA
                       organism = synthetic construct
SEQUENCE: 33
tagacatcca ctattcccca gc                                          22

SEQ ID NO: 34          moltype = RNA  length = 23
FEATURE                Location/Qualifiers
source                 1..23
                       mol_type = other RNA
                       organism = synthetic construct
SEQUENCE: 34
agaaaaccca aattctcatc ttg                                         23

SEQ ID NO: 35          moltype = RNA  length = 23
FEATURE                Location/Qualifiers
source                 1..23
                       mol_type = other RNA
                       organism = synthetic construct
SEQUENCE: 35
agaaaaccca aattctcatc tgg                                         23
```

```
SEQ ID NO: 36          moltype = RNA  length = 22
FEATURE                Location/Qualifiers
source                 1..22
                       mol_type = other RNA
                       organism = synthetic construct
SEQUENCE: 36
agaaaaccca aattctcatc tg                                           22

SEQ ID NO: 37          moltype = RNA  length = 22
FEATURE                Location/Qualifiers
source                 1..22
                       mol_type = other RNA
                       organism = synthetic construct
SEQUENCE: 37
agaaaaccca aattctcatc cg                                           22

SEQ ID NO: 38          moltype = RNA  length = 23
FEATURE                Location/Qualifiers
source                 1..23
                       mol_type = other RNA
                       organism = synthetic construct
SEQUENCE: 38
tatccatcta gcatcaggta gat                                          23

SEQ ID NO: 39          moltype = RNA  length = 22
FEATURE                Location/Qualifiers
source                 1..22
                       mol_type = other RNA
                       organism = synthetic construct
SEQUENCE: 39
tatccatcta gcatcaggta ga                                           22

SEQ ID NO: 40          moltype = RNA  length = 22
FEATURE                Location/Qualifiers
source                 1..22
                       mol_type = other RNA
                       organism = synthetic construct
SEQUENCE: 40
tatccatcta gcatcaggta gg                                           22

SEQ ID NO: 41          moltype = RNA  length = 23
FEATURE                Location/Qualifiers
source                 1..23
                       mol_type = other RNA
                       organism = synthetic construct
SEQUENCE: 41
tcatcaatga cagtaattgg gtc                                          23

SEQ ID NO: 42          moltype = RNA  length = 23
FEATURE                Location/Qualifiers
source                 1..23
                       mol_type = other RNA
                       organism = synthetic construct
SEQUENCE: 42
aaagcattga tgttcacttg gtt                                          23

SEQ ID NO: 43          moltype = RNA  length = 23
FEATURE                Location/Qualifiers
source                 1..23
                       mol_type = other RNA
                       organism = synthetic construct
SEQUENCE: 43
acaaagtact cagacaccac acg                                          23

SEQ ID NO: 44          moltype = RNA  length = 23
FEATURE                Location/Qualifiers
source                 1..23
                       mol_type = other RNA
                       organism = synthetic construct
SEQUENCE: 44
tcaacttgaa tgaaacgact tct                                          23

SEQ ID NO: 45          moltype = RNA  length = 22
FEATURE                Location/Qualifiers
source                 1..22
                       mol_type = other RNA
                       organism = synthetic construct
SEQUENCE: 45
tctacctgat gctagatgga ta                                           22
```

```
SEQ ID NO: 46          moltype = RNA  length = 22
FEATURE                Location/Qualifiers
source                 1..22
                       mol_type = other RNA
                       organism = synthetic construct
SEQUENCE: 46
tcctggtgtt agatggatca ga                                           22

SEQ ID NO: 47          moltype = RNA  length = 22
FEATURE                Location/Qualifiers
source                 1..22
                       mol_type = other RNA
                       organism = synthetic construct
SEQUENCE: 47
tagatgagaa tttgggtttt ct                                           22

SEQ ID NO: 48          moltype = RNA  length = 22
FEATURE                Location/Qualifiers
source                 1..22
                       mol_type = other RNA
                       organism = synthetic construct
SEQUENCE: 48
tggatgagaa tttgggtttt ct                                           22

SEQ ID NO: 49          moltype = RNA  length = 22
FEATURE                Location/Qualifiers
source                 1..22
                       mol_type = other RNA
                       organism = synthetic construct
SEQUENCE: 49
tctggggaat agtggatgtc ta                                           22

SEQ ID NO: 50          moltype = RNA  length = 22
FEATURE                Location/Qualifiers
source                 1..22
                       mol_type = other RNA
                       organism = synthetic construct
SEQUENCE: 50
tatggggaat agtggatgtc ta                                           22

SEQ ID NO: 51          moltype = RNA  length = 22
FEATURE                Location/Qualifiers
source                 1..22
                       mol_type = other RNA
                       organism = synthetic construct
SEQUENCE: 51
tgggagtaat ggatgtctgc aa                                           22

SEQ ID NO: 52          moltype = RNA  length = 22
FEATURE                Location/Qualifiers
source                 1..22
                       mol_type = other RNA
                       organism = synthetic construct
SEQUENCE: 52
tgggagtaat ggatgtctac aa                                           22

SEQ ID NO: 53          moltype = RNA  length = 22
FEATURE                Location/Qualifiers
source                 1..22
                       mol_type = other RNA
                       organism = synthetic construct
SEQUENCE: 53
taggagtaat ggatgtctac aa                                           22

SEQ ID NO: 54          moltype = RNA  length = 22
FEATURE                Location/Qualifiers
source                 1..22
                       mol_type = other RNA
                       organism = synthetic construct
SEQUENCE: 54
ttctggagag ggtagagatc aa                                           22

SEQ ID NO: 55          moltype = RNA  length = 22
FEATURE                Location/Qualifiers
source                 1..22
                       mol_type = other RNA
                       organism = synthetic construct
SEQUENCE: 55
```

-continued

```
tgaagcggaa cctggagata ga                                            22

SEQ ID NO: 56          moltype = RNA  length = 22
FEATURE                Location/Qualifiers
source                 1..22
                       mol_type = other RNA
                       organism = synthetic construct
SEQUENCE: 56
ttcggaagaa ggtctacatc aa                                            22

SEQ ID NO: 57          moltype = RNA  length = 22
FEATURE                Location/Qualifiers
source                 1..22
                       mol_type = other RNA
                       organism = synthetic construct
SEQUENCE: 57
tgtgctagat ggatcagaca ga                                            22

SEQ ID NO: 58          moltype = RNA  length = 22
FEATURE                Location/Qualifiers
source                 1..22
                       mol_type = other RNA
                       organism = synthetic construct
SEQUENCE: 58
tgtgctagat ggatcagata ga                                            22

SEQ ID NO: 59          moltype = RNA  length = 22
FEATURE                Location/Qualifiers
source                 1..22
                       mol_type = other RNA
                       organism = synthetic construct
SEQUENCE: 59
tgtgctagat ggatcagaaa ga                                            22

SEQ ID NO: 60          moltype = RNA  length = 21
FEATURE                Location/Qualifiers
source                 1..21
                       mol_type = other RNA
                       organism = synthetic construct
SEQUENCE: 60
gagctgctcc ctgcacagga t                                             21

SEQ ID NO: 61          moltype = RNA  length = 21
FEATURE                Location/Qualifiers
source                 1..21
                       mol_type = other RNA
                       organism = synthetic construct
SEQUENCE: 61
gagctgctcc ctgcacagaa t                                             21

SEQ ID NO: 62          moltype = RNA  length = 21
FEATURE                Location/Qualifiers
source                 1..21
                       mol_type = other RNA
                       organism = synthetic construct
SEQUENCE: 62
gagctgctcc ctgcacaaga t                                             21

SEQ ID NO: 63          moltype = RNA  length = 23
FEATURE                Location/Qualifiers
source                 1..23
                       mol_type = other RNA
                       organism = synthetic construct
SEQUENCE: 63
tgtgagtgat gagatctctt tca                                           23

SEQ ID NO: 64          moltype = RNA  length = 23
FEATURE                Location/Qualifiers
source                 1..23
                       mol_type = other RNA
                       organism = synthetic construct
SEQUENCE: 64
tgggaggatt atctggatgt cta                                           23

SEQ ID NO: 65          moltype = RNA  length = 22
FEATURE                Location/Qualifiers
source                 1..22
                       mol_type = other RNA
                       organism = synthetic construct
```

```
SEQUENCE: 65
tggcttccaa gaaagacaat ga                                          22

SEQ ID NO: 66          moltype = RNA  length = 22
FEATURE                Location/Qualifiers
source                 1..22
                       mol_type = other RNA
                       organism = synthetic construct
SEQUENCE: 66
tgaagcggga cctggagata ga                                          22

SEQ ID NO: 67          moltype = RNA  length = 22
FEATURE                Location/Qualifiers
source                 1..22
                       mol_type = other RNA
                       organism = synthetic construct
SEQUENCE: 67
tggaggtcta catcaagaat ga                                          22

SEQ ID NO: 68          moltype = RNA  length = 22
FEATURE                Location/Qualifiers
source                 1..22
                       mol_type = other RNA
                       organism = synthetic construct
SEQUENCE: 68
tcaggctcca tgaacatcta ca                                          22

SEQ ID NO: 69          moltype = RNA  length = 23
FEATURE                Location/Qualifiers
source                 1..23
                       mol_type = other RNA
                       organism = synthetic construct
SEQUENCE: 69
tggggagtaa tggatgtctg caa                                         23

SEQ ID NO: 70          moltype = RNA  length = 23
FEATURE                Location/Qualifiers
source                 1..23
                       mol_type = other RNA
                       organism = synthetic construct
SEQUENCE: 70
tgggagtaat ggatgtctgc aat                                         23

SEQ ID NO: 71          moltype = RNA  length = 24
FEATURE                Location/Qualifiers
source                 1..24
                       mol_type = other RNA
                       organism = synthetic construct
SEQUENCE: 71
tggggagtaa tggatgtctg caat                                        24

SEQ ID NO: 72          moltype = RNA  length = 21
FEATURE                Location/Qualifiers
source                 1..21
                       mol_type = other RNA
                       organism = synthetic construct
SEQUENCE: 72
ctggggaata gtggatgtct a                                           21

SEQ ID NO: 73          moltype = RNA  length = 22
FEATURE                Location/Qualifiers
source                 1..22
                       mol_type = other RNA
                       organism = synthetic construct
SEQUENCE: 73
ctggggaata gtggatgtct at                                          22

SEQ ID NO: 74          moltype = RNA  length = 23
FEATURE                Location/Qualifiers
source                 1..23
                       mol_type = other RNA
                       organism = synthetic construct
SEQUENCE: 74
tgctggggaa tagtggatgt cta                                         23

SEQ ID NO: 75          moltype = RNA  length = 23
FEATURE                Location/Qualifiers
source                 1..23
                       mol_type = other RNA
```

```
                        organism = synthetic construct
SEQUENCE: 75
caagatgaga atttgggttt tct                                              23

SEQ ID NO: 76           moltype = RNA  length = 23
FEATURE                 Location/Qualifiers
source                  1..23
                        mol_type = other RNA
                        organism = synthetic construct
SEQUENCE: 76
ccagatgaga atttgggttt tct                                              23

SEQ ID NO: 77           moltype = RNA  length = 23
FEATURE                 Location/Qualifiers
source                  1..23
                        mol_type = other RNA
                        organism = synthetic construct
SEQUENCE: 77
tcagatgaga atttgggttt tct                                              23

SEQ ID NO: 78           moltype = RNA  length = 22
FEATURE                 Location/Qualifiers
source                  1..22
                        mol_type = other RNA
                        organism = synthetic construct
SEQUENCE: 78
cagatgagaa tttgggtttt ct                                               22

SEQ ID NO: 79           moltype = RNA  length = 22
FEATURE                 Location/Qualifiers
source                  1..22
                        mol_type = other RNA
                        organism = synthetic construct
SEQUENCE: 79
cggatgagaa tttgggtttt ct                                               22

SEQ ID NO: 80           moltype = RNA  length = 23
FEATURE                 Location/Qualifiers
source                  1..23
                        mol_type = other RNA
                        organism = synthetic construct
SEQUENCE: 80
ttctacctga tgctagatgg ata                                              23

SEQ ID NO: 81           moltype = RNA  length = 23
FEATURE                 Location/Qualifiers
source                  1..23
                        mol_type = other RNA
                        organism = synthetic construct
SEQUENCE: 81
tcctacctga tgctagatgg ata                                              23

SEQ ID NO: 82           moltype = RNA  length = 23
FEATURE                 Location/Qualifiers
source                  1..23
                        mol_type = other RNA
                        organism = synthetic construct
SEQUENCE: 82
tctacctgat gctagatgga tat                                              23

SEQ ID NO: 83           moltype = RNA  length = 24
FEATURE                 Location/Qualifiers
source                  1..24
                        mol_type = other RNA
                        organism = synthetic construct
SEQUENCE: 83
tcctacctga tgctagatgg atat                                             24

SEQ ID NO: 84           moltype = RNA  length = 15
FEATURE                 Location/Qualifiers
source                  1..15
                        mol_type = other RNA
                        organism = synthetic construct
SEQUENCE: 84
taatttgggt tttct                                                       15

SEQ ID NO: 85           moltype = RNA  length = 12
FEATURE                 Location/Qualifiers
source                  1..12
```

```
                        mol_type = other RNA
                        organism = synthetic construct
SEQUENCE: 85
tttgggtttt ct                                                    12

SEQ ID NO: 86           moltype = RNA  length = 24
FEATURE                 Location/Qualifiers
source                  1..24
                        mol_type = other RNA
                        organism = synthetic construct
SEQUENCE: 86
agctggggaa tagtggatgt ctat                                       24

SEQ ID NO: 87           moltype = RNA  length = 14
FEATURE                 Location/Qualifiers
source                  1..14
                        mol_type = other RNA
                        organism = synthetic construct
SEQUENCE: 87
aatttgggtt ttct                                                  14

SEQ ID NO: 88           moltype = RNA  length = 13
FEATURE                 Location/Qualifiers
source                  1..13
                        mol_type = other RNA
                        organism = synthetic construct
SEQUENCE: 88
atttgggttt tct                                                   13

SEQ ID NO: 89           moltype = RNA  length = 23
FEATURE                 Location/Qualifiers
source                  1..23
                        mol_type = other RNA
                        organism = synthetic construct
SEQUENCE: 89
agctggggaa tagtggatgt cta                                        23

SEQ ID NO: 90           moltype = RNA  length = 22
FEATURE                 Location/Qualifiers
source                  1..22
                        mol_type = other RNA
                        organism = synthetic construct
SEQUENCE: 90
aagatgagaa tttgggtttt ct                                         22

SEQ ID NO: 91           moltype = RNA  length = 22
FEATURE                 Location/Qualifiers
source                  1..22
                        mol_type = other RNA
                        organism = synthetic construct
SEQUENCE: 91
tgggagtaat ggatgtttgc aa                                         22

SEQ ID NO: 92           moltype = RNA  length = 21
FEATURE                 Location/Qualifiers
source                  1..21
                        mol_type = other RNA
                        organism = synthetic construct
SEQUENCE: 92
cccaattact gtcattgatg a                                          21

SEQ ID NO: 93           moltype = RNA  length = 21
FEATURE                 Location/Qualifiers
source                  1..21
                        mol_type = other RNA
                        organism = synthetic construct
```

```
SEQUENCE: 93
ccaagtgaac atcaatgctt t                                            21

SEQ ID NO: 94          moltype = RNA  length = 21
FEATURE                Location/Qualifiers
source                 1..21
                       mol_type = other RNA
                       organism = synthetic construct
SEQUENCE: 94
tgtggtgtct gagtactttg t                                            21

SEQ ID NO: 95          moltype = RNA  length = 21
FEATURE                Location/Qualifiers
source                 1..21
                       mol_type = other RNA
                       organism = synthetic construct
SEQUENCE: 95
aagtcgtttc attcaagttg a                                            21

SEQ ID NO: 96          moltype = RNA  length = 21
FEATURE                Location/Qualifiers
source                 1..21
                       mol_type = other RNA
                       organism = synthetic construct
SEQUENCE: 96
aaagcattga tgttcacttg g                                            21

SEQ ID NO: 97          moltype = RNA  length = 23
FEATURE                Location/Qualifiers
source                 1..23
                       mol_type = other RNA
                       organism = synthetic construct
SEQUENCE: 97
tagacatcca gataatcctc cct                                          23

SEQ ID NO: 98          moltype = RNA  length = 21
FEATURE                Location/Qualifiers
source                 1..21
                       mol_type = other RNA
                       organism = synthetic construct
SEQUENCE: 98
tagacatcca gataatcctc c                                            21

SEQ ID NO: 99          moltype = RNA  length = 23
FEATURE                Location/Qualifiers
source                 1..23
                       mol_type = other RNA
                       organism = synthetic construct
SEQUENCE: 99
aaagcattga tgttcgcttg gtt                                          23

SEQ ID NO: 100         moltype = RNA  length = 22
FEATURE                Location/Qualifiers
source                 1..22
                       mol_type = other RNA
                       organism = synthetic construct
SEQUENCE: 100
tagacatcca gataatcctt cc                                           22

SEQ ID NO: 101         moltype = RNA  length = 23
FEATURE                Location/Qualifiers
source                 1..23
                       mol_type = other RNA
                       organism = synthetic construct
SEQUENCE: 101
tcaacttgaa tgaaacggct tct                                          23

SEQ ID NO: 102         moltype = RNA  length = 23
FEATURE                Location/Qualifiers
source                 1..23
                       mol_type = other RNA
                       organism = synthetic construct
```

-continued

```
SEQUENCE: 102
tcattgtctt tcttggaagc caa                                           23

SEQ ID NO: 103         moltype = RNA  length = 22
FEATURE                Location/Qualifiers
source                 1..22
                       mol_type = other RNA
                       organism = synthetic construct
SEQUENCE: 103
accaagtgaa catcaatgct tt                                            22

SEQ ID NO: 104         moltype = RNA  length = 22
FEATURE                Location/Qualifiers
source                 1..22
                       mol_type = other RNA
                       organism = synthetic construct
SEQUENCE: 104
tccaagtgaa catcaatgct tt                                            22

SEQ ID NO: 105         moltype = RNA  length = 22
FEATURE                Location/Qualifiers
source                 1..22
                       mol_type = other RNA
                       organism = synthetic construct
SEQUENCE: 105
gtgagtgatg agatctcttt ca                                            22

SEQ ID NO: 106         moltype = RNA  length = 22
FEATURE                Location/Qualifiers
source                 1..22
                       mol_type = other RNA
                       organism = synthetic construct
SEQUENCE: 106
gggaggatta tctggatgtc ta                                            22

SEQ ID NO: 107         moltype = RNA  length = 22
FEATURE                Location/Qualifiers
source                 1..22
                       mol_type = other RNA
                       organism = synthetic construct
SEQUENCE: 107
tggaggatta tctggatgtc ta                                            22

SEQ ID NO: 108         moltype = RNA  length = 22
FEATURE                Location/Qualifiers
source                 1..22
                       mol_type = other RNA
                       organism = synthetic construct
SEQUENCE: 108
accaagcgaa catcaatgct tt                                            22

SEQ ID NO: 109         moltype = RNA  length = 23
FEATURE                Location/Qualifiers
source                 1..23
                       mol_type = other RNA
                       organism = synthetic construct
SEQUENCE: 109
tggaaggatt atctggatgt cta                                           23

SEQ ID NO: 110         moltype = RNA  length = 22
FEATURE                Location/Qualifiers
source                 1..22
                       mol_type = other RNA
                       organism = synthetic construct
SEQUENCE: 110
gaagccgttt cattcaagtt ga                                            22
```